US012733858B2

(12) United States Patent
Hatakeyama et al.

(10) Patent No.: US 12,733,858 B2
(45) Date of Patent: Sep. 15, 2026

(54) BIO-ELECTRODE COMPOSITION, BIO-ELECTRODE, AND METHOD FOR MANUFACTURING BIO-ELECTRODE

(71) Applicant: SHIN-ETSU CHEMICAL CO., LTD., Tokyo (JP)

(72) Inventors: Jun Hatakeyama, Joetsu (JP); Takayuki Nagasawa, Joetsu (JP); Joe Ikeda, Joetsu (JP)

(73) Assignee: SHIN-ETSU CHEMICAL CO., LTD., Tokyo (JP)

(*) Notice: Subject to any disclaimer, the term of this patent is extended or adjusted under 35 U.S.C. 154(b) by 258 days.

(21) Appl. No.: 18/524,312

(22) Filed: Nov. 30, 2023

(65) Prior Publication Data

US 2024/0215891 A1 Jul. 4, 2024

(30) Foreign Application Priority Data

Dec. 5, 2022 (JP) ................................ 2022-194520
May 23, 2023 (JP) .................................. 2023-84852

(51) Int. Cl.
*A61B 5/268* (2021.01)

(52) U.S. Cl.
CPC .................................. *A61B 5/268* (2021.01)

(58) Field of Classification Search
CPC ............................... A61B 5/257; A61B 5/268
See application file for complete search history.

(56) References Cited

U.S. PATENT DOCUMENTS

2015/0175722 A1 6/2015 Hatakeyama et al.
2015/0340118 A1 11/2015 Nagasawa et al.
(Continued)

FOREIGN PATENT DOCUMENTS

EP 3067897 A1 9/2016
EP 3995548 A1 5/2022
(Continued)

OTHER PUBLICATIONS

Office Action and Search Report mailed Jun. 27, 2024, in corresponding Taiwanese Application No. 112147214 (including English translation).
Araki, et al.; Non-contact Laser Printing of Ag N anowire-based Electrode with Photodegradable Polymers; Journal of Photopolymer Science and Technology, vol. 32, No. 3 (2019) 429-434; published Jun. 24, 2019.
Extended Search Report mailed May 7, 2024, in corresponding European Application No. 23211286.2.
(Continued)

*Primary Examiner* — Eun Hwa Kim
(74) *Attorney, Agent, or Firm* — Harness, Dickey & Pierce, P.L.C.

(57) ABSTRACT

The present invention is a bio-electrode composition containing: an electro-conductive polymer composite including (A) a π-conjugated polymer and (B) a dopant polymer containing a repeating unit-a1 having a hydroxy group and/or a carboxy group and a repeating unit-a2 having a sulfonic acid, fluorosulfonimide, and N-carbonyl-fluorosulfonamide, the dopant polymer having a weight-average molecular weight of 1,000 to 500,000; and (C) a crosslinking agent. This provides: a bio-electrode composition that allows a thin film of high transparency, has high sensitivity to biological signals, has excellent biocompatibility, is lightweight, can be manufactured at low cost, can control significant reduction in sensitivity to biological signals when soaked in water for a long time or when attached to the skin for a long time, causes no itchiness, red spots, rashes, etc. of the skin, and is comfortable; a bio-electrode; and a method for manufacturing a bio-electrode.

14 Claims, 3 Drawing Sheets

(56) References Cited

U.S. PATENT DOCUMENTS

| | | | | |
|---|---|---|---|---|
| 2016/0064112 | A1 | 3/2016 | Hatakeyama et al. | |
| 2016/0064113 | A1 | 3/2016 | Hatakeyama et al. | |
| 2016/0067702 | A1 | 3/2016 | Hatakeyama et al. | |
| 2016/0268015 | A1* | 9/2016 | Hatakeyama .......... | H01B 1/122 |
| 2017/0062089 | A1 | 3/2017 | Hatakeyama et al. | |
| 2017/0233596 | A1 | 8/2017 | Hatakeyama et al. | |
| 2018/0072930 | A1 | 3/2018 | Hatakeyama et al. | |
| 2018/0085019 | A1 | 3/2018 | Hatakeyama et al. | |
| 2018/0086948 | A1 | 3/2018 | Hatakeyama et al. | |
| 2018/0168470 | A1 | 6/2018 | Hatakeyama et al. | |
| 2018/0193632 | A1* | 7/2018 | Hatakeyama .......... | A61B 5/259 |
| 2018/0229024 | A1 | 8/2018 | Hatakeyama et al. | |
| 2018/0240564 | A1 | 8/2018 | Hatakeyama et al. | |
| 2019/0209740 | A1* | 7/2019 | Hatakeyama ........ | A61B 5/0531 |
| 2020/0040125 | A1 | 2/2020 | Hatakeyama et al. | |
| 2020/0259094 | A1 | 8/2020 | Nagasawa et al. | |
| 2022/0135763 | A1 | 5/2022 | Hatakeyama | |

FOREIGN PATENT DOCUMENTS

| | | | |
|---|---|---|---|
| JP | 2015-100673 | A | 6/2015 |
| JP | 2015-134905 | A | 7/2015 |
| JP | 6271378 | B2 | 1/2018 |
| JP | 2018-044147 | A | 3/2018 |
| JP | 2018-059050 | A | 4/2018 |
| JP | 2018-059052 | A | 4/2018 |
| JP | 6335138 | B2 | 5/2018 |
| JP | 2018-099504 | A | 6/2018 |
| JP | 2018-110845 | A | 7/2018 |
| JP | 2018-130534 | A | 8/2018 |
| JP | 6407107 | B2 | 10/2018 |
| JP | 6438348 | B2 | 12/2018 |
| JP | 6450661 | B2 | 1/2019 |
| JP | 6483518 | B2 | 3/2019 |
| JP | 6496258 | B2 | 4/2019 |
| JP | 2020-023668 | A | 2/2020 |
| JP | 6661212 | B2 | 3/2020 |
| KR | 1020160110163 | A | 9/2016 |
| TW | 202043361 | A | 12/2020 |
| WO | 2013039151 | A1 | 3/2013 |

OTHER PUBLICATIONS

Trulove, et al.; Electrochemical Properties of Ionic Liquids; pp. 103-126; published Feb. 26, 2003.

Yang, et al.; Facile fabrication of stretchable Ag nanowire/polyurethane electrodes using high intensity pulsed light; Nano Research 2016, 9(2): 401-414; published Jan. 7, 2016.

Korean Office Action in application No. 2023-0170666 issued on Sep. 4, 2025.

Japanese Notification of Reasons for Refusal in application No. 2023-084852 issued on Jan. 20, 2026.

Shogo Saito, Electronic Properties of Aromatic Polymers, Polymers, 1984, vol. 33, 760-764.

* cited by examiner

[FIG. 1]
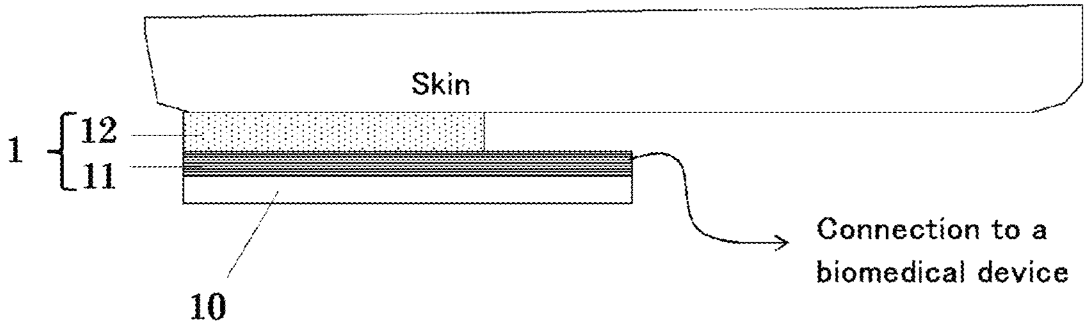
[FIG. 2]
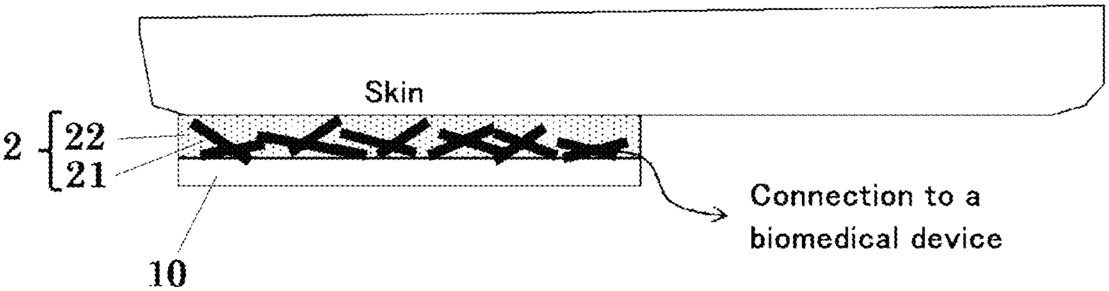
[FIG. 3]
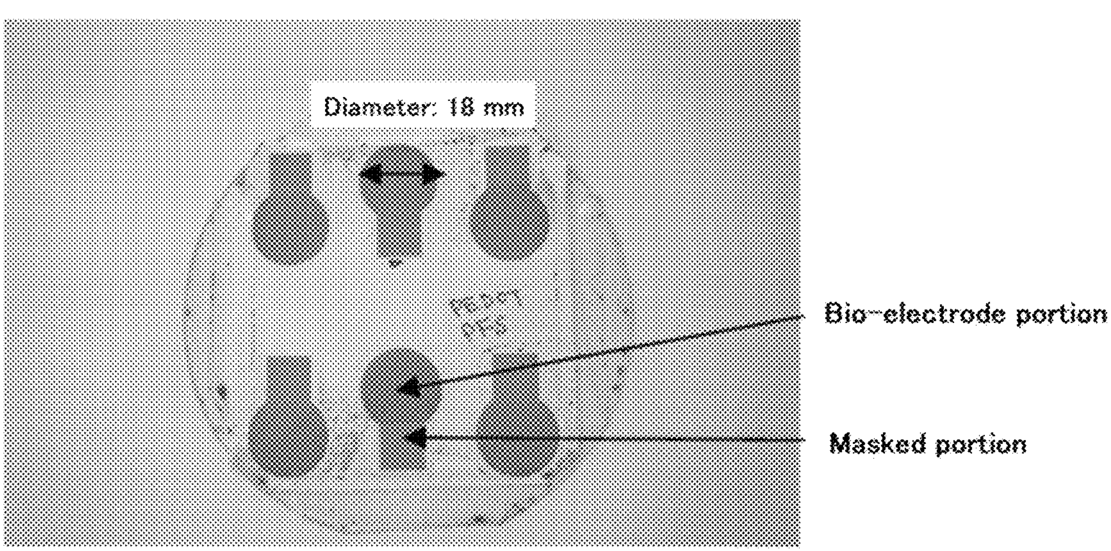

[FIG. 4]
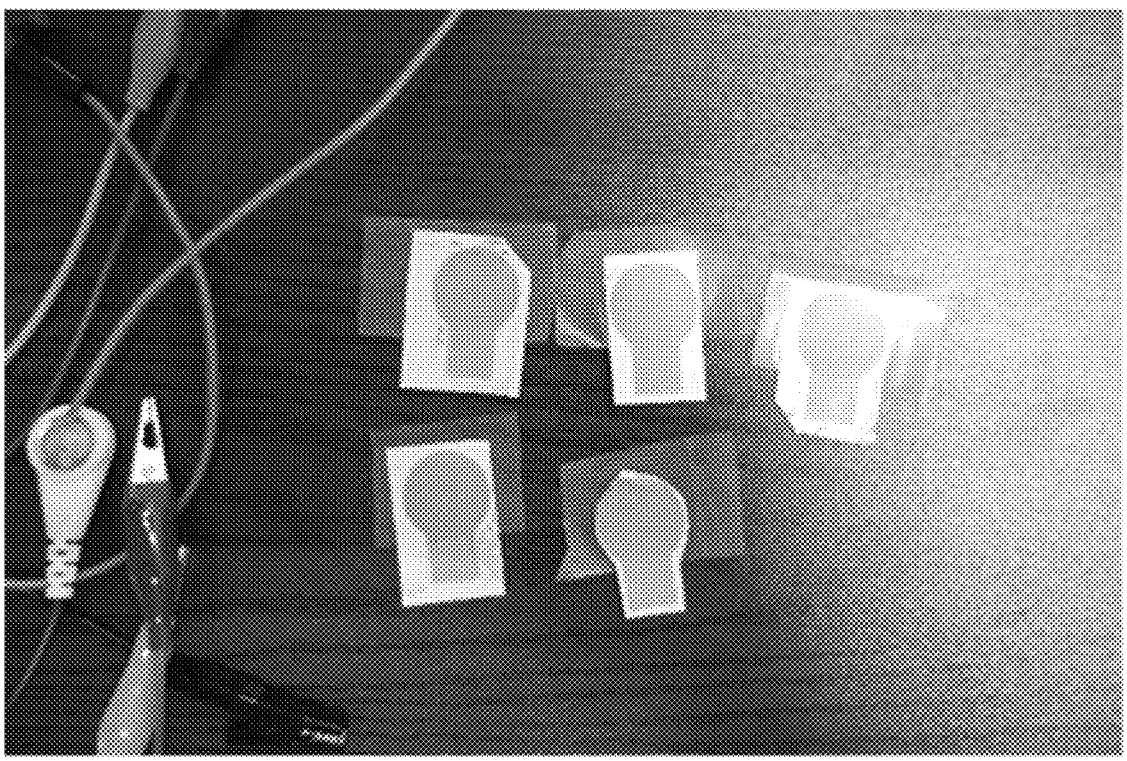
[FIG. 5]
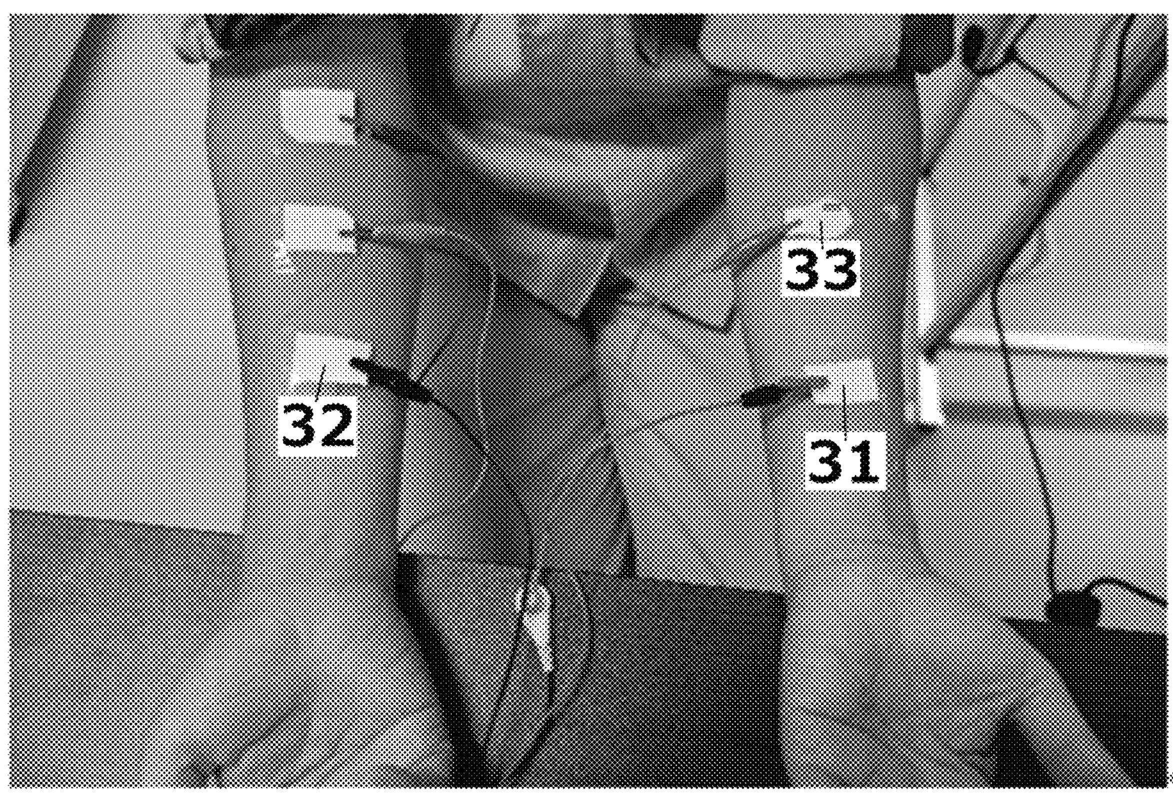

[FIG. 6]
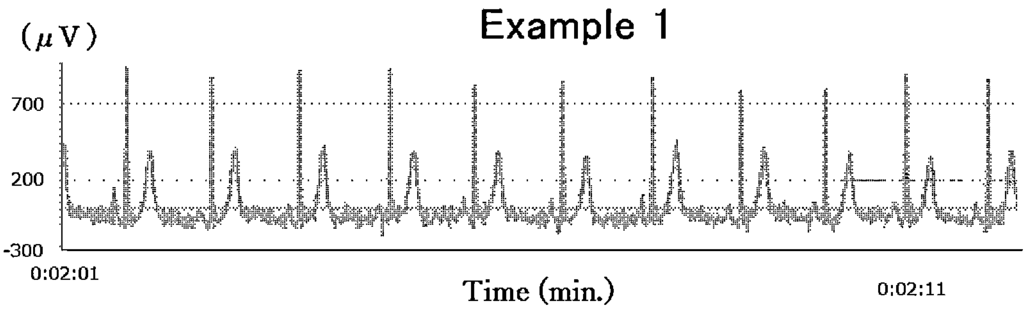

BIO-ELECTRODE COMPOSITION, BIO-ELECTRODE, AND METHOD FOR MANUFACTURING BIO-ELECTRODE

TECHNICAL FIELD

The present invention relates to: a bio-electrode composition; a bio-electrode; and a method for manufacturing a bio-electrode.

BACKGROUND ART

A recent growing popularity of Internet of Things (IoT) has accelerated the development of wearable devices. Even in the fields of medicine and sports, wearable devices for constantly monitoring the user's physical state are increasingly demanded, and such technological development is expected to be further encouraged. In particular, there is a serious strain on medical services due to worldwide spread of novel coronavirus (COVID-19), and there is a call for the need for and acceleration of home care for people who are not infected with the virus.

In the field of medicine, wearable devices are sold for monitoring the state of human organs by sensing extremely weak current, such as an electrocardiogram which detects an electric signal to measure the motion of the heart. The electrocardiogram measurement is conducted by attaching an electrode coated with a hydrated gel to a body, but this is a single (not continuous), short-time measurement. On the other hand, development of the above medical wearable device is aimed at devices for continuously monitoring the health condition for a few weeks. Accordingly, a bio-electrode used in a medical wearable device is required to be capable of collecting biological signals even in long-time use in daily life involving showers, bathing, perspiration, etc., cause no itching or skin allergy, and be comfortable. In addition to these, it is also required that a bio-electrode is so light-weight and thin as to cause no feeling of attachment and can be produced at low cost and high productivity.

It is becoming possible to obtain an electrocardiogram by using watch-type devices, such as Apple Watch, or by non-contact sensing using radar. However, high-accuracy electrocardiograms for medical purposes require a type of electrocardiograph in which bio-electrodes are attached to a number of places on the body.

Medical wearable devices are classified into two types: a type which is directly attached to the body and a type which is incorporated into clothes. As the type which is attached to the body, widely used is a bio-electrode of the above-mentioned hydrated gel material, for example, a hydrophilic gel disclosed in Patent Document 1 containing water and electrolytes. The hydrophilic gel contains sodium, potassium, or calcium as the electrolyte in a hydrophilic polymer for retaining water, and converts changes of the concentration of ions from skin into electric signals by a reduction reaction of silver chloride contacting the hydrophilic gel. There are problems that if the gel dries, conductivity is lost, so that the function as a bio-electrode is lost, and that the gel swells during bathing or a shower and falls off.

On the other hand, as the type which is incorporated into clothes, there has been proposed a means to use cloth in which an electro-conductive polymer such as PEDOT-PSS (poly-3,4-ethylenedioxythiophene-polystyrenesulfonate) or silver paste is incorporated into the fibers for electrodes (Patent Document 2). PEDOT-PSS has a characteristic that the polymer disperses in water, and therefore, films and fibers coated with PEDOT-PSS also have a problem of falling off if immersed in water for a long time.

A bio-electrode sheet having stretchability and high conductivity is being developed (Non Patent Document 1). Here, silver nanowires are applied to a polyurethane film, the surfaces of the silver nanowires are heated and melted at 500° C. or higher instantaneously by flash annealing, and the silver nanowires are fused together.

Metallic bio-electrodes of gold thin films, silver nanowires, etc. have a metallic color, and are not transparent. If it is possible to develop a bio-electrode that is transparent and through which the skin can be seen, there is an advantage that there is no incongruity in appearance when the bio-electrode is attached to the skin.

Here, as a transparent conductive film to replace ITO for organic EL use, PEDOT-PSS is studied. Combination of silver nanowires and PEDOT-PSS is also carried out (Non Patent Document 2). However, PEDOT-PSS has a blue appearance, and is not transparent. In order to improve transparency, there has been indicated the application, to a transparent conductive film, of polythiophene combined with a dopant to which fluorine is introduced (Patent Documents 3 to 10).

CITATION LIST

Patent Literature

Patent Document 1: WO 2013/039151 A1
Patent Document 2: JP 2015-100673 A
Patent Document 3: JP 6661212 B2
Patent Document 4: JP 6450661 B2
Patent Document 5: JP 6335138 B2
Patent Document 6: JP 6271378 B2
Patent Document 7: JP 6407107 B2
Patent Document 8: JP 6496258 B2
Patent Document 9: JP 6483518 B2
Patent Document 10: JP 6438348 B2
Patent Document 11: JP 2020-023668 A
Patent Document 12: JP 2018-044147 A
Patent Document 13: JP 2018-059050 A
Patent Document 14: JP 2018-059052 A
Patent Document 15: JP 2018-130534 A

Non Patent Literature

Non Patent Document 1: Nano Res. 9, 401 (2016)
Non Patent Document 2: J. Photopolymer Sci. and Tech. Vol 32 No. 3 p 429 (2019)
Non Patent Document 3: Trulove C, Mantz R. 2003.Ionic Liquids in Synthesis, Chapter 3.6: Electrochemical Properties of Ionic Liquids.

SUMMARY OF INVENTION

Technical Problem

The present invention has been made to solve the problems. An object of the present invention is to provide: a bio-electrode composition that allows a thin film of high transparency, has high sensitivity to biological signals, has excellent biocompatibility, is light-weight, can be manufactured at low cost, can control significant reduction in sensitivity to biological signals when soaked in water for a long time or when attached to the skin for a long time, causes no itchiness, red spots, rashes, etc. of the skin, and is comfortable; a bio-electrode; and a method for manufacturing a bio-electrode.

Solution to Problem

The present invention has been made to achieve the object, and provides a bio-electrode composition comprising:

an electro-conductive polymer composite including (A) a π-conjugated polymer and (B) a dopant polymer containing a repeating unit-a1 having a hydroxy group and/or a carboxy group and a repeating unit-a2 having a sulfonic acid, fluorosulfonimide, and N-carbonyl-fluorosulfonamide, the dopant polymer having a weight-average molecular weight of 1,000 to 500,000; and (C) a crosslinking agent.

Such a bio-electrode composition makes it possible to provide a composition containing: a π-conjugated polymer compounded with a dopant polymer into which a repeating unit of a crosslinkable group and a sulfonic acid residue has been introduced; and a crosslinking agent. It is also possible to provide a bio-electrode which includes a combination of a living body contact layer, being a cured product of the composition, and an electro-conductive base material. Such a bio-electrode can be used without significant reduction in sensitivity to biological signals even when soaked in water for a long time.

In this event, the crosslinking agent may have a reactive group selected from an isocyanate group, a blocked isocyanate group, a carbodiimide group, and an aziridine group.

In this manner, it is possible to prevent the electro-conductive polymer composite from falling off or swelling in water.

In this event, the π-conjugated polymer (A) may be a polymerized product of one or more precursor monomers selected from the group consisting of monocyclic aromatic compounds, polycyclic aromatic compounds, acetylenes, and derivatives thereof.

In this manner, ease of polymerization and stability in air can be enhanced.

In this event, the monocyclic aromatic compounds may be pyrroles, thiophenes, thiophenevinylenes, selenophenes, tellurophenes, phenylenes, phenylenevinylenes, or anilines, and the polycyclic aromatic compounds may be acenes.

In this manner, ease of polymerization and stability in air can be enhanced with more certainty.

In this event, the repeating unit-a1, having a hydroxy group and/or a carboxy group in the dopant polymer (B), may have a repeating unit A1-1 and/or a repeating unit A1-2 represented by the following general formulae (1), (1)

A1-1

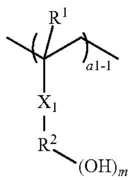

-continued

A1-2

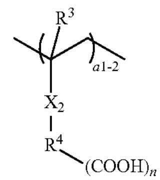

wherein $R^1$ and $R^3$ each independently represent a hydrogen atom or a methyl group; $X_1$ and $X_2$ each independently represent a single bond, a phenylene group, a naphthylene group, an ether group, an ester group, or an amide group; $R^2$ and $R^4$ each independently represent a single bond or a linear, branched, or cyclic hydrocarbon group having 1 to 20 carbon atoms and optionally having an ether group or an ester group; "m" and "n" each represent an integer of 1 to 5; and a1-1 and a1-2 satisfy $0 \leq (a1\text{-}1) < 1.0$, $0 \leq (a1\text{-}2) < 1.0$, and $0 < (a1\text{-}1)+(a1\text{-}2) < 1.0$.

This allows a reaction with the crosslinking agent certainly, and prevents the electro-conductive polymer composite from being detached or swelling in water.

In this event, the dopant polymer (B) may contain, as the repeating unit-a2, partial structures represented by the following general formulae (2)-1 to (2)-4, (2)-1

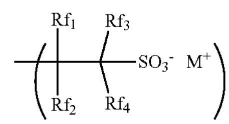

(2)-2

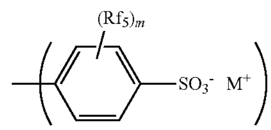

(2)-3

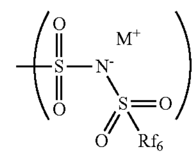

(2)-4

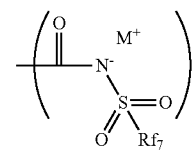

wherein $Rf_1$ to $Rf_4$ each represent a hydrogen atom, a fluorine atom, or a trifluoromethyl group, $Rf_1$ and $Rf_2$ optionally forming a carbonyl group together; $Rf_5$ represents a hydrogen atom, a fluorine atom, or a linear or branched alkyl group having 1 to 4 carbon atoms, optionally being substituted with a fluorine atom; $Rf_6$ and $Rf_7$ each represent a fluorine atom or a linear or branched alkyl group having 1 to 4 carbon atoms, having at least one fluorine atom; "m" represents an integer of 0 to 4; and $M^+$ represents an ion selected from a hydrogen ion, an ammonium ion, a sodium ion, and a potassium ion.

In this manner, the bio-electrode has excellent conductivity and biocompatibility, is light-weight, and can control significant reduction in conductivity either when soaked in water or dried.

In this event, the dopant polymer (B) may contain, as the repeating unit-a2, one or more repeating units selected from repeating units A2-1 to A2-7 represented by the following general formulae (2), (2)

A2-1

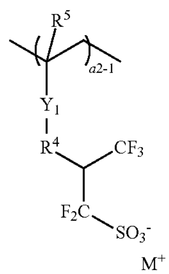

A2-2

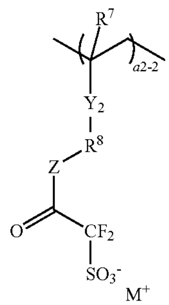

A2-3

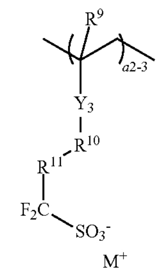

A2-4

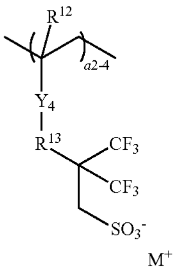

A2-5

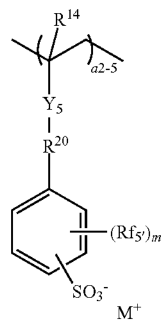

-continued

A2-6

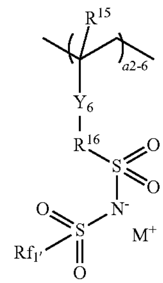

A2-7

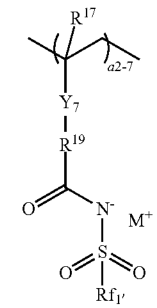

wherein $R^5$, $R^7$, $R^9$, $R^{12}$, $R^{14}$, $R^{15}$, and $R^{17}$ each independently represent a hydrogen atom or a methyl group; $R^6$, $R^8$, $R^{10}$, $R^{13}$, $R^{16}$, $R^{19}$, and $R^{20}$ each independently represent a single bond or a linear, branched, or cyclic hydrocarbon group having 1 to 13 carbon atoms, the hydrocarbon group optionally having one or more selected from an ester group, an ether group, an amide group, a carbamate group, a thiocarbamate group, and a urea group; $R^{11}$ represents a linear or branched alkylene group having 1 to 4 carbon atoms, one or two hydrogen atoms in $R^{11}$ optionally being substituted with a fluorine atom; $Y_1$, $Y_2$, $Y_3$, $Y_4$, $Y_6$, and $Y_7$ each independently represent a single bond, a phenylene group, a naphthylene group, an ether group, an ester group, or an amide group; $Y_5$ represents a single bond, an ether group, or an ester group; Z represents an oxygen atom or an —$NR^{18}$— group; $R^{18}$ represents a hydrogen atom, a linear, branched or cyclic alkyl group having 2 to 12 carbon atoms, or a phenyl group and optionally has one or more selected from an ether group, a carbonyl group, an ester group, and an amide group; Z optionally forms a ring together with $R^8$; $Rf_1$, and $Rf_5$, each represent a fluorine atom, a trifluoromethyl group, or a linear or branched alkyl group having 1 to 4 carbon atoms, having at least one fluorine atom; "m" represents an integer of 0 to 4; a2-1, a2-2, a2-3, a2-4, a2-5, a2-6, and a2-7 satisfy $0 \leq (a2\text{-}1) < 1.0$, $0 \leq (a2\text{-}2) < 1.0$, $0 \leq (a2\text{-}3) < 1.0$, $0 \leq (a2\text{-}4) < 1.0$, $0 \leq (a2\text{-}5) < 1.0$, $0 \leq (a2\text{-}6) < 1.0$, $0 \leq (a2\text{-}7) < 1.0$, and $0 < (a2\text{-}1)+(a2\text{-}2)+(a2\text{-}3)+(a2\text{-}4)+(a2\text{-}5)+(a2\text{-}6)+(a2\text{-}7) < 1.0$; $M^+$ represents an ion selected from a hydrogen ion, an ammonium ion, a sodium ion, and a potassium ion.

In this manner, the advantageous effects of the present invention can be enhanced further.

In this event, the $Rf_1$, may have at least one fluorine atom, and the $Rf_5$, may be a fluorine atom or a trifluoromethyl group in the general formulae (2).

In this manner, the bio-electrode, with certainty, has excellent conductivity and biocompatibility, is light-weight, and can control significant reduction in conductivity either when soaked in water or dried.

In this event, the dopant polymer (B) may contain, as the ammonium ion, an ammonium ion represented by the following general formula (3), (3)

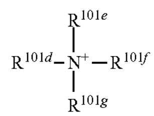

wherein $R^{101d}$, $R^{101e}$, $R^{101f}$, and $R^{101g}$ each represent a hydrogen atom, a linear, branched, or cyclic alkyl group having 1 to 15 carbon atoms, a linear, branched, or cyclic alkenyl group or alkynyl group having 2 to 12 carbon atoms, or an aromatic group having 4 to 20 carbon atoms, $R^{101d}$, $R^{101e}$, $R^{101f}$, and $R^{101g}$ optionally having one or more selected from an ether group, a carbonyl group, an ester group, a hydroxy group, a carboxy group, an amino group, a nitro group, a sulfonyl group, a sulfinyl group, a halogen atom, and a sulfur atom; and $R^{101d}$ and $R^{101e}$, or $R^{101d}$, $R^{101e}$, and $R^{101f}$ optionally form a ring together with a nitrogen atom bonded to $R^{101d}$ and $R^{101e}$, or $R^{101d}$, $R^{101e}$, and $R^{101f}$ and when a ring is formed, $R^{101d}$ and $R^{101e}$, or $R^{101d}$, $R^{101e}$, and $R^{101f}$ form an alkylene group having 3 to 10 carbon atoms or a heteroaromatic ring having, in the ring, the nitrogen atom in the general formula (3).

In this manner, the bio-electrode more certainly has high sensitivity to biological signals, is light-weight, can be manufactured at low cost, can control significant reduction in sensitivity to biological signals either when soaked in water, dried, or attached to the skin for a long time, causes no itchiness, red spots, rashes, etc. of the skin, and can be used comfortably.

In this event, the inventive bio-electrode composition may comprise, in addition to the components (A), (B), and (C), a component (D) containing one or more resins selected from a (meth)acrylate resin, a (meth)acrylamide resin, a urethane resin, polyvinyl alcohol, polyvinylpyrrolidone, polyoxazoline, polyglycerin, polyglycerin-modified silicone, cellulose, polyethylene glycol, and polypropylene glycol.

In this manner, the resin is made compatible with salts and prevents elution of the composite, and can hold an electric conductivity improver such as a metal powder, a carbon powder, a silicon powder, and a lithium titanate powder.

In this event, the inventive bio-electrode composition may further comprise, as a component (E), one or more selected from a carbon powder, a metal powder, a silicon powder, and a lithium titanate powder.

In this manner, the carbon powder and the metal powder can enhance electron conductivity, and the silicon powder and the lithium titanate powder can enhance ion reception sensitivity.

In this event, the carbon powder may be one or both of carbon black and carbon nanotube.

In this manner, electron conductivity can be enhanced more certainly.

In this event, the metal powder may be any of gold nanoparticles, silver nanoparticles, copper nanoparticles, gold nanowire, silver nanowire, and copper nanowire.

In this manner, electron conductivity can be enhanced more certainly.

The present invention has been made to achieve the above-described object, and provides a bio-electrode comprising an electro-conductive base material and a living body contact layer formed on the electro-conductive base material, wherein the living body contact layer comprises the electro-conductive polymer composite comprised in the above-described bio-electrode composition.

Such a bio-electrode has high sensitivity to biological signals, has excellent biocompatibility, is a thin film and is light-weight, has high transparency, can be manufactured at low cost, can control significant reduction in sensitivity to biological signals either when soaked in water for a long time or attached to the skin for a long time, causes no itchiness, red spots, or rashes of the skin, and can be used comfortably.

In this event, the electro-conductive base material may comprise one or more selected from the group consisting of gold, silver, silver chloride, platinum, aluminum, magnesium, tin, tungsten, iron, copper, nickel, stainless steel, chromium, titanium, and carbon.

In this manner, electron conductivity can be enhanced more certainly.

The present invention has been made to achieve the above-described object, and provides a method for manufacturing a bio-electrode having an electro-conductive base material and a living body contact layer formed on the electro-conductive base material, the method comprising:

applying the above-described bio-electrode composition onto the electro-conductive base material; and curing the bio-electrode composition to form the living body contact layer.

According to such a method for manufacturing a bio-electrode, it is possible to manufacture a bio-electrode that has high sensitivity to biological signals, has excellent biocompatibility, is a thin film and is light-weight, has high transparency, can be manufactured at low cost, can control significant reduction in sensitivity to biological signals either when soaked in water for a long time or attached to the skin for a long time, causes no itchiness, red spots, or rashes of the skin, and can be used comfortably.

Advantageous Effects of Invention

As described above, the inventive bio-electrode composition and bio-electrode have high sensitivity to biological signals, have excellent biocompatibility, can achieve a thin film, light-weight, and high transparency, can be manufactured at low cost, can control significant reduction in sensitivity to biological signals either when soaked in water for a long time or attached to the skin for a long time, cause no itchiness, red spots, rashes, etc. of the skin, and can be used comfortably.

According to the inventive method for manufacturing a bio-electrode, it is possible to manufacture a bio-electrode that has high sensitivity to biological signals, has excellent biocompatibility, is a thin film and is light-weight, has high transparency, can be manufactured at low cost, can control significant reduction in sensitivity to biological signals either when soaked in water for a long time or attached to the skin for a long time, causes no itchiness, red spots, rashes, etc. of the skin, and can be used comfortably.

BRIEF DESCRIPTION OF DRAWINGS

FIG. 1 is a cross-sectional view showing an example of the inventive bio-electrode, where the bio-electrode is in contact with skin.

FIG. 2 is a cross-sectional view showing a different example of the inventive bio-electrode, where the bio-electrode is in contact with skin.

FIG. 3 is a photograph in which an electro-conductive polymer composite solution used for the inventive bio-electrode has been applied to a quartz wafer on which has been placed a TPU film having a silver paste screen-printed in a keyhole shape.

FIG. 4 is a photograph of bio-electrodes obtained by cutting the TPU film having the keyhole-shaped screen print and having a film of the electro-conductive polymer composite used for the inventive bio-electrode, and attaching a cellophane adhesive tape on the backside.

FIG. 5 is a photograph where biological signals are being measured with the bio-electrodes shown in FIG. 4 attached to the arms.

FIG. 6 shows an ECG signal when the bio-electrodes shown in FIG. 5 were attached to the arms.

DESCRIPTION OF EMBODIMENTS

Hereinafter, the present invention will be described in detail, but the present invention is not limited thereto.

As explained above, there have been desired: a bio-electrode composition that has excellent high conductivity for achieving biological signals with high sensitivity and low noise, has excellent biocompatibility, can achieve a thin film of high transparency and light weight, can be manufactured at low cost, allows measurement of biological signals either when soaked in water or dried, causes no roughness or itchiness of the skin even when attached to the skin for a long time, and can form a light-weight thin film; a bio-electrode; and a method for manufacturing a bio-electrode.

The surface of skin releases ions of sodium, potassium, and calcium in accordance with heartbeat. A bio-electrode has to convert the increase and decrease of ions released from skin to electric signals. Accordingly, the bio-electrode requires a material that is excellent in ionic conductivity to transmit the increase and decrease of ions. In accordance with heartbeat, electric potential on the surface of the skin also fluctuates. This fluctuation in electric potential is slight, and electron conductivity for conducting an extremely weak current to a device is also necessary.

A hydrophilic gel containing sodium chloride or potassium chloride has high ionic conductivity and electron conductivity, but loses conductivity if the water dries. Conductivity is also degraded by the sodium chloride or potassium chloride being eluted from the bio-electrode due to bathing or a shower.

A bio-electrode containing a metal such as gold or silver detects only extremely weak currents, and has low ionic conductivity, and therefore, has low sensitivity as a bio-electrode. Carbon has electron conductivity, as does metal, but has lower electron conductivity than metal, and therefore, has even lower sensitivity as a bio-electrode than metal.

Electro-conductive polymers, including PEDOT-PSS, have both electron conductivity and ionic conductivity, but have low polarization, and therefore, have low ionic conductivity. In addition, a film of PEDOT-PSS coating has a problem that the film falls off from the substrate when immersed in water for a long time.

Acids and salts of fluorosulfonic acid, fluorosulfonimide, and N-carbonyl-fluorosulfonamide have high polarizability, and have high ionic conductivity. By compounding these dopant polymers with a π-conjugated polymer, such as polythiophene, it is possible to realize both high ionic conductivity and electron conductivity.

Furthermore, reactive hydroxy groups and carboxy groups contained in the dopant polymer and an added crosslinking agent that reacts with the groups prevent dissolution of a film of the electro-conductive polymer composite in water and detachment of the composite. Thus, it is possible to obtain biological signals even when the user bathes, takes a shower, or does exercise that accompanies perspiration, while the bio-electrode is attached to the skin.

The present inventors have thus earnestly studied the above problems and information, and found out a bio-electrode composition, a bio-electrode, and a method for manufacturing a bio-electrode having the following features. Thus, the present invention has been completed.

That is, the present invention is "a bio-electrode composition comprising:

an electro-conductive polymer composite including (A) a π-conjugated polymer and (B) a dopant polymer containing a repeating unit-a1 having a hydroxy group and/or a carboxy group and a repeating unit-a2 having a sulfonic acid, fluorosulfonimide, and N-carbonyl-fluorosulfonamide, the dopant polymer having a weight-average molecular weight of 1,000 to 500,000; and (C) a crosslinking agent", "a bio-electrode comprising an electro-conductive base material and a living body contact layer formed on the electro-conductive base material, wherein the living body contact layer comprises the electro-conductive polymer composite comprised in the above-described bio-electrode composition", and "a method for manufacturing a bio-electrode having an electro-conductive base material and a living body contact layer formed on the electro-conductive base material, the method comprising:

applying the above-described bio-electrode composition onto the electro-conductive base material; and curing the bio-electrode composition to form the living body contact layer".

The living body contact layer, containing the electro-conductive polymer composite, contacts the electro-conductive base material, and the electro-conductive base material conveys biological signals to a device. The electro-conductive base material contains one or more selected from the group consisting of gold, silver, silver chloride, platinum, aluminum, magnesium, tin, tungsten, iron, copper, nickel, stainless steel, chromium, titanium, and carbon.

The living body contact layer may be formed on a surface of a film of the electro-conductive base material or may be formed on a surface of fibers of the electro-conductive base material.

It is possible to measure not only electrocardiograms, but also electromyograms, electroencephalograms, and respiratory rate. Furthermore, it is possible not only to measure signals released from the skin, but also to convey signals to muscles or control brainwaves by giving electric signals to the skin. For example, use of the bio-electrode may be considered for stimulating muscles during swimming for enhancing performance or reducing fatigue or for enhancing relaxation during bathing.

For constituting a high-sensitivity bio-electrode, high electron conductivity is necessary, as well as high ionic conductivity. Electron conductivity is guaranteed by the π-conjugated polymer, but to enhance the electron conductivity further, it is effective to incorporate a metal powder or a carbon powder in addition to the electro-conductive polymer composite.

Hereinafter, the present invention will be described with reference to the drawings.

First Embodiment

<Bio-Electrode>

Firstly, an example of the inventive bio-electrode will be described.

FIG. 1 is a cross-sectional view showing an example of the inventive bio-electrode where the bio-electrode is in contact with the skin.

As shown in FIG. 1, a bio-electrode 1 according to a first embodiment of the present invention has an electro-conductive base material 11 and a living body contact layer 12 formed on the electro-conductive base material 11.

Incidentally, although a base material 10 is provided under the electro-conductive base material 11 in FIG. 1, the base material 10 is not an essential feature.

In addition, FIG. 1 shows a state in which the living body contact layer 12 is in contact with the skin.

One side of the living body contact layer 12 is in contact with the skin, and the other side is in contact with the electro-conductive base material 11.

The base material 10 is preferably a flexible and stretchable film. A foamed film or a non-woven fabric is lightweight, has high stretchability, has high permeability of perspiration and allows dermal respiration, and is preferable.

(Living Body Contact Layer)

The living body contact layer 12 is a part that actually contacts the living body when the bio-electrode is used.

The living body contact layer 12 contains an electro-conductive polymer composite contained in the inventive bio-electrode composition.

The living body contact layer 12 is a film containing the electro-conductive polymer composite.

A film containing an electro-conductive polymer composite has low adhesion, and therefore, an adhesive layer may be provided in this area.

The adhesive layer preferably has an adhesive strength in a range of 0.5 N/25 mm or more and 20 N/25 mm or less. The adhesive strength is commonly measured by the method described in JIS Z 0237, in which a metal substrate such as a stainless steel (SUS) substrate or a polyethylene terephthalate (PET) substrate can be used as a base material. Alternatively, human skin can be used for measuring. Human skin has lower surface energy than metals and various plastics, and the energy is as low as that of Teflon (registered trademark). It is hard to make the layer adhere to human skin.

The living body contact layer 12 (the film of the electro-conductive polymer composite) preferably has a thickness of 1 nm or more and 1 mm or less, more preferably 2 nm or more and 0.5 mm or less.

The living body contact layer 12 (the film of the electro-conductive polymer composite) is in contact with the electro-conductive base material 11, and the electro-conductive base material 11 conveys biological signals to a device.

(Electro-Conductive Base Material)

The electro-conductive base material 11 preferably contains one or more selected from the group consisting of gold, silver, silver chloride, platinum, aluminum, magnesium, tin, tungsten, iron, copper, nickel, stainless steel, chromium, titanium, and carbon.

Second Embodiment

Secondly, a different example of the inventive bio-electrode will be described.

FIG. 2 is a cross-sectional view showing a different example of the inventive bio-electrode where the bio-electrode is in contact with the skin.

As shown in FIG. 2, a bio-electrode 2 according to a second embodiment of the present invention has an electro-conductive base material 21 and a living body contact layer 22 formed on the electro-conductive base material 21.

Incidentally, although a base material 10 is provided under the electro-conductive base material 21 in FIG. 2, the base material 10 is not an essential feature. In addition, FIG. 2 shows a state in which the living body contact layer 22 is in contact with the skin.

In the bio-electrode 2 according to the second embodiment of the present invention, the electro-conductive base material 21 is a network, and the living body contact layer 22 is formed so as to cover the network and enter a mesh of the network. In other respects, the bio-electrode 2 has the same features as the bio-electrode 1 according to the first embodiment of the present invention.

In a case where the electro-conductive base material 21 has a fiber-form or a wire-form, the bio-electrode 2 is formed to have the electro-conductive polymer composite buried in spaces in the fibers or wires. When the electro-conductive base material 21 is a freestanding film having a fiber-form or the like, the base material 10 is not necessarily needed.

The living body contact layer includes a bio-electrode composition containing:

an electro-conductive polymer composite including (A) a π-conjugated polymer and (B) a dopant polymer containing a repeating unit-a1 having a hydroxy group and/or a carboxy group and a repeating unit-a2 having a sulfonic acid, fluorosulfonimide, and N-carbonyl-fluorosulfonamide, the dopant polymer having a weight-average molecular weight of 1,000 to 500,000; and (C) a crosslinking agent.

<Bio-Electrode Composition>

In the following, each component of the inventive bio-electrode composition is described in further detail.

[(A) π-Conjugated Polymer]

The component (A) of the electro-conductive polymer composite contained in the bio-electrode composition, being a material for forming the living body contact layer of the inventive bio-electrode, may be a polymer containing a precursor monomer (organic monomer molecule) for forming a π-conjugated chain (a structure in which a single bond and a double bond are alternately continued).

Examples of such a precursor monomer include monocyclic aromatics, such as pyrroles, thiophenes, thiophenevinylenes, selenophenes, tellurophenes, phenylenes, phenylenevinylenes, and anilines; polycyclic aromatics, such as acenes; and acetylenes. A homopolymer or a copolymer of these monomers can be used as the component (A).

Among the monomers, from the viewpoints of easiness in polymerization and stability in air, pyrrole, thiophene, selenophene, tellurophene, aniline, polycyclic aromatic compounds, and derivatives thereof are preferable, and pyrrole, thiophene, aniline, and derivatives thereof are particularly preferable. However, the monomers are not limited thereto.

In addition, the component (A) can give sufficient conductivity even when the monomer constituting the n-conjugated polymer is not substituted. Nevertheless, for higher conductivity, a monomer substituted by an alkyl group, a carboxy group, a sulfo group, an alkoxy group, a hydroxy group, a cyano group, a halogen atom, or the like may be used.

Specific examples of the monomers of pyrroles, thiophenes, and anilines include pyrrole, N-methylpyrrole, 3-methylpyrrole, 3-ethylpyrrole, 3-n-propylpyrrole, 3-butylpyrrole, 3-octylpyrrole, 3-decylpyrrole, 3-dodecylpyrrole, 3,4-dimethylpyrrole, 3,4-dibutylpyrrole, 3-carboxypyrrole, 3-methyl-4-carboxypyrrole, 3-methyl-4- carboxyethylpyrrole, 3-methyl-4-carboxybutylpyrrole, 3-hydroxypyrrole, 3-methoxypyrrole, 3-ethoxypyrrole, 3-butoxypyrrole, 3-hexyloxypyrrole, 3-methyl-4-hexyloxypyrrole; thiophene, 3-methylthiophene, 3-ethylthiophene, 3-propylthiophene, 3-butylthiophene, 3-hexylthiophene, 3-heptylthiophene, 3-octylthiophene, 3-decylthiophene, 3-dodecylthiophene, 3-octadecylthiophene, 3-bromothiophene, 3-chlorothiophene, 3-iodothiophene, 3-cyanothiophene, 3-phenylthiophene, 3,4-dimethylthiophene, 3,4-dibutylthiophene, 3-hydroxythiophene, 3-methoxythiophene, 3-ethoxythiophene, 3-butoxythiophene, 3-hexyloxythiophene, 3-heptyloxythiophene, 3-octyloxythiophene, 3-decyloxythiophene, 3-dodecyloxythiophene, 3-octadecyloxythiophene, 3,4-dihydroxythiophene, 3,4-dimethoxythiophene, 3,4-diethoxythiophene, 3,4-dipropoxythiophene, 3,4-dibutoxythiophene, 3,4-dihexyloxythiophene, 3,4-diheptyloxythiophene, 3,4-dioctyloxythiophene, 3,4-didecyloxythiophene, 3,4-didodecyloxythiophene, 3,4-ethylenedioxythiophene, 3,4-propylenedioxythiophene, 3,4-butenedioxythiophene, 3-methyl-4-methoxythiophene, 3-methyl-4-ethoxythiophene, 3-carboxythiophene, 3-methyl-4-carboxythiophene, 3-methyl-4-carboxyethylthiophene, 3-methyl-4-carboxybutylthiophene; aniline, 2-methylaniline, 3-isobutylaniline, 2-methoxyaniline, 2-ethoxyaniline, 2-anilinesulfonic acid, 3-anilinesulfonic acid; etc.

Particularly, a (co)polymer containing one or more selected from pyrrole, thiophene, N-methylpyrrole, 3-methylthiophene, 3-methoxythiophene, and 3,4-ethylenedioxythiophene is suitably used from the viewpoints of a resistance value and reactivity. Moreover, a homopolymer of pyrrole or 3,4-ethylenedioxythiophene is more preferable because the conductivity is high.

For practical reasons, the number of these repeating units (precursor monomers) in the component (A) is preferably 2 to 20, more preferably 6 to 15.

The molecular weight of the component (A) is preferably about 130 to 5,000.

The component (A) is preferably contained in an amount of 5 to 150 parts by mass based on 100 parts by mass of the component (B) dopant polymer.

[(B) Dopant Polymer (Salt)]

The dopant polymer (B) of the electro-conductive polymer composite contained in the bio-electrode composition, being a material for forming the living body contact layer of the inventive bio-electrode, contains a repeating unit-a1 having a hydroxy group and/or a carboxy group and a repeating unit-a2 having a sulfonic acid, fluorosulfonimide, and N-carbonyl-fluorosulfonamide, and the dopant polymer has a weight-average molecular weight of 1,000 to 500,000. In addition, the dopant polymer (B) may contain, as an ionic material, a polymer having an ionic repeating unit-a2 selected from, for example, a hydrogen ion, an ammonium salt, a sodium salt, and a potassium salt of fluorosulfonic acid, fluorosulfonimide, or N-carbonyl-fluorosulfonamide.

The repeating unit-a1, having a hydroxy group and/or a carboxy group in the dopant polymer (B), preferably has a repeating unit A1-1 and/or a repeating unit A1-2 represented by the following general formulae (1).

(1)

A1-1

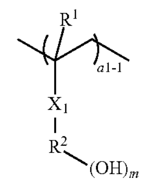

A1-2

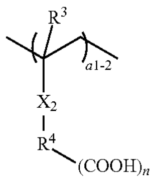

In the formulae, $R^1$ and $R^3$ each independently represent a hydrogen atom or a methyl group. $X_1$ and $X_2$ each independently represent a single bond, a phenylene group, a naphthylene group, an ether group, an ester group, or an amide group. $R^2$ and $R^4$ each independently represent a single bond or a linear, branched, or cyclic hydrocarbon group having 1 to 20 carbon atoms and optionally having an ether group or an ester group. "m" and "n" each represent an integer of 1 to 5. a1-1 and a1-2 satisfy $0 \le (a1\text{-}1) < 1.0$, $0 \le (a1\text{-}2) < 1.0$, and $0 \le (a1\text{-}1)+(a1\text{-}2) < 1.0$.

Specific examples of a monomer to give the repeating unit-a1 having a hydroxy group and/or a carboxy group include the following.

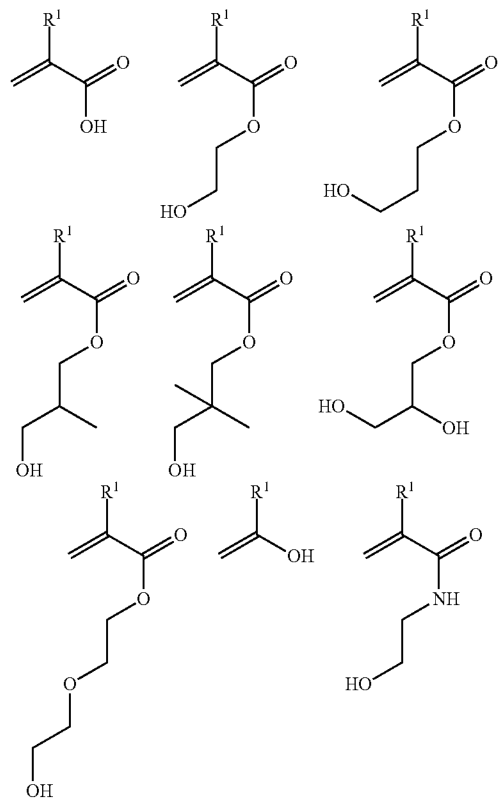

-continued
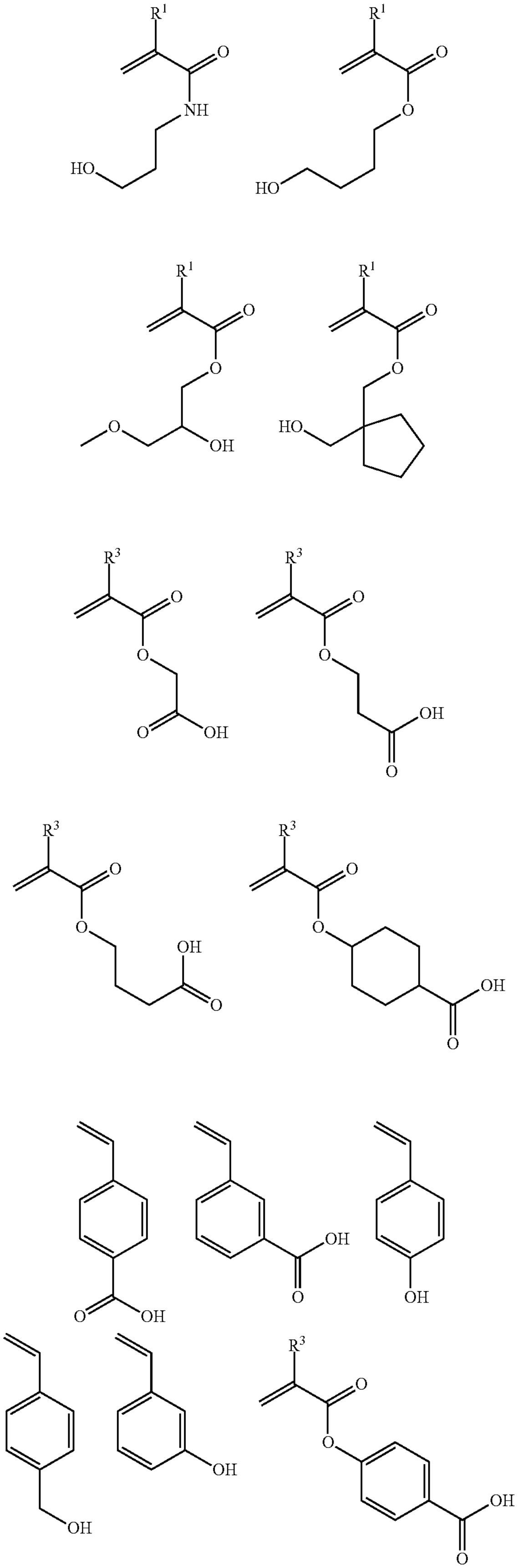
-continued
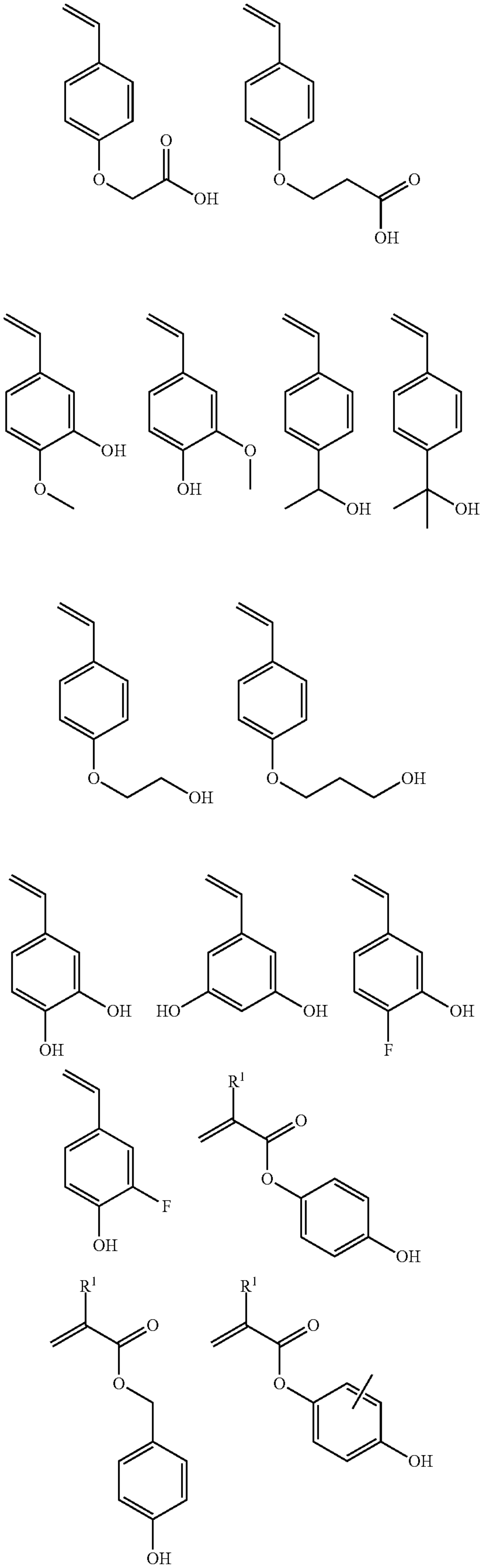

-continued
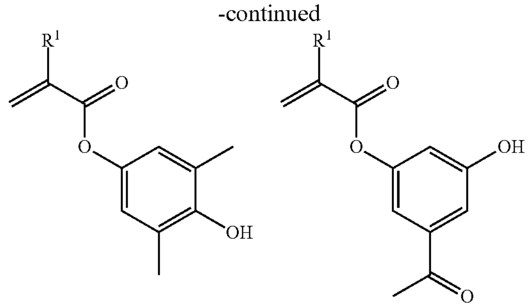
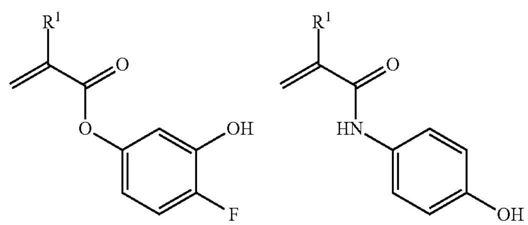
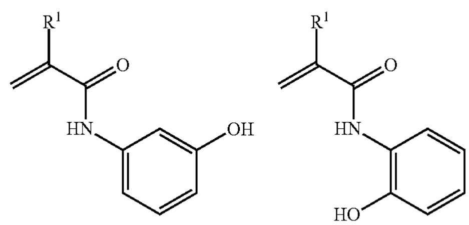
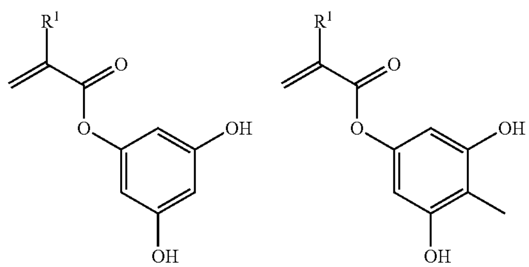
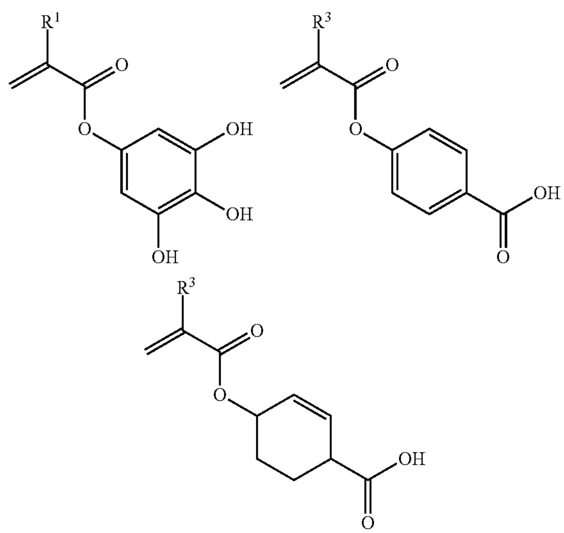
-continued
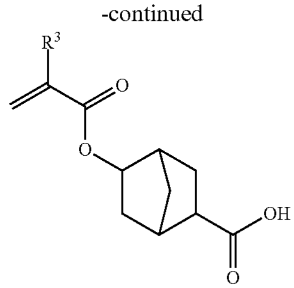
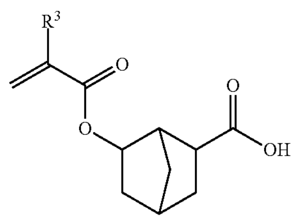
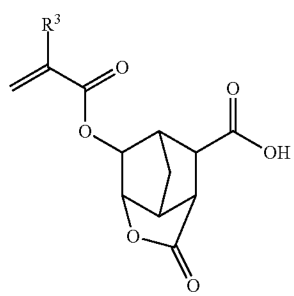
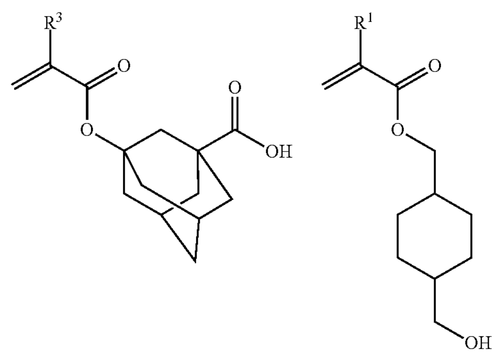
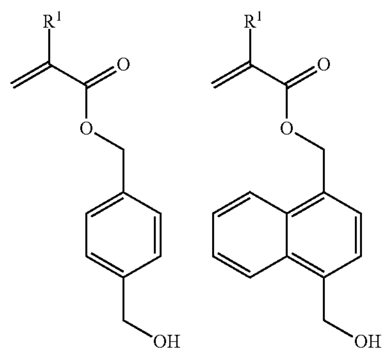

-continued

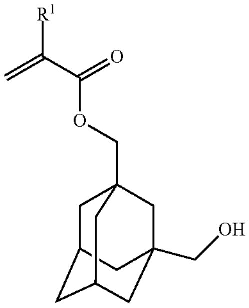

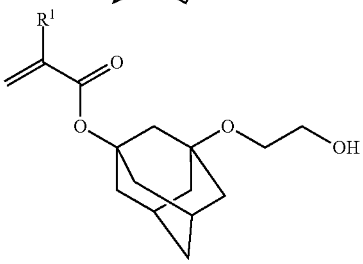

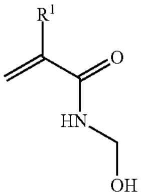

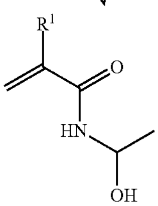

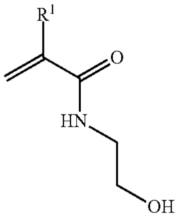

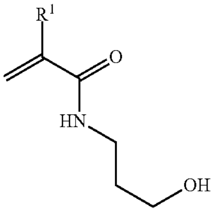

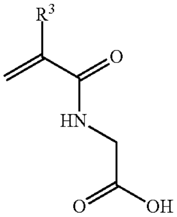

In the formulae, $R^1$ and $R^3$ are as defined above.

The ionic material selected from, for example, a hydrogen ion, an ammonium salt, a sodium salt, and a potassium salt of one of sulfonic acid, fluorosulfonimide, and N-carbonyl-fluorosulfonamide may have a partial structure represented by the following general formulae (2)-1 to (2)-5.

(2)-1

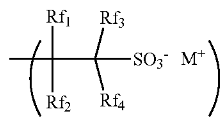

(2)-2

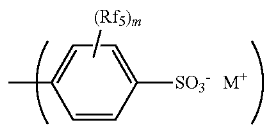

-continued (2)-3

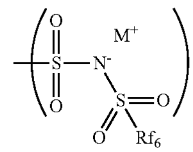

(2)-4

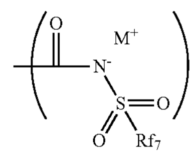

(2)-5

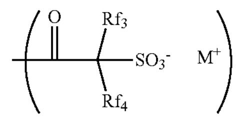

In the formulae, $Rf_1$ to $Rf_4$ each represent a hydrogen atom, a fluorine atom, or a trifluoromethyl group. $Rf_5$ represents a hydrogen atom, a fluorine atom, or a linear or branched alkyl group having 1 to 4 carbon atoms alkyl group is unsubstituted or substituted with a fluorine atom. $Rf_6$ and $Rf_7$ each represent a fluorine atom or a linear or branched alkyl group having 1 to 4 carbon atoms, having at least one fluorine atom. "m" represents an integer of 0 to 4. $M^+$ represents an ion selected from a hydrogen ion, an ammonium ion, a sodium ion, and a potassium ion.

The dopant polymer (B) preferably contains, as the repeating unit-a2, one or more repeating units selected from repeating units A2-1 to A2-7 represented by the following general formulae (2). In addition, the one or more repeating units selected from the hydrogen ion, ammonium salt, sodium salt, and potassium salt of the sulfonic acid represented by the general formula (2)-1 or (2)-2, the fluorosulfonimide represented by (2)-3, or the N-carbonyl-fluorosulfonamide represented by (2)-4 are preferably ionic polymers having one or more repeating units selected from repeating units A2-1 to A2-7 represented by the following general formulae (2).

(2)

A2-1

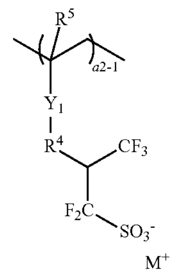

-continued

A2-2

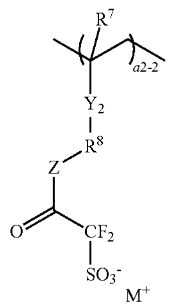

A2-3

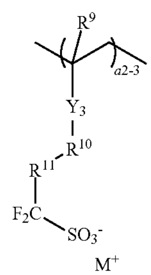

A2-4

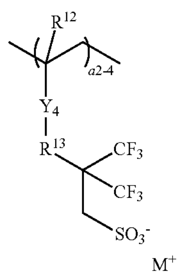

A2-5

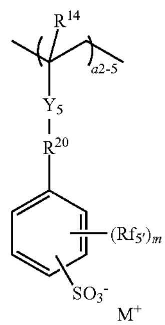

A2-6

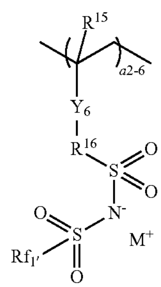

-continued

A2-7

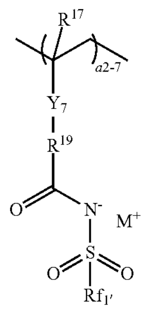

In the general formulae (2), $R^5$, $R^7$, $R^9$, $R^{12}$, $R^{14}$, $R^{15}$, and $R^{17}$ each independently represent a hydrogen atom or a methyl group. $R^6$, $R^8$, $R^{10}$, $R^{13}$, $R^{16}$, $R^{19}$, and $R^{20}$ each independently represent a single bond or a linear, branched, or cyclic hydrocarbon group having 1 to 13 carbon atoms, the hydrocarbon group optionally having one or more selected from an ester group, an ether group, an amide group, a carbamate group, a thiocarbamate group, and a urea group. $R^{11}$ represents a linear or branched alkylene group having 1 to 4 carbon atoms, one or two hydrogen atoms in $R^{11}$ optionally being substituted with a fluorine atom. $Y_1$, $Y_2$, $Y_3$, $Y_4$, $Y_6$, and $Y_7$ each independently represent a single bond, a phenylene group, a naphthylene group, an ether group, an ester group, or an amide group. $Y_5$ represents a single bond, an ether group, or an ester group. Z represents an oxygen atom or an —$NR^{18}$— group. $R^{18}$ represents a hydrogen atom, a linear, branched or cyclic alkyl group having 2 to 12 carbon atoms, or a phenyl group and optionally has one or more selected from an ether group, a carbonyl group, an ester group, and an amide group. Z optionally forms a ring together with $R^8$. $Rf_1$, and $Rf_5$, each represent a fluorine atom, a trifluoromethyl group, or a linear or branched alkyl group having 1 to 4 carbon atoms, having at least one fluorine atom. "m" represents an integer of 0 to 4. a2-1, a2-2, a2-3, a2-4, a2-5, a2-6, and a2-7 satisfy $0 \leq (a2\text{-}1) < 1.0$, $0 \leq (a2\text{-}2) < 1.0$, $0 \leq (a2\text{-}3) < 1.0$, $0 \leq (a2\text{-}4) < 1.0$, $0 \leq (a2\text{-}5) < 1.0$, $0 \leq (a2\text{-}6) < 1.0$, $0 \leq (a2\text{-}7) < 1.0$, and $0 < (a2\text{-}1)+(a2\text{-}2)+(a2\text{-}3)+(a2\text{-}4)+(a2\text{-}5)+(a2\text{-}6)+(a2\text{-}7) < 1.0$. $M^+$ represents an ion selected from a hydrogen ion, an ammonium ion, a sodium ion, and a potassium ion.

The $Rf_1$, preferably has at least one fluorine atom, and the $Rf_5$, is preferably a fluorine atom or a trifluoromethyl group in the general formulae (2).

(Repeating Units A2-1 to A2-7)

Specific examples of fluorosulfonic acid monomers and fluorosulfonic acid salt monomers for obtaining the repeating units A2-1 to A2-5 represented by the general formulae (2) include the following.

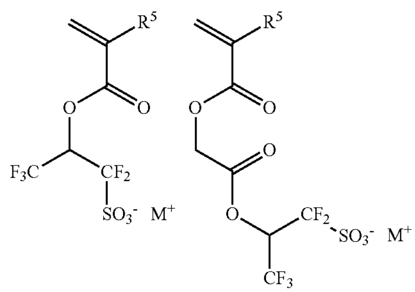

-continued
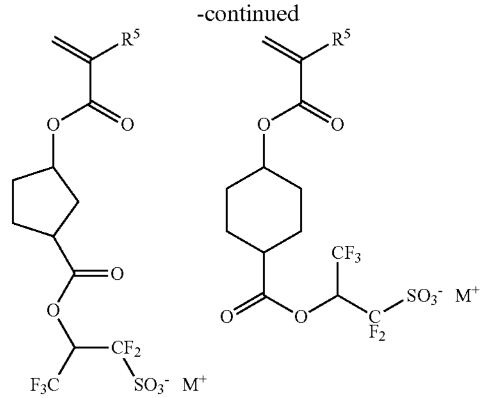
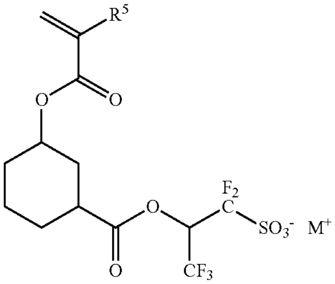
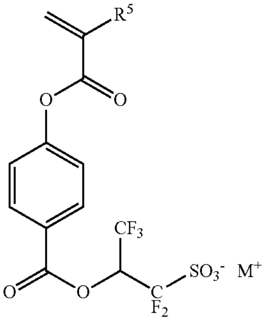
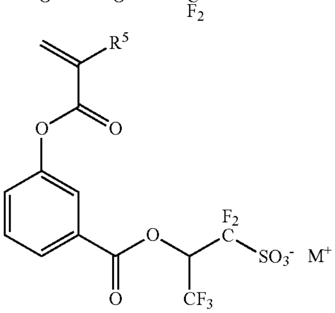
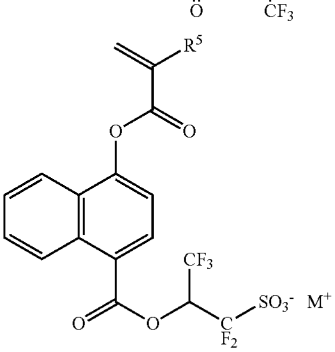
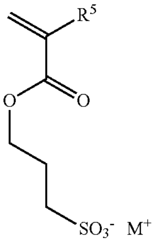
-continued
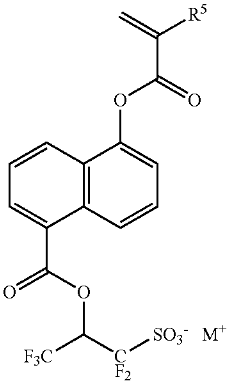
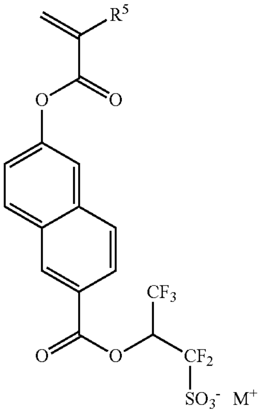
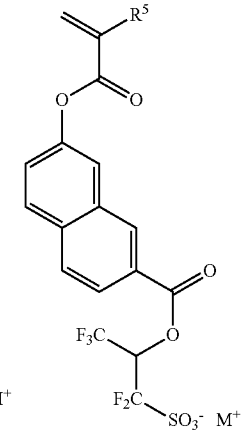
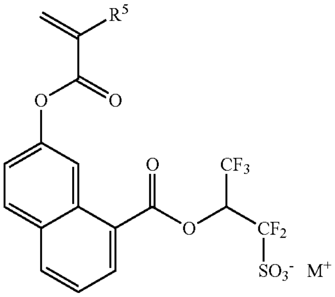
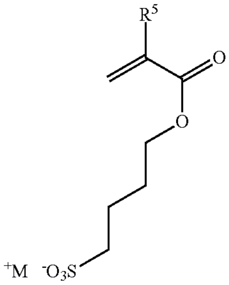
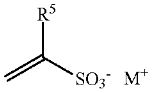
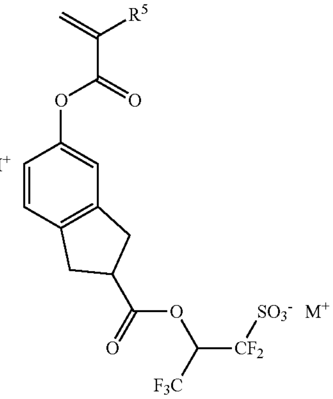

-continued
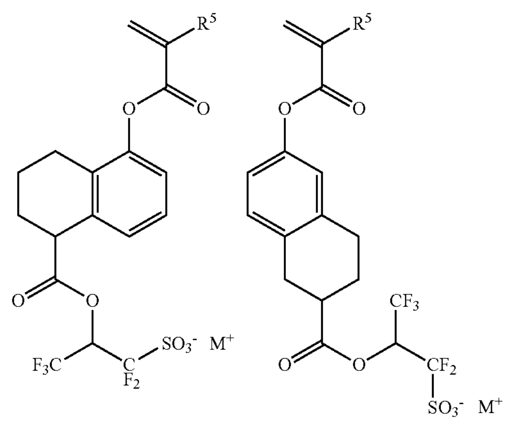
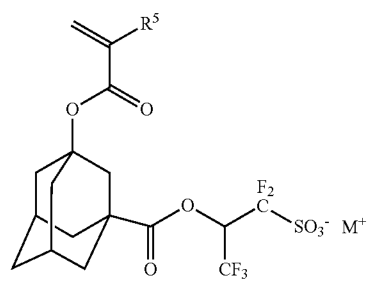
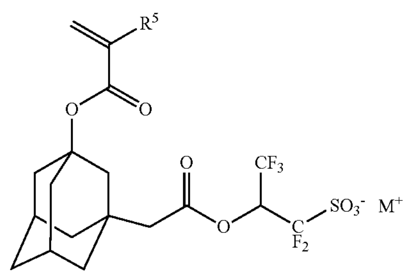
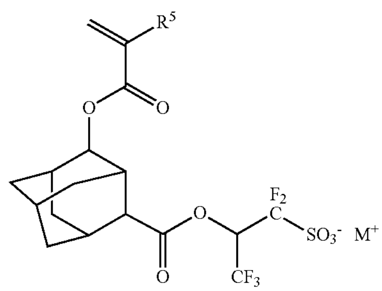
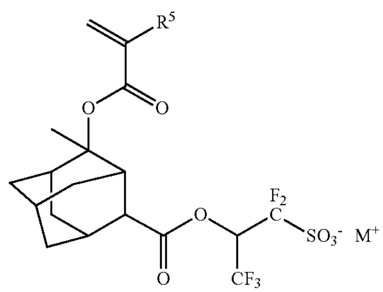
-continued
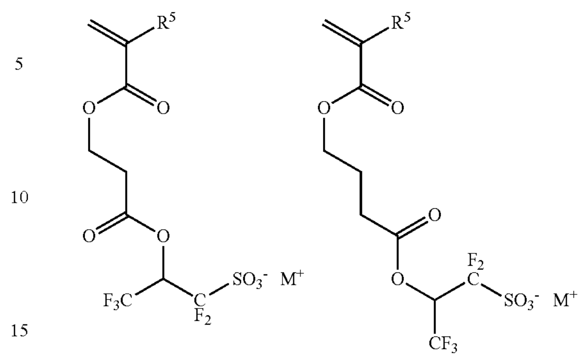
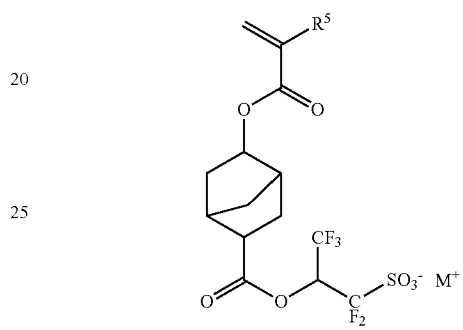
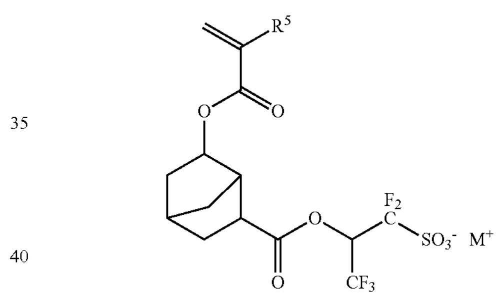
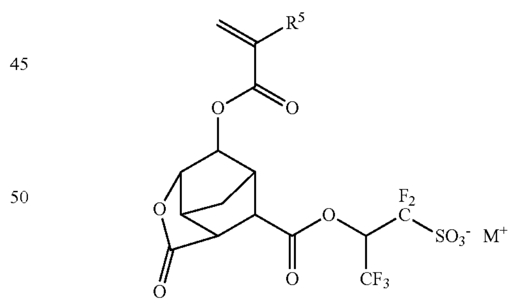
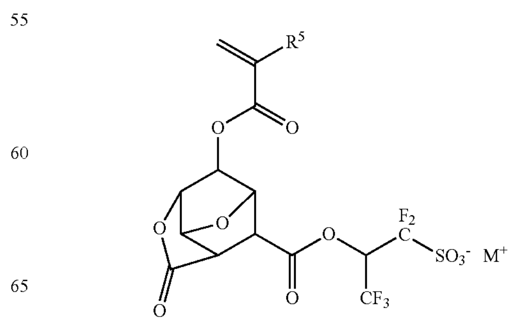

-continued
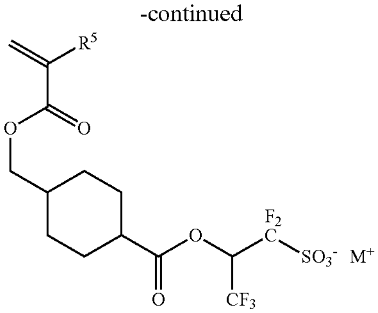
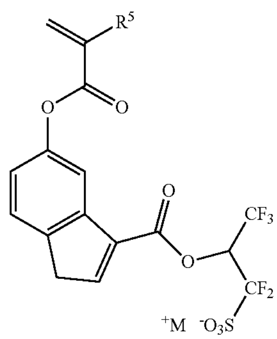
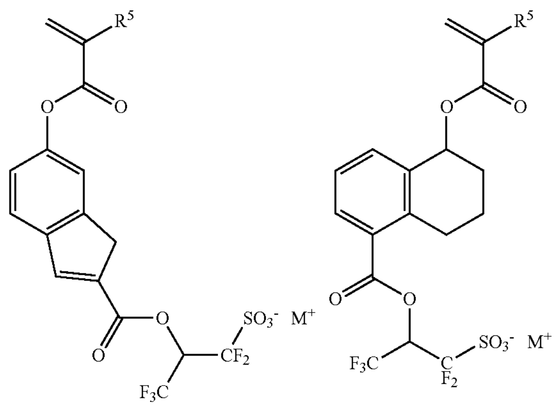
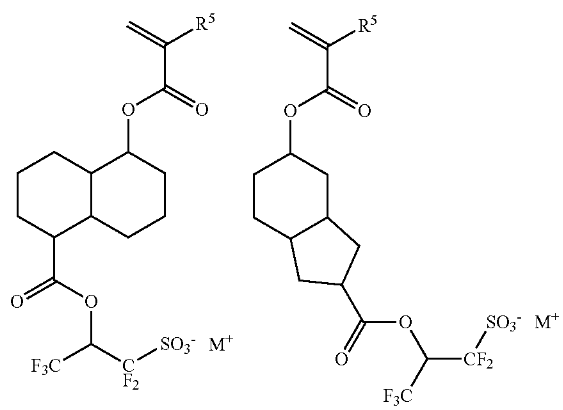
-continued
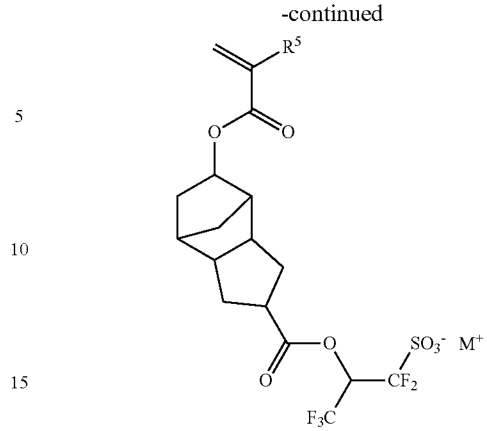
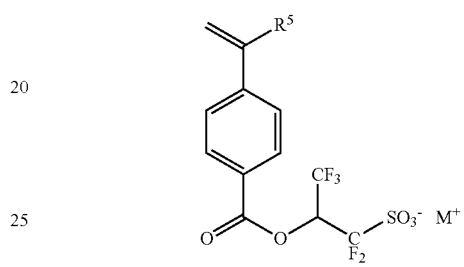
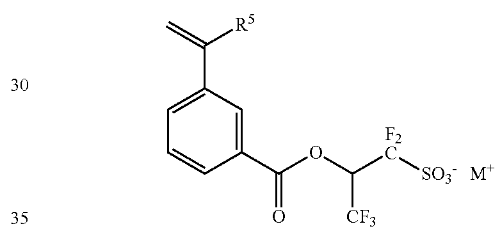
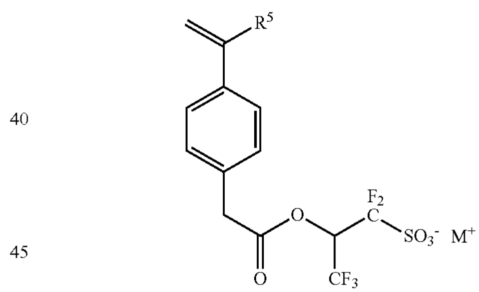
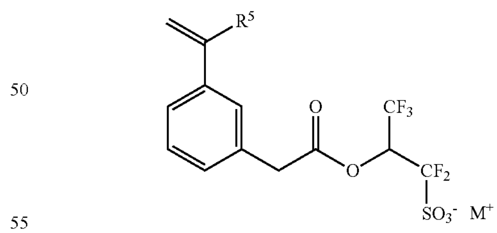
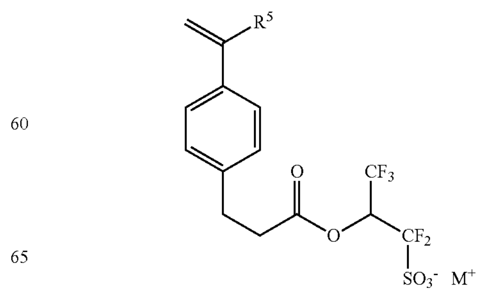

-continued
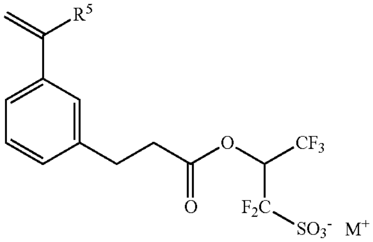
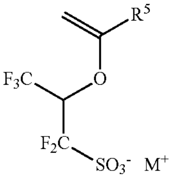
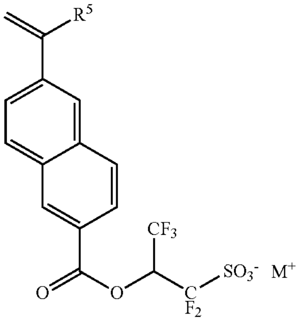
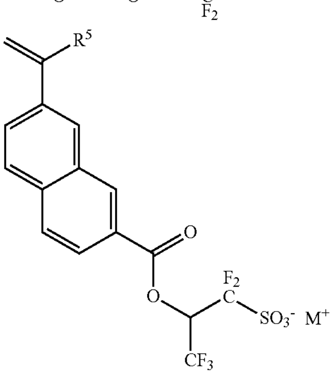
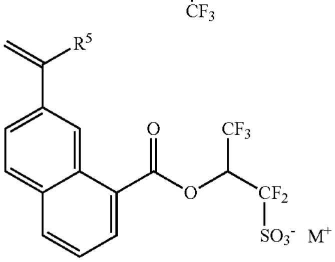
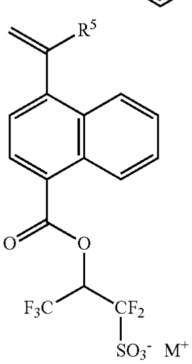
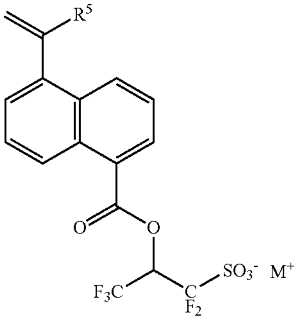
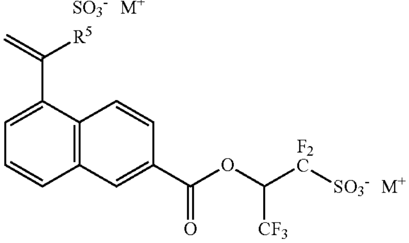
-continued
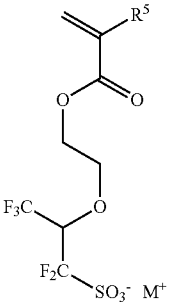
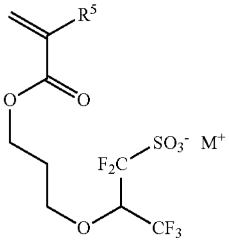
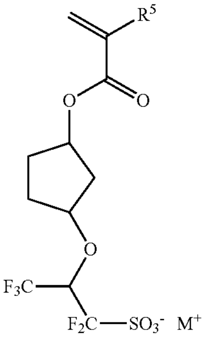
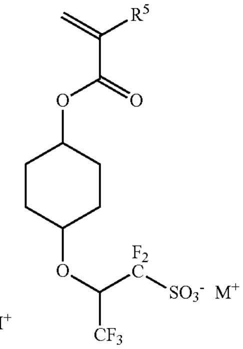
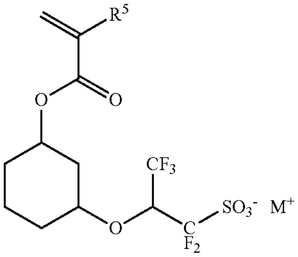
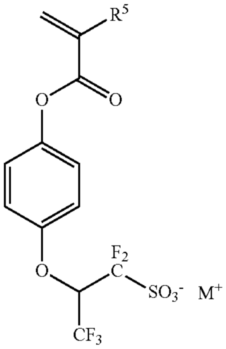
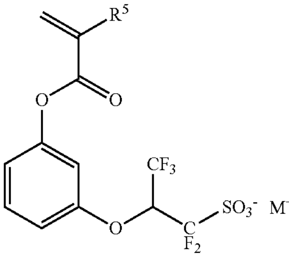
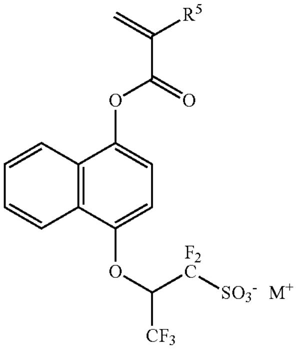
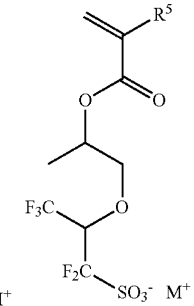

-continued
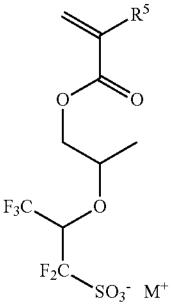
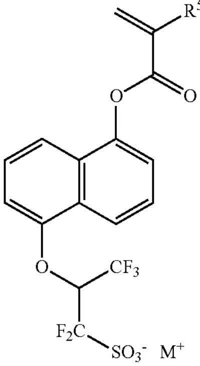
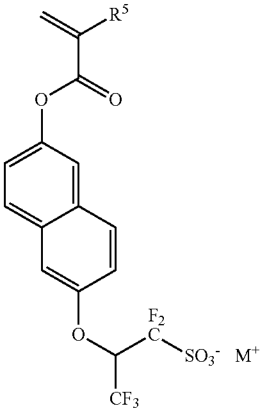
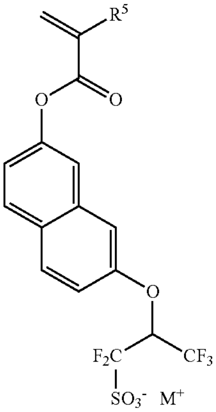
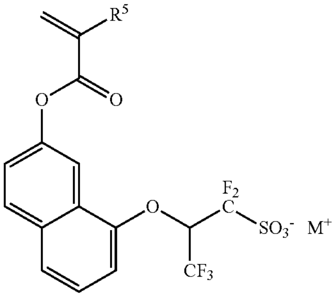
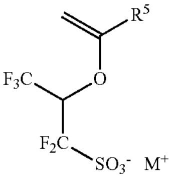
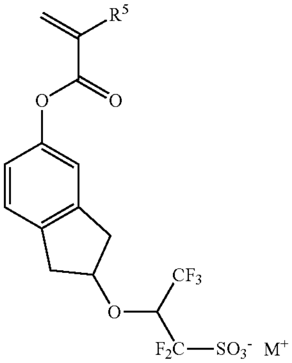
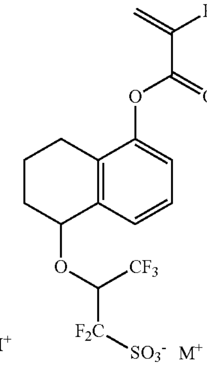
-continued
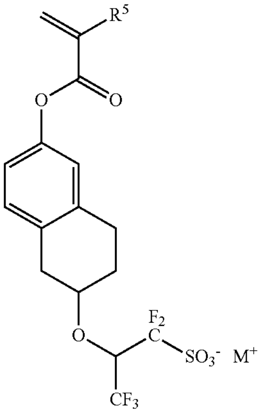
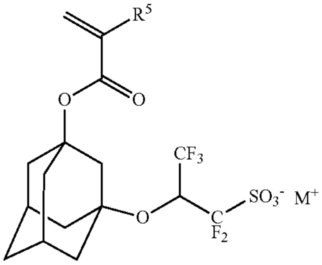
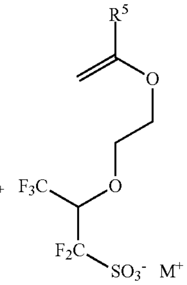
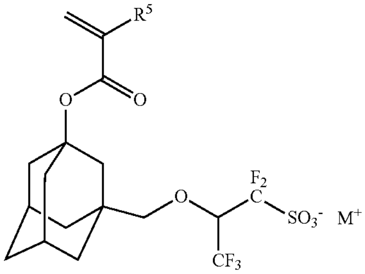
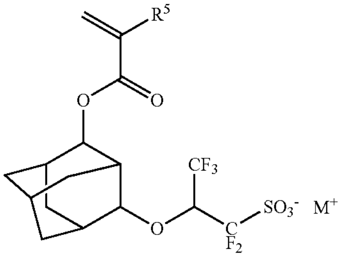
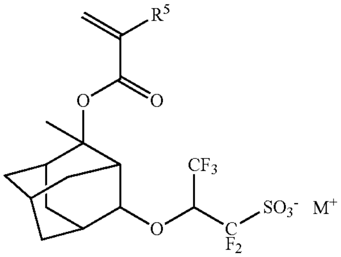

-continued
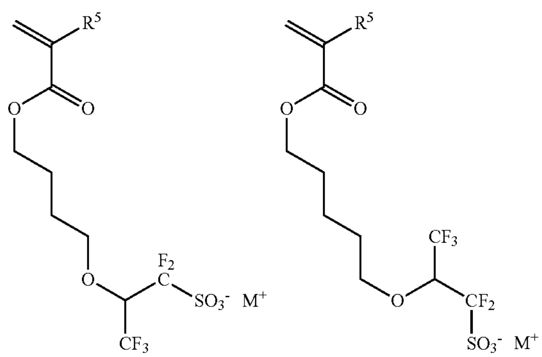
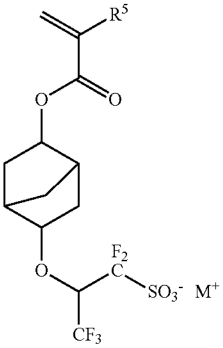
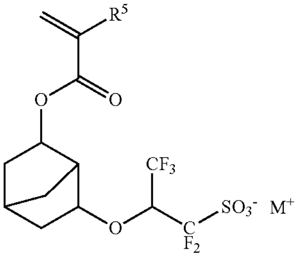
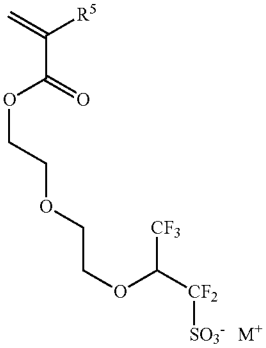
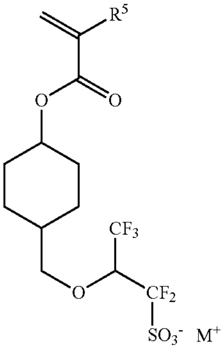
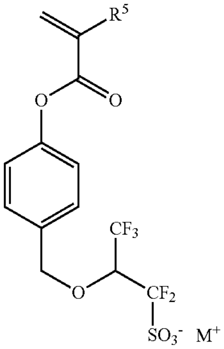
-continued
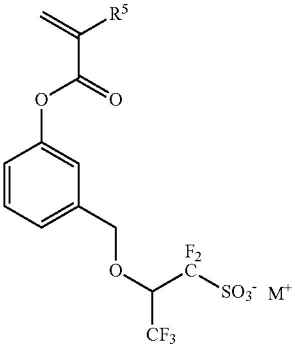
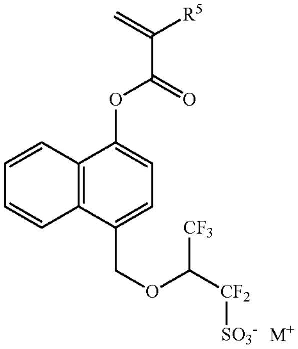
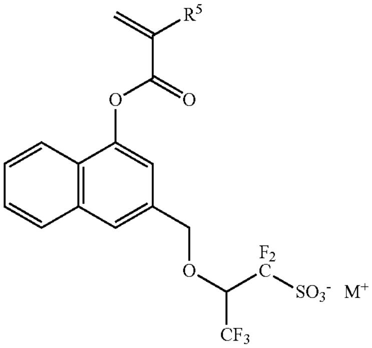
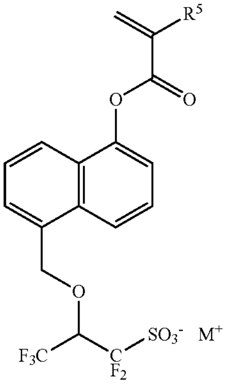
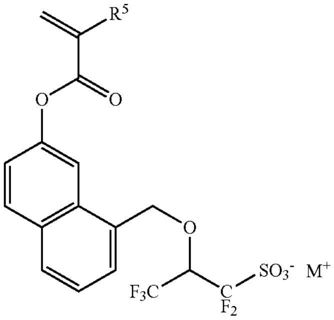

-continued
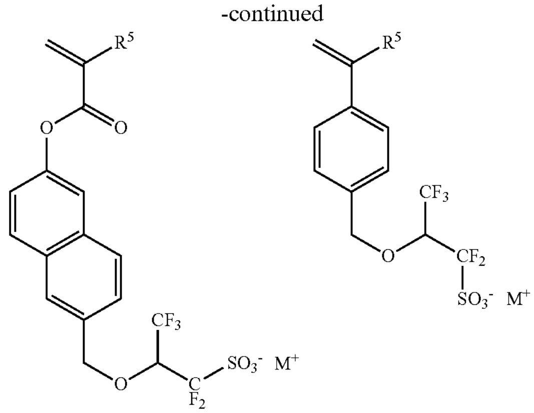
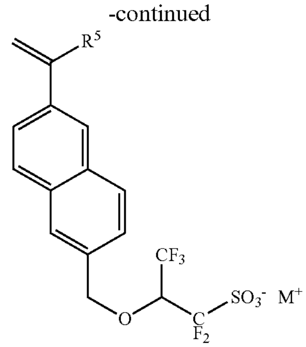
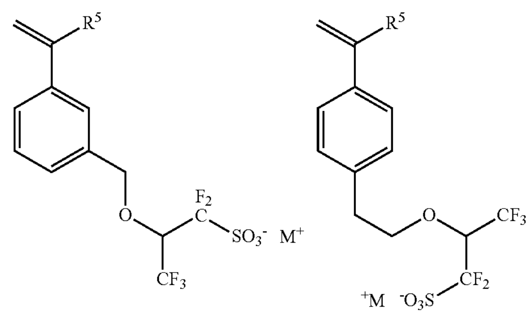
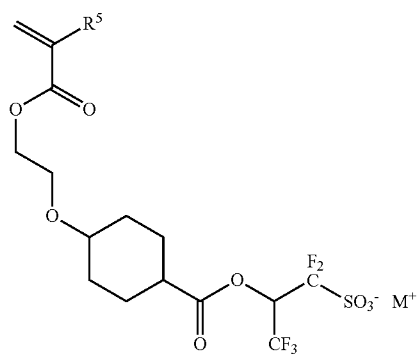
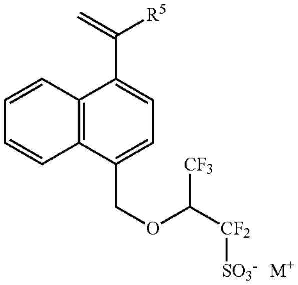
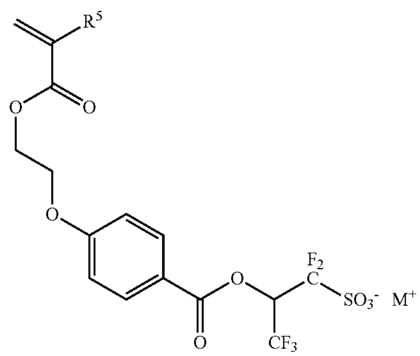
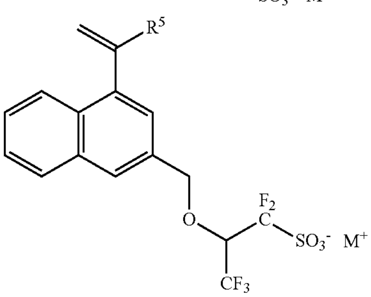
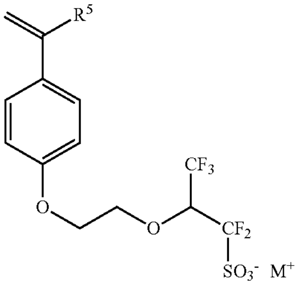
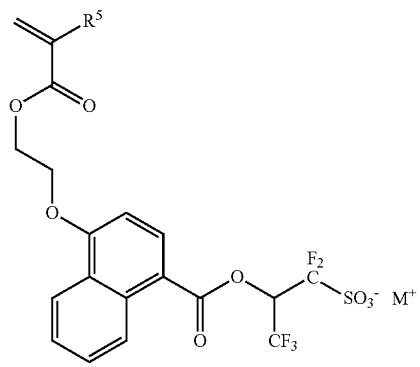

-continued
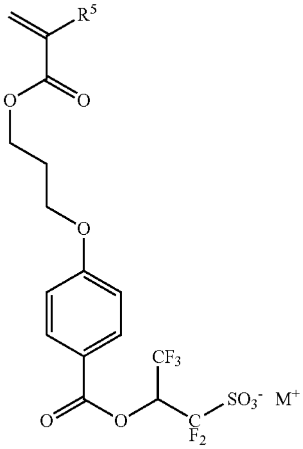
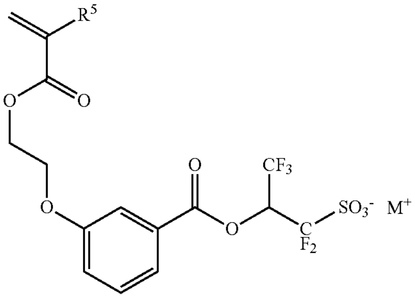
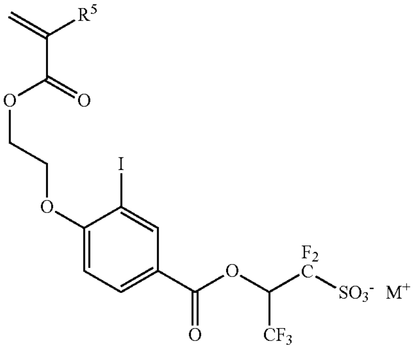
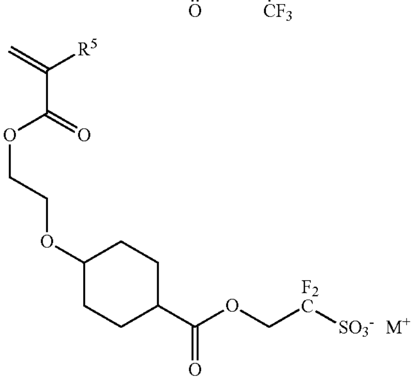
-continued
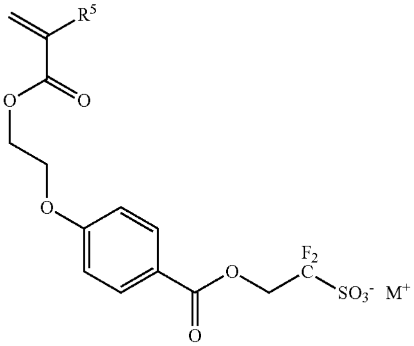
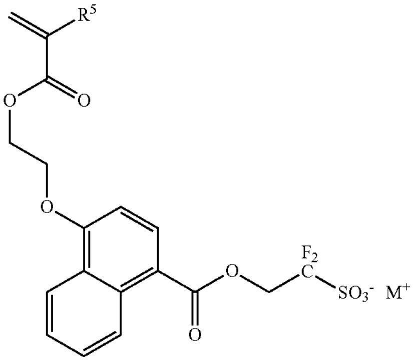
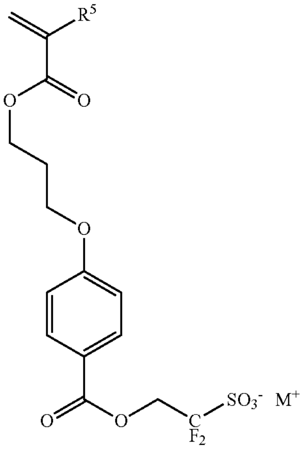
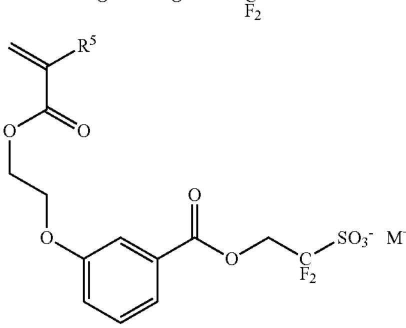

-continued
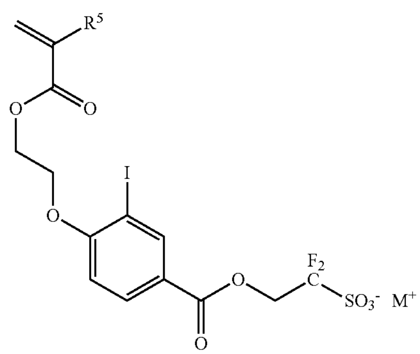
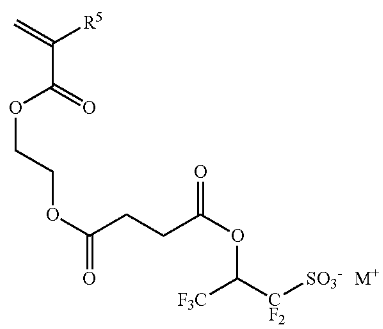
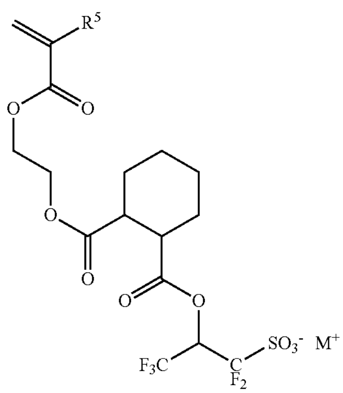
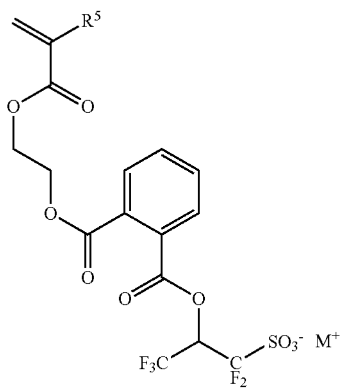
-continued
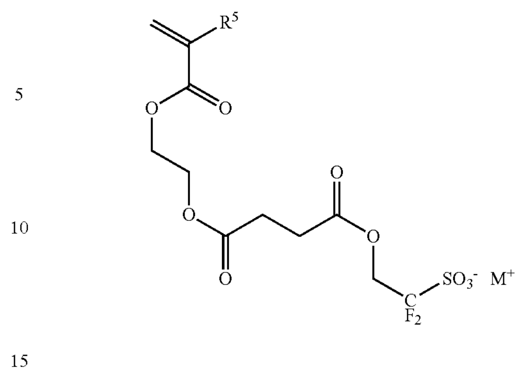
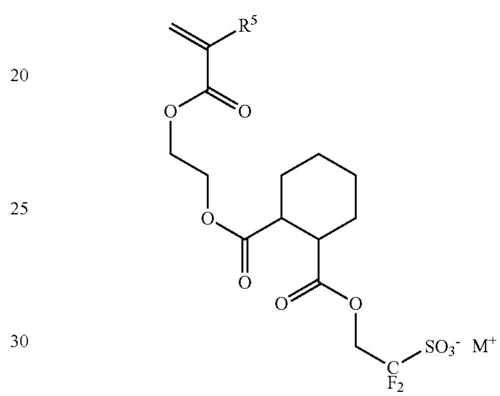
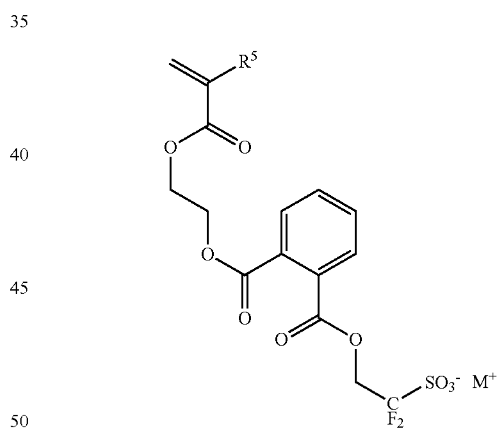
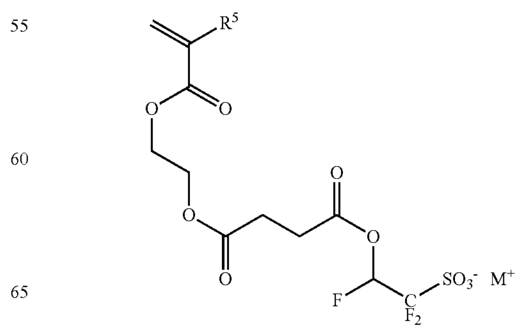

-continued
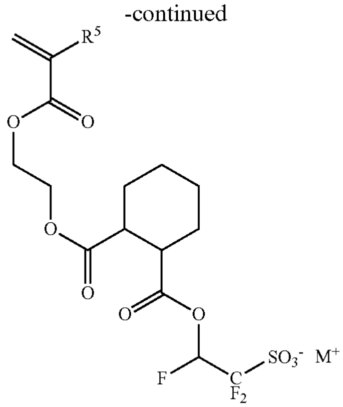
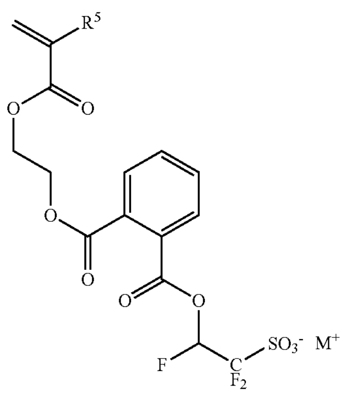
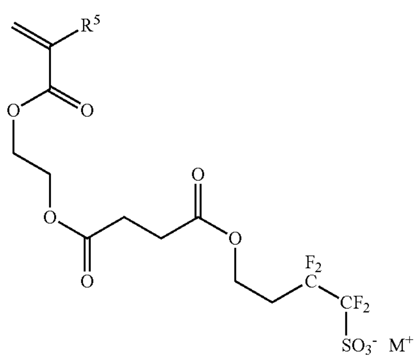
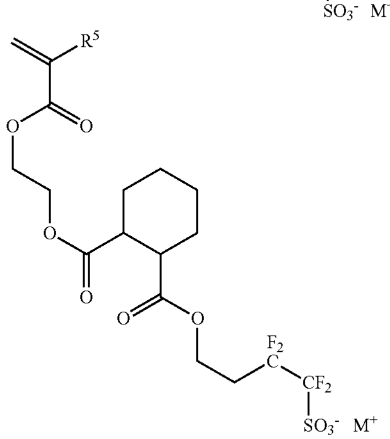
-continued
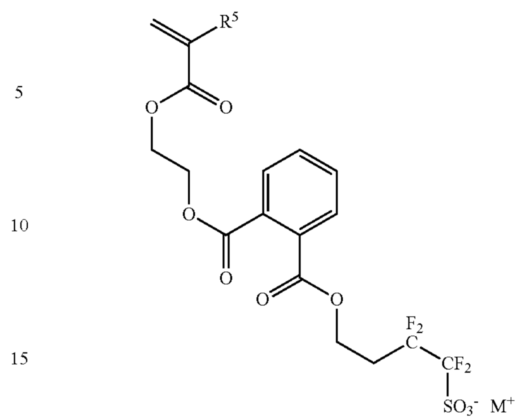
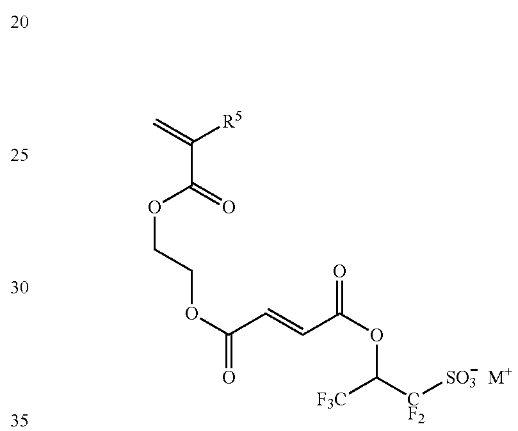
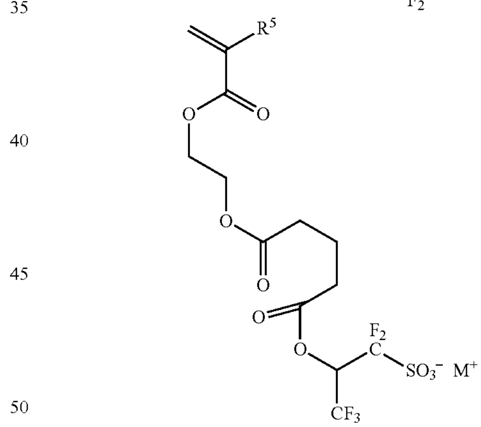
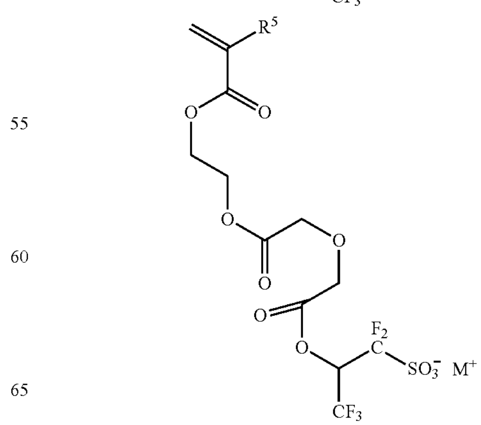

-continued
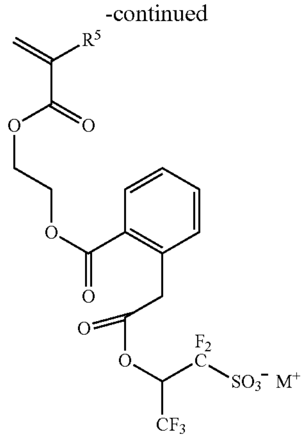
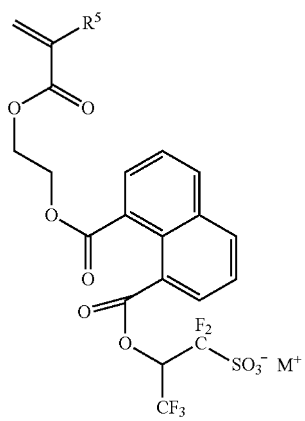
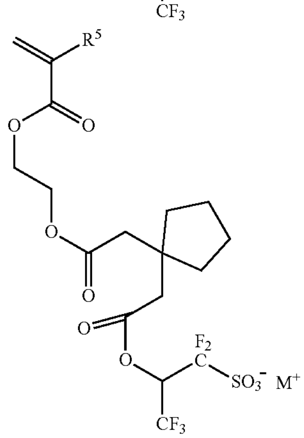
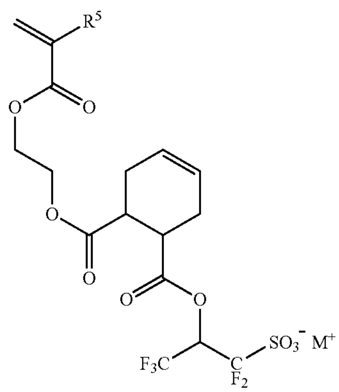
-continued
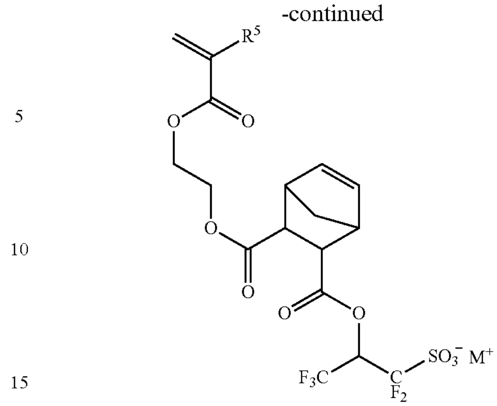
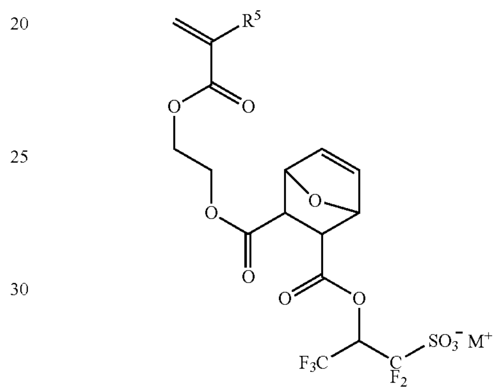
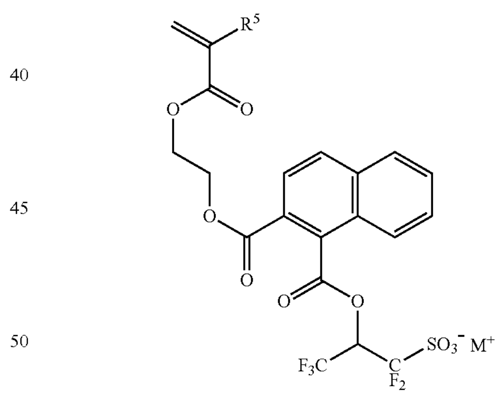
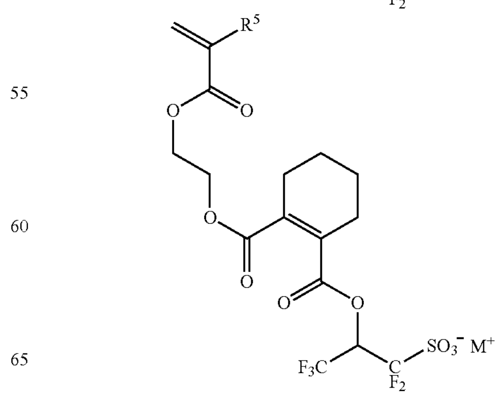

-continued
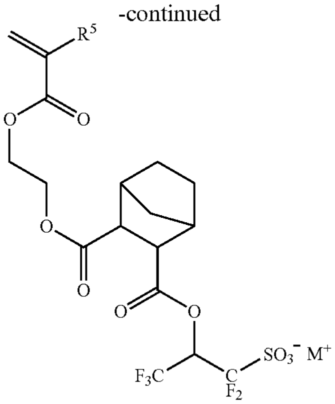
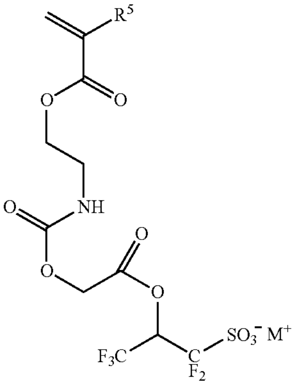
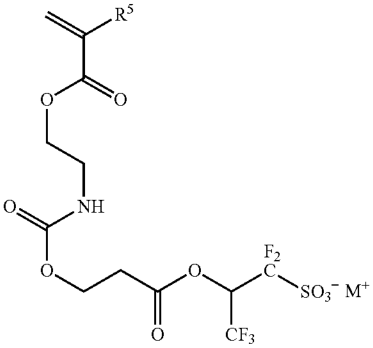
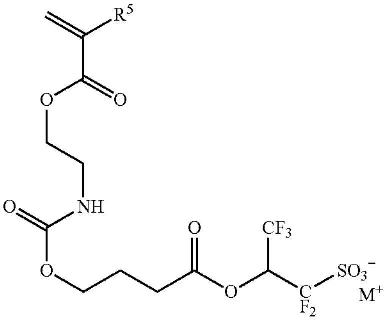
-continued
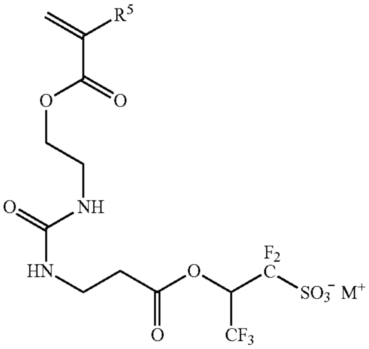
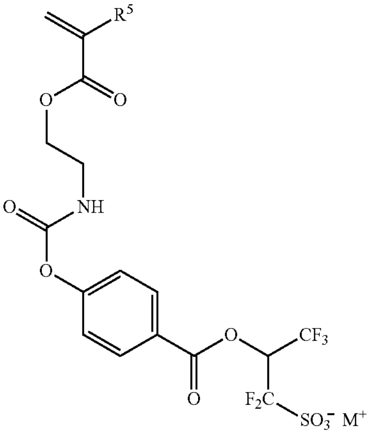
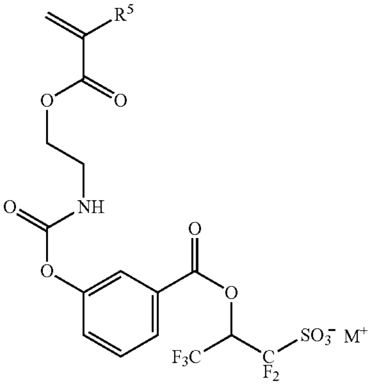
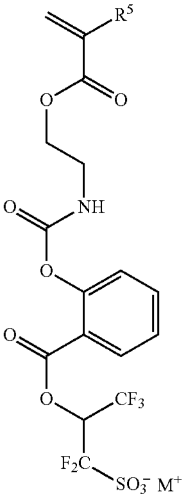

-continued
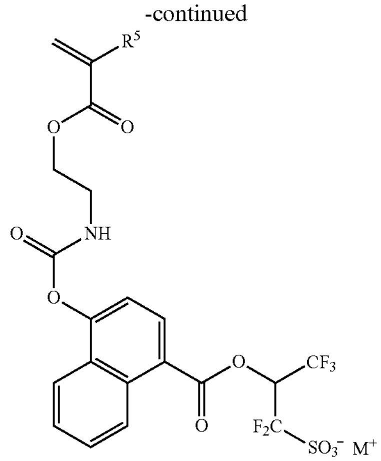
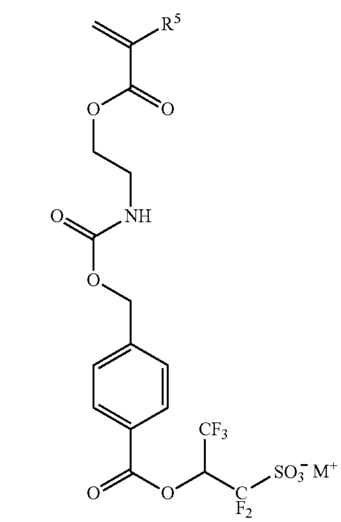
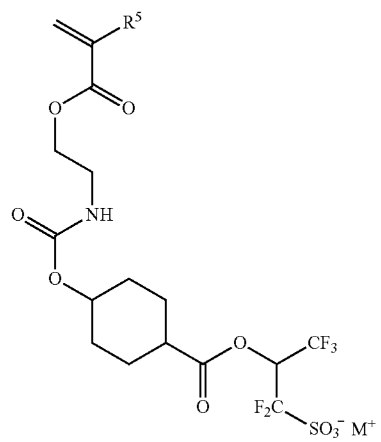
-continued
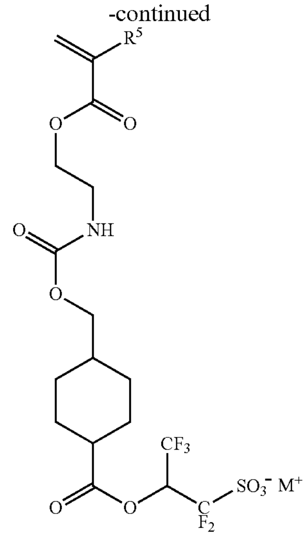
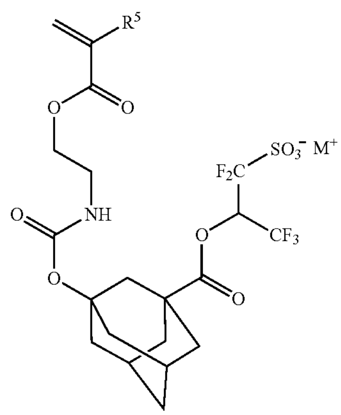
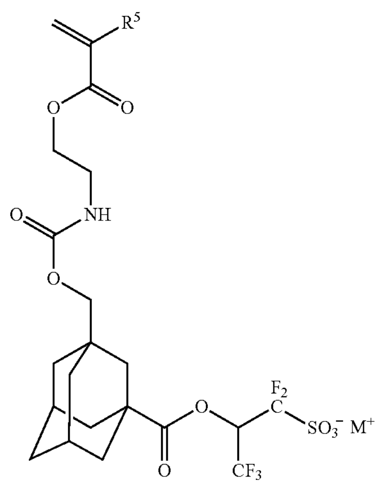

-continued
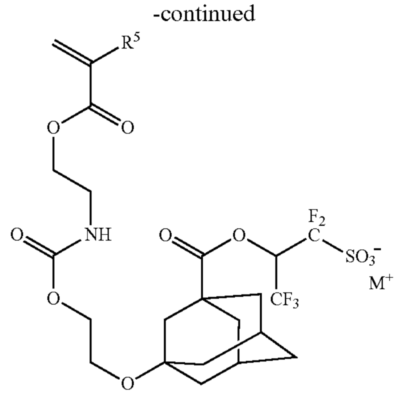
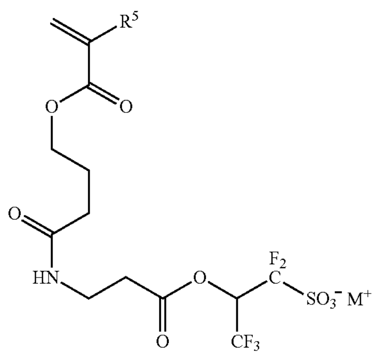
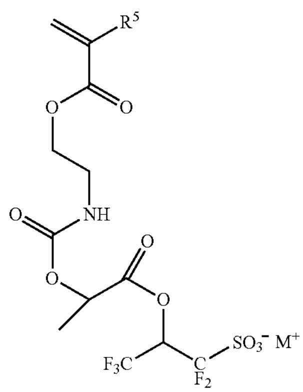
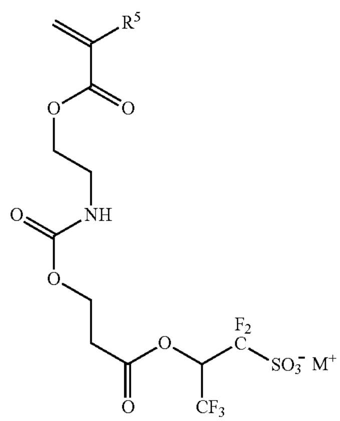
-continued
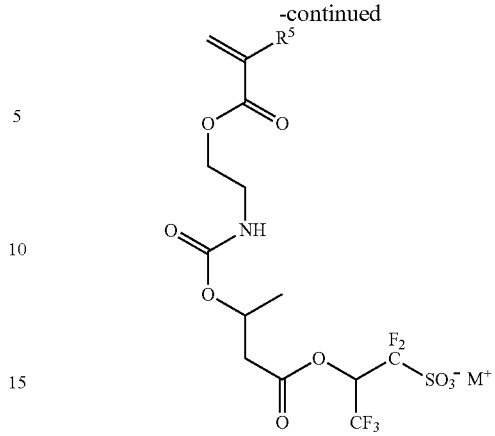
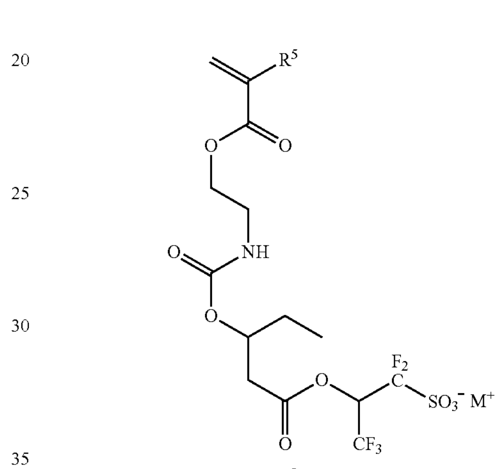
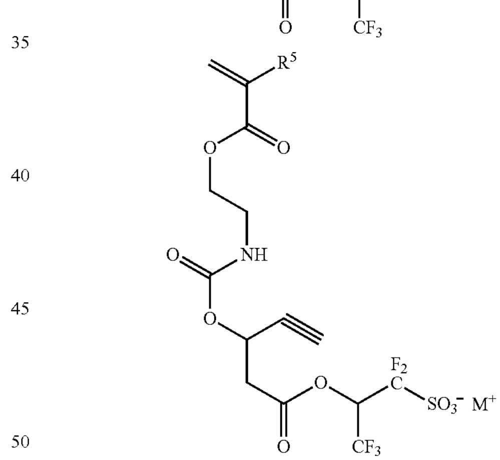
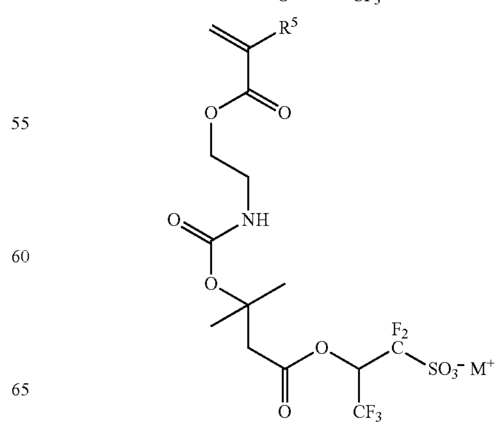

-continued
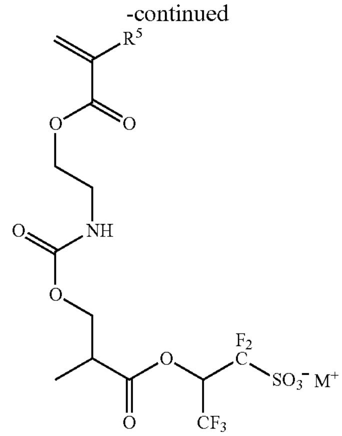
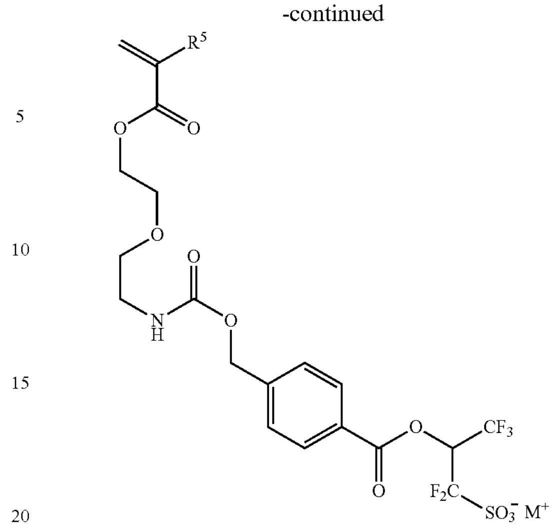
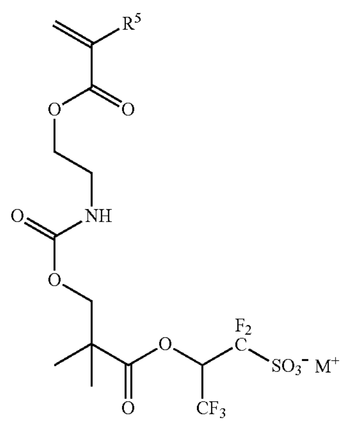
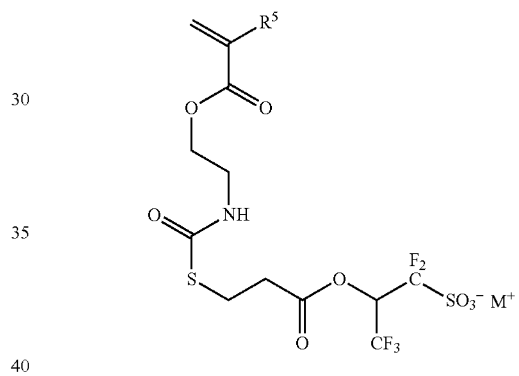
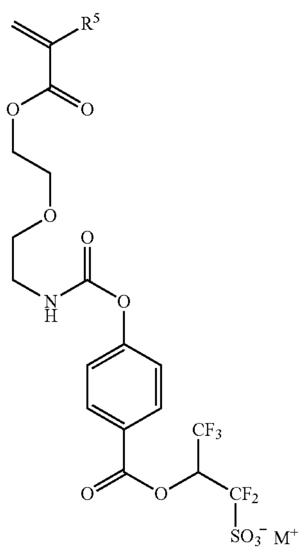
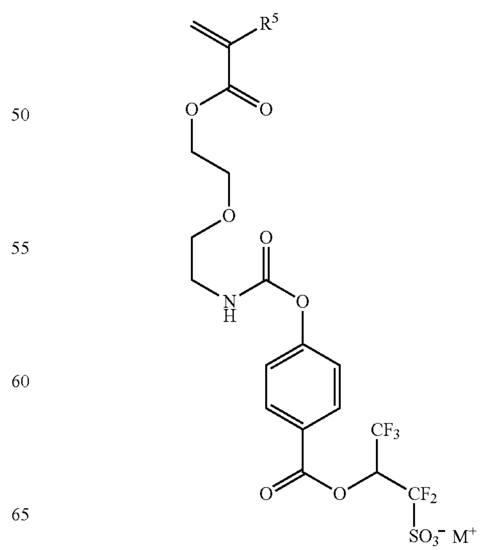

-continued
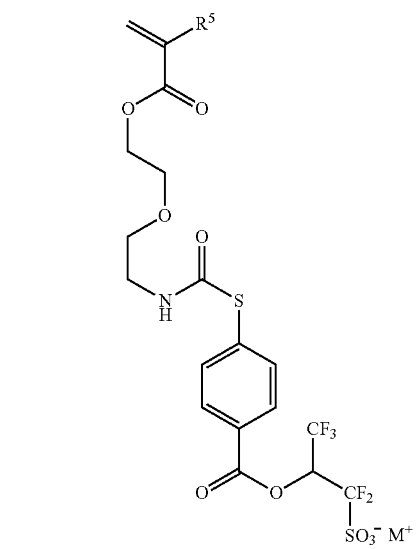
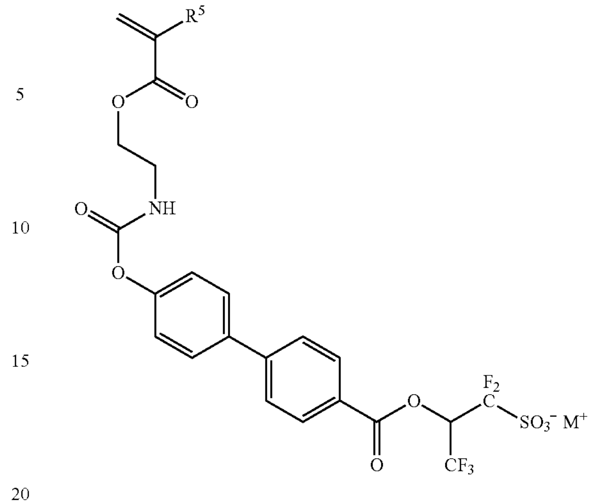
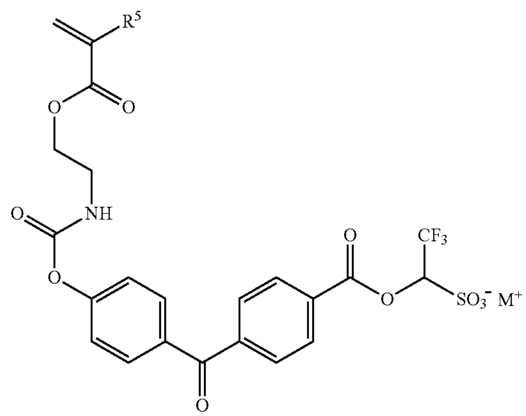
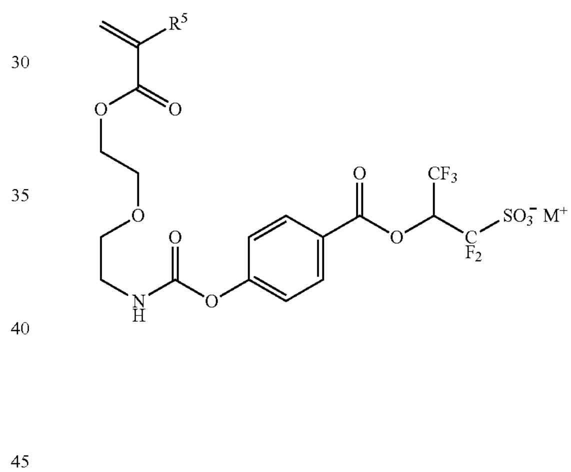
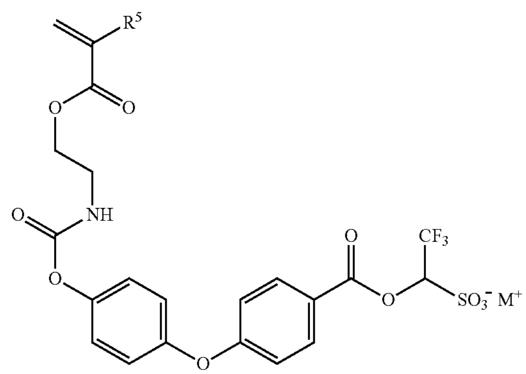
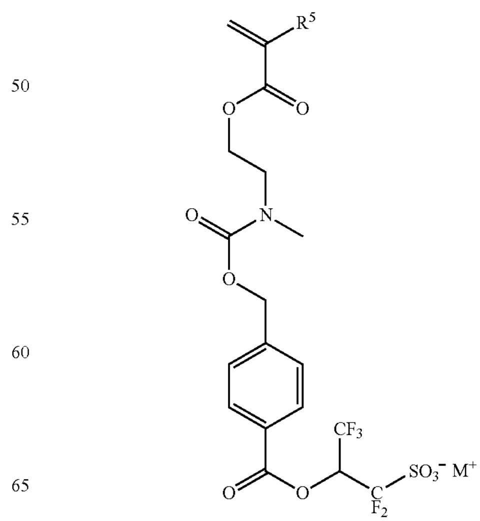
-continued -continued
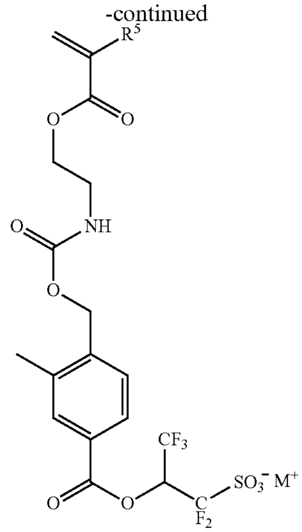
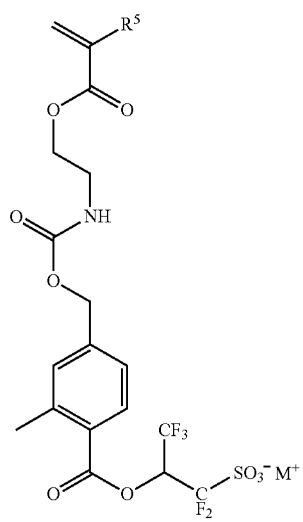
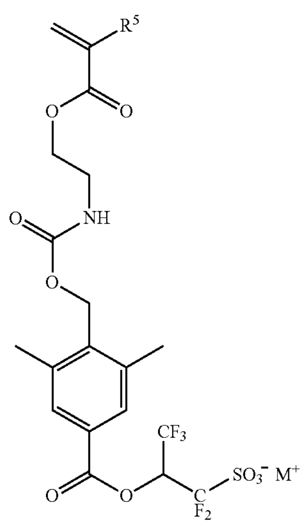
-continued
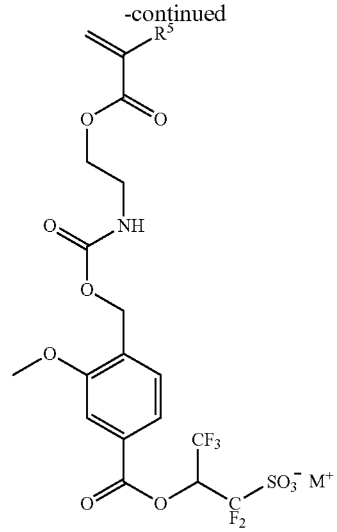
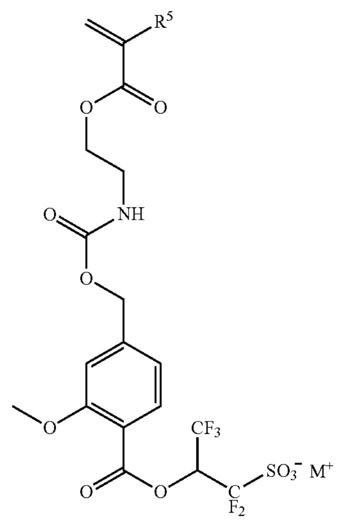
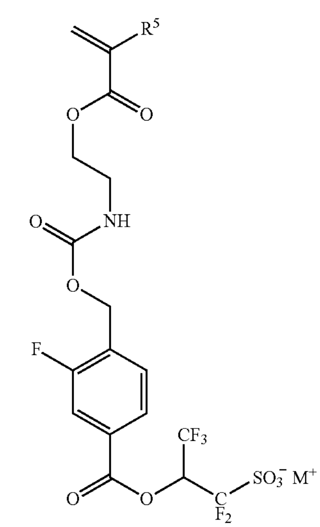

-continued
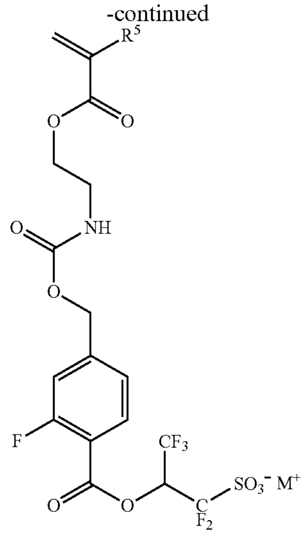
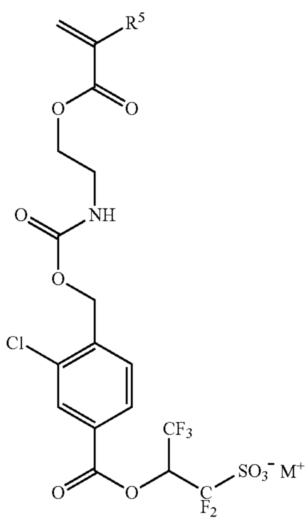
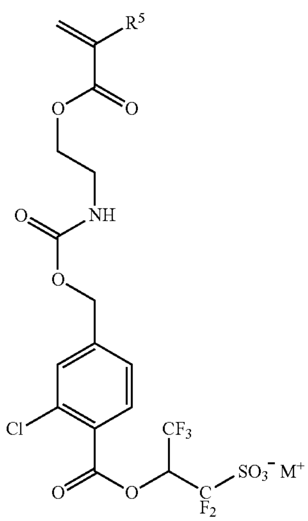
-continued
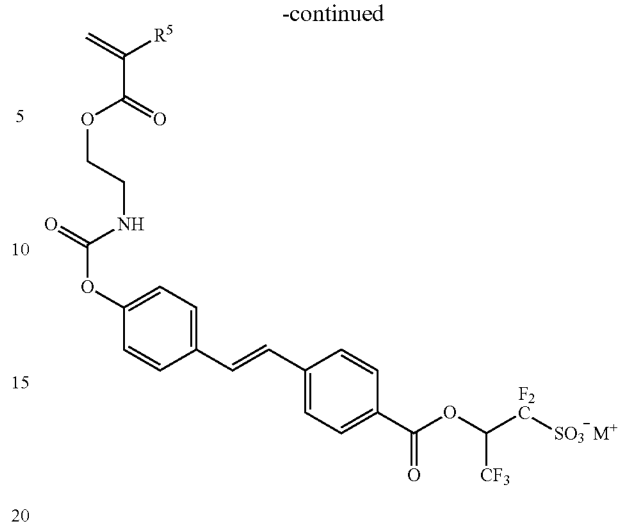
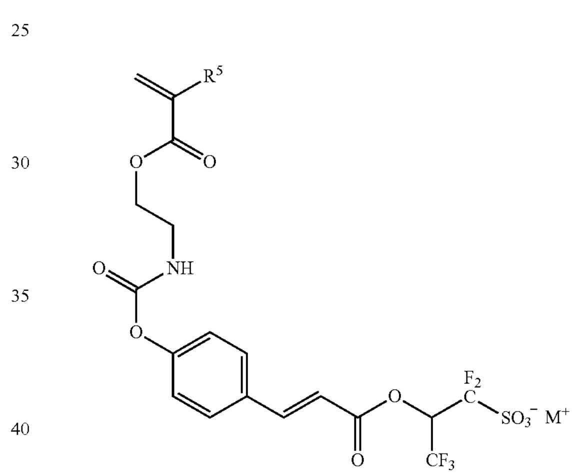
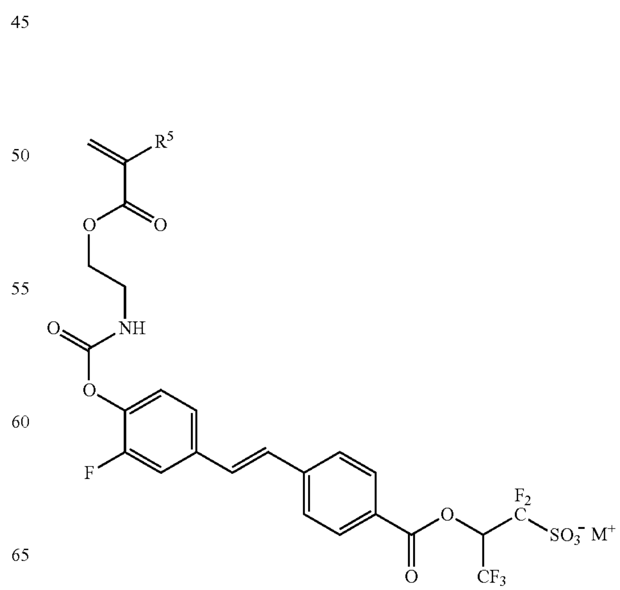

-continued
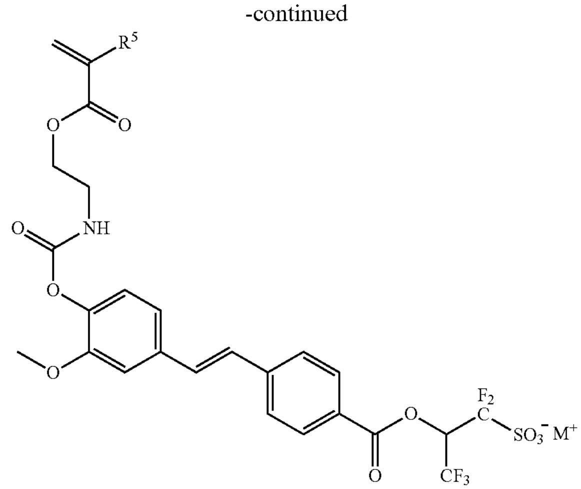
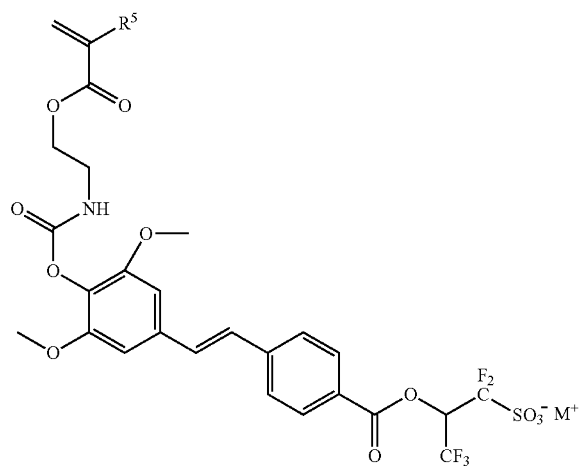
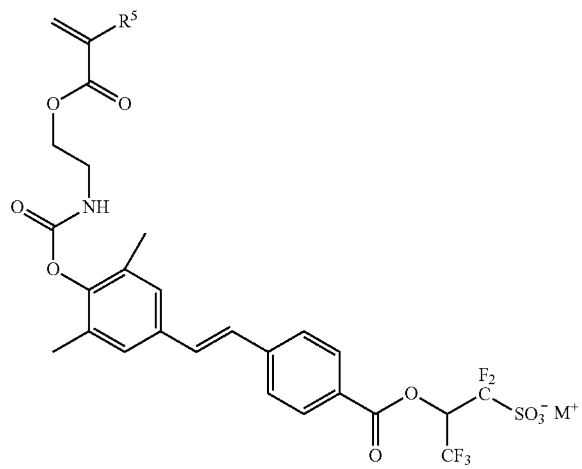
-continued
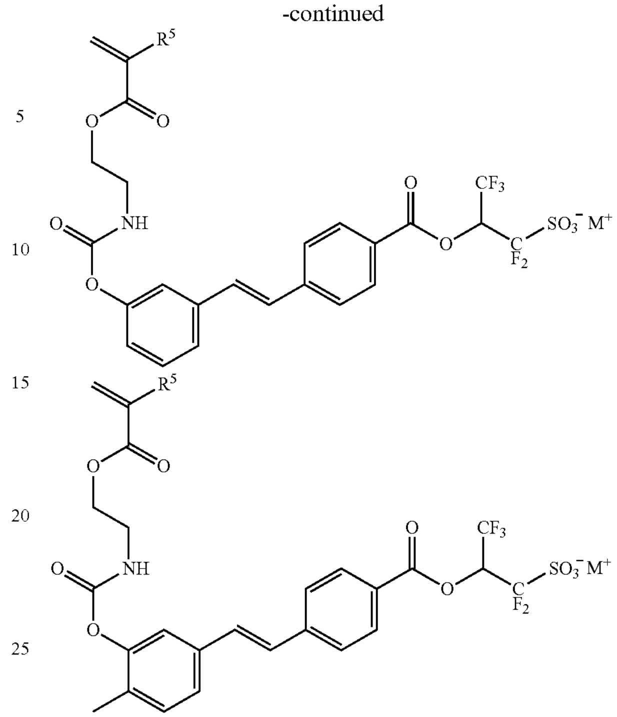
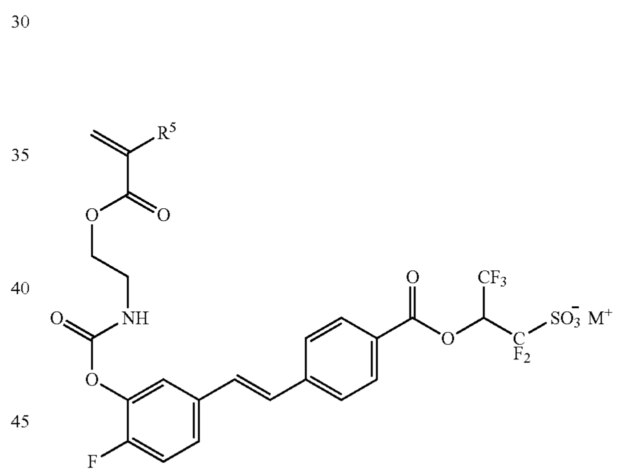
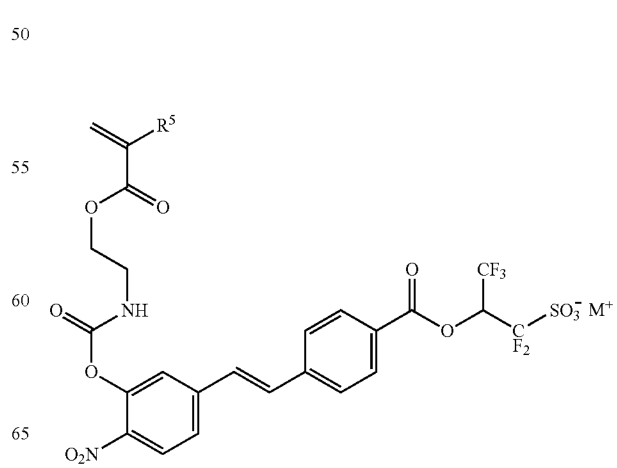

-continued
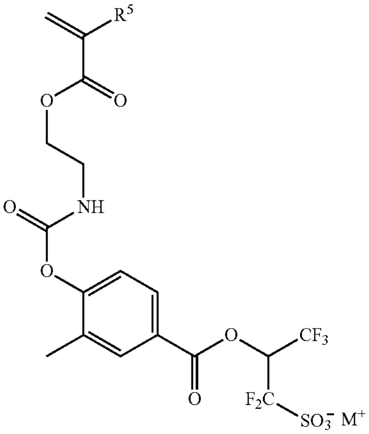
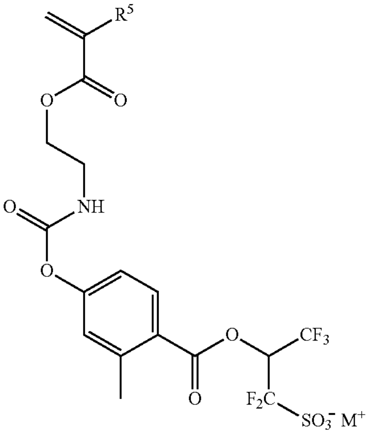
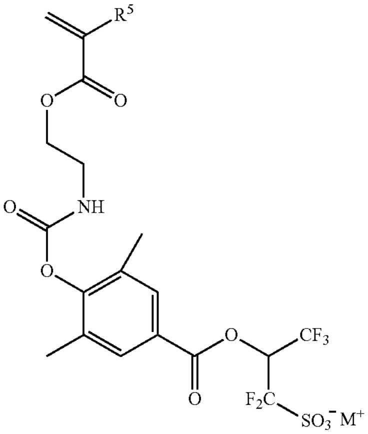
-continued
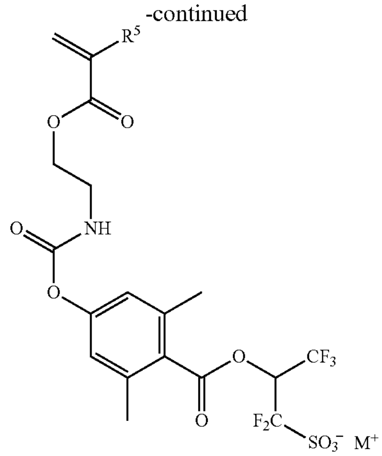
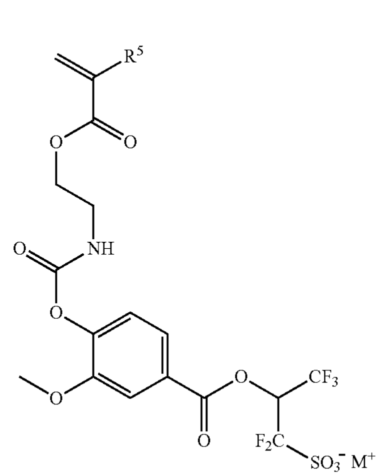
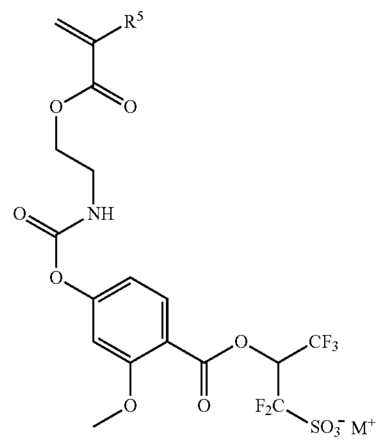

-continued
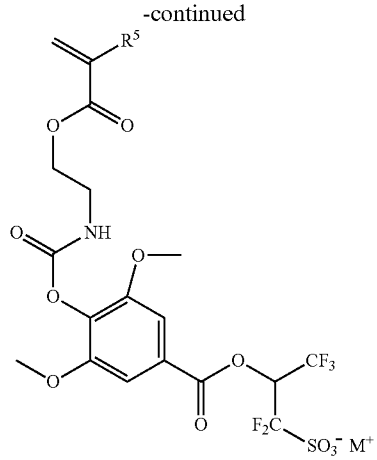
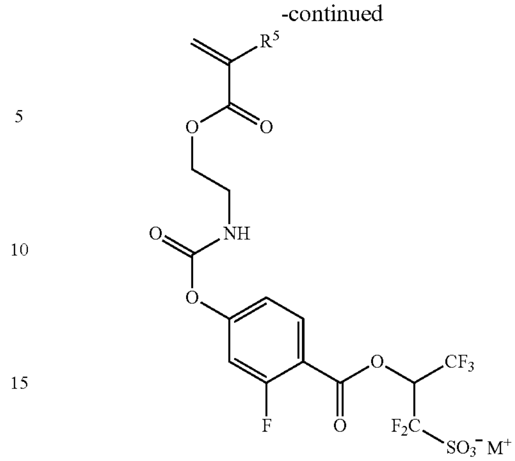
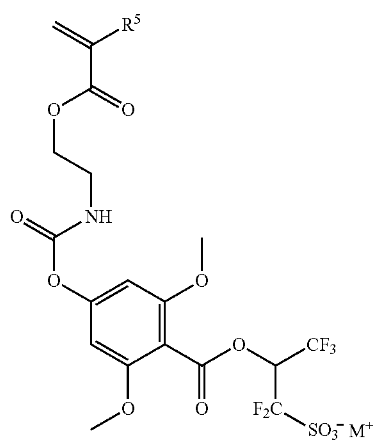
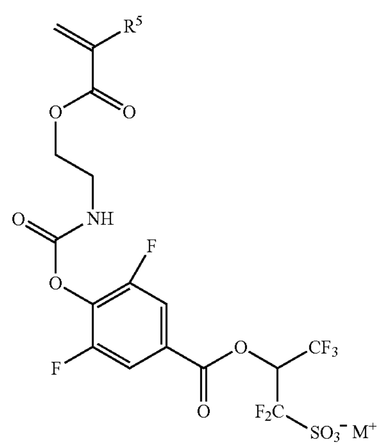
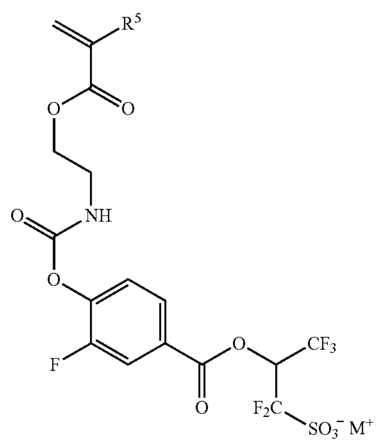
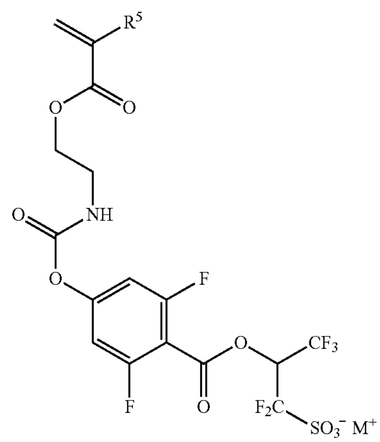
-continued -continued
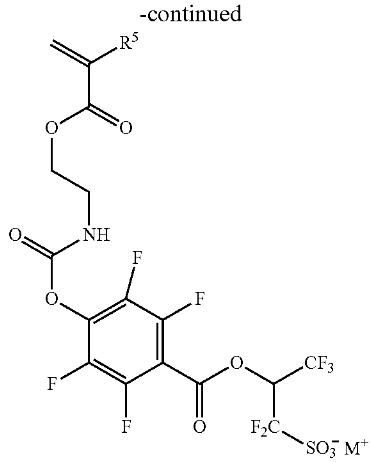
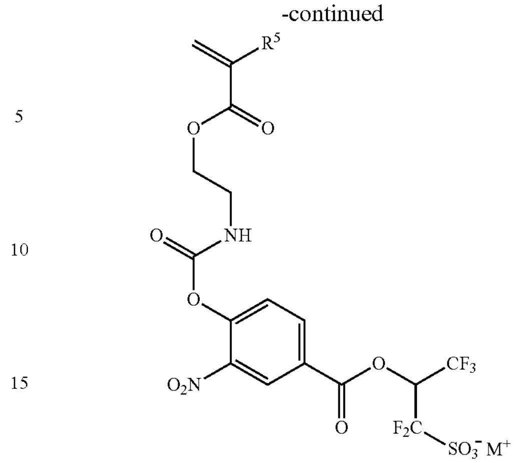
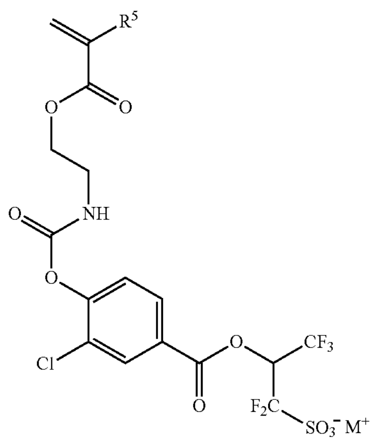
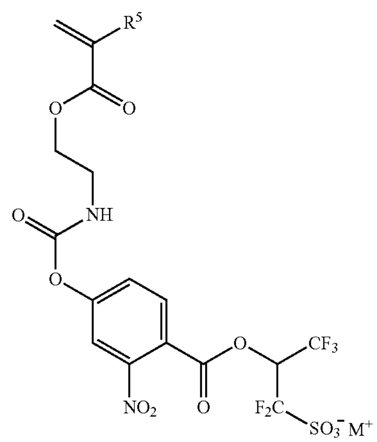
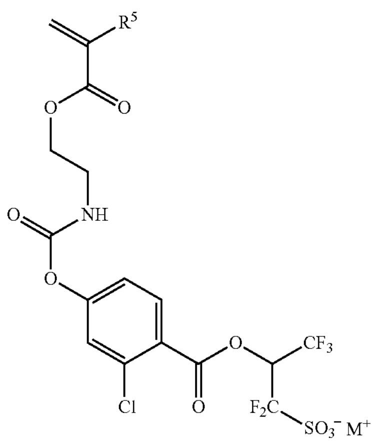
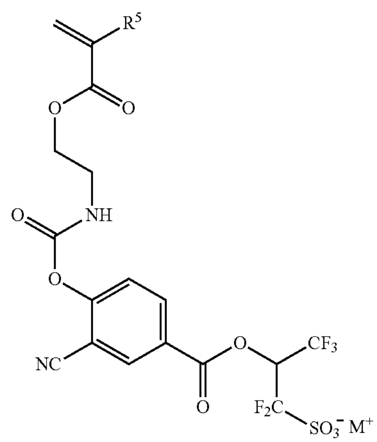

-continued
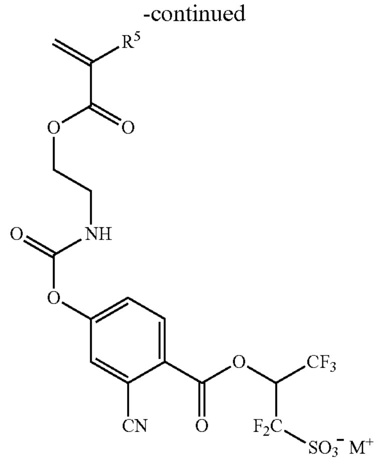
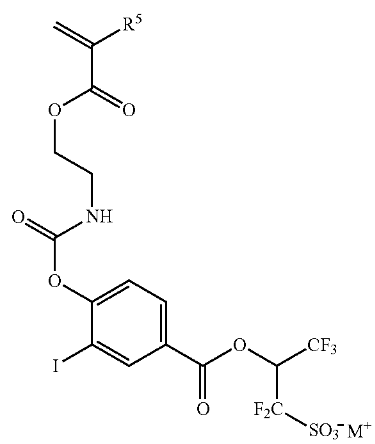
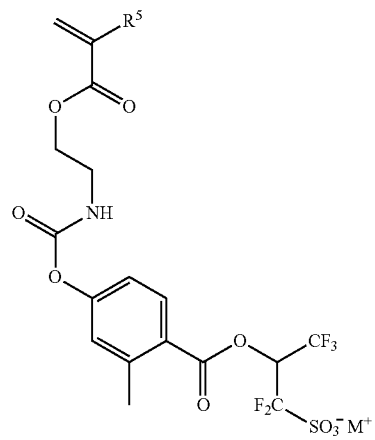
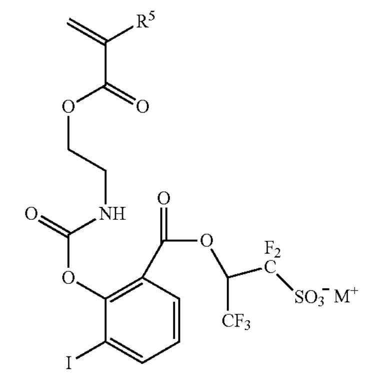
-continued
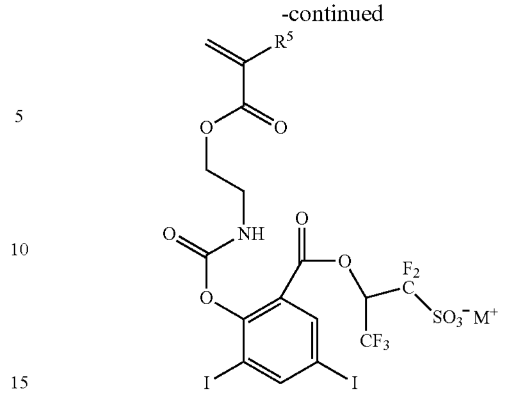
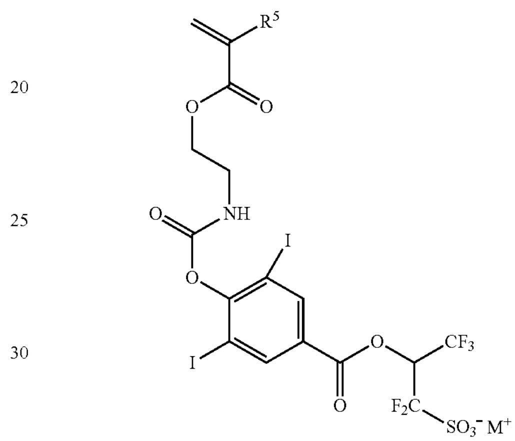
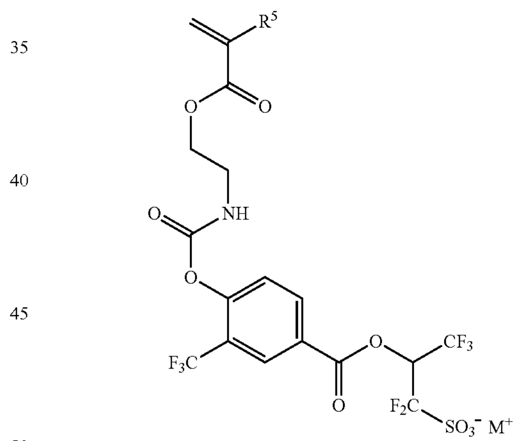
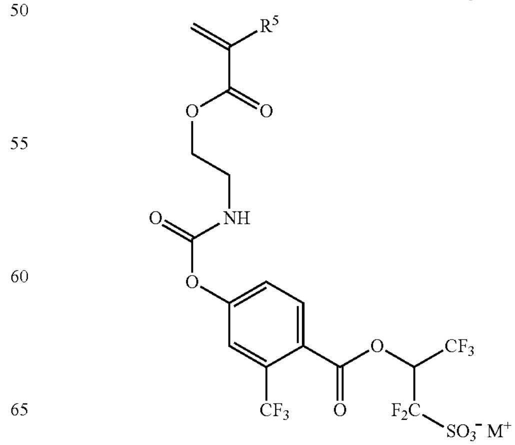

-continued
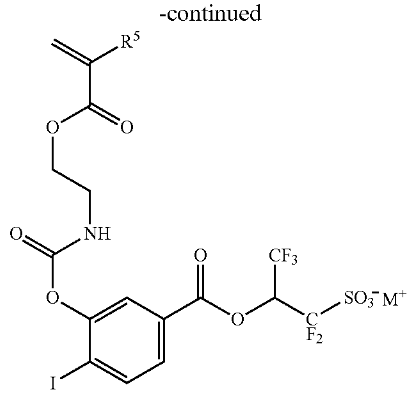
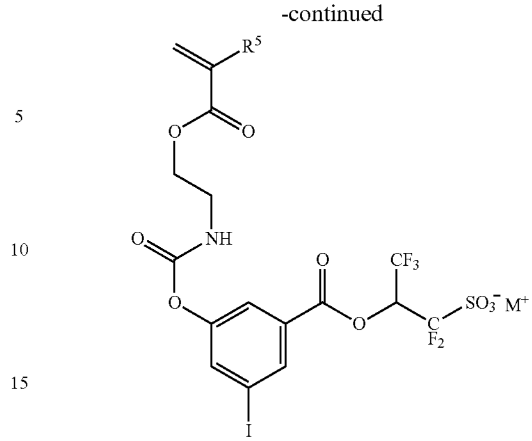
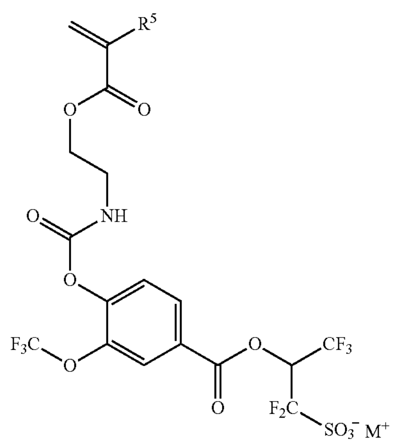
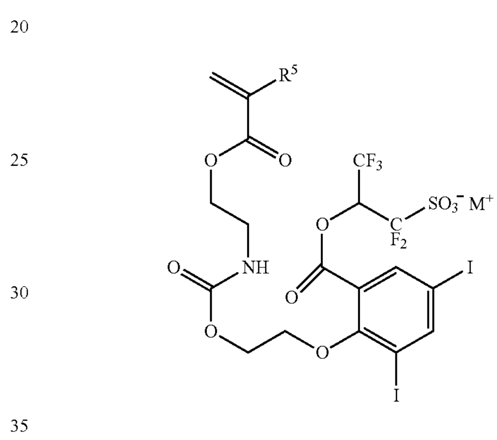
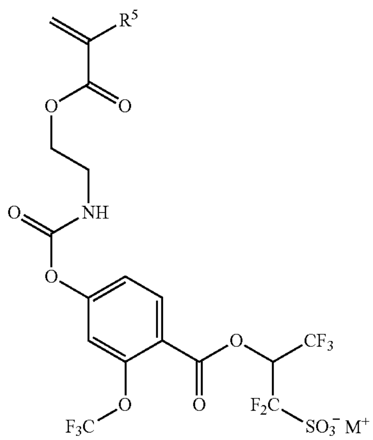
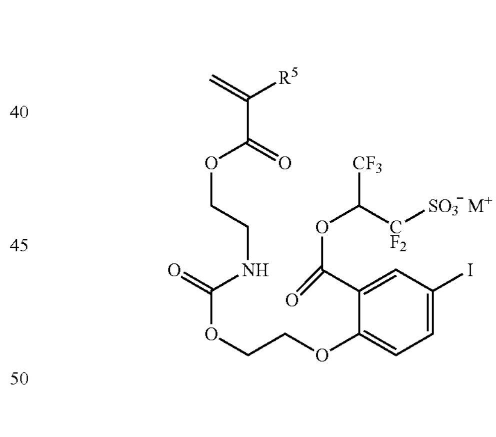
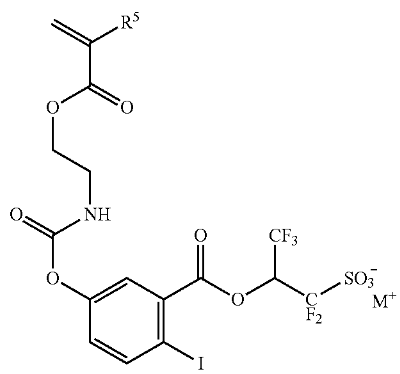
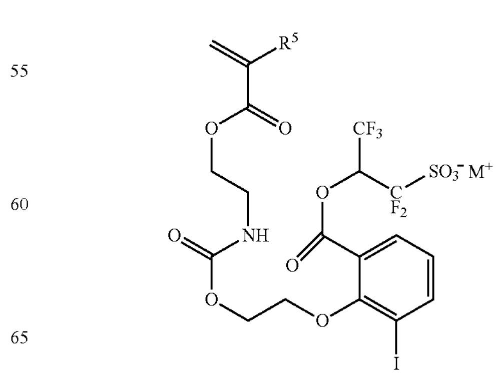

-continued
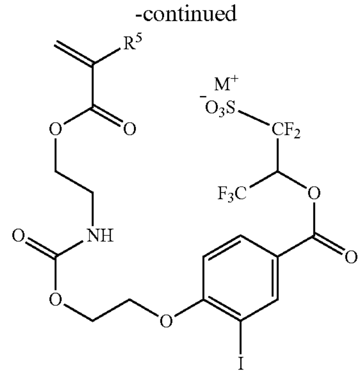
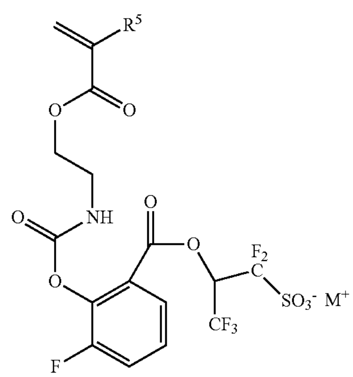
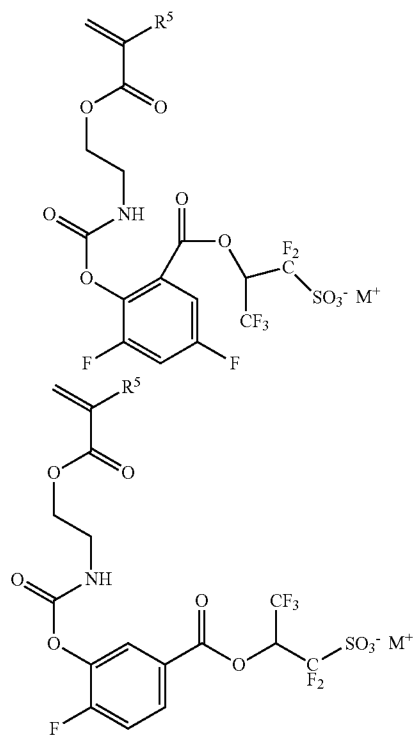
-continued
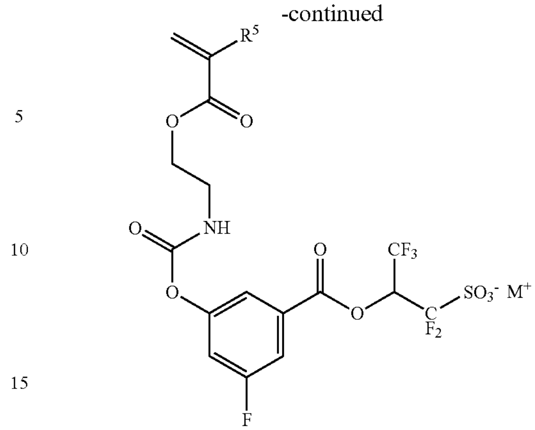
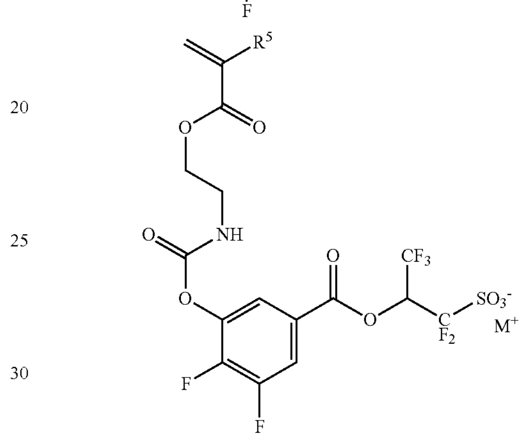
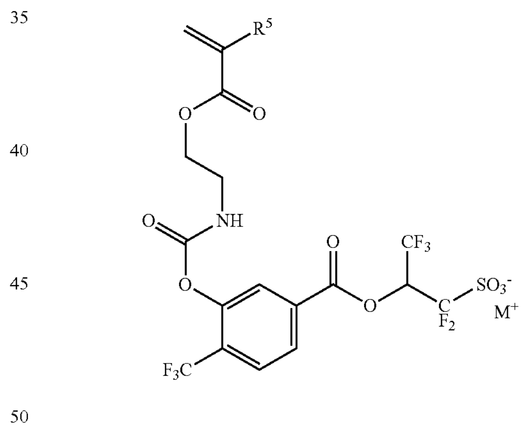
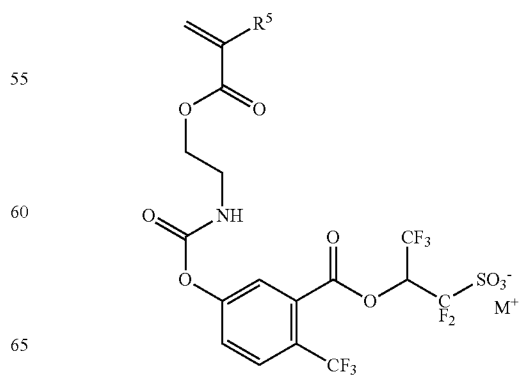

-continued
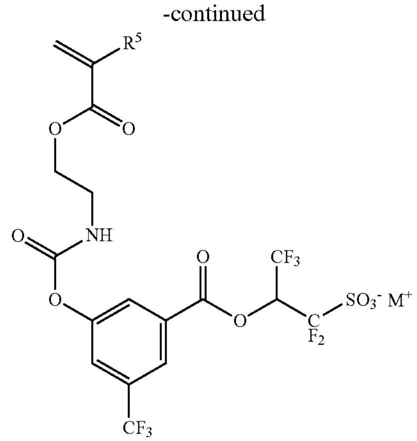
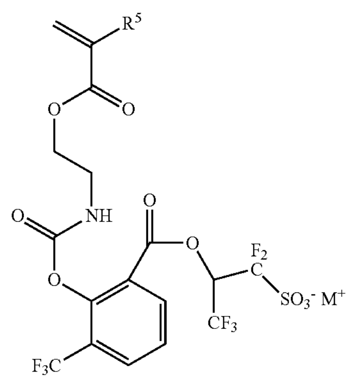
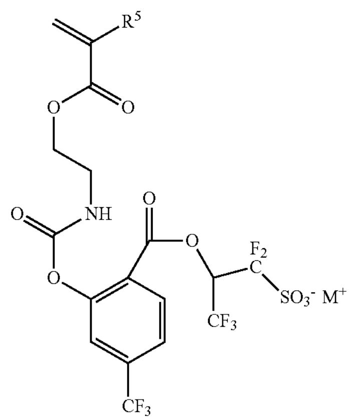
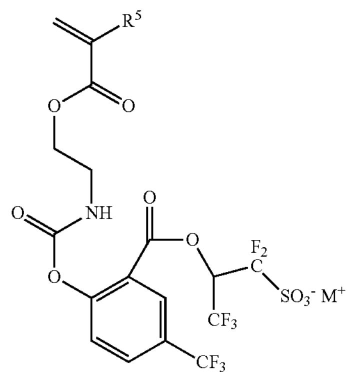
-continued
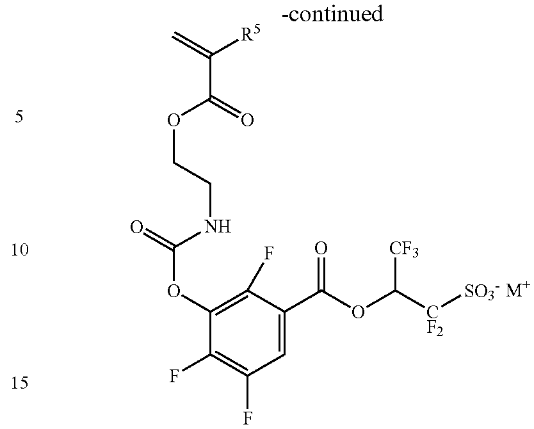
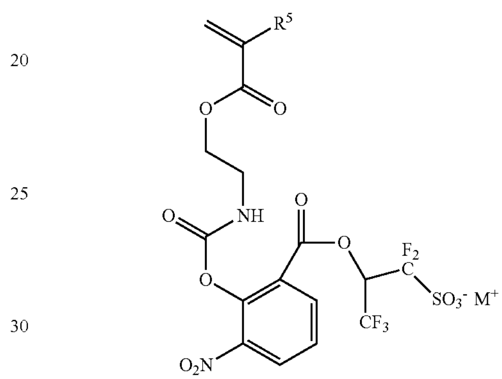
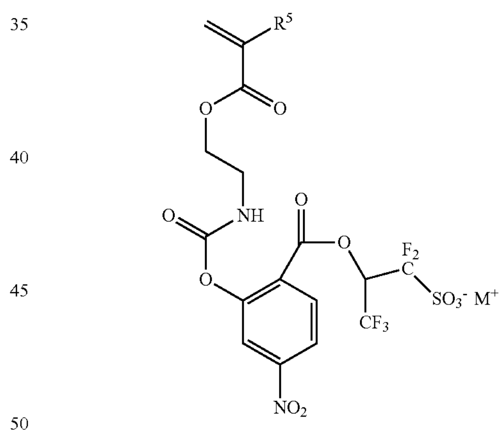
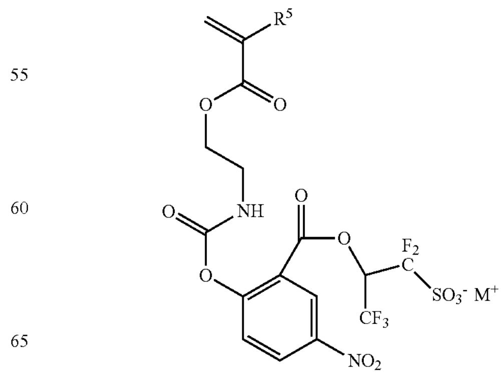

-continued
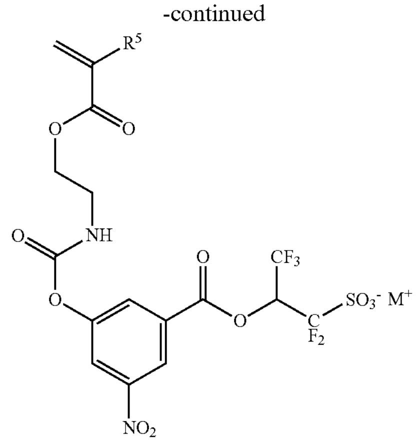
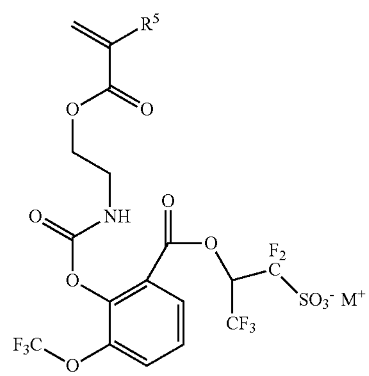
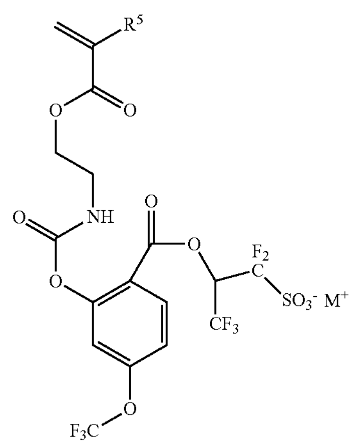
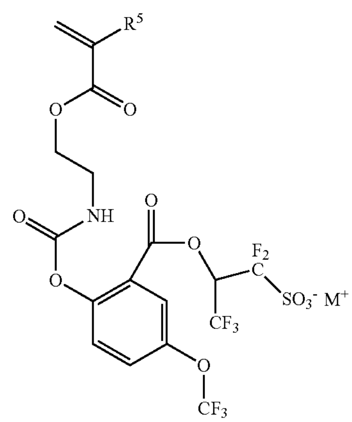
-continued
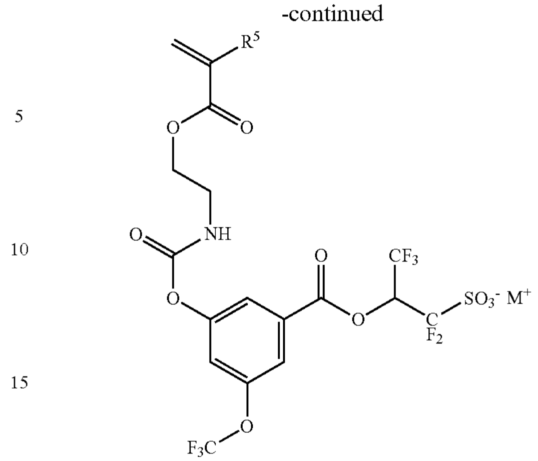
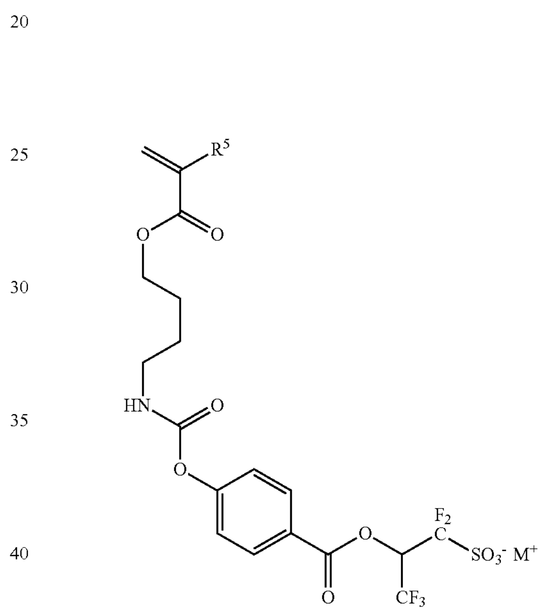
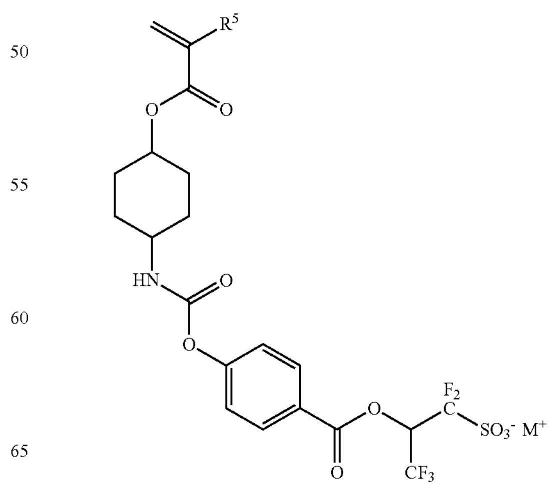

-continued
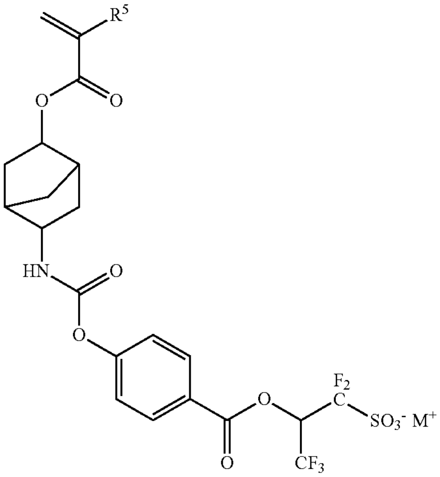
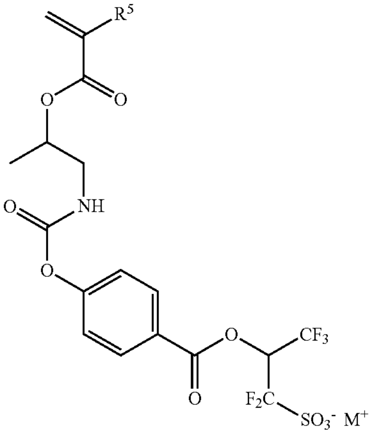
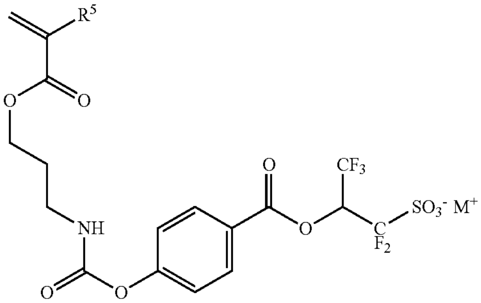
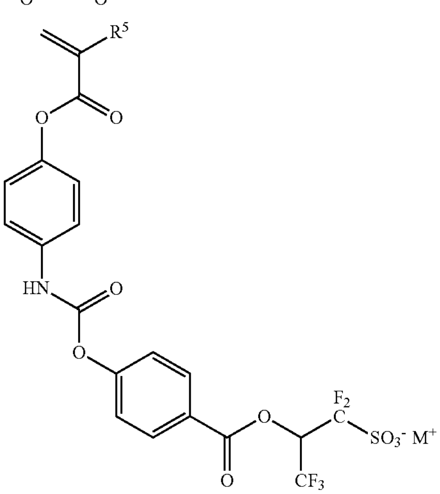
-continued
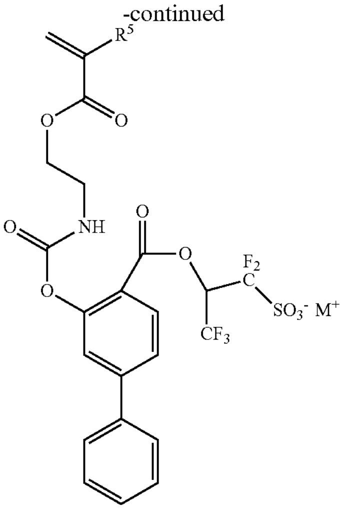
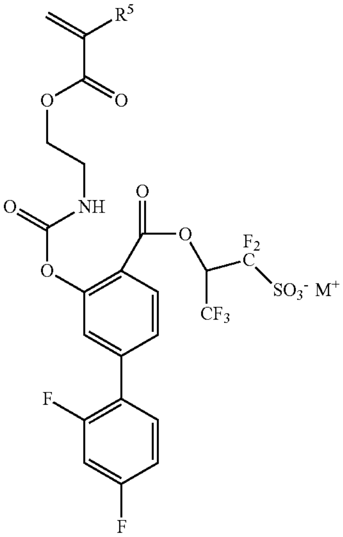
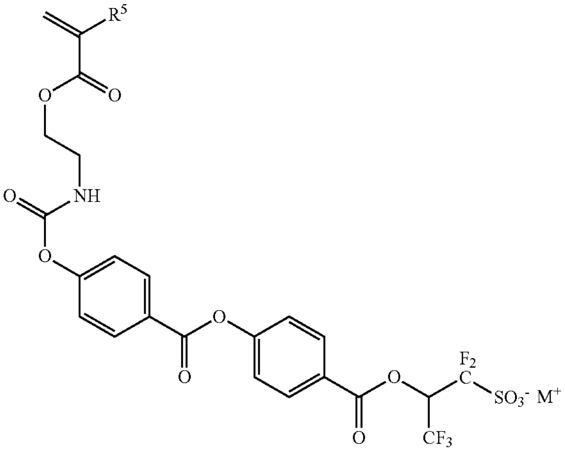

-continued
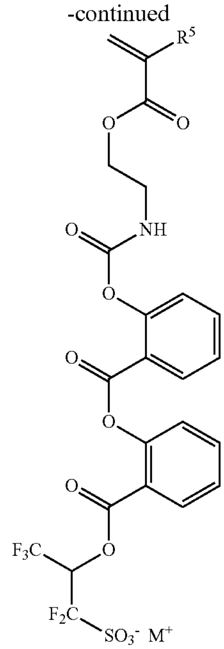
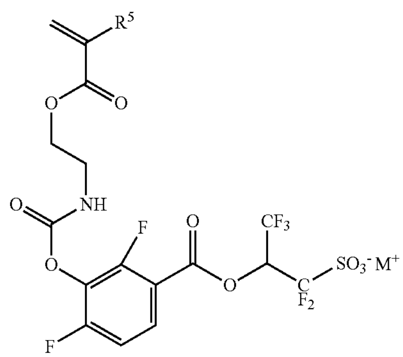
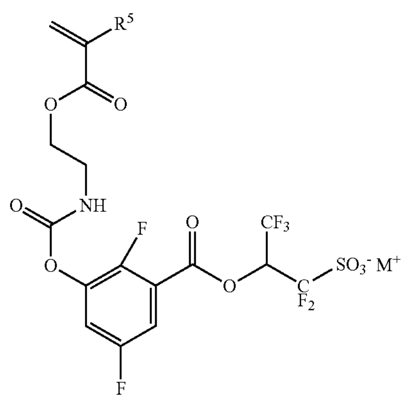
-continued
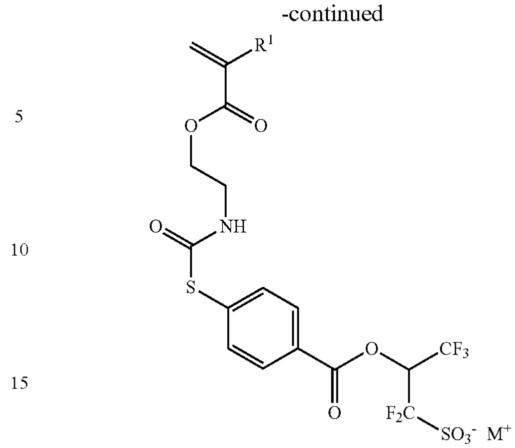
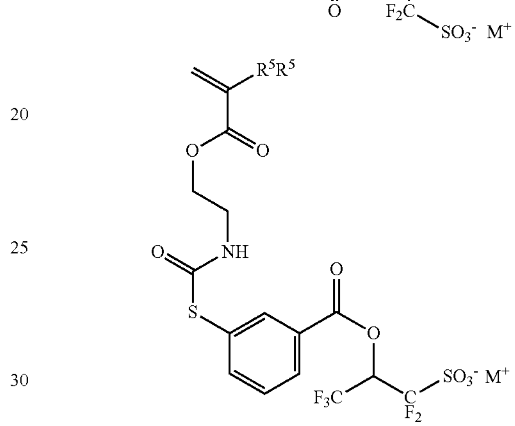
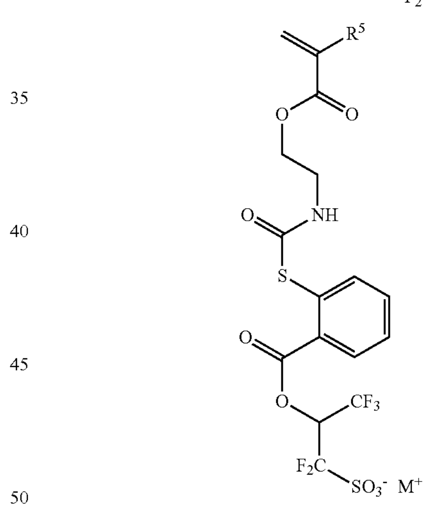
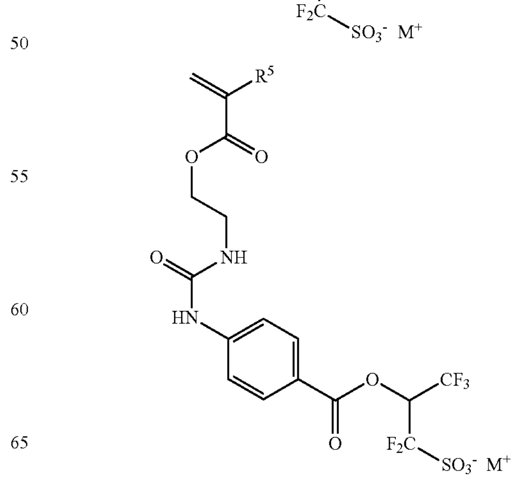

-continued
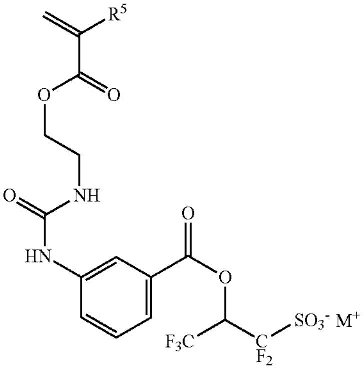
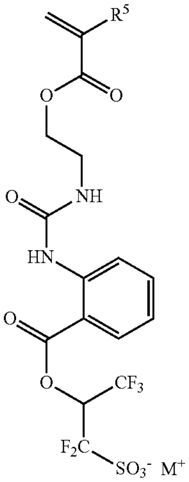
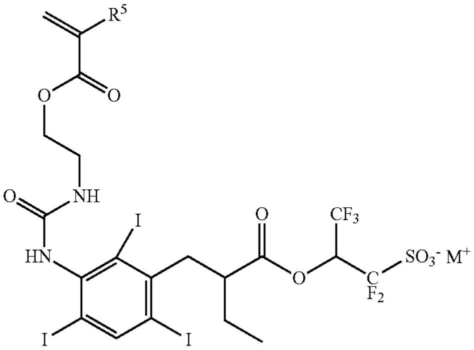
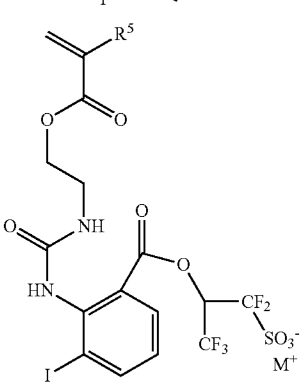
-continued
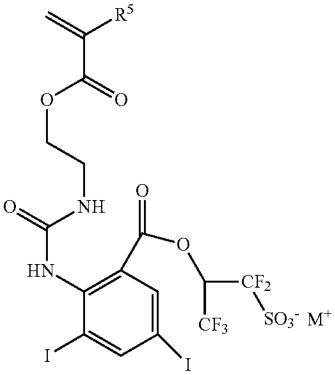
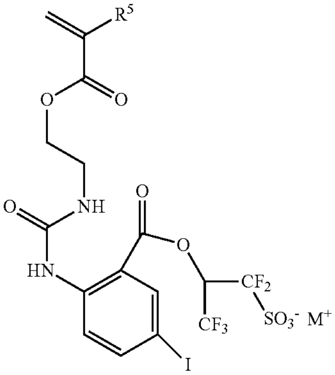
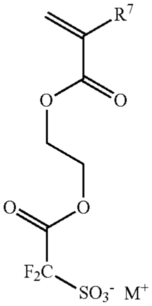
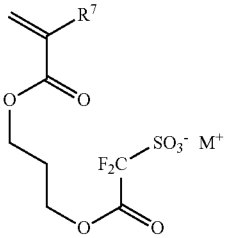
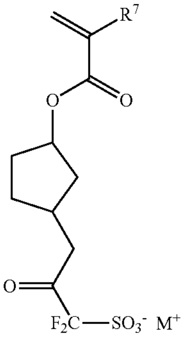
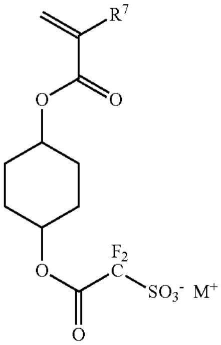
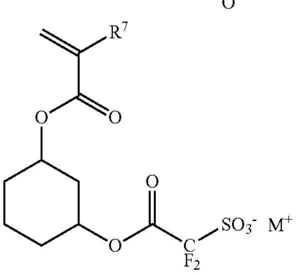

-continued
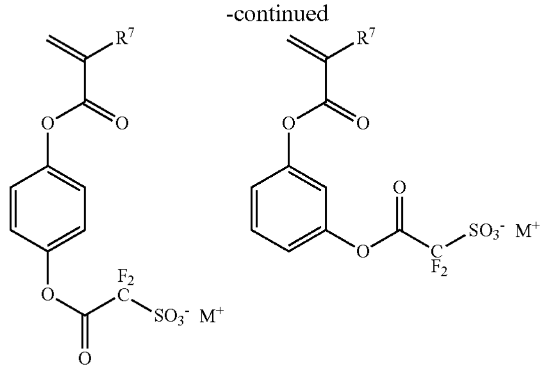
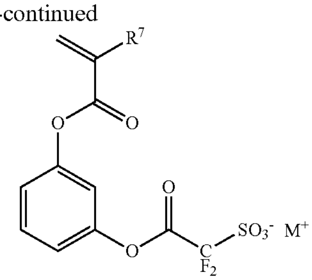
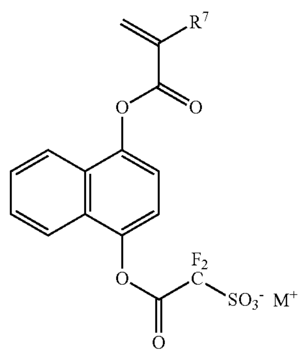
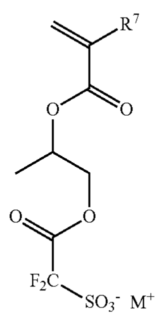
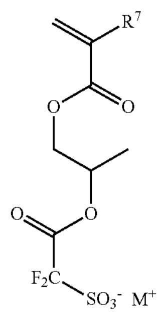
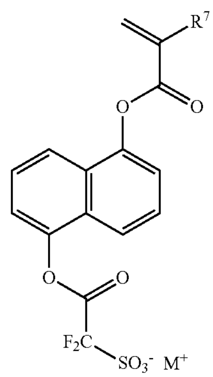
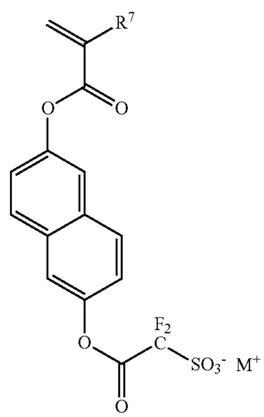
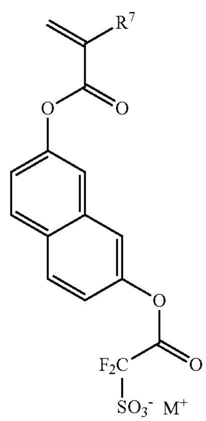
-continued
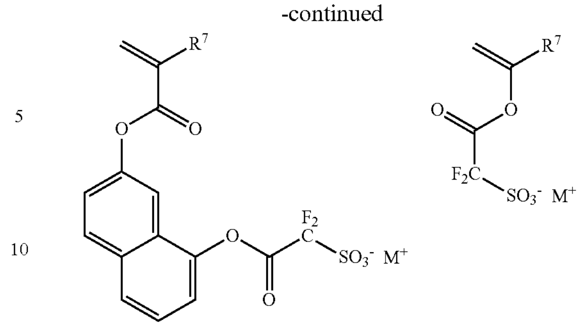
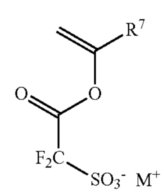
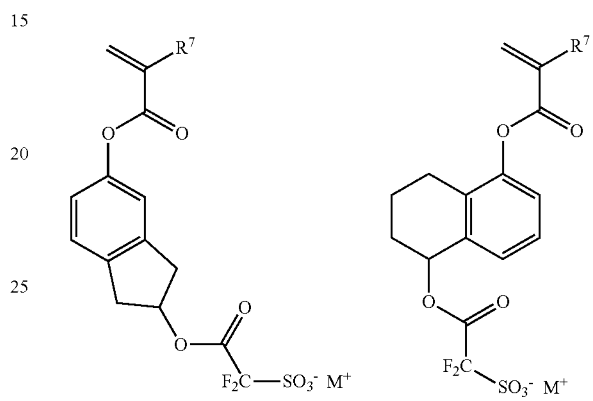
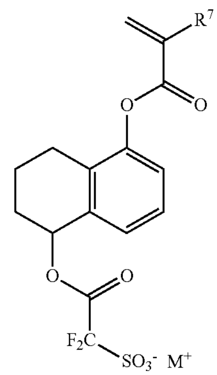
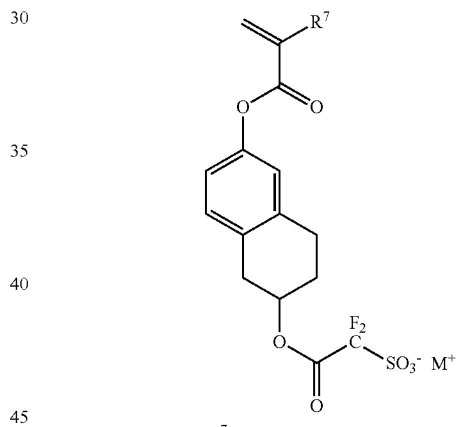
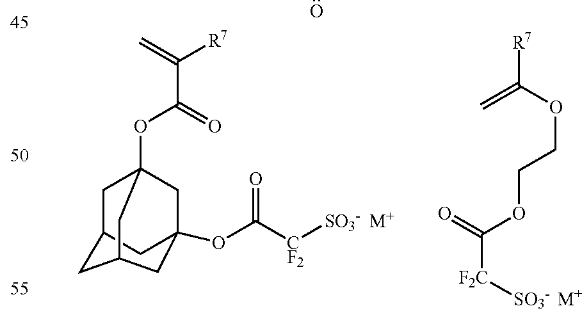
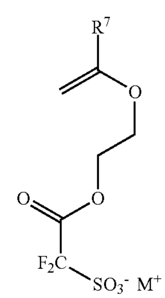
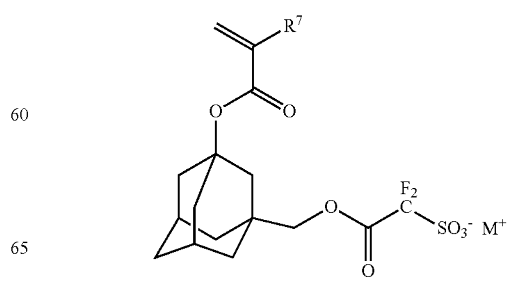

-continued
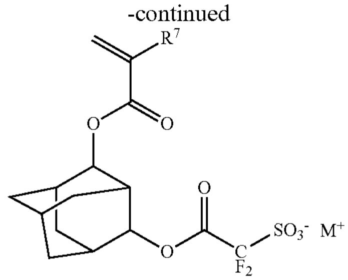
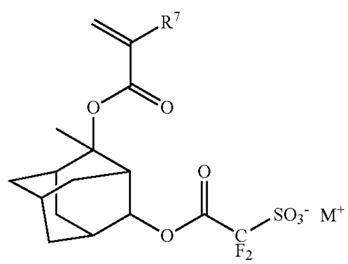
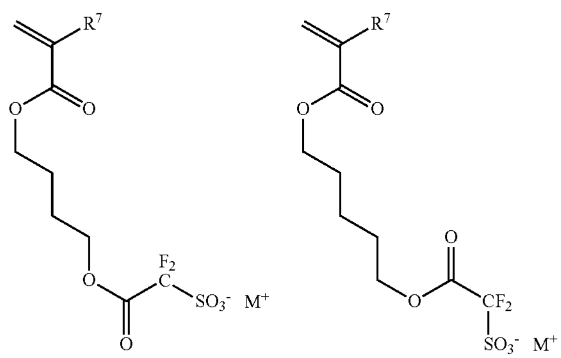
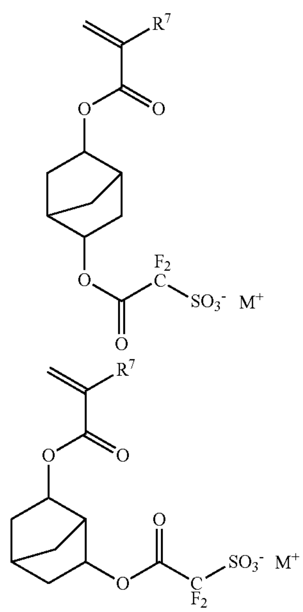
-continued
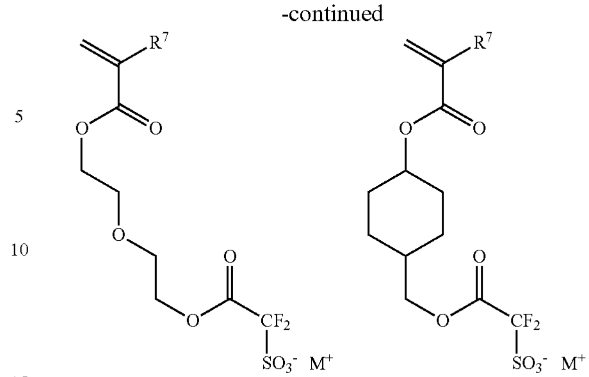
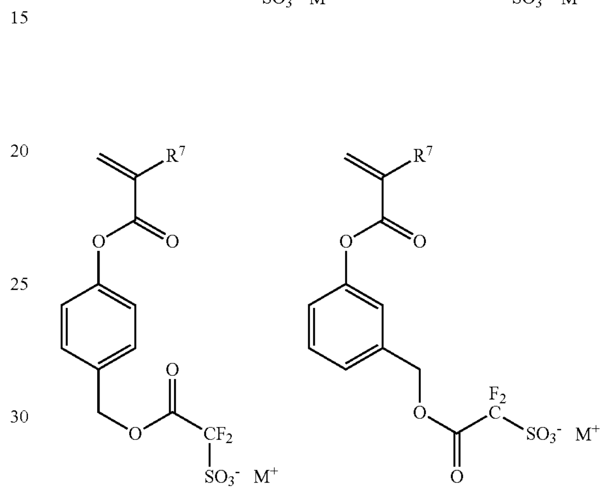
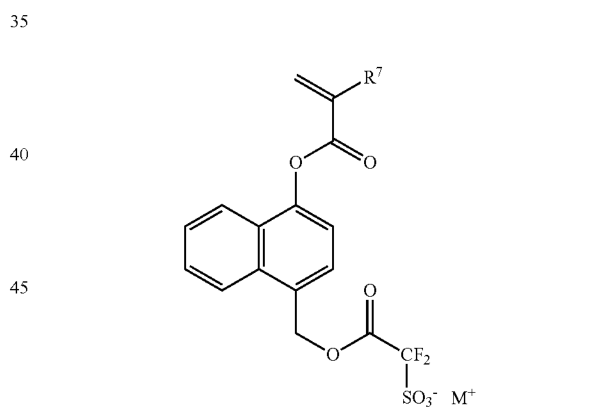
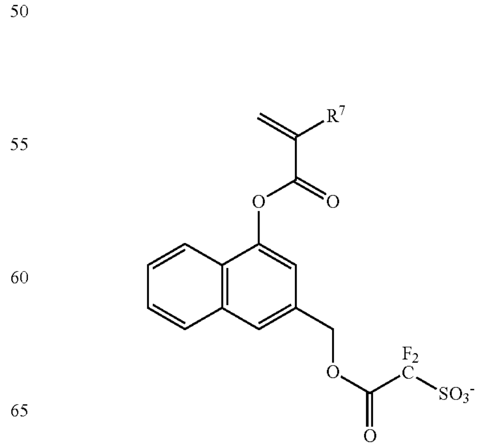

-continued
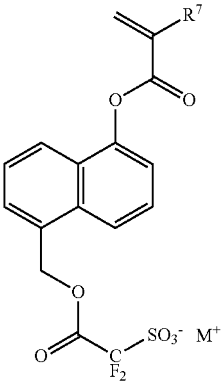
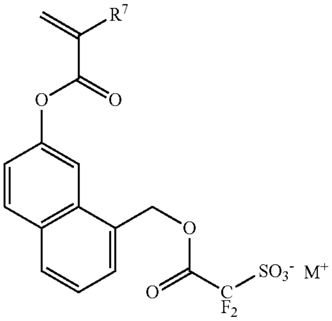
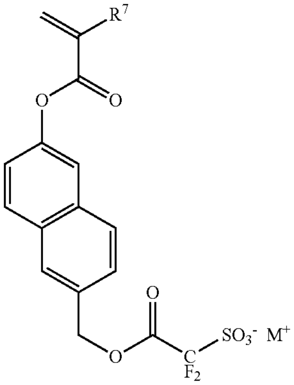
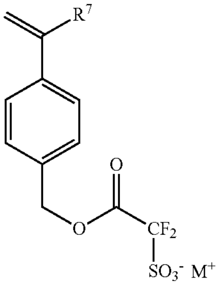
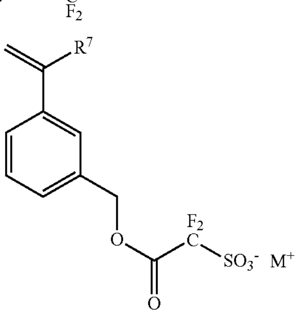
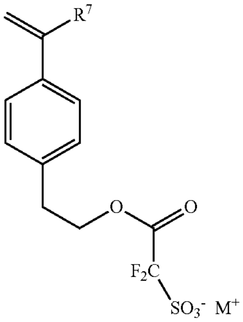
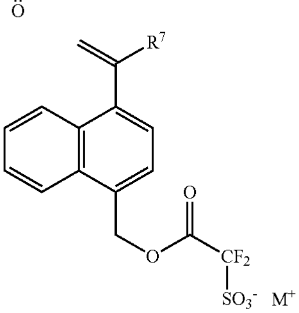
-continued
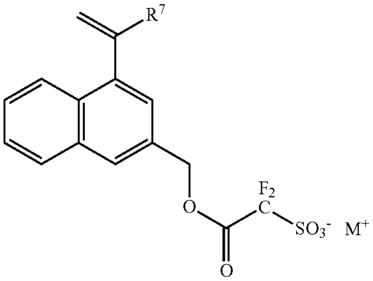
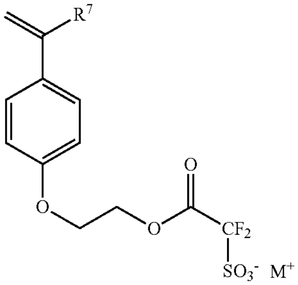
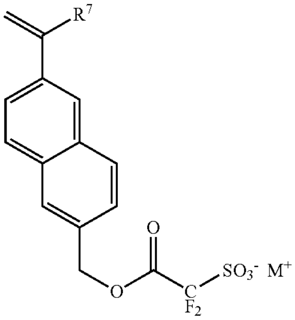
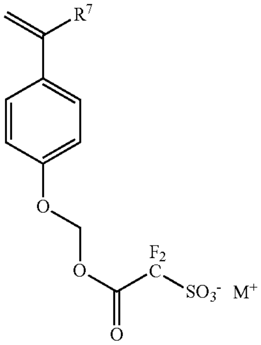
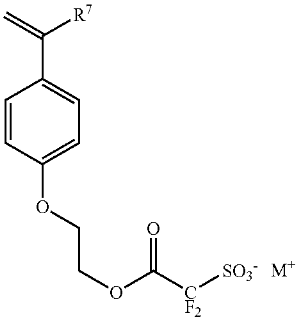

-continued
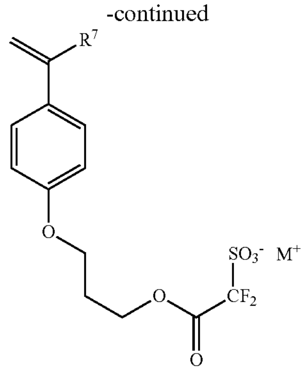
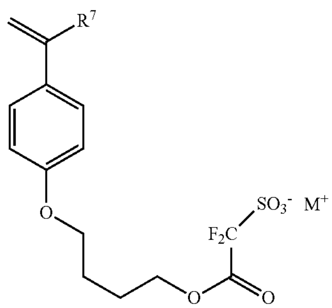
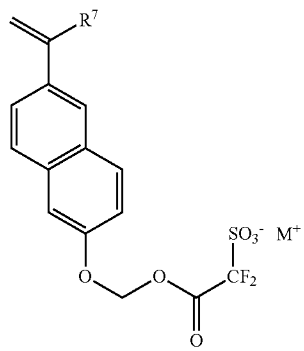
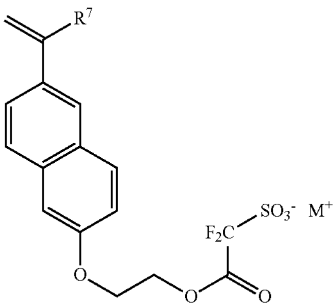
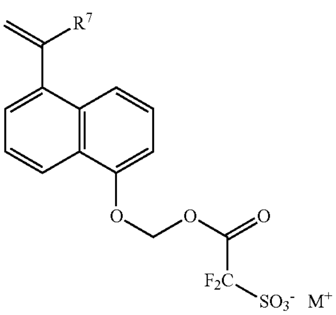
-continued
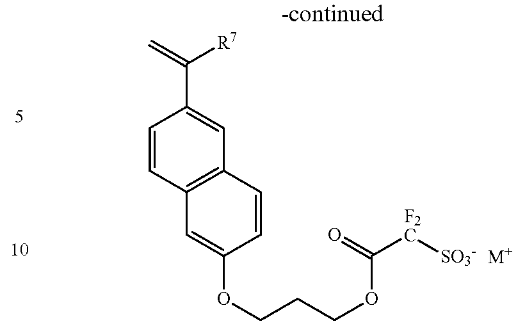
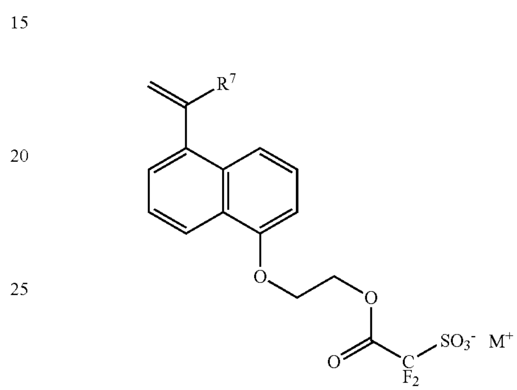
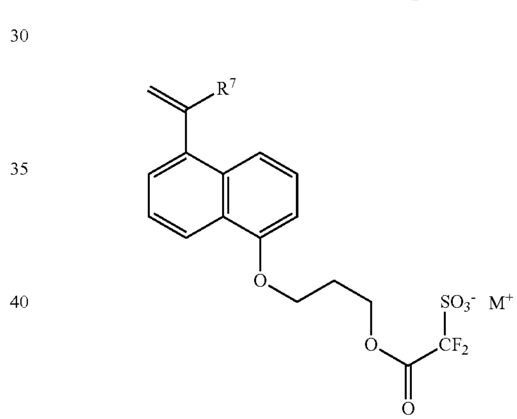
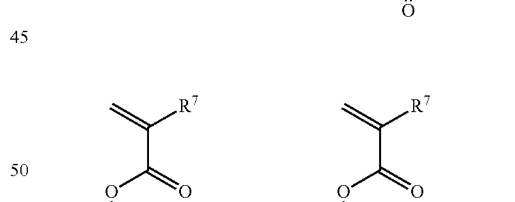
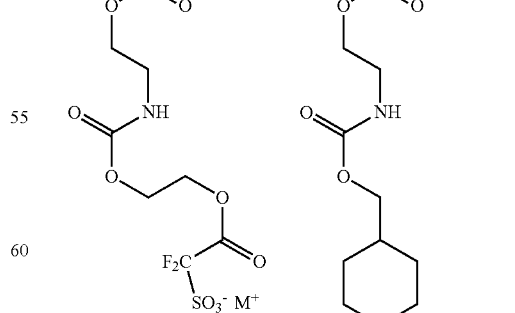
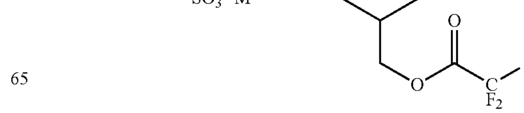

-continued
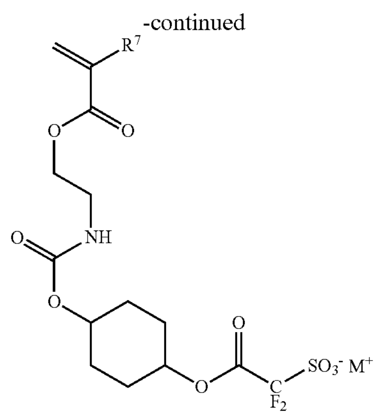
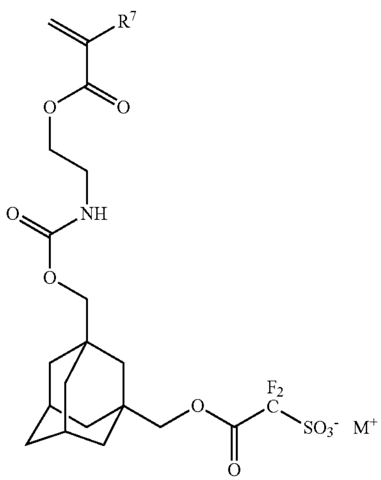
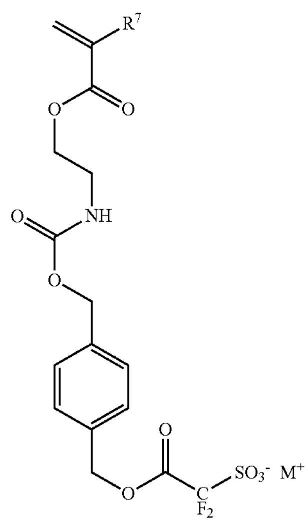
-continued
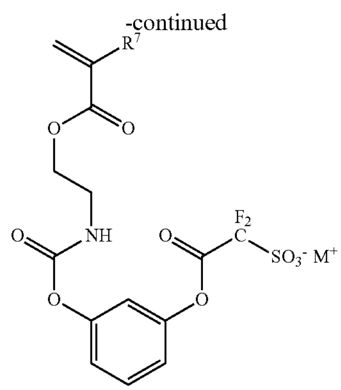
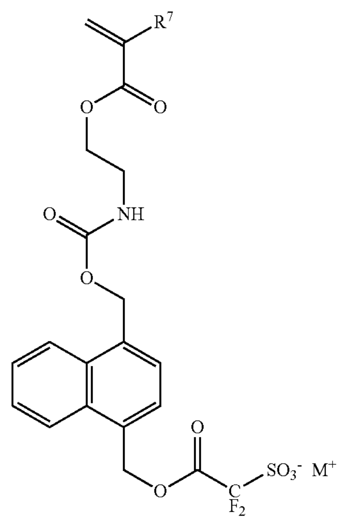
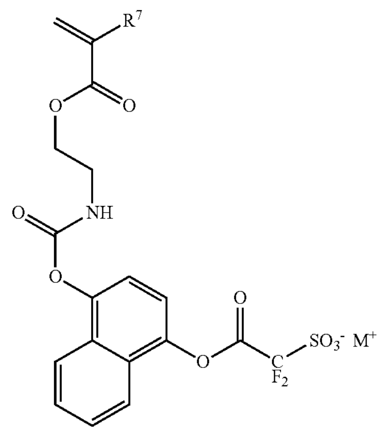

-continued
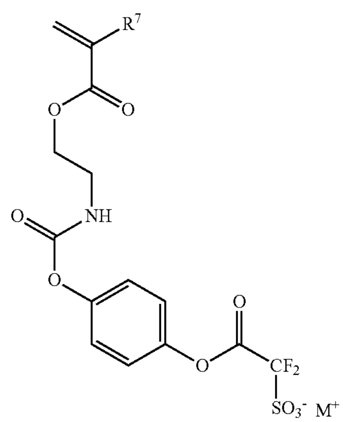
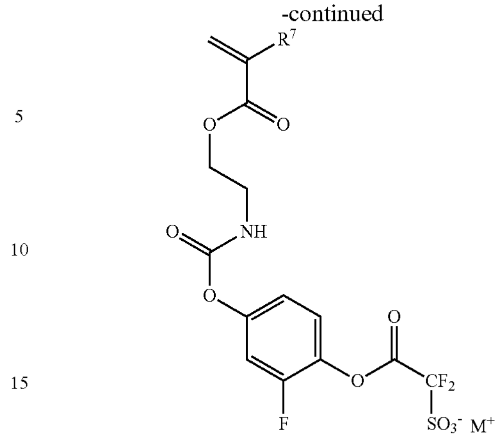
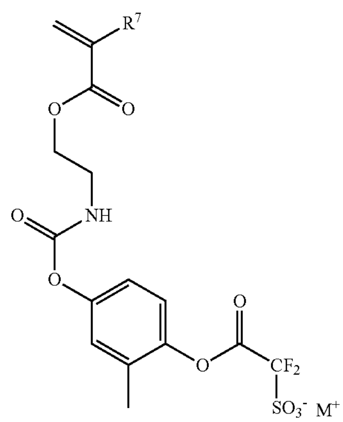
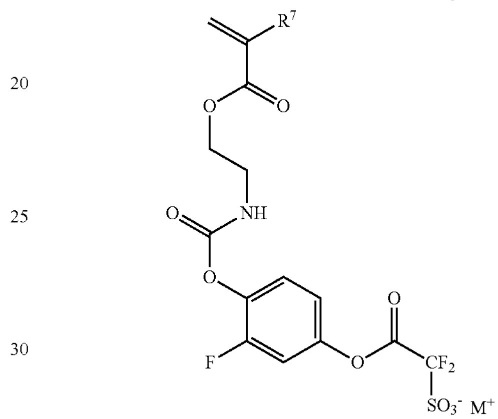
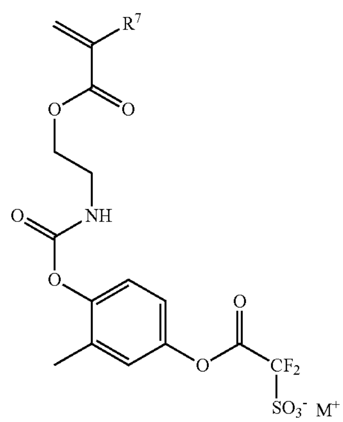
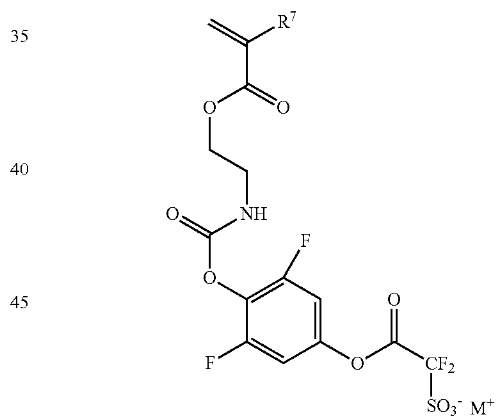
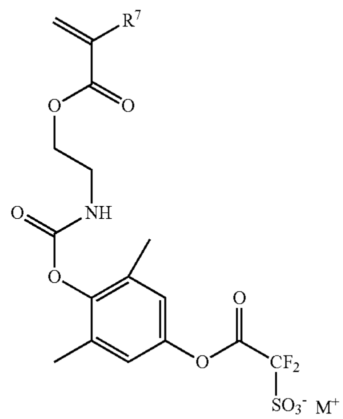
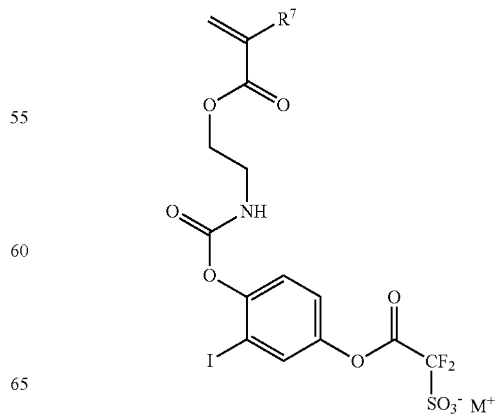

-continued
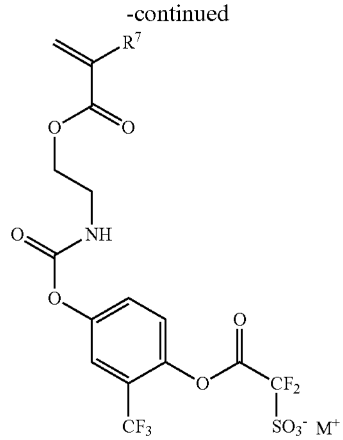
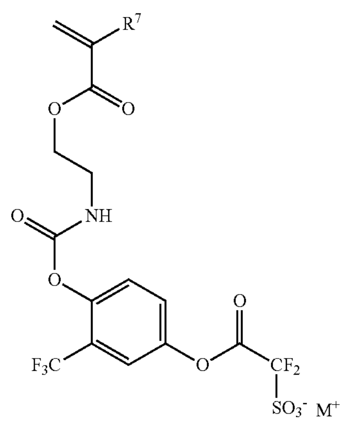
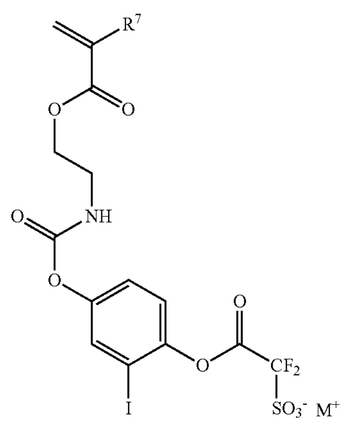
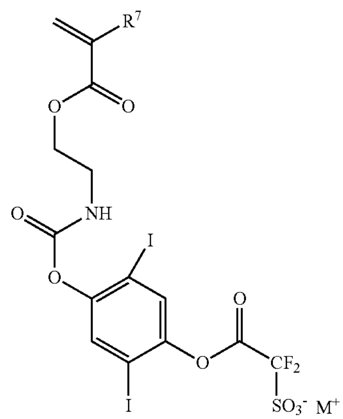
-continued
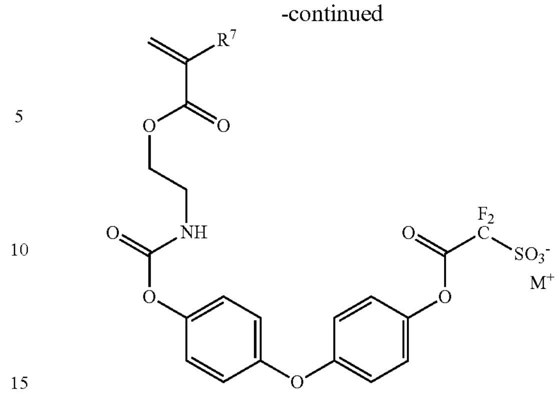
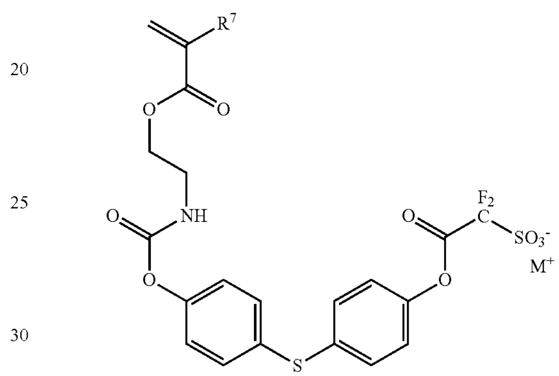
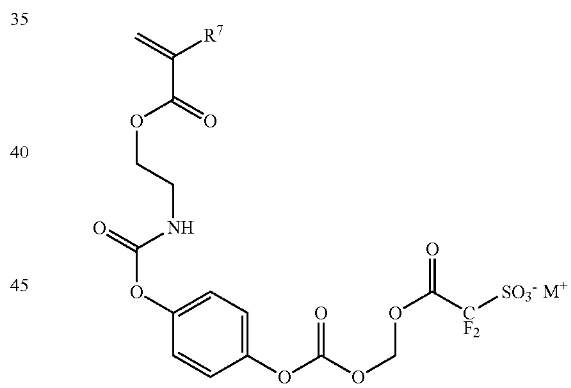
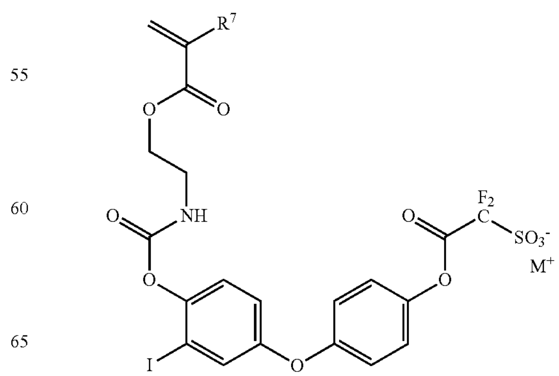

-continued
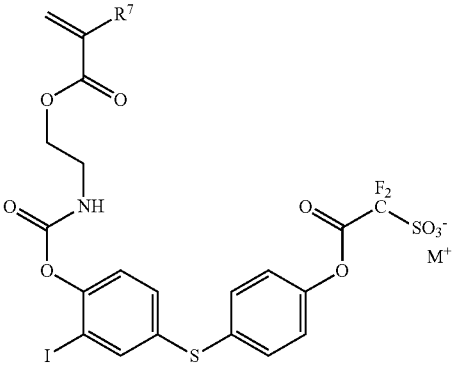
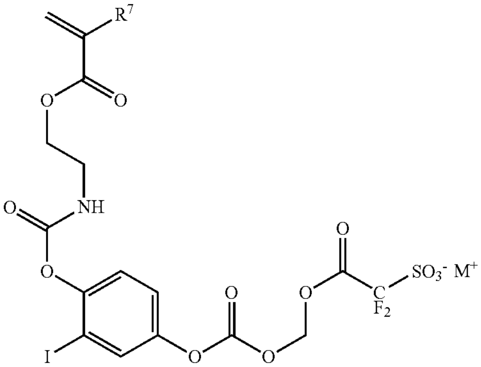
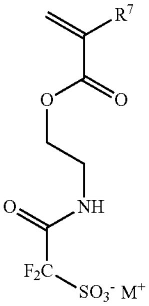
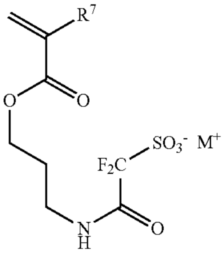
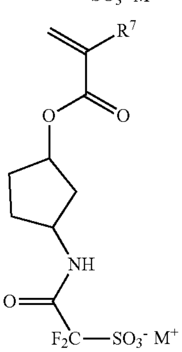
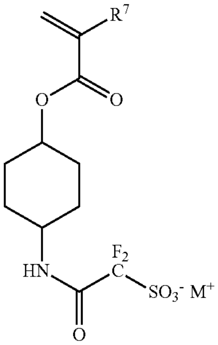
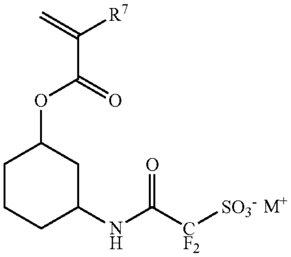
-continued
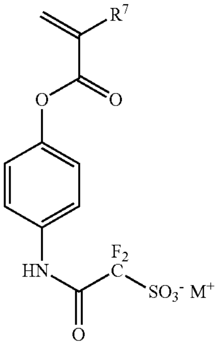
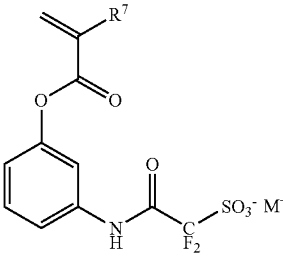
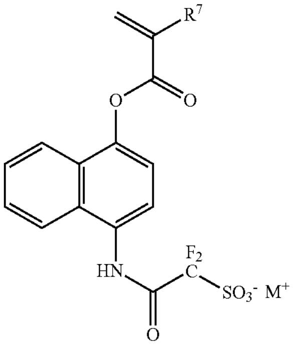
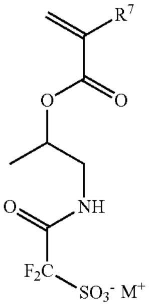
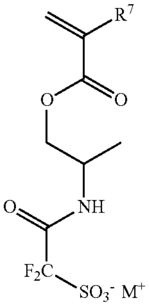
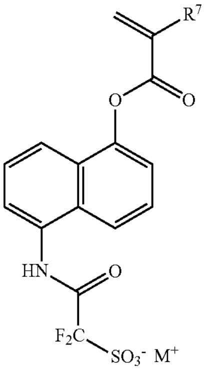
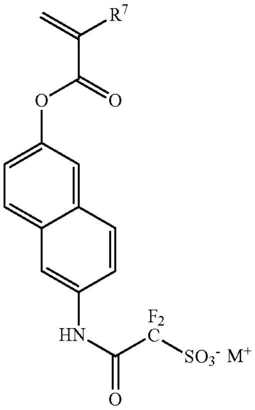
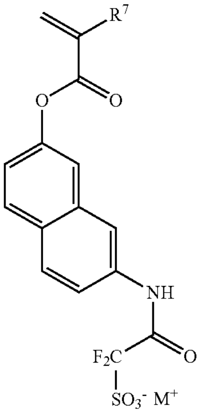

-continued
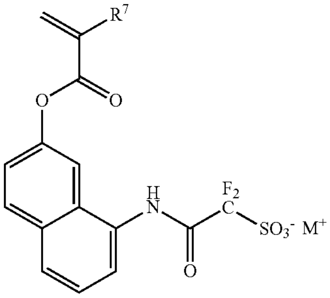
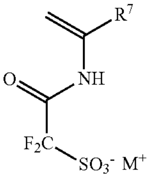
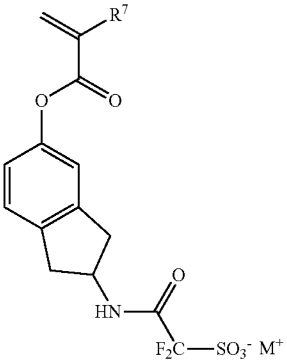
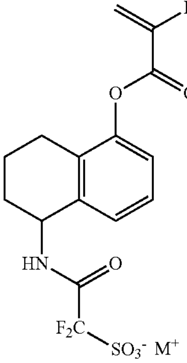
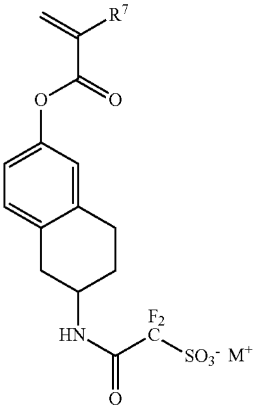
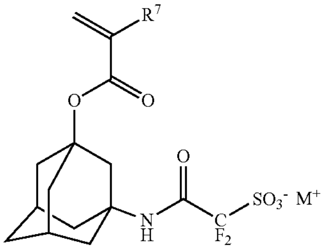
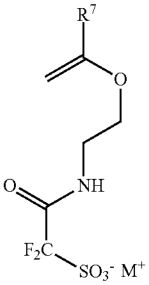
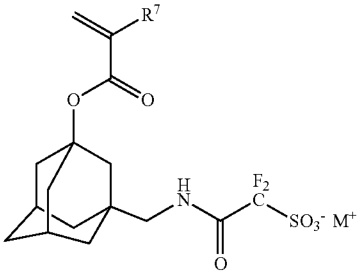
-continued
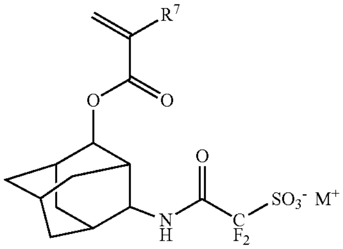
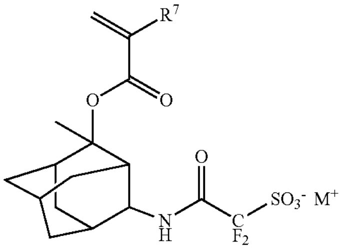
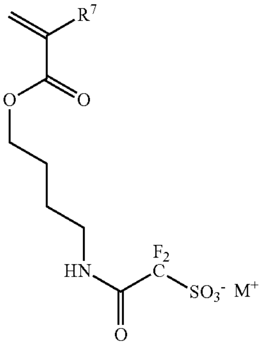
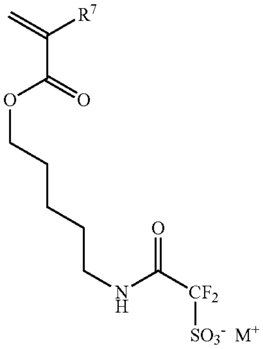
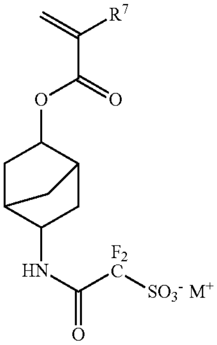
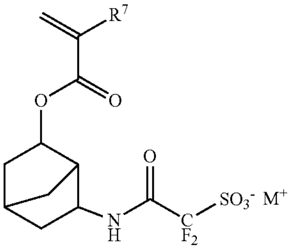
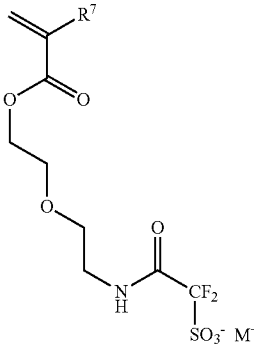

-continued
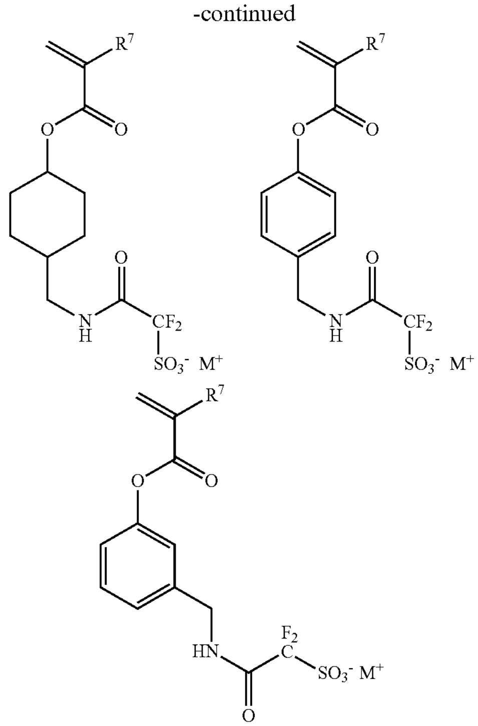
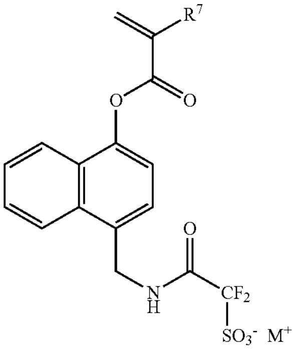
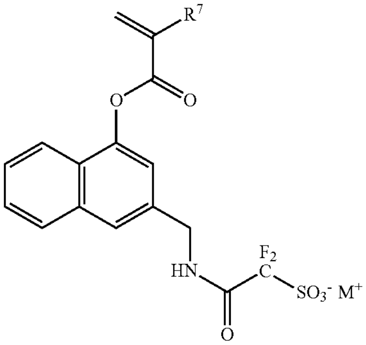
-continued
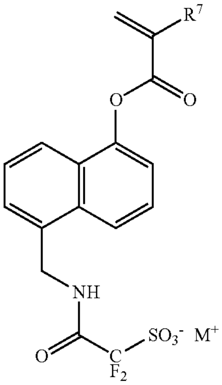
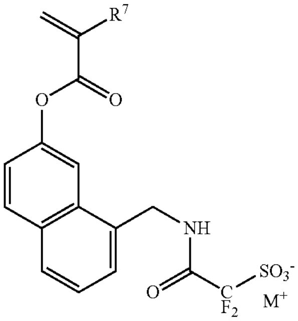
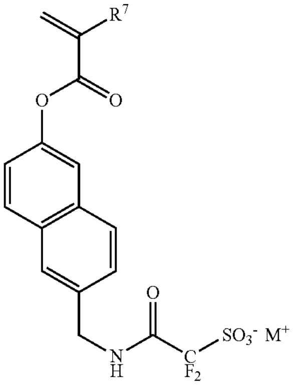
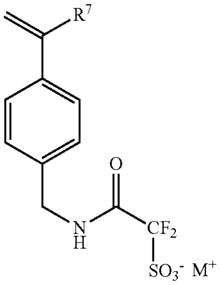
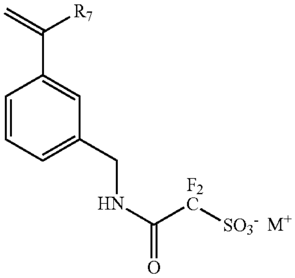
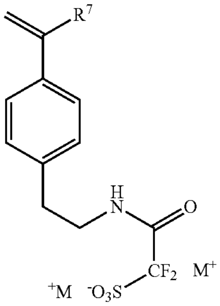
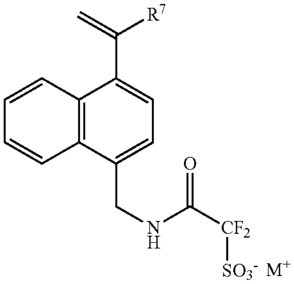

-continued
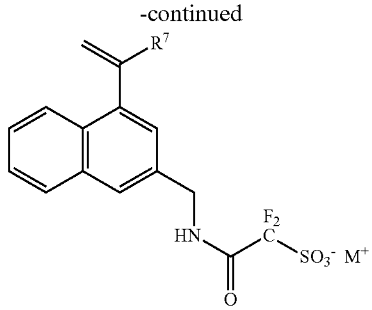
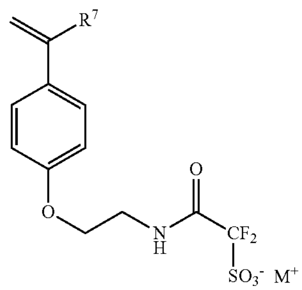
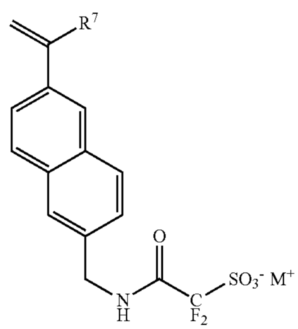
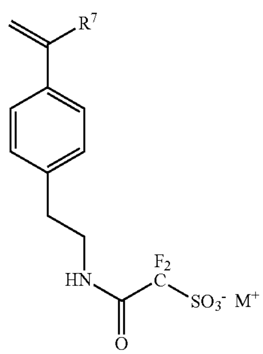
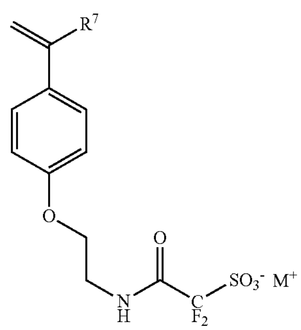
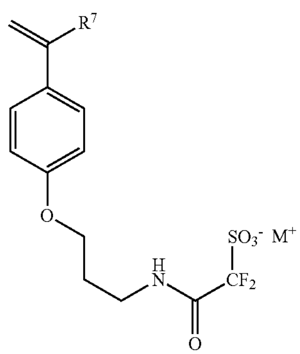
-continued
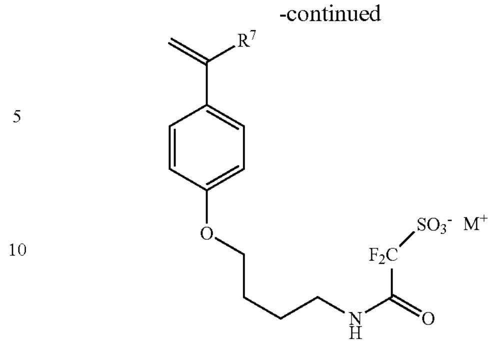
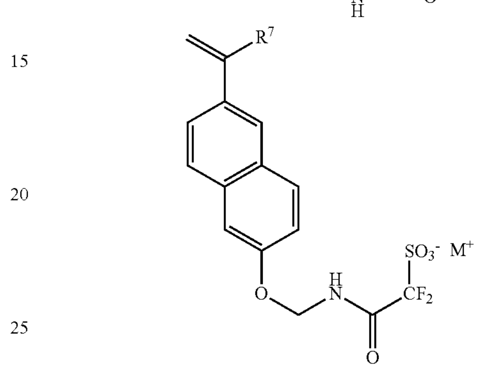
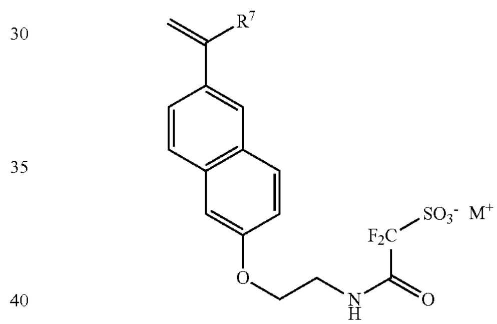
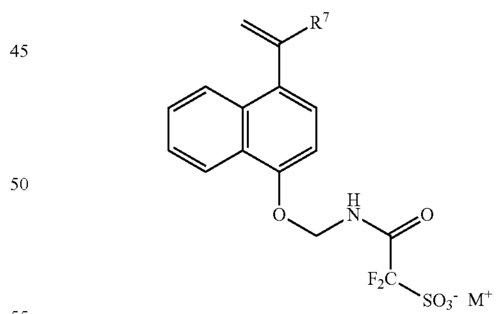
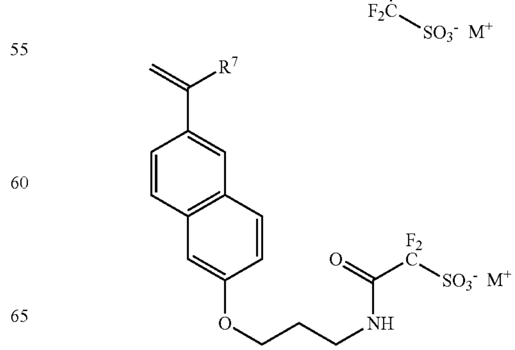

-continued
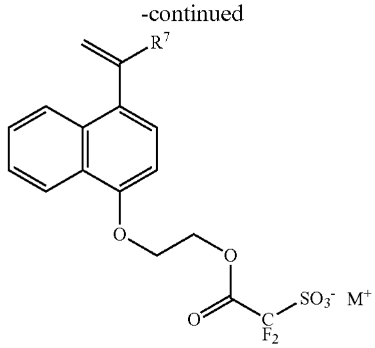
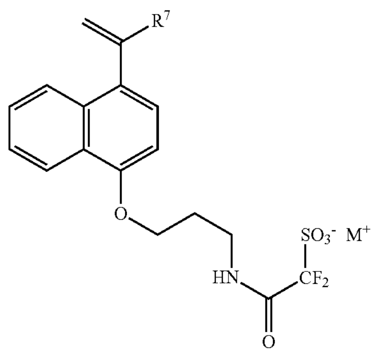
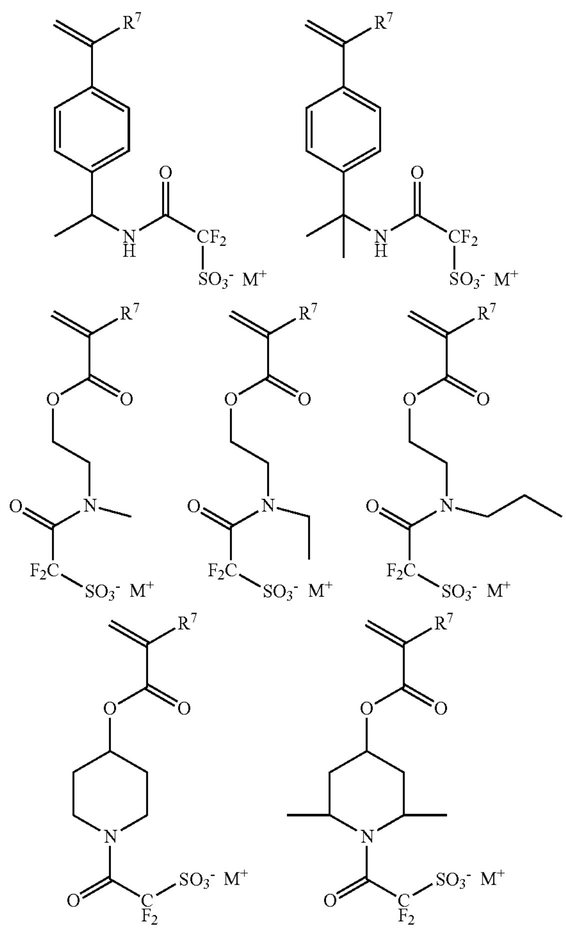
-continued
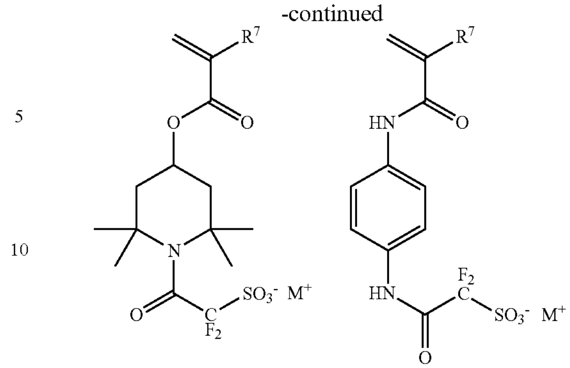
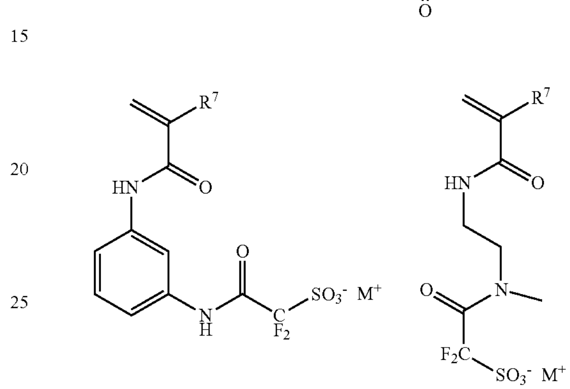
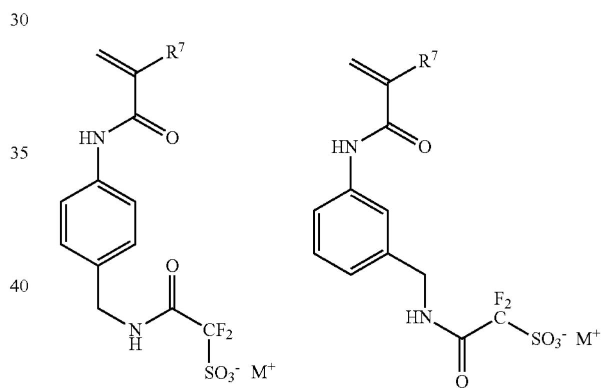
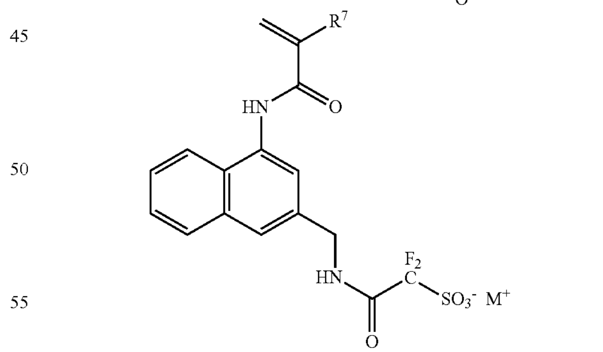
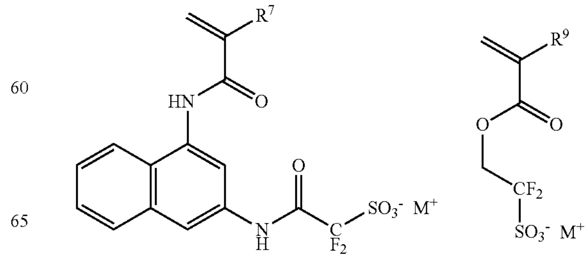

-continued
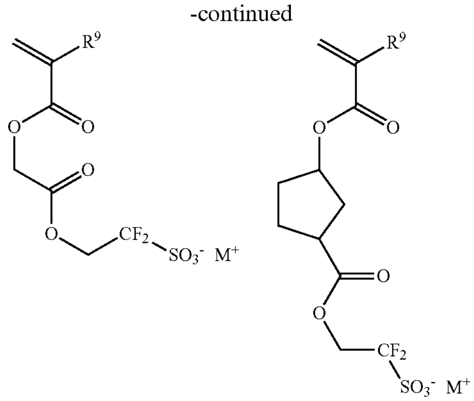
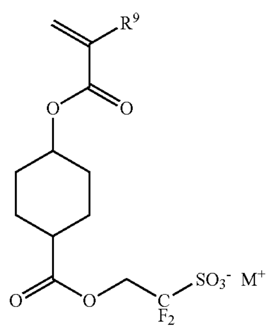
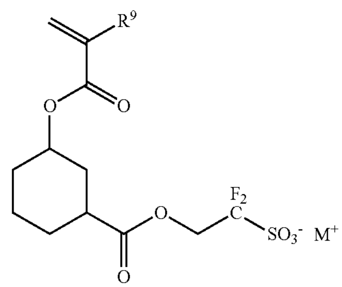
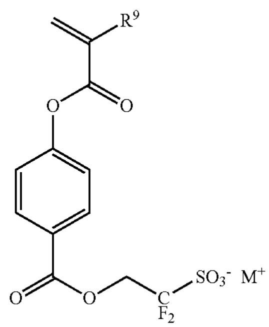
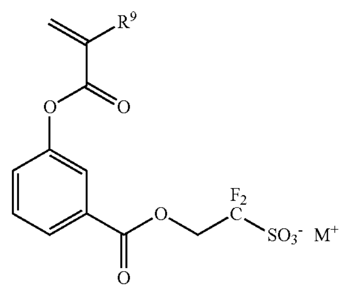
-continued
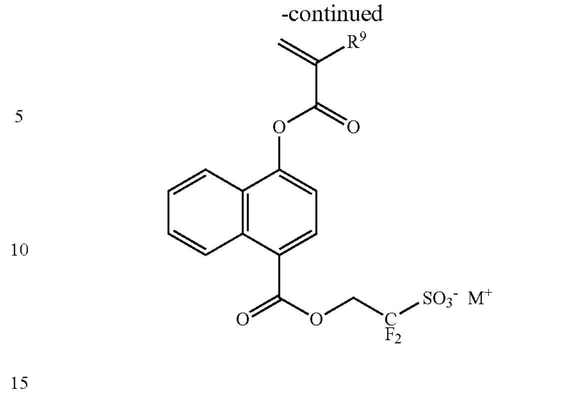
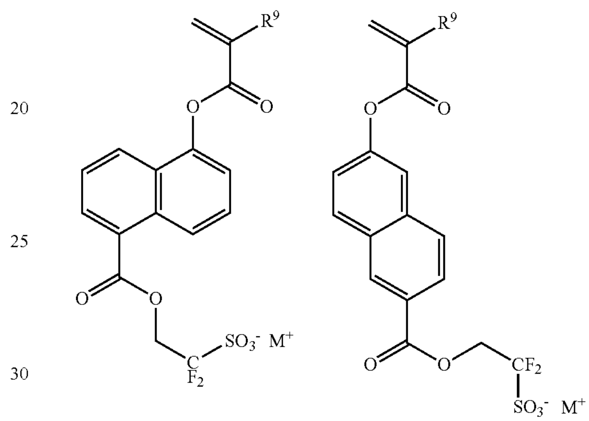
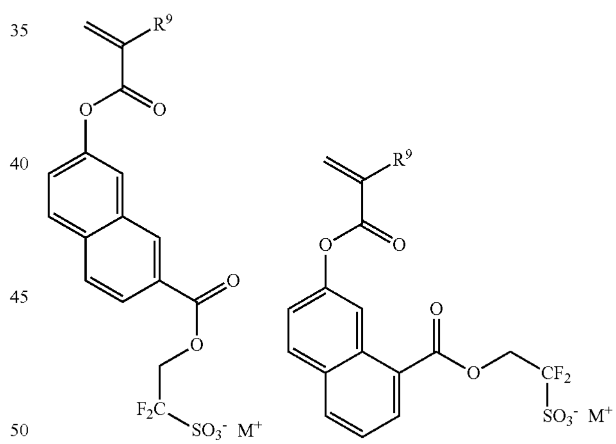
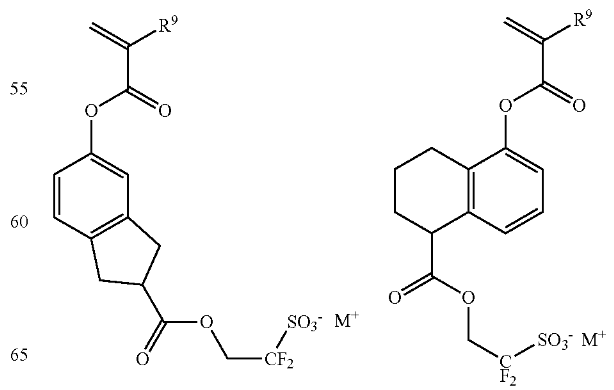

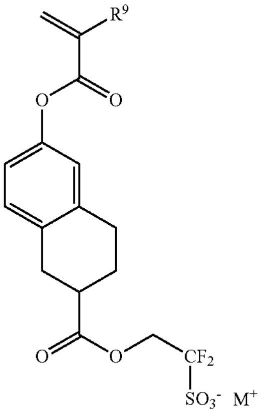
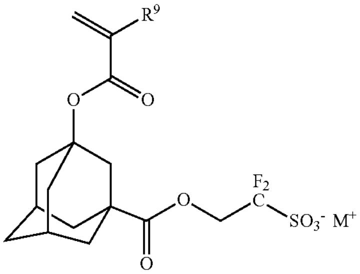
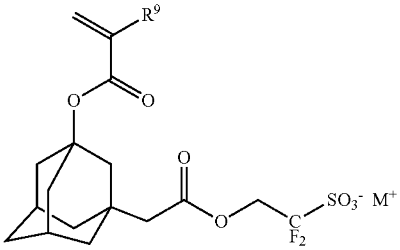
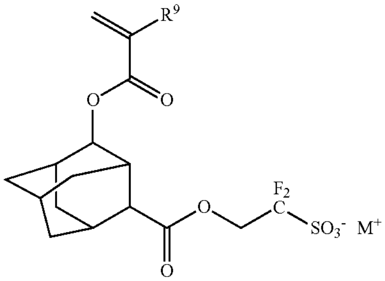
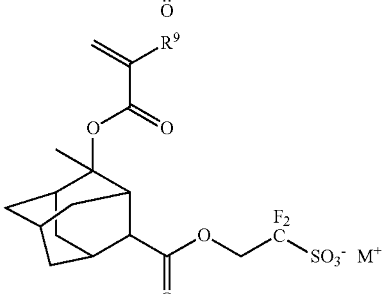
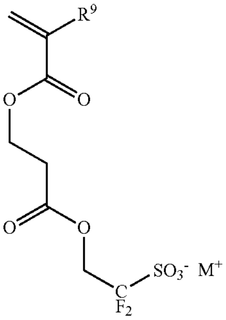
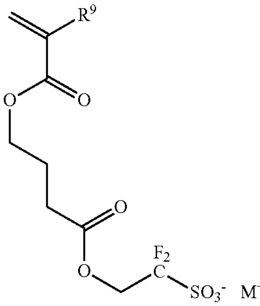
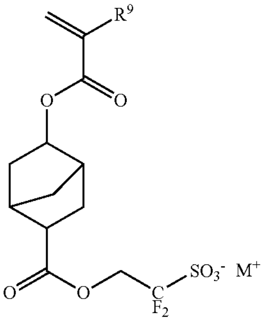
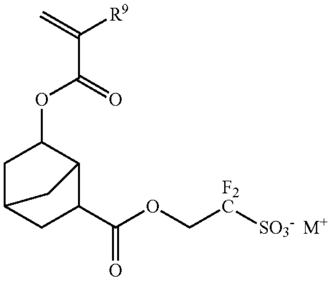
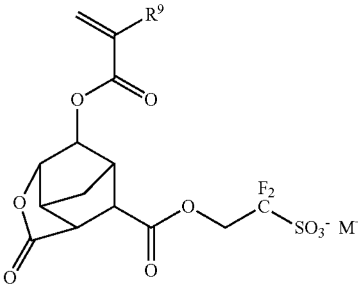
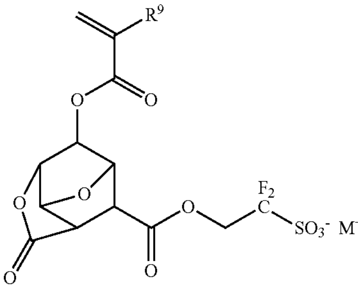

-continued
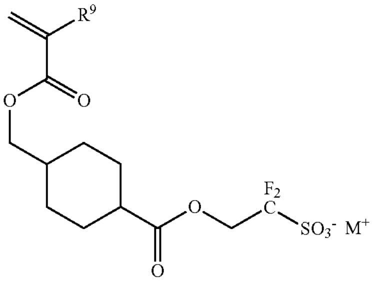
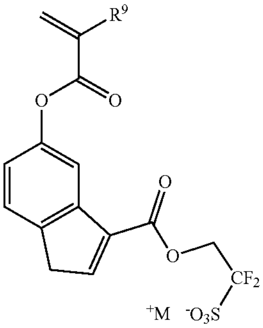
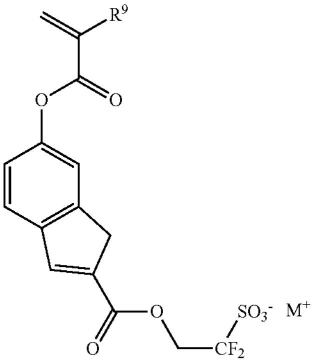
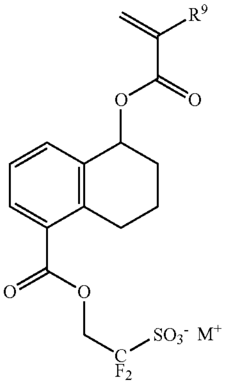
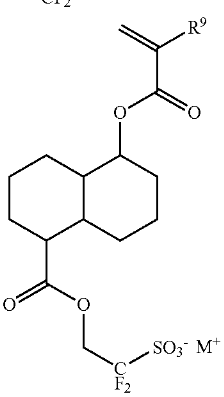
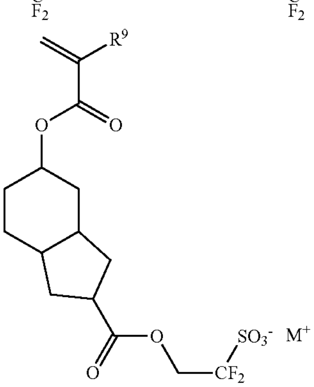
-continued
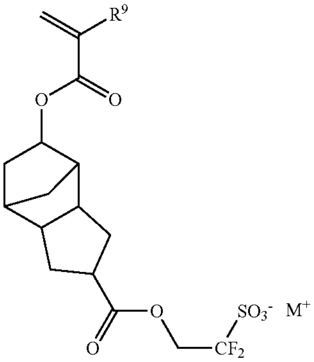
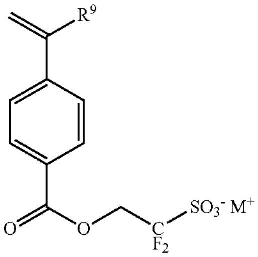
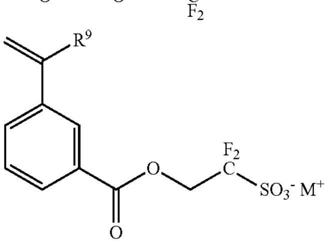
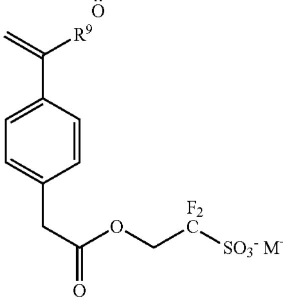
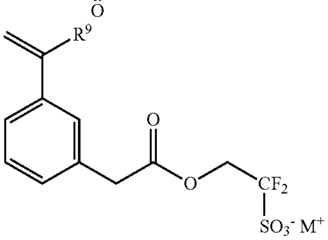
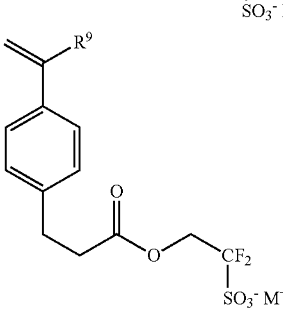

-continued
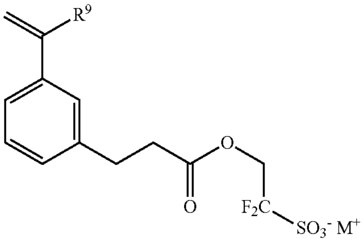
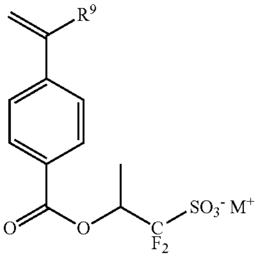
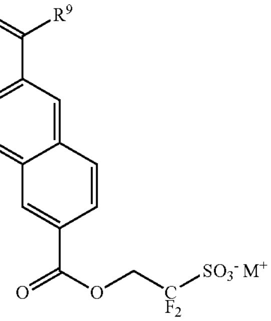
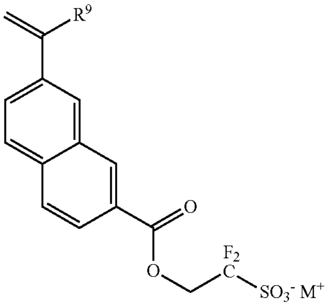
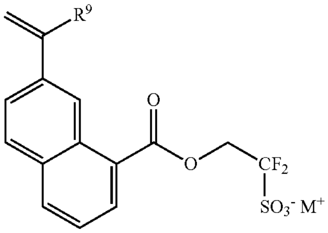
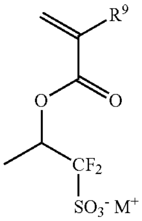
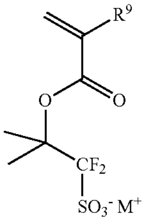
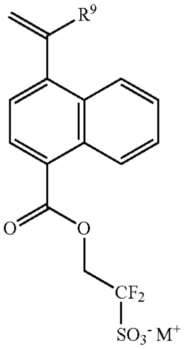
-continued
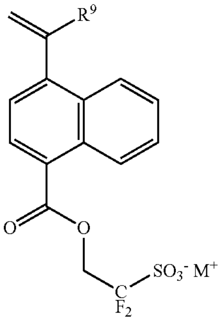
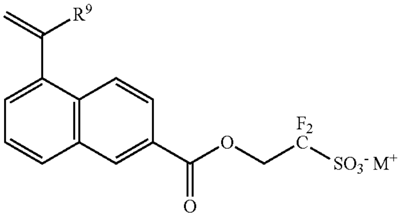
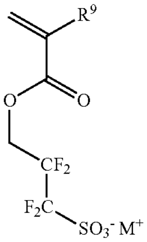
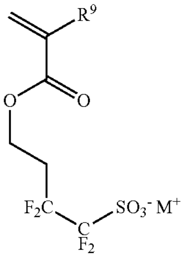
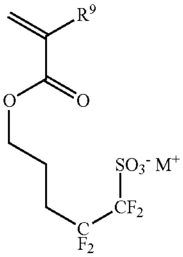
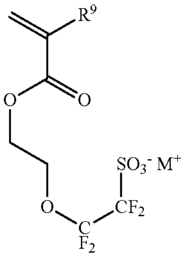
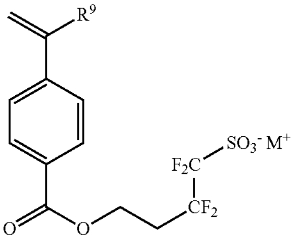
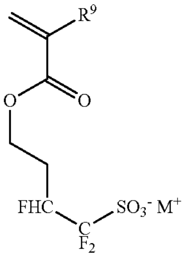
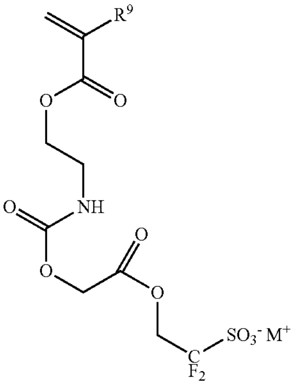

-continued
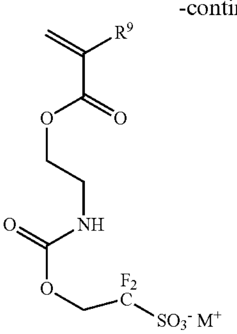
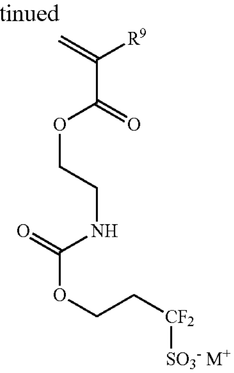
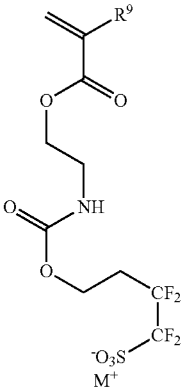
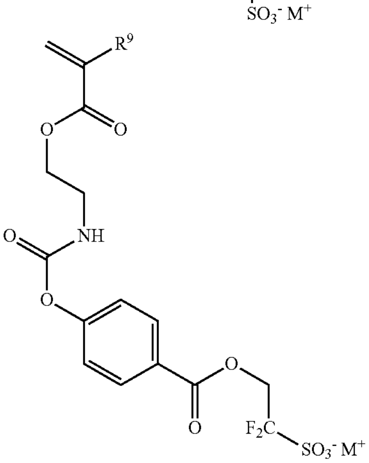
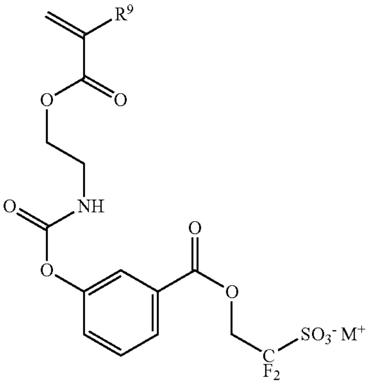
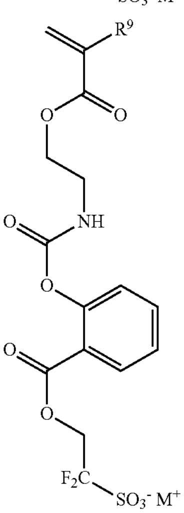
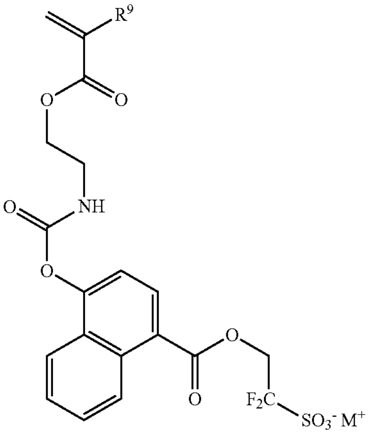
-continued
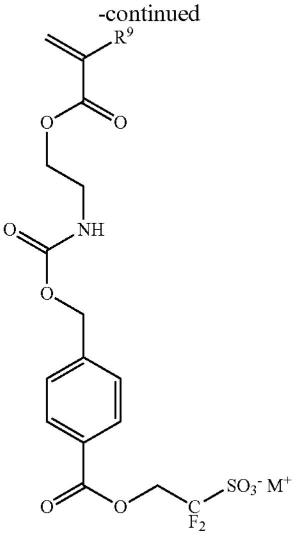
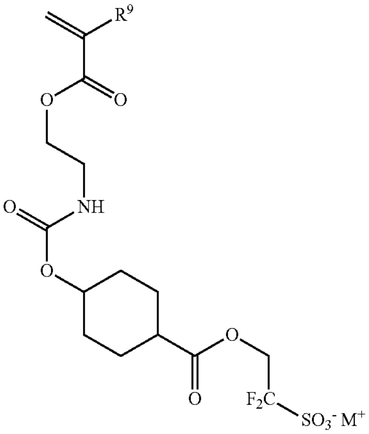
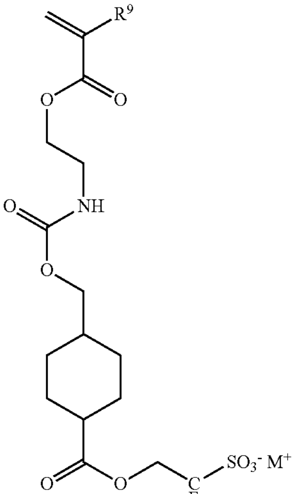

-continued
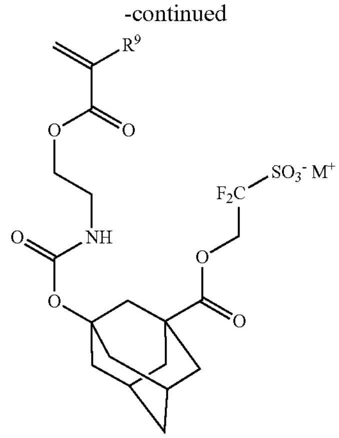
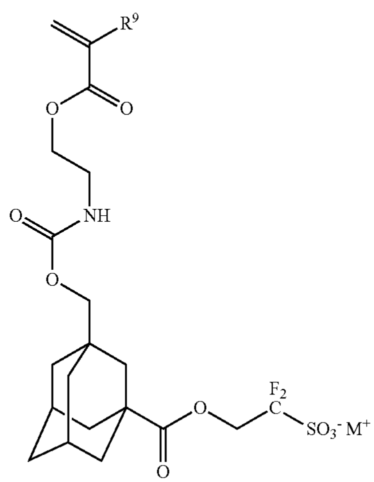
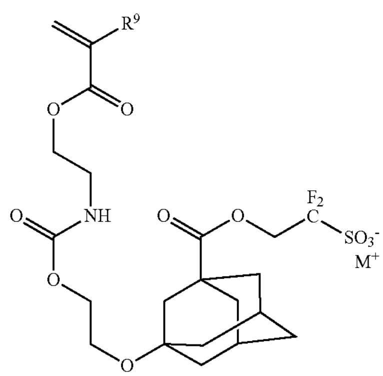
-continued
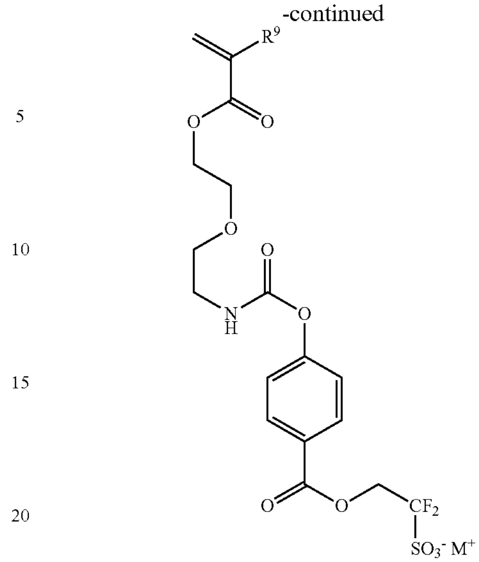
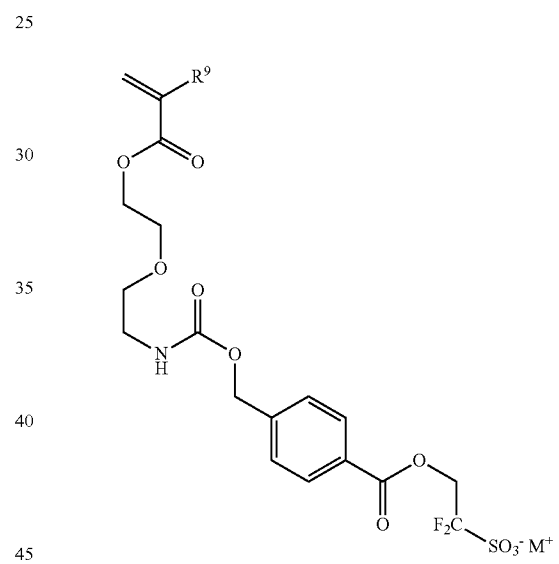
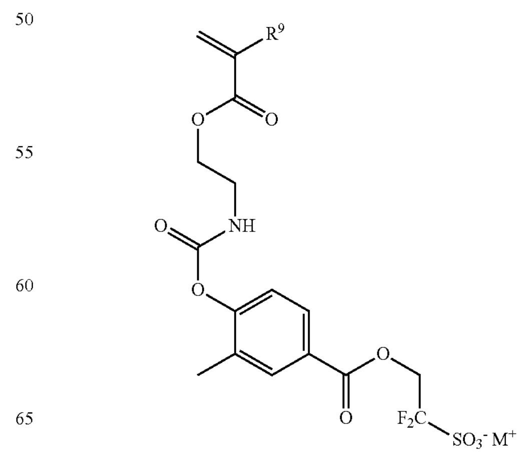

-continued
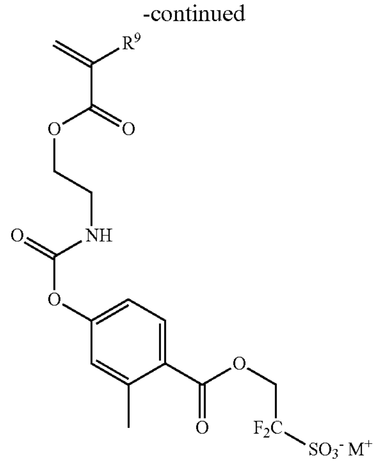
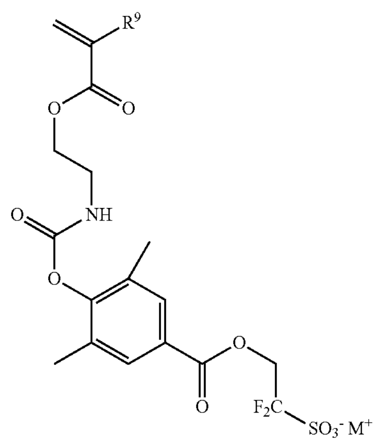
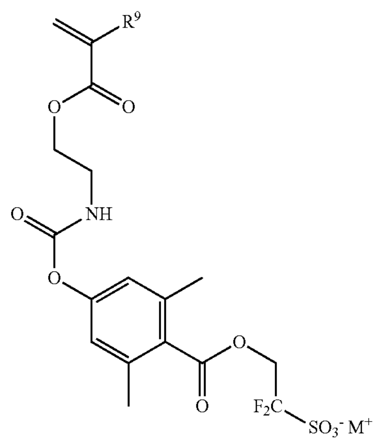
-continued
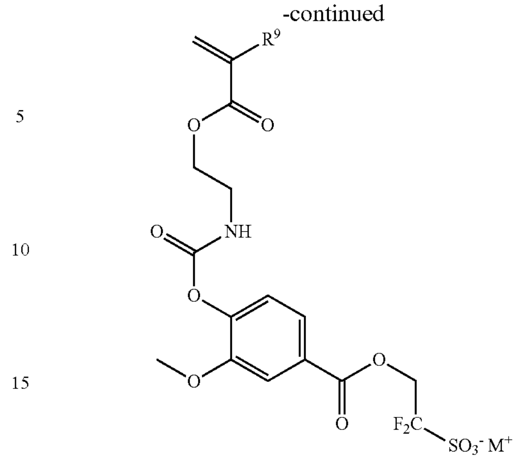
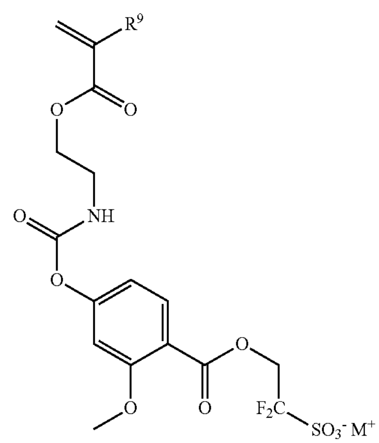
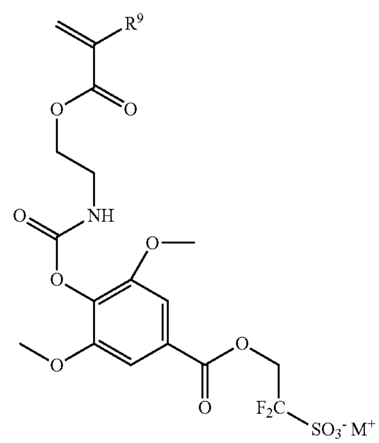

-continued
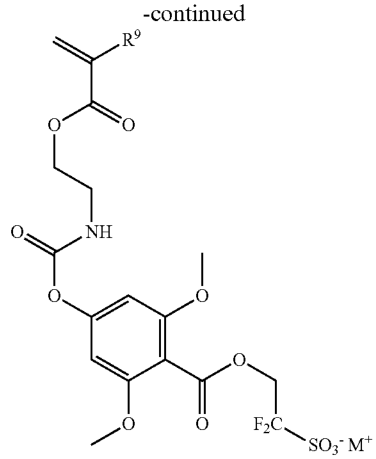
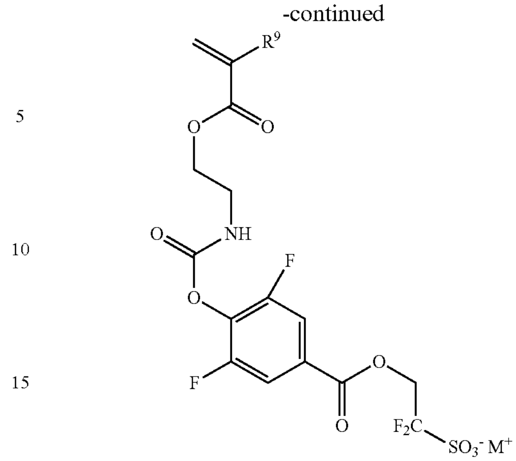
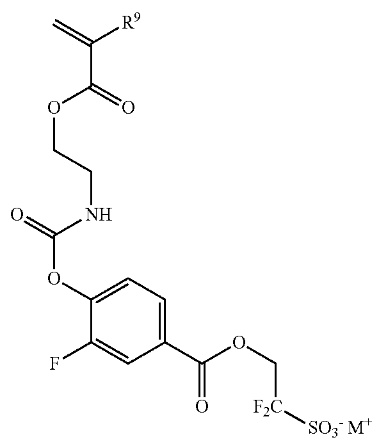
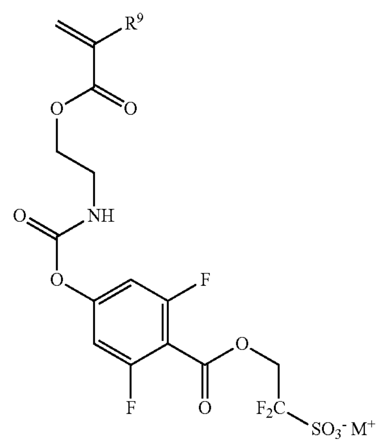
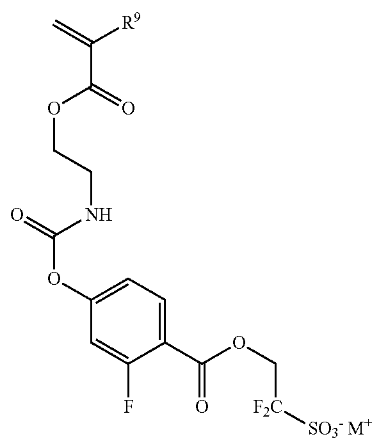
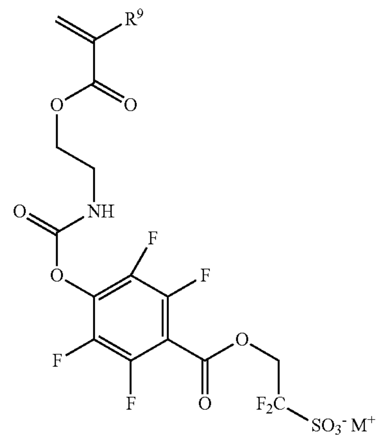
-continued -continued
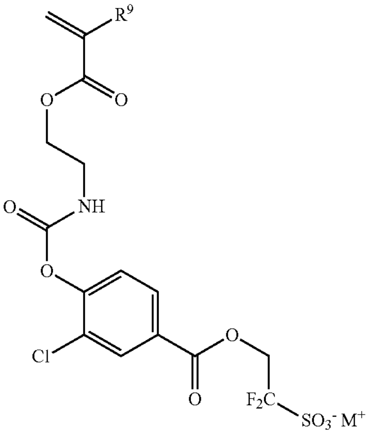
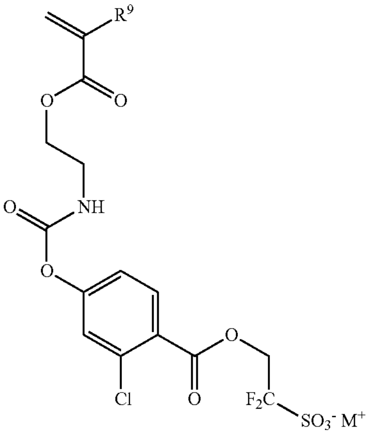
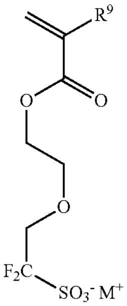
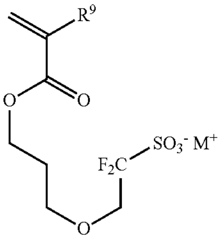
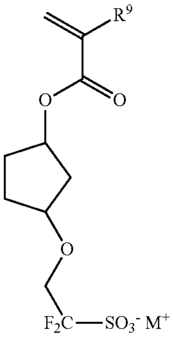
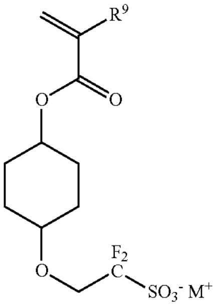
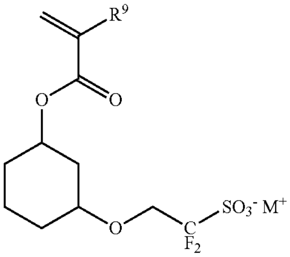
-continued
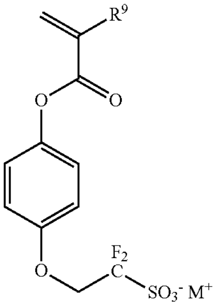
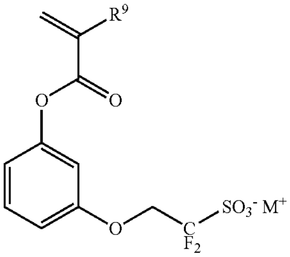
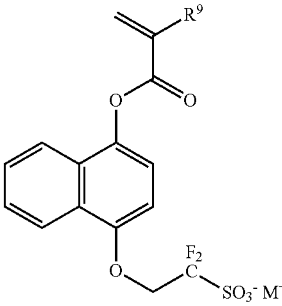
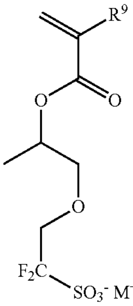
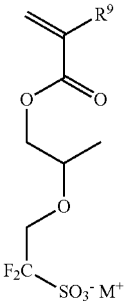
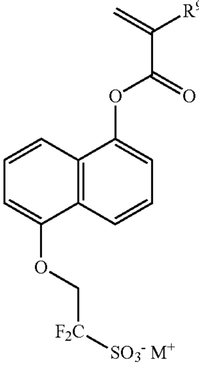
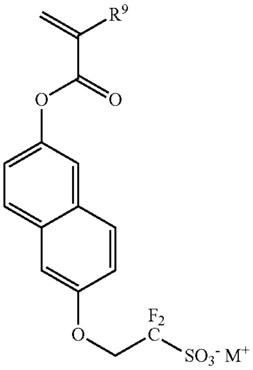
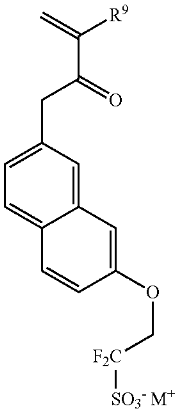
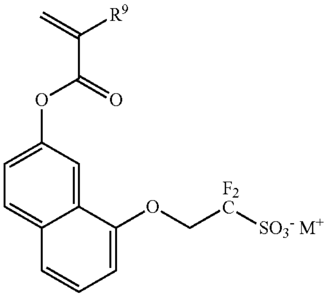

-continued
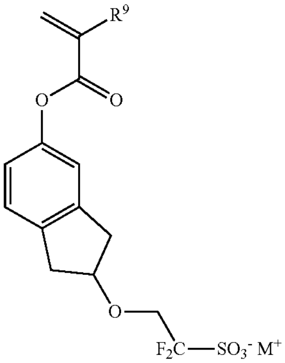
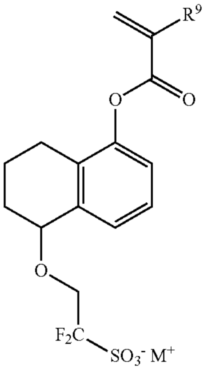
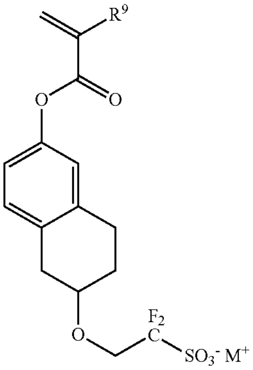
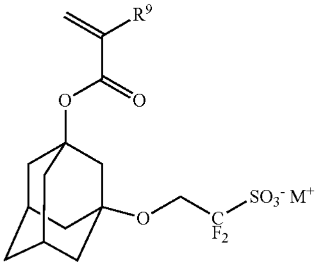
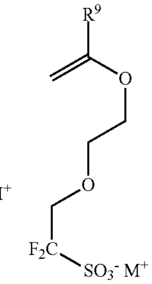
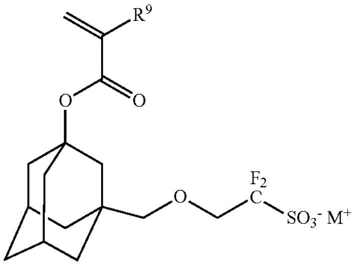
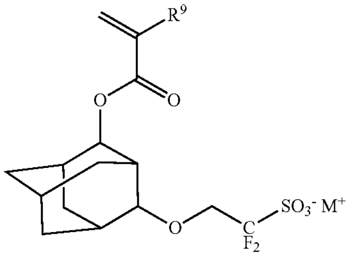
-continued
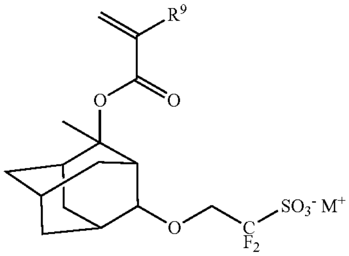
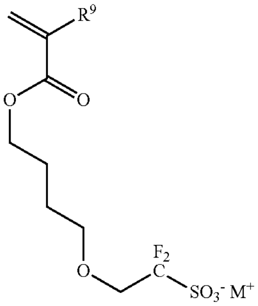
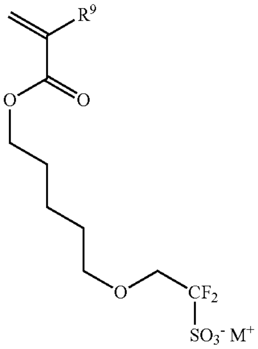
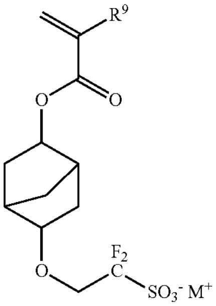
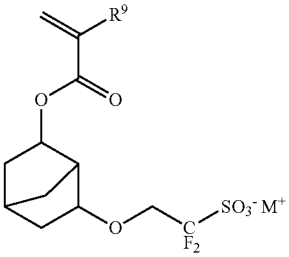
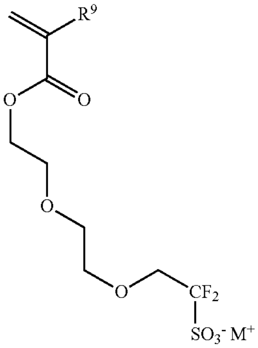
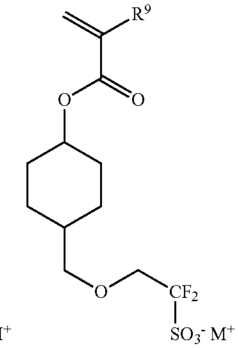
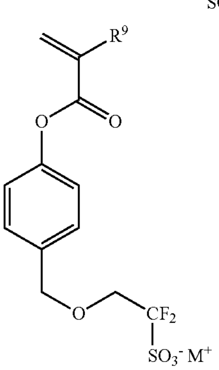
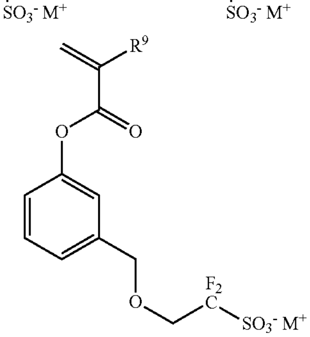

-continued
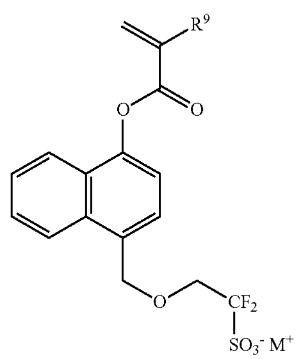
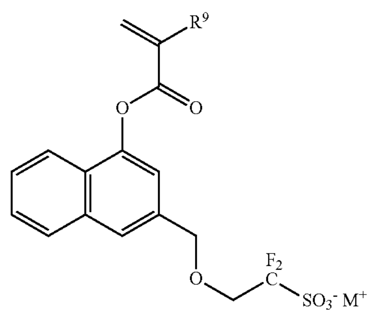
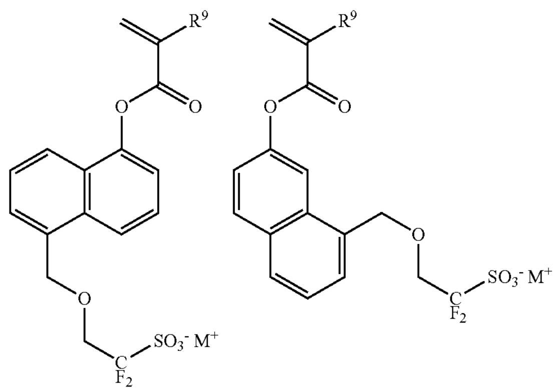
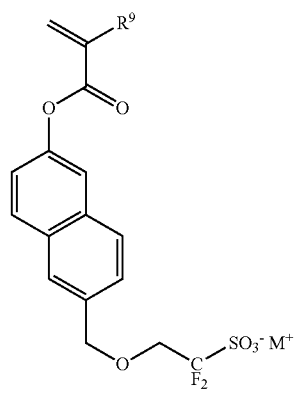
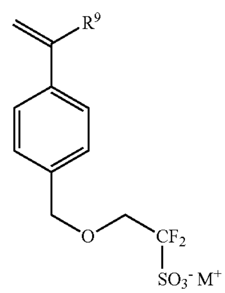
-continued
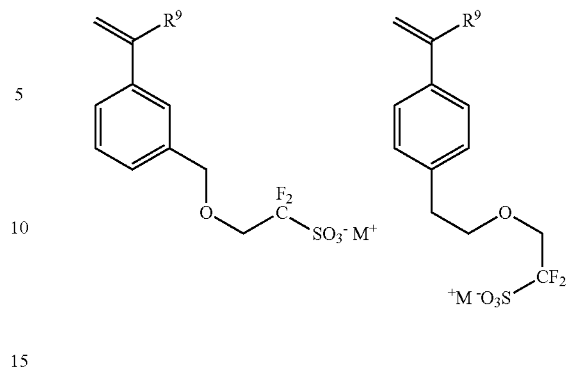
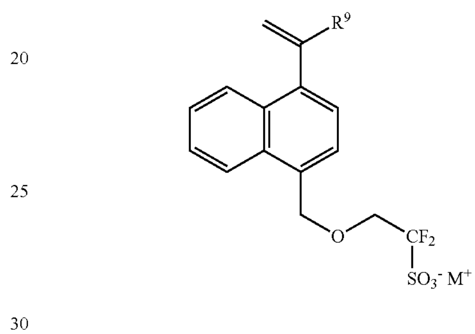
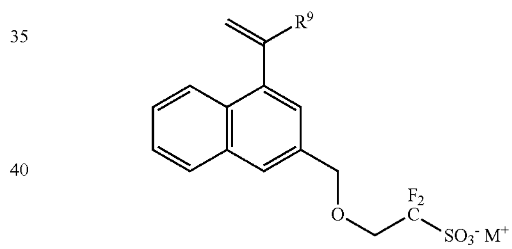
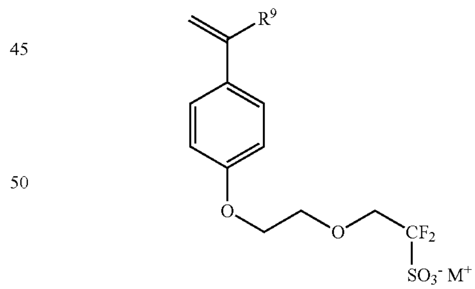
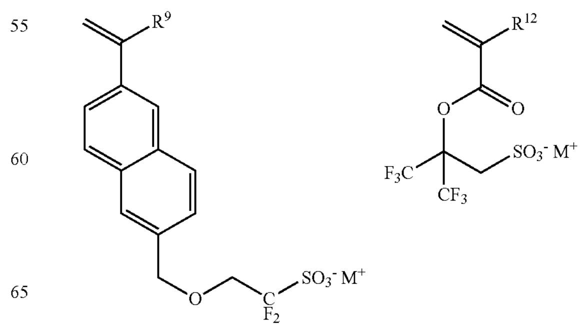

-continued
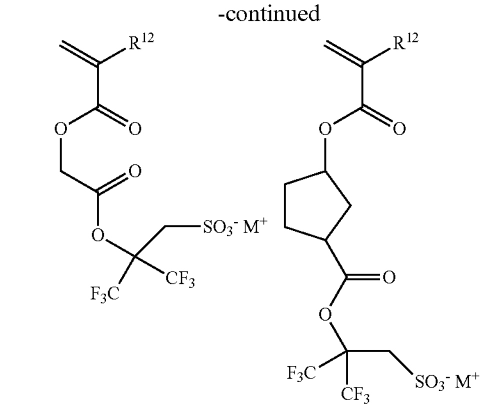
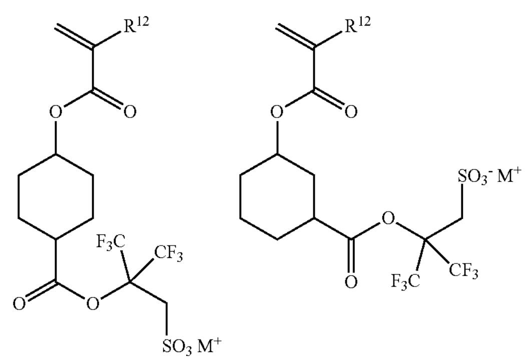
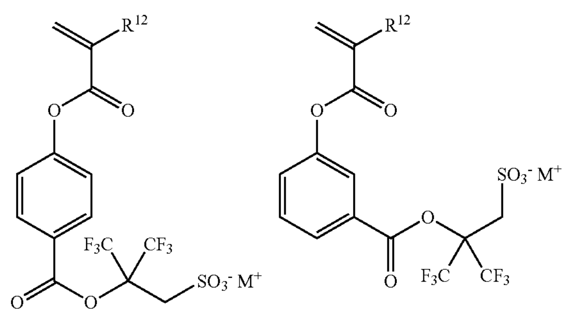
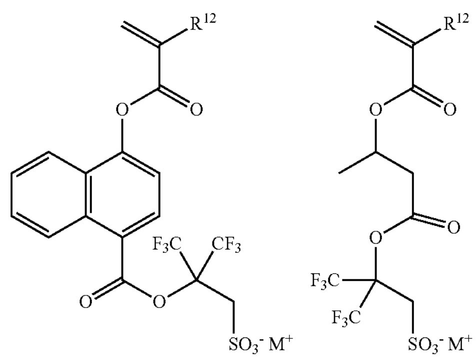
-continued
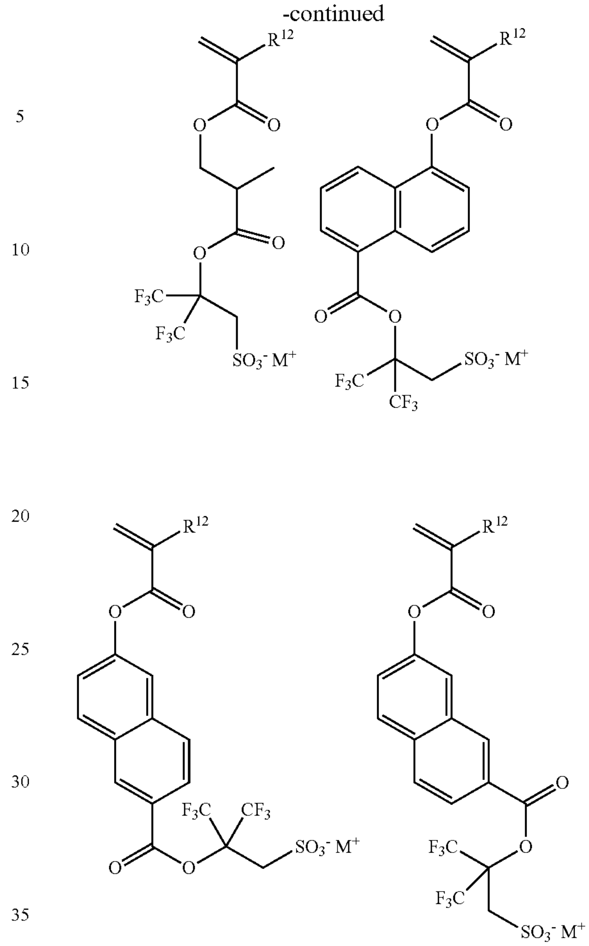
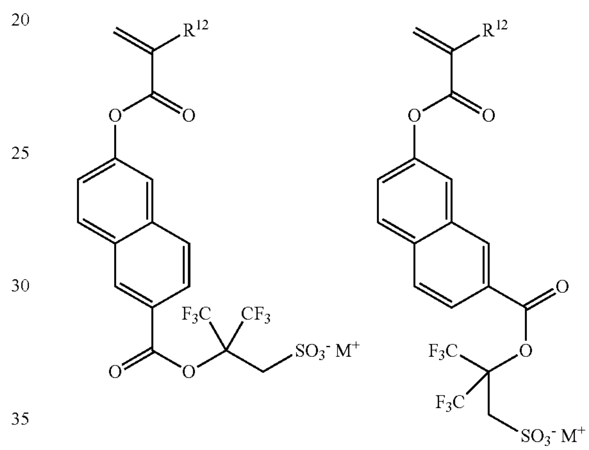
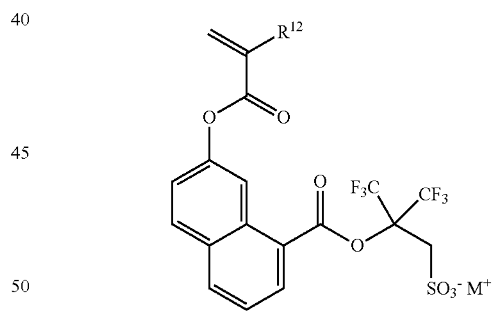
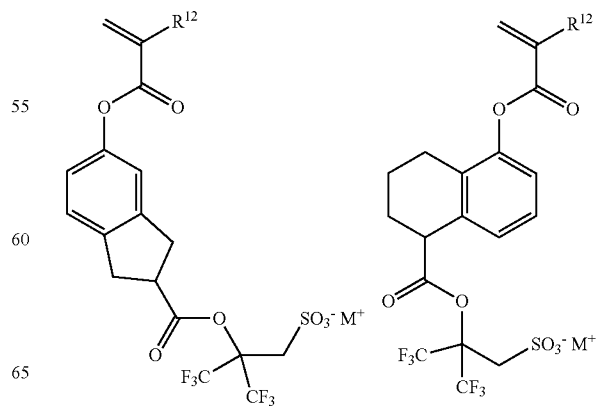

-continued
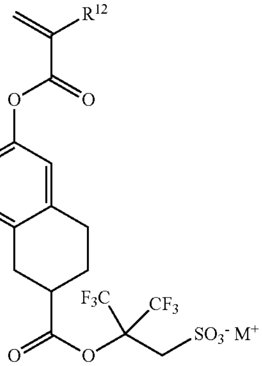
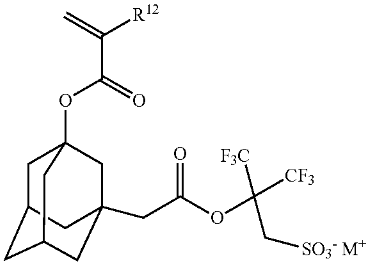
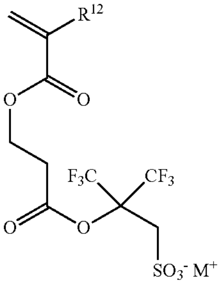
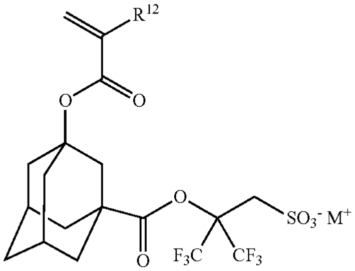
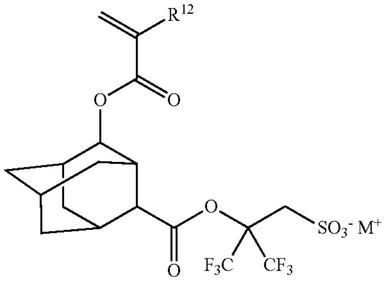
-continued
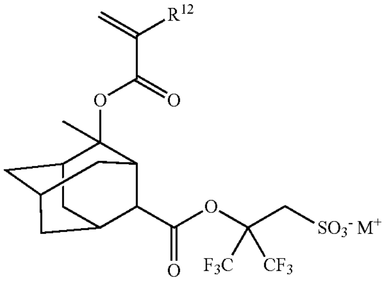
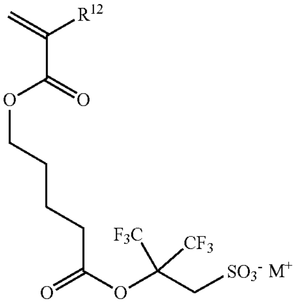
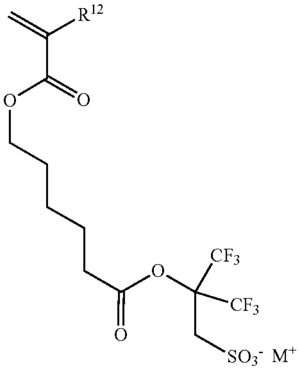
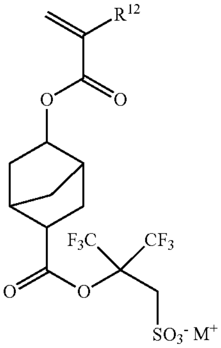
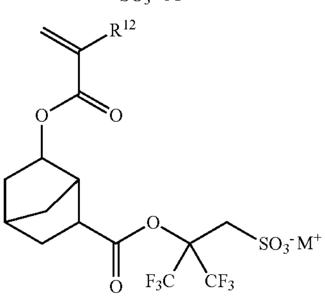
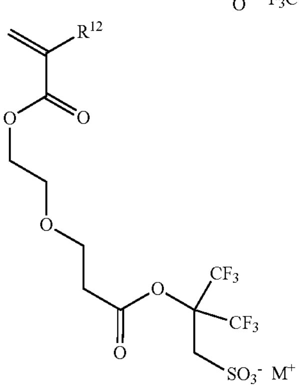
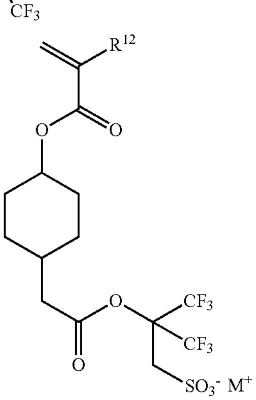

-continued
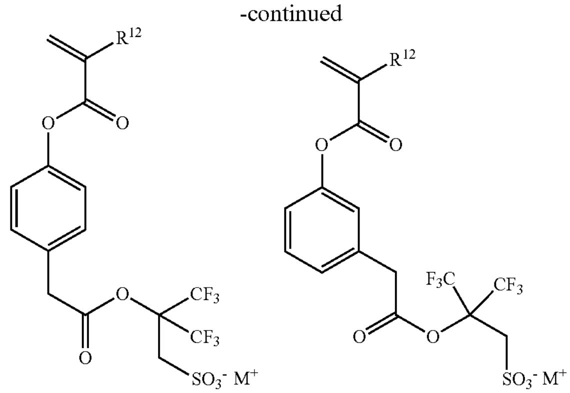
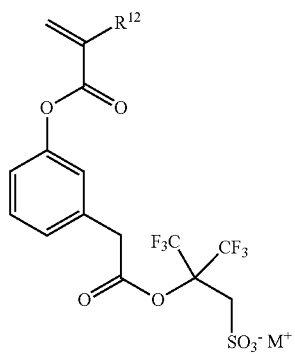
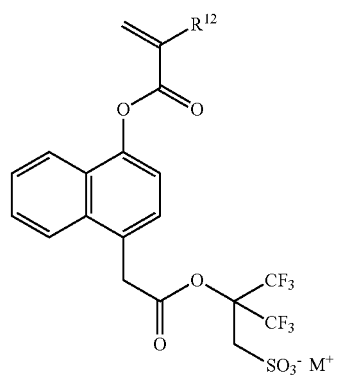
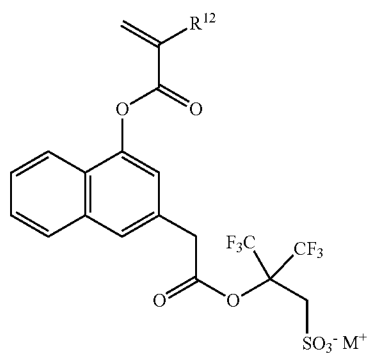
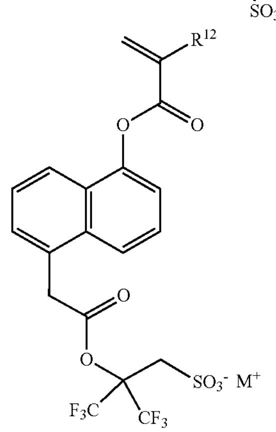
-continued
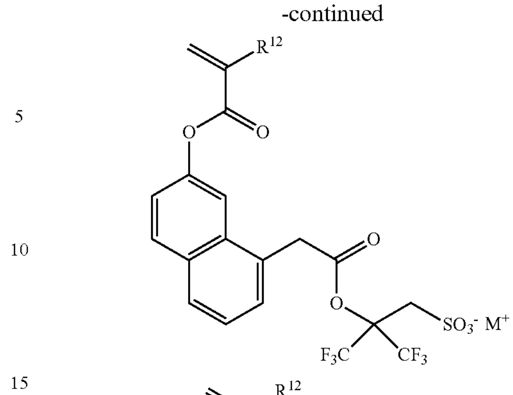
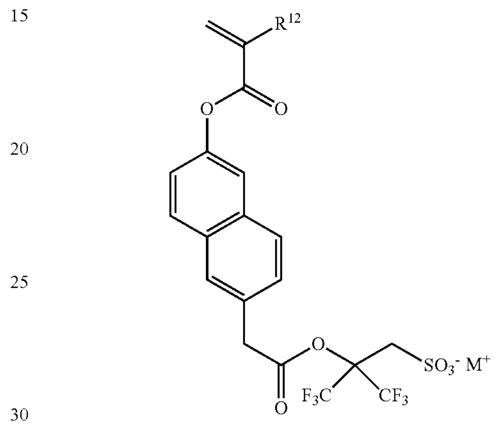
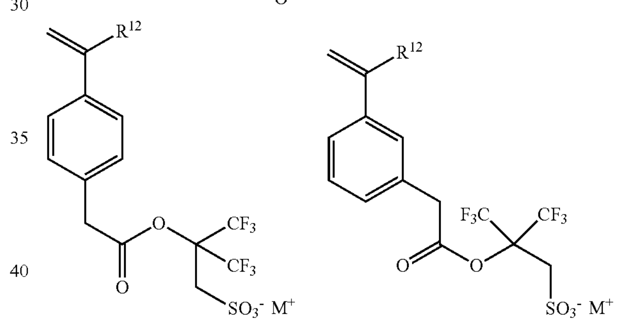
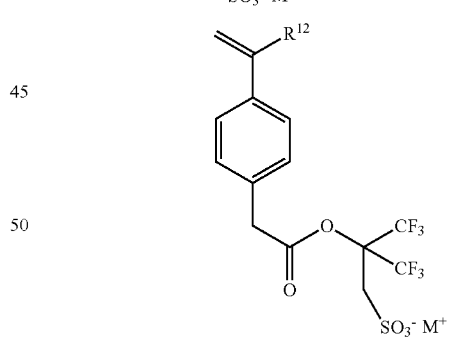
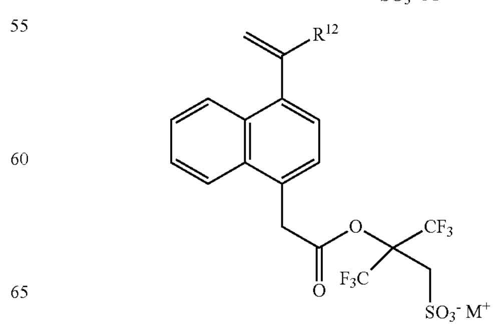

-continued
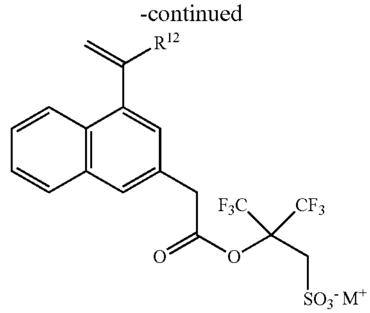
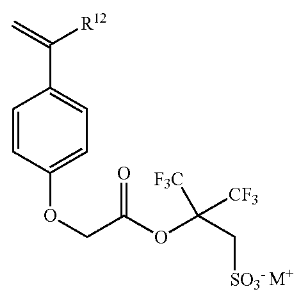
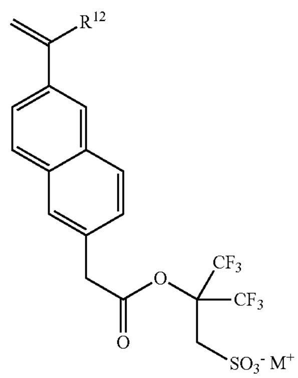
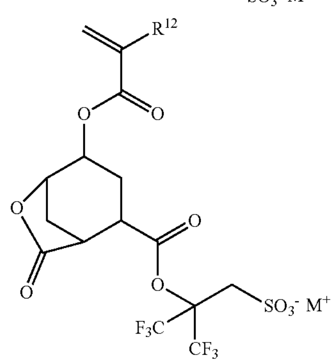
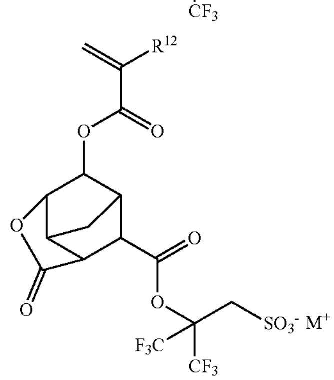
-continued
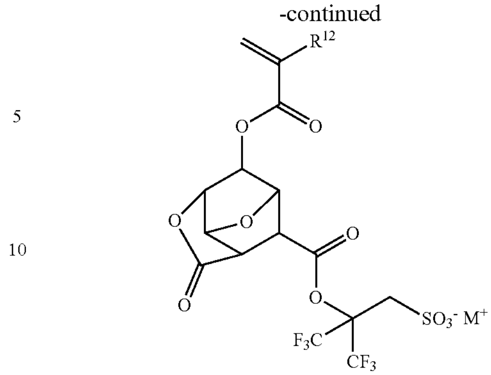
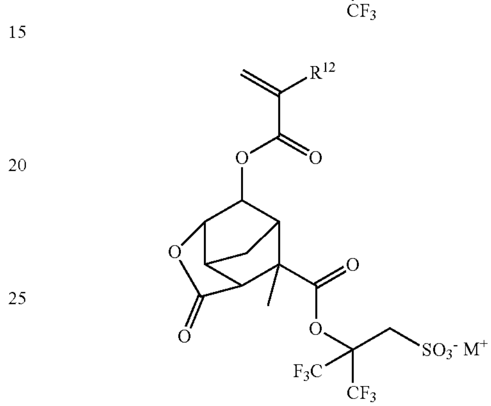
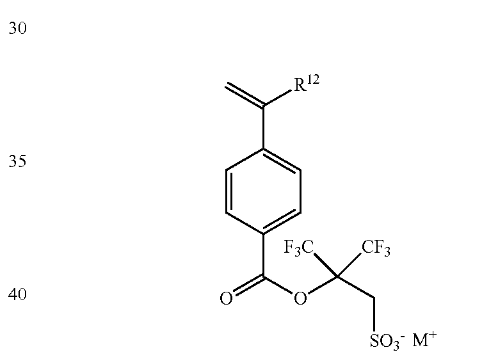
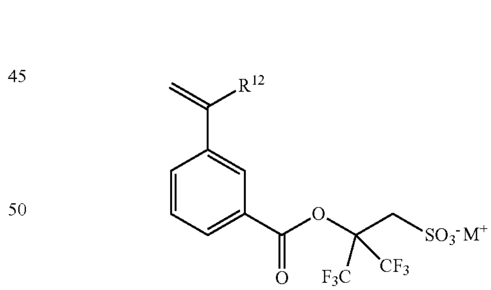
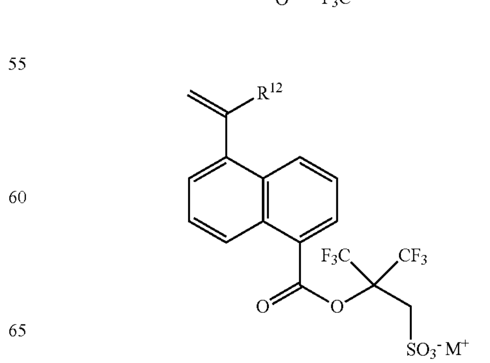

-continued
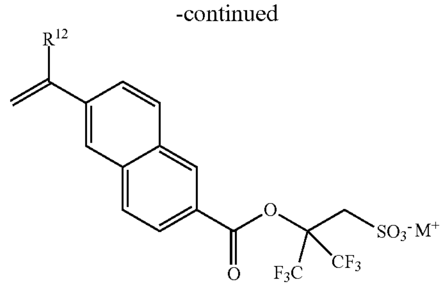
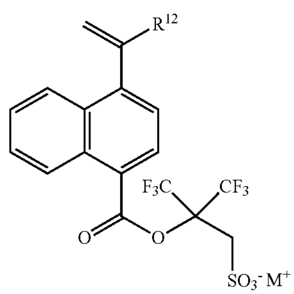
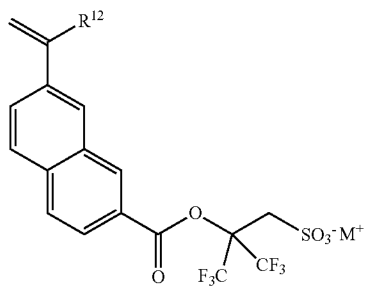
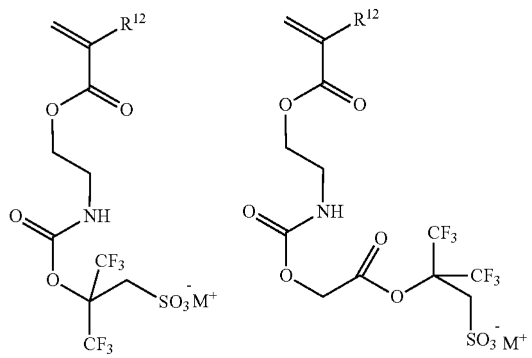
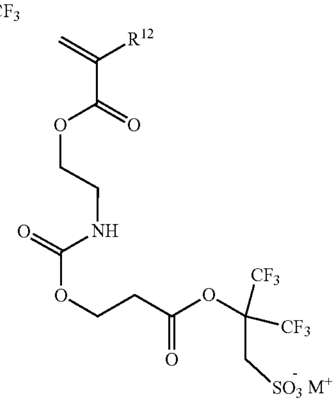
-continued
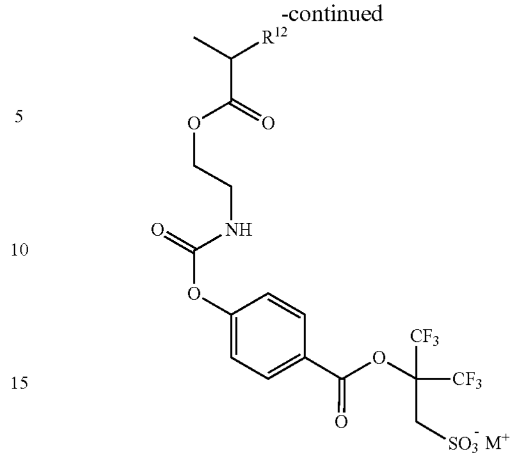
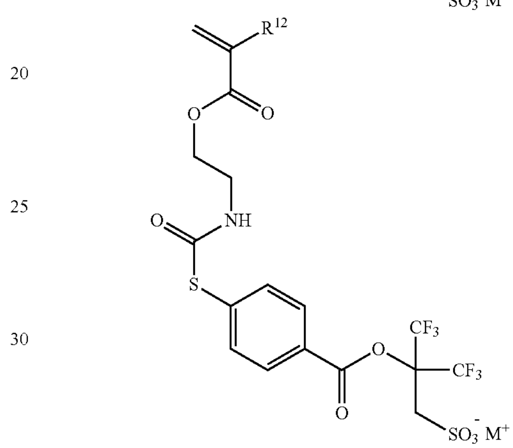
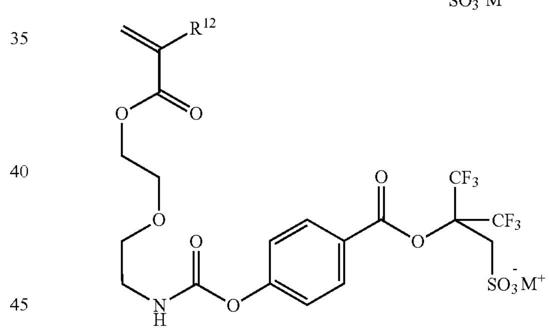
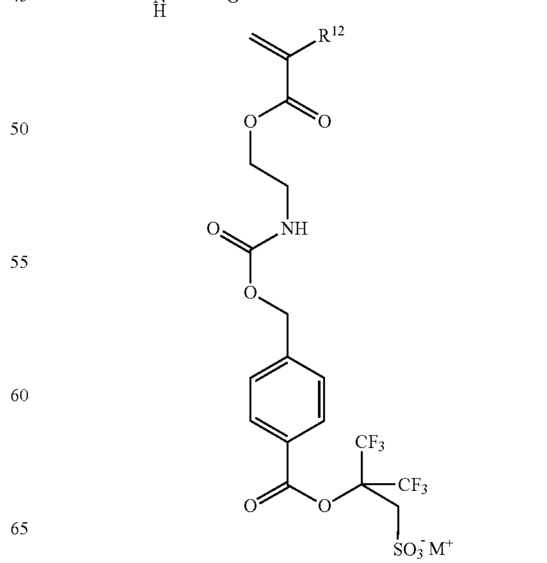

-continued
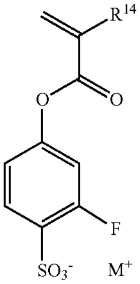
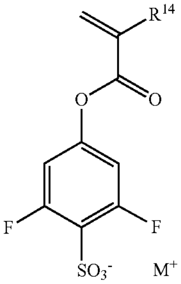
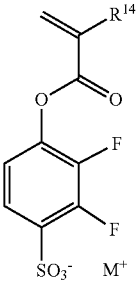
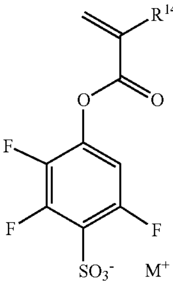
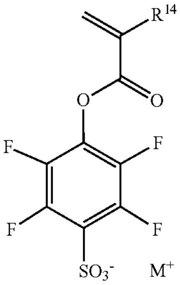
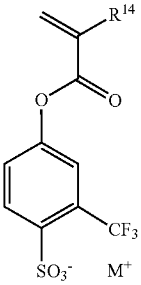
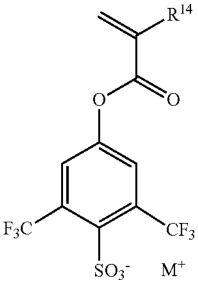
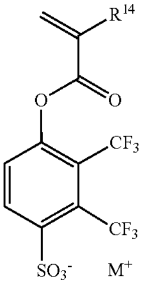
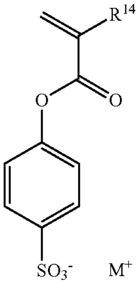
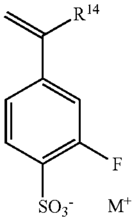
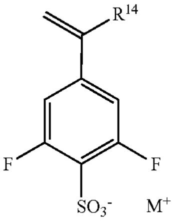
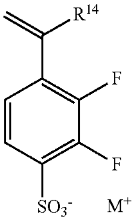
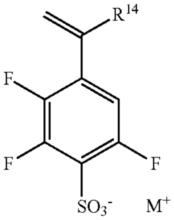
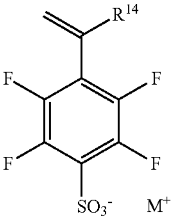
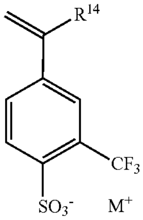
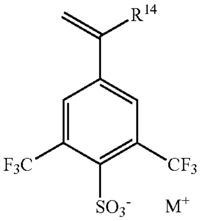
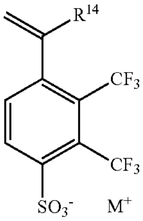
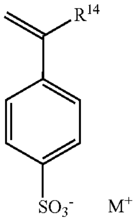
-continued
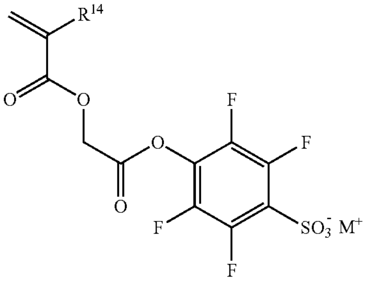
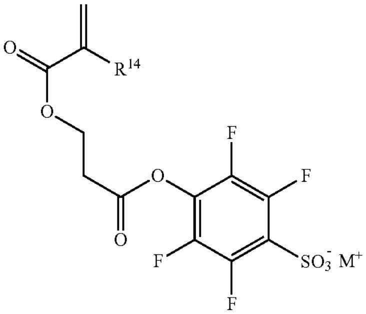
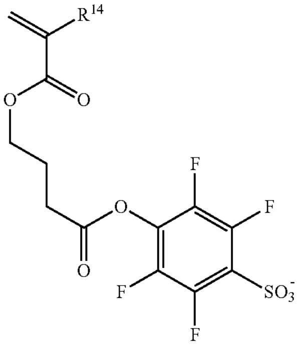
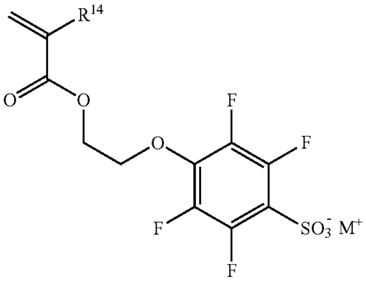
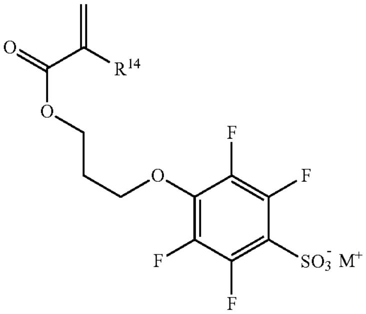

-continued
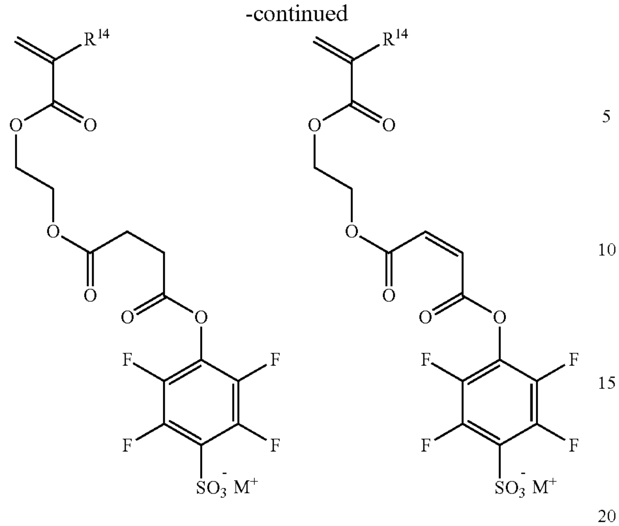
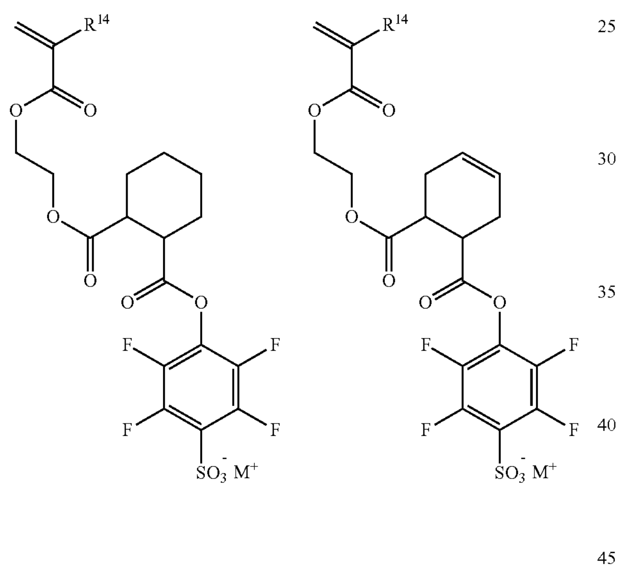
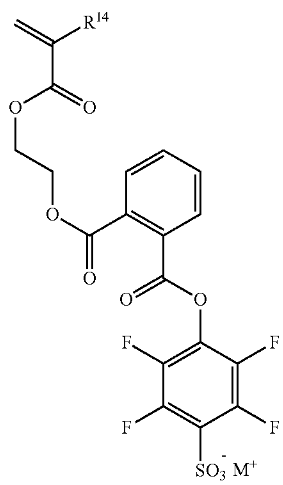
-continued
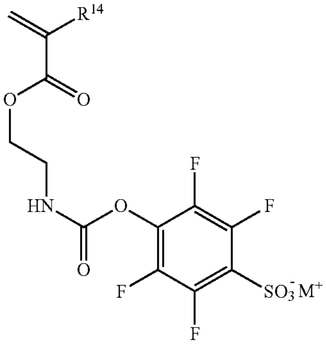
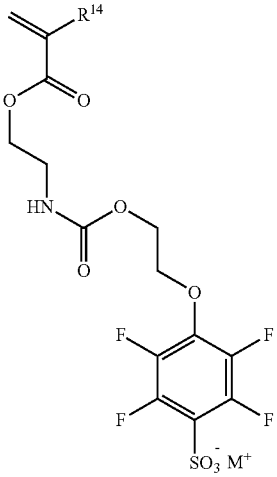
Specific examples of fluorosulfonimide monomers and fluorosulfonimide salt monomers for obtaining the repeating unit A2-6 include the following.
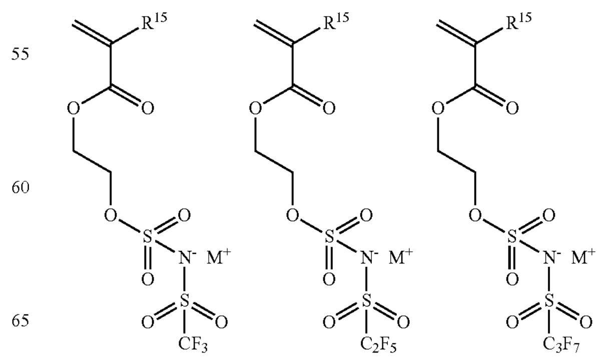

-continued
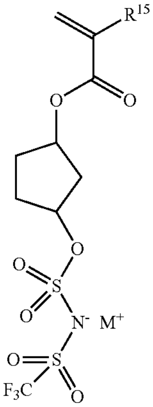
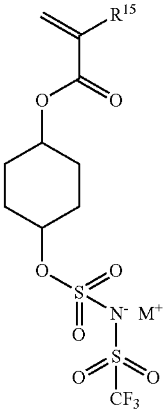
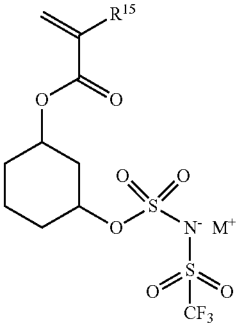
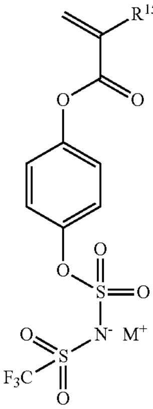
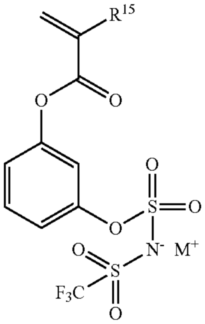
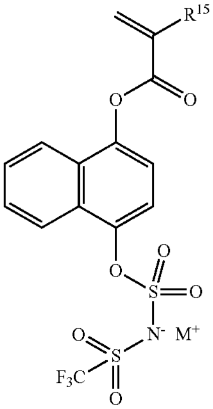
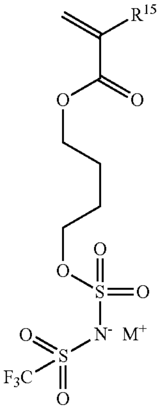
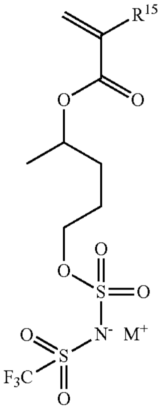
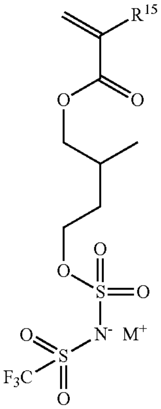
-continued
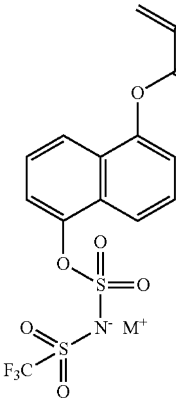
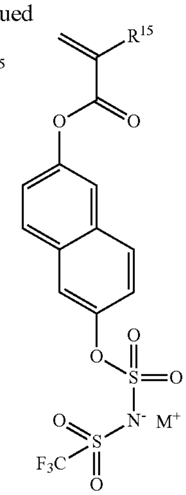
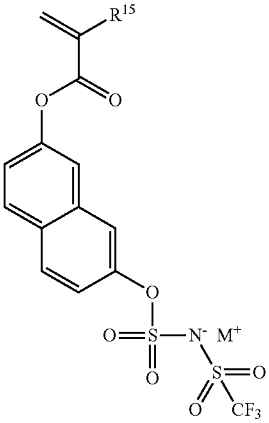
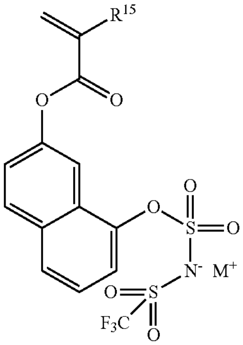
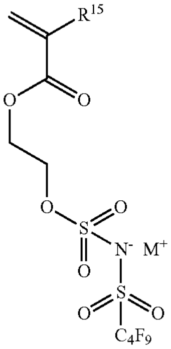
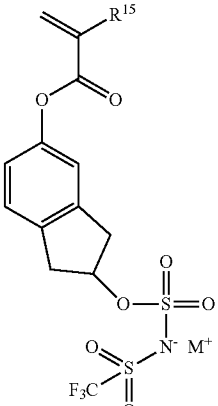

-continued
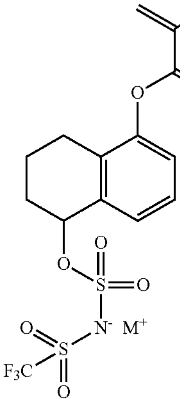
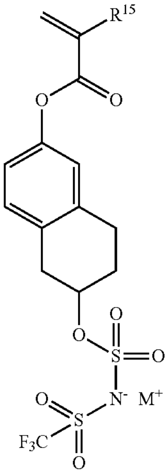
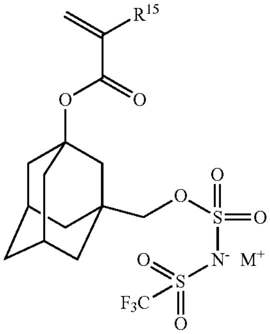
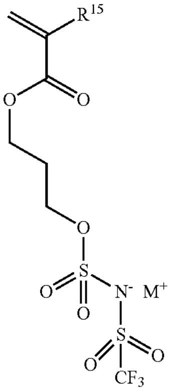
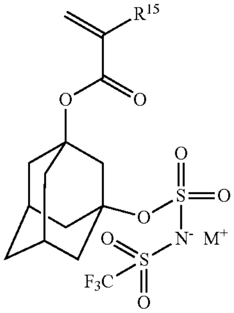
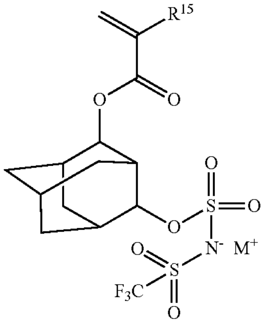
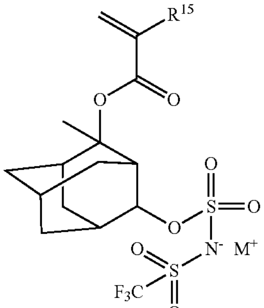
-continued
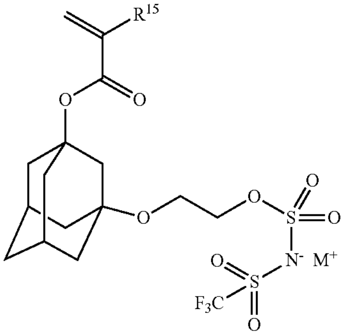
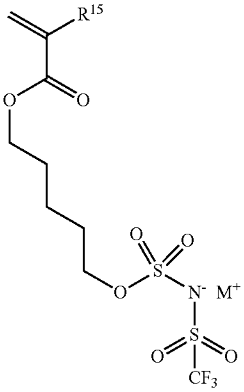
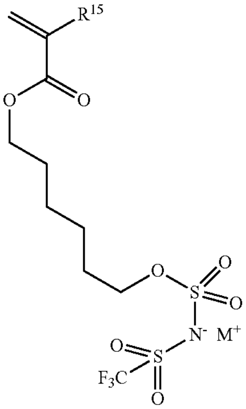
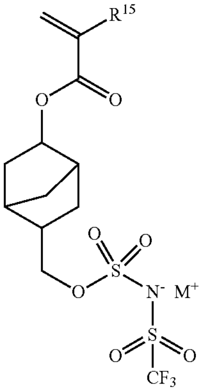
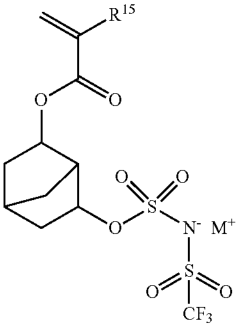
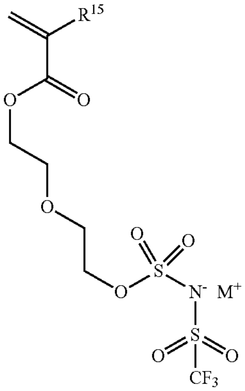
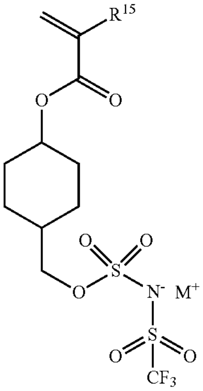

-continued
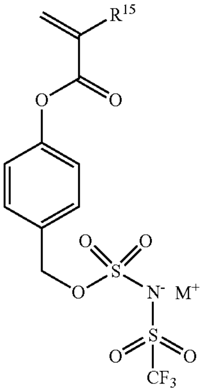
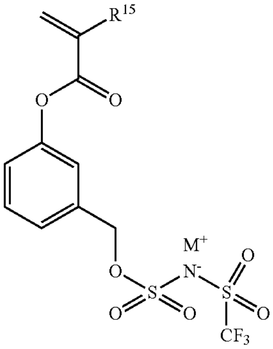
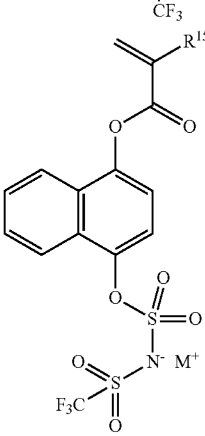
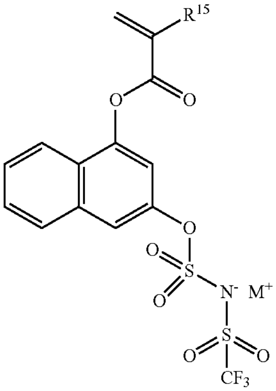
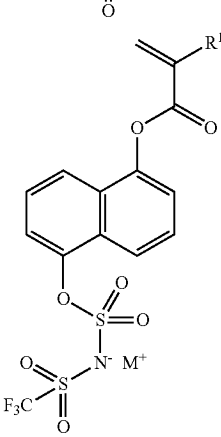
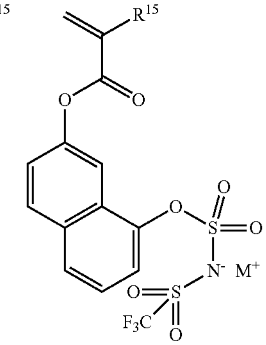
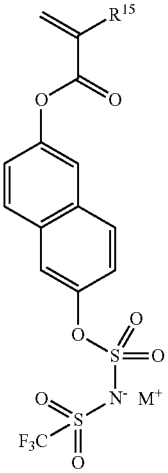
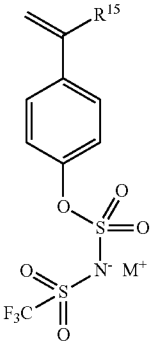
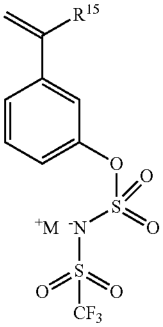
-continued
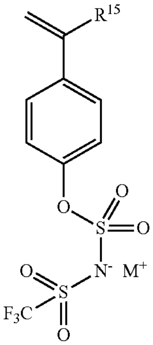
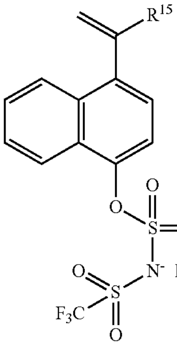
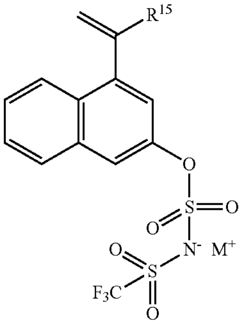
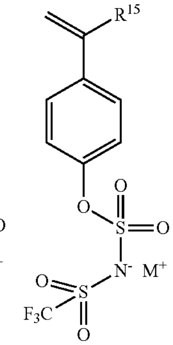
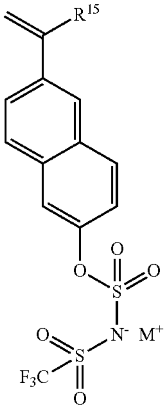
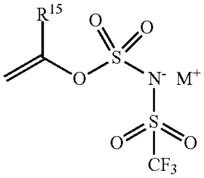
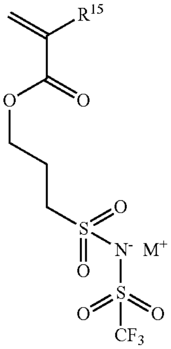
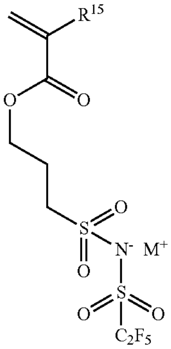
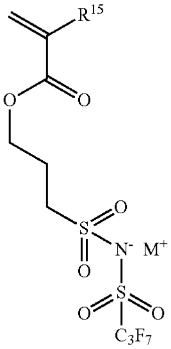
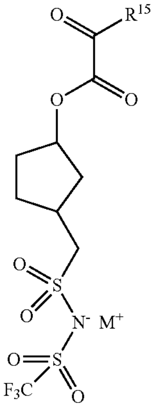

-continued
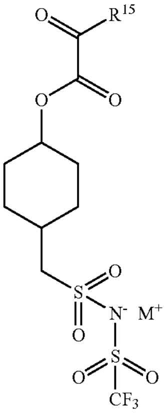
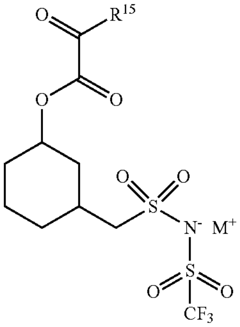
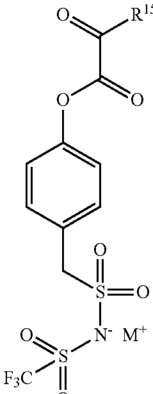
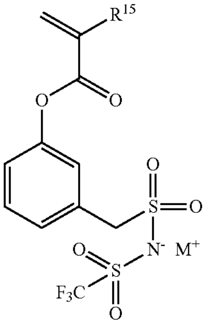
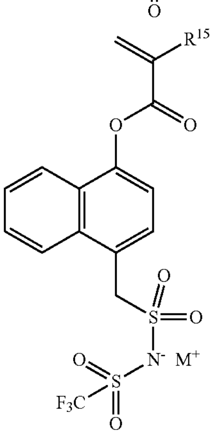
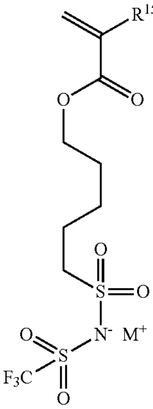
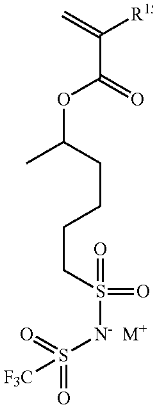
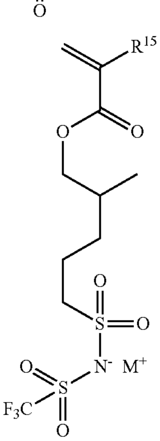
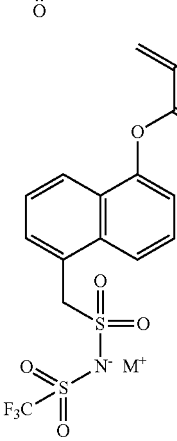
-continued
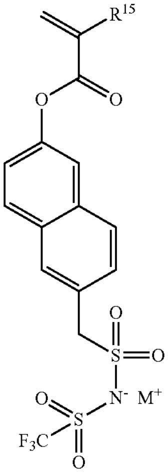
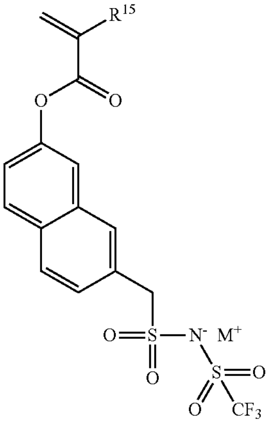
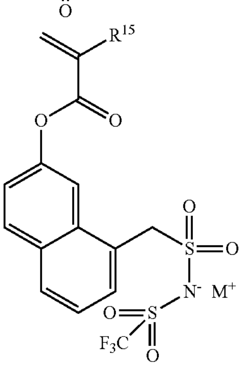
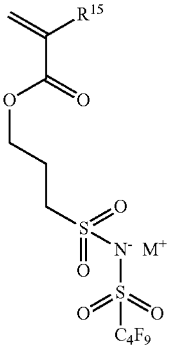
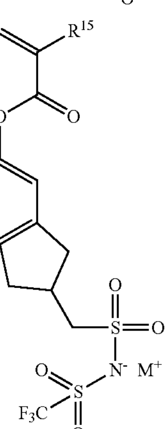
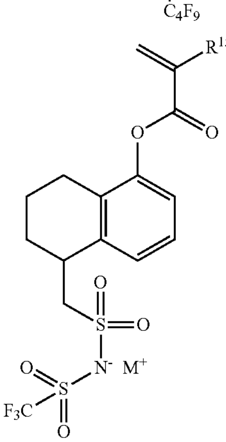
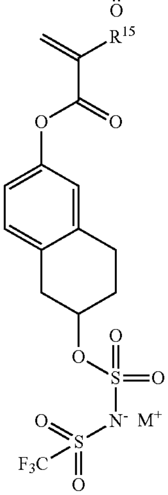
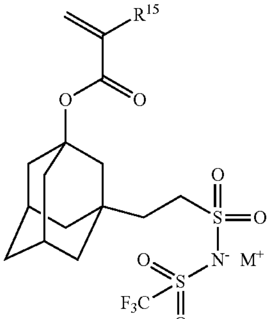

-continued
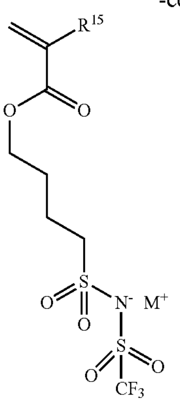
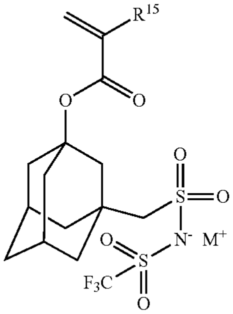
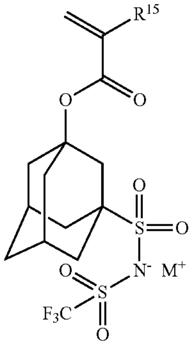
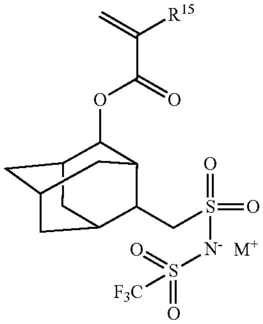
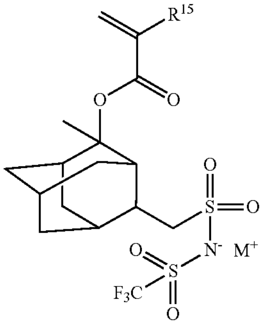
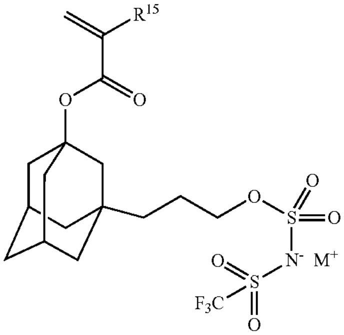
-continued
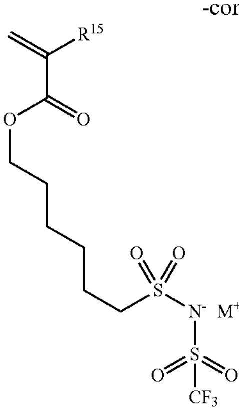
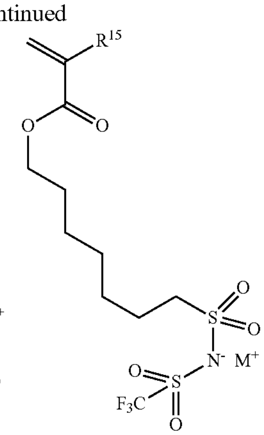
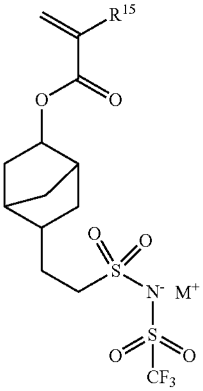
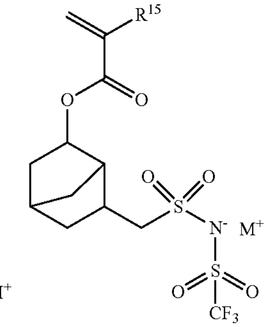
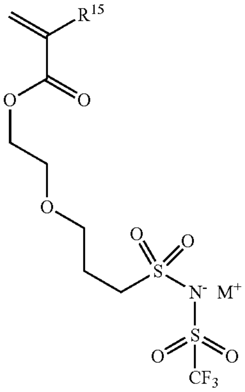
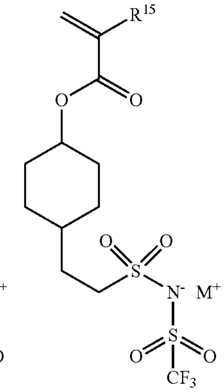
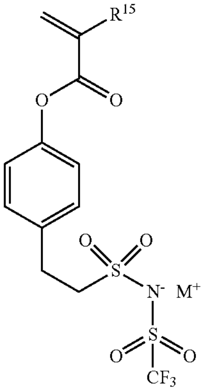
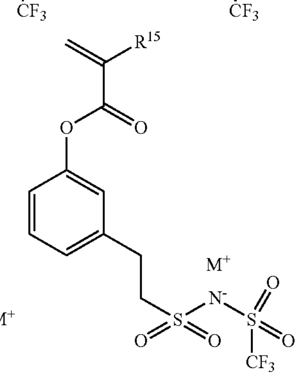

-continued
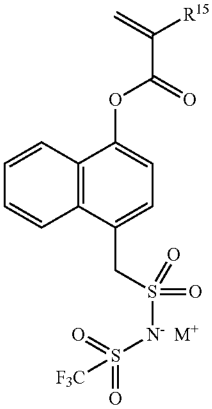
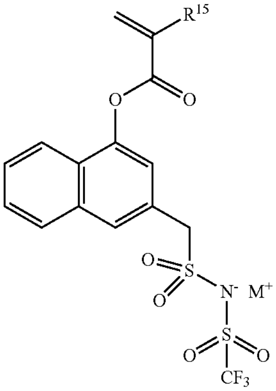
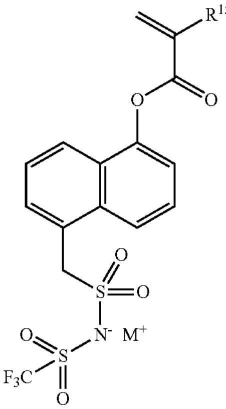
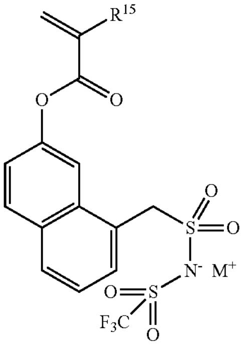
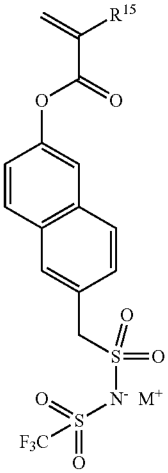
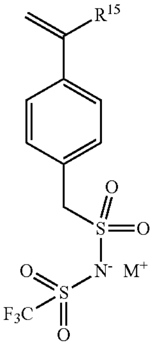
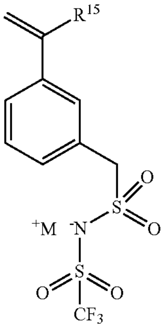
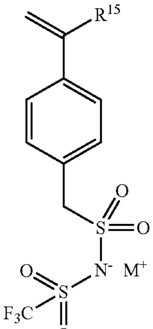
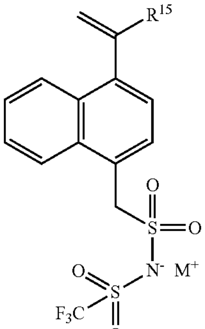
-continued
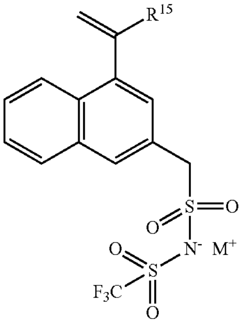
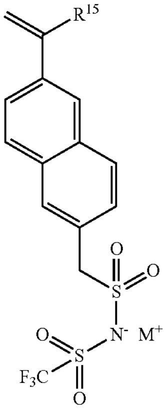
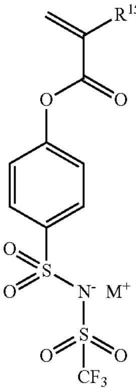
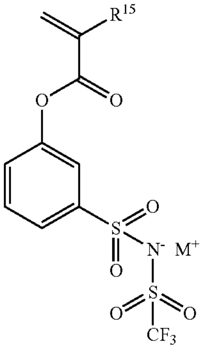
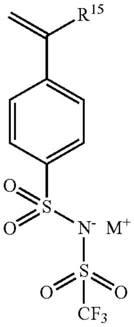
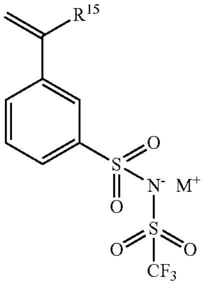
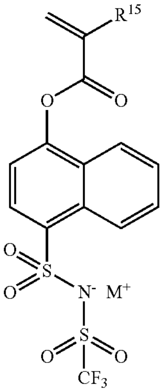
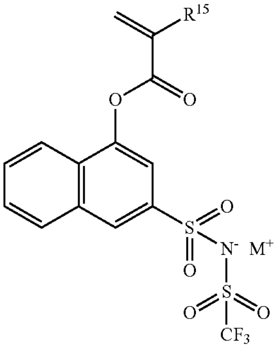
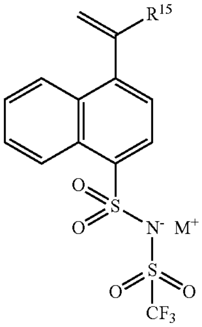
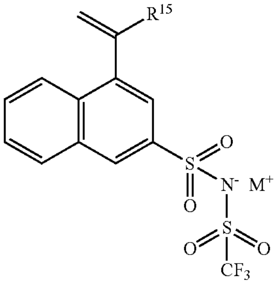

-continued
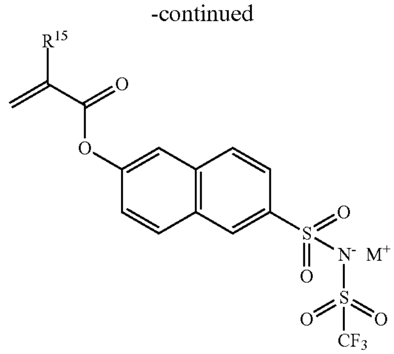
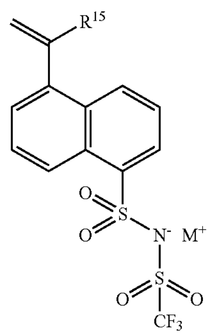
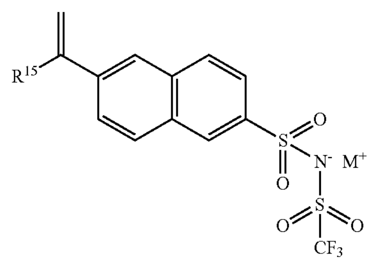
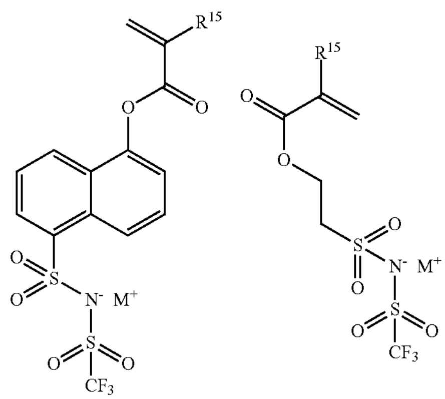
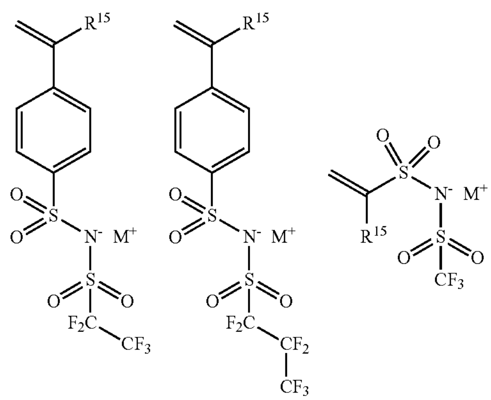
-continued
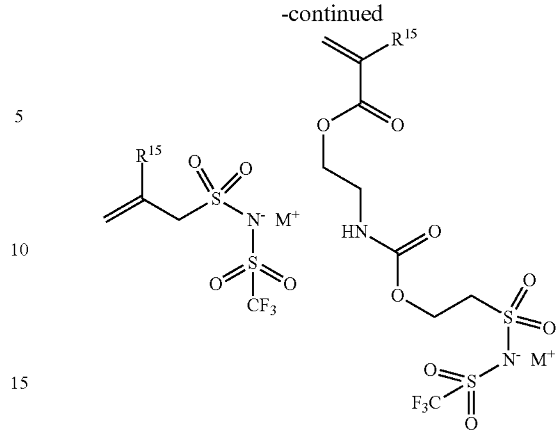
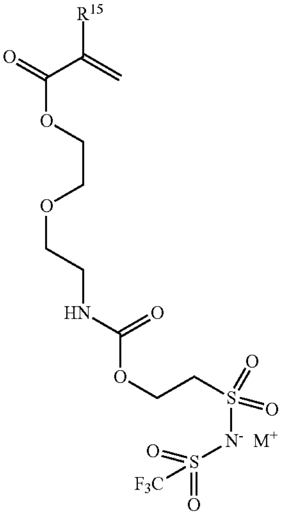
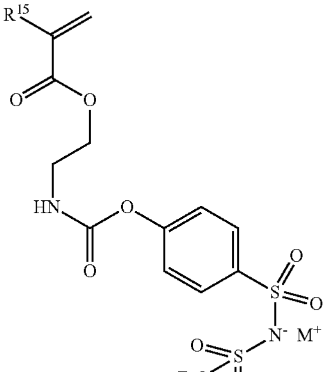

-continued
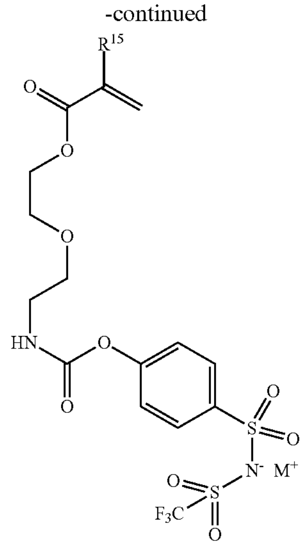
Specific examples of N-carbonyl-fluorosulfonamide monomers and N-carbonyl-fluorosulfonamide salt monomers for obtaining the repeating unit A2-7 include the following.
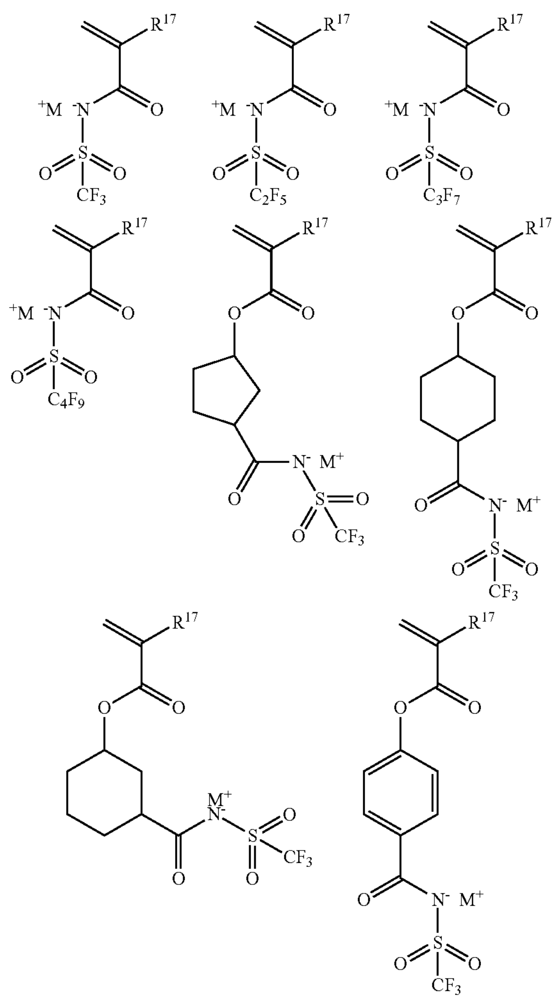
-continued
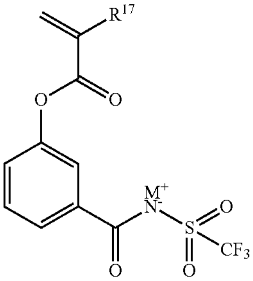
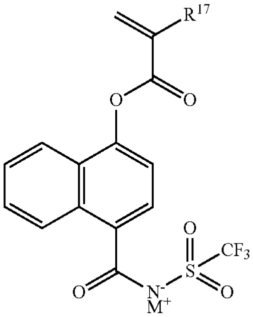
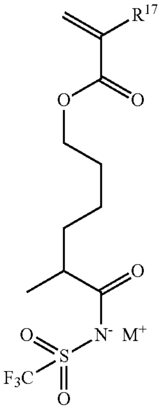
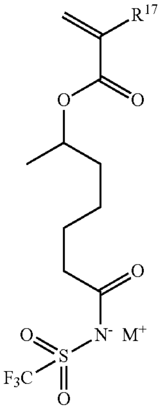
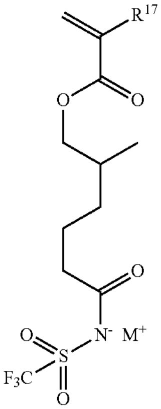
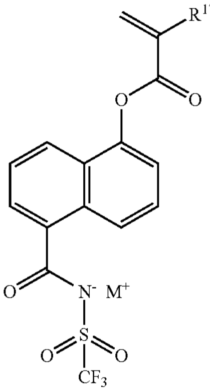
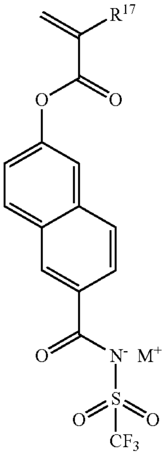
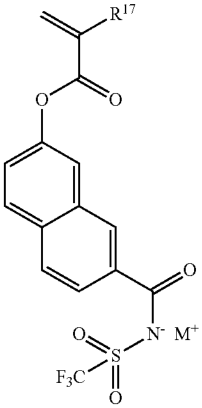
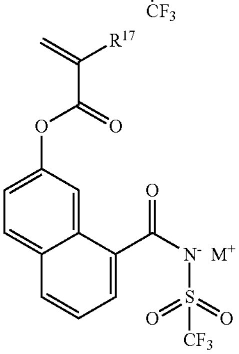

-continued
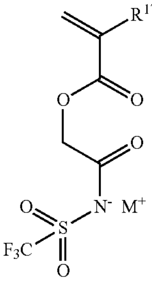
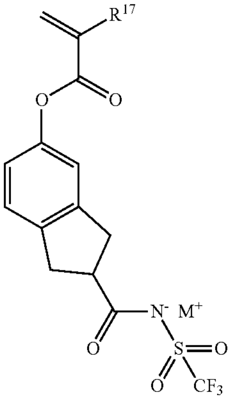
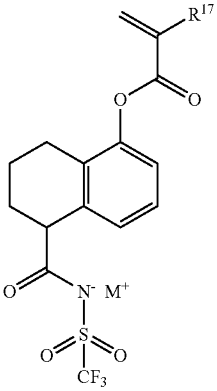
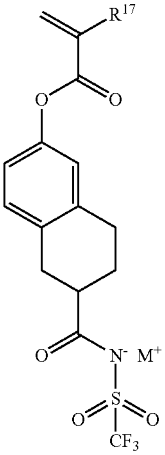
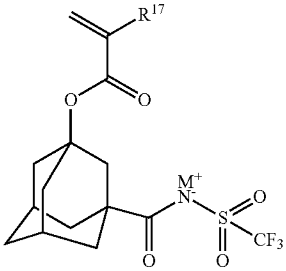
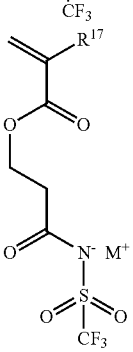
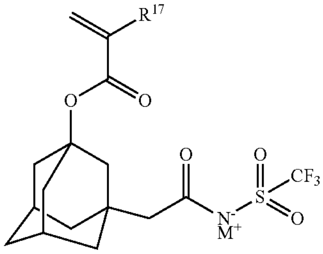
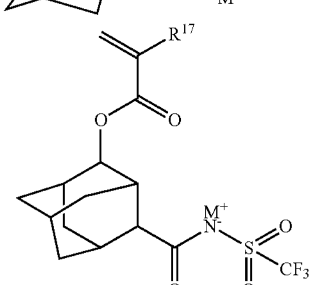
-continued
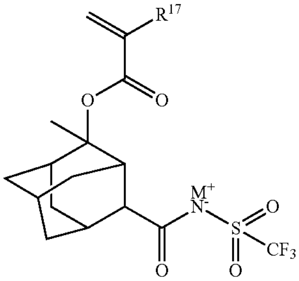
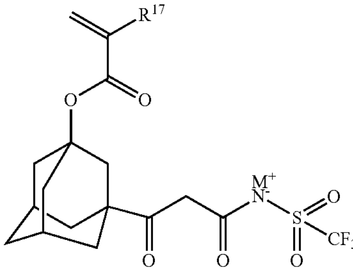
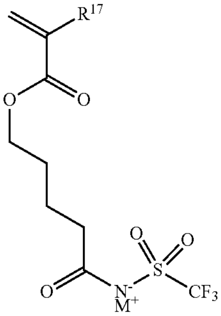
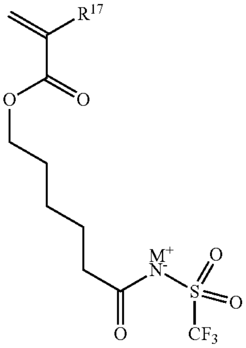
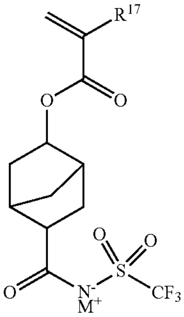
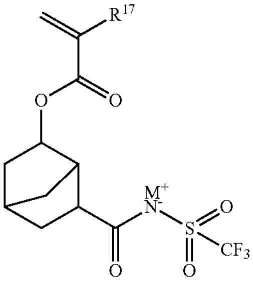
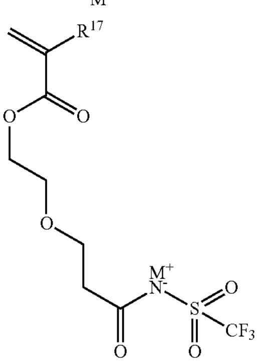
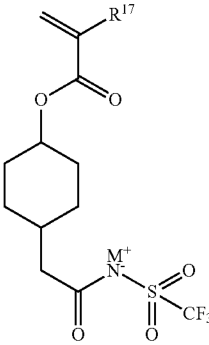

-continued
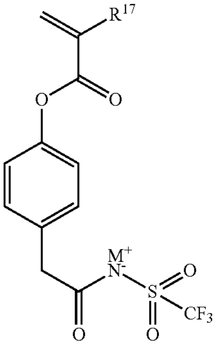
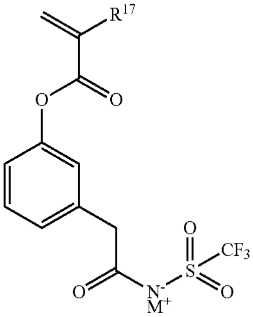
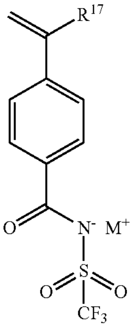
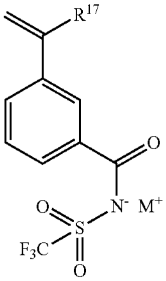
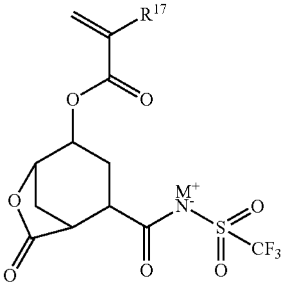
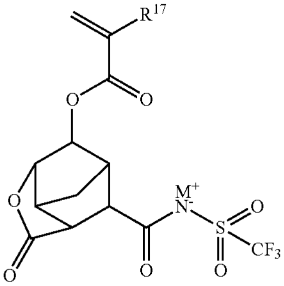
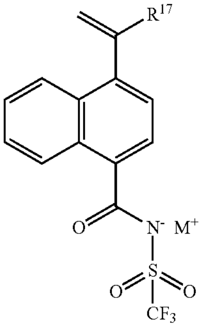
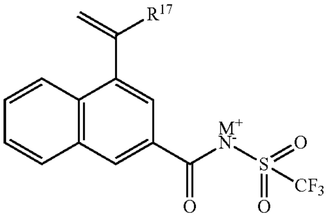
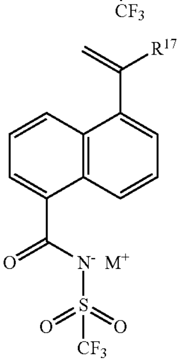
-continued
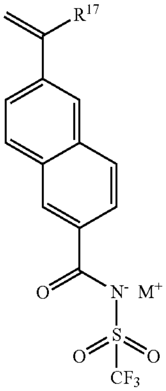
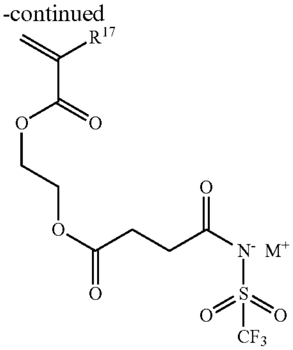
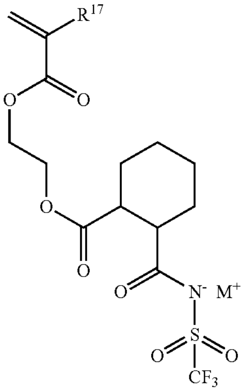
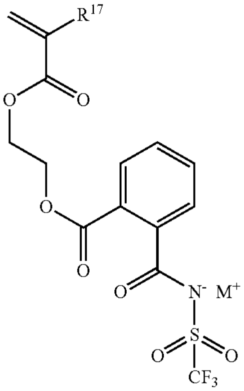
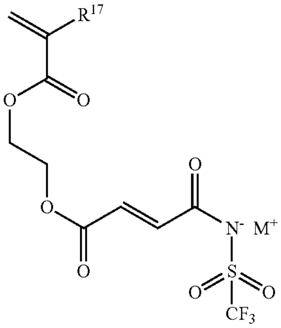
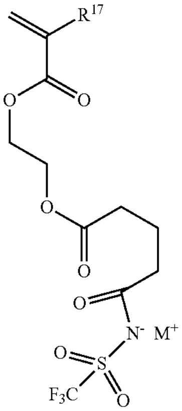
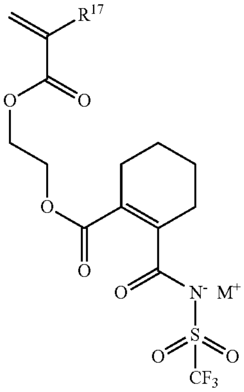
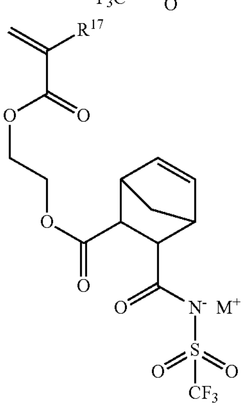

-continued
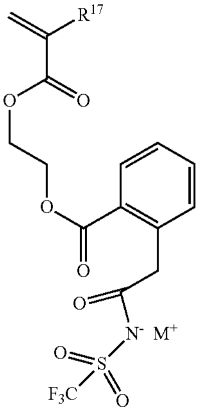
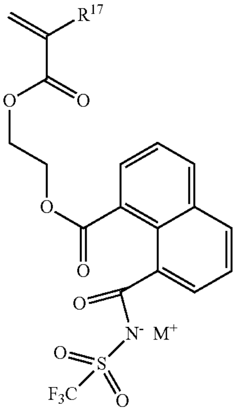
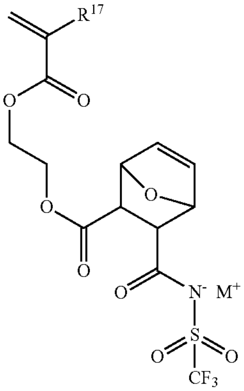
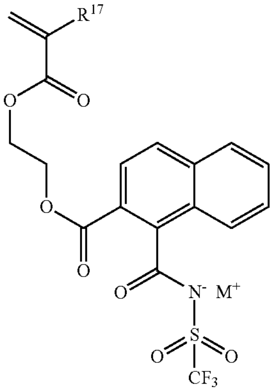
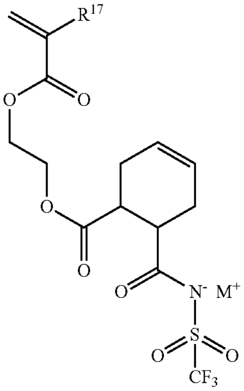
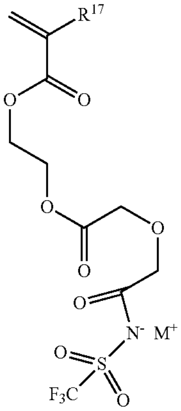
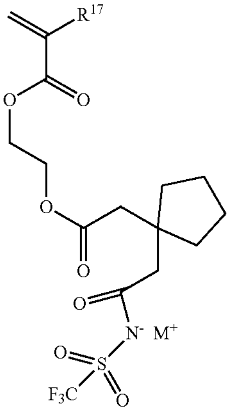
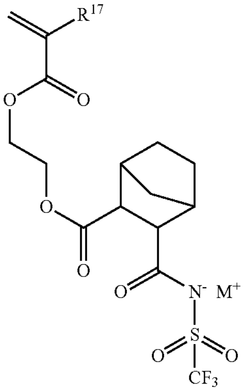
-continued
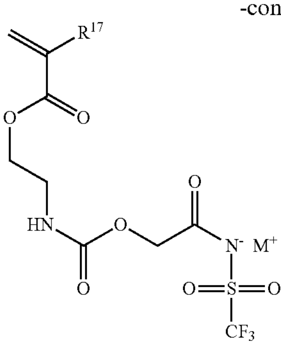
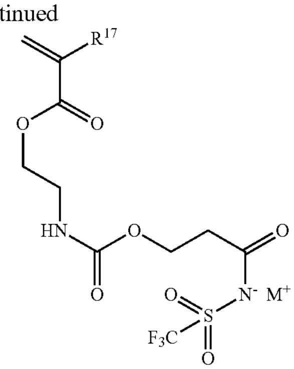
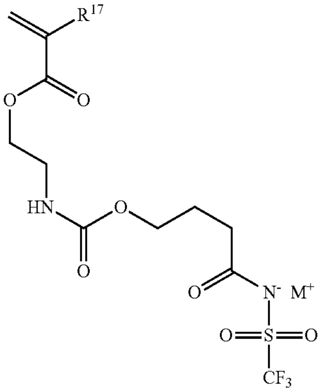
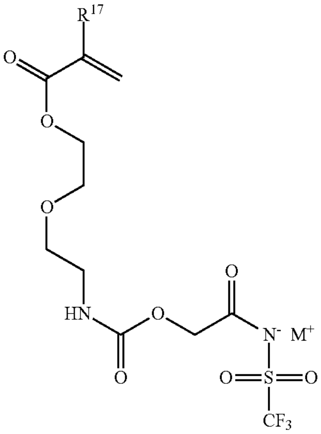
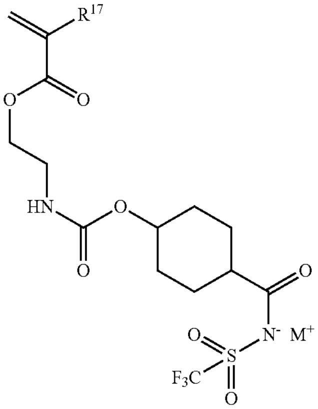

-continued

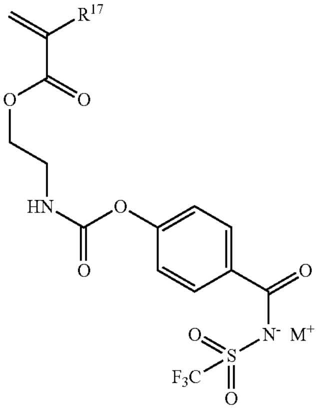

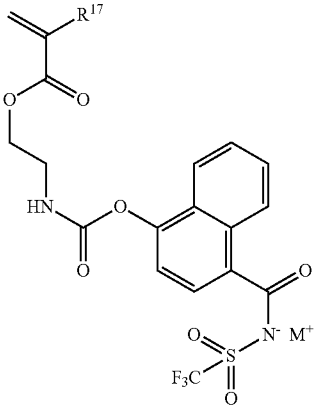

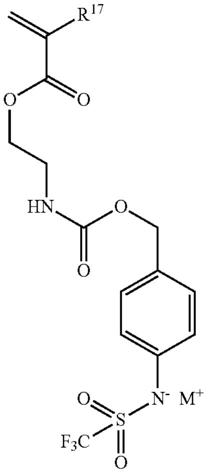

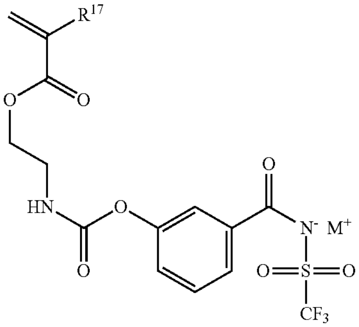

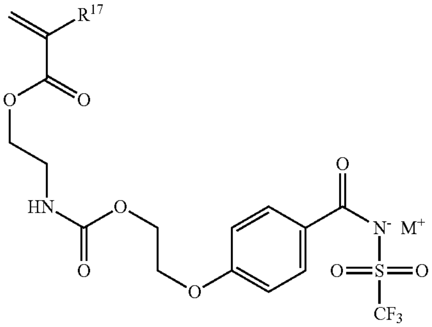

-continued

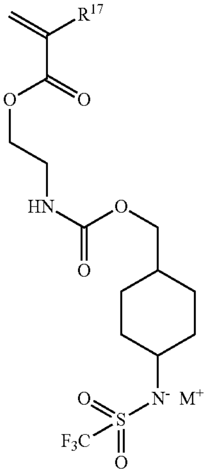

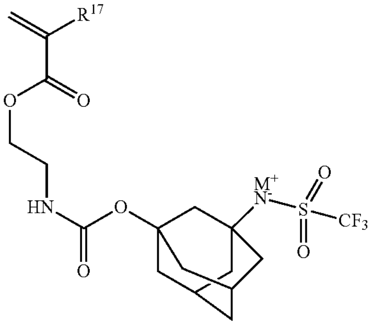

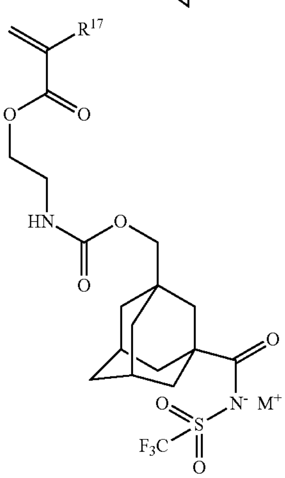

In the formulae, $R^5$, $R^7$, $R^9$, $R^{12}$, $R^{14}$, $R^{15}$, and $R^{17}$ are as defined above.

(Repeating Unit-b)

In the component (B) dopant polymer of the inventive bio-electrode composition, a repeating unit-b having a glyme chain can also be copolymerized in addition to the repeating units A1-1, A1-2, and A2-1 to A2-7 in order to enhance ionic conductivity. Specific examples of a monomer for obtaining the repeating unit-b having a glyme chain include the following. The copolymerization with the repeating unit having a glyme chain facilitates the movement of ions released from the skin in a dry electrode film, and thus can increase the sensitivity of a dry electrode.

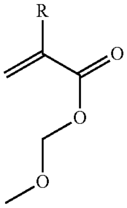
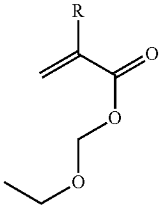
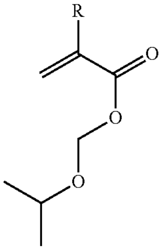
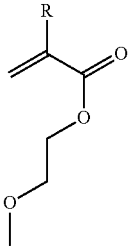
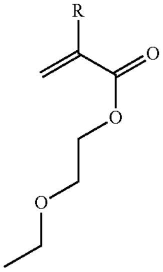
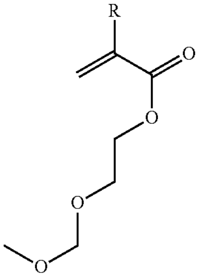
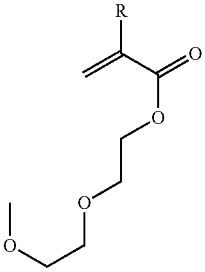
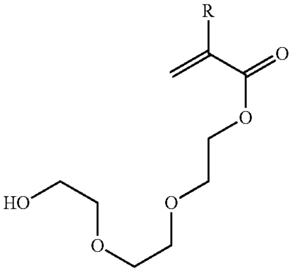
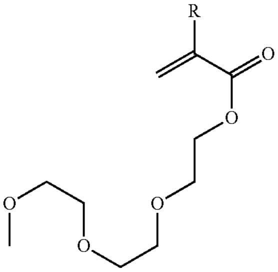
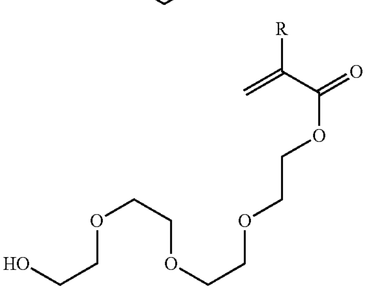
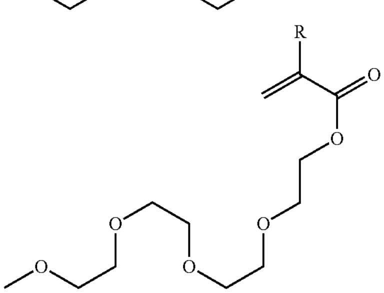
-continued
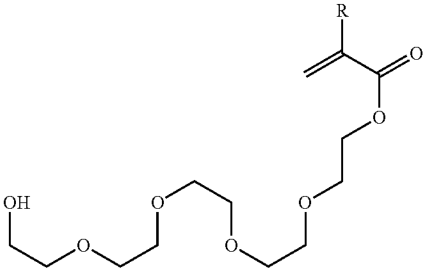
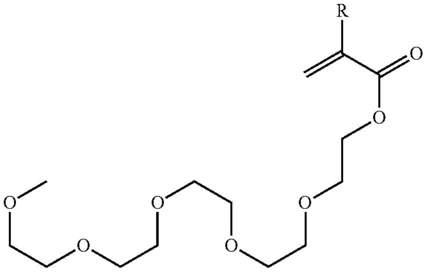
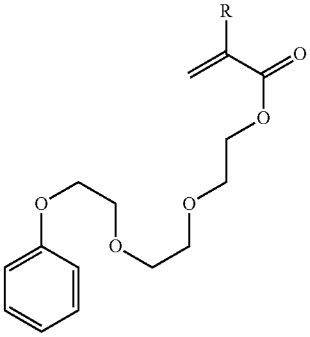
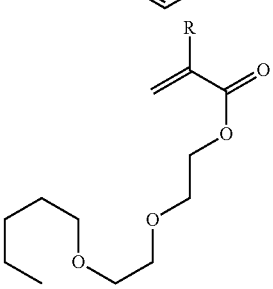
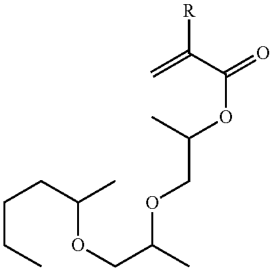
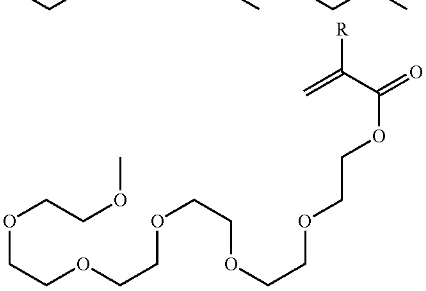
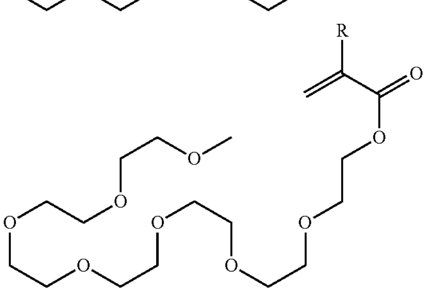

-continued
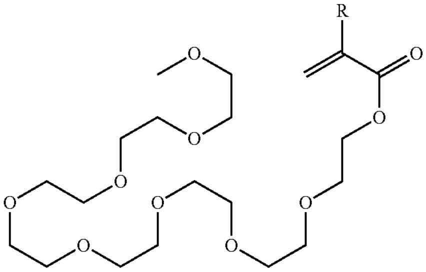
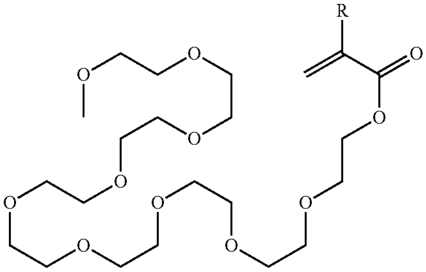
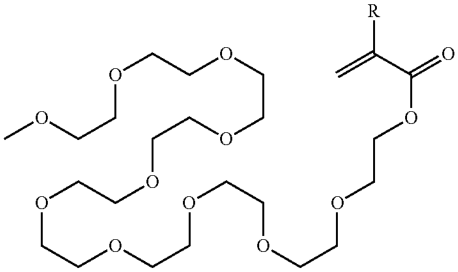
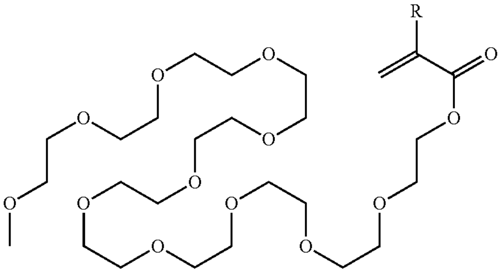
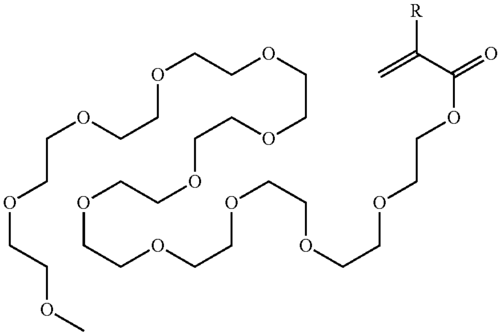
-continued
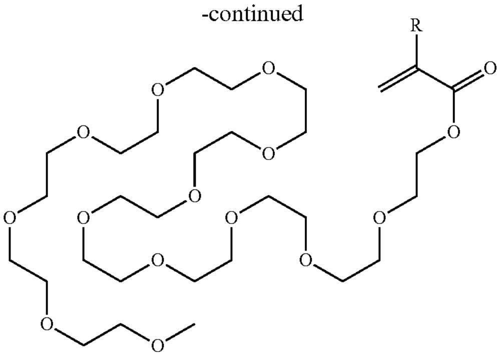
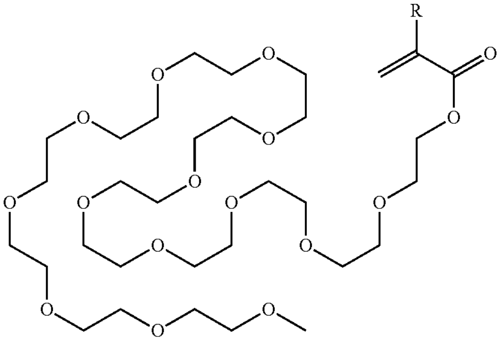
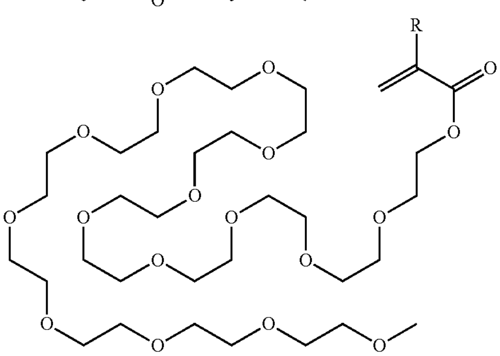
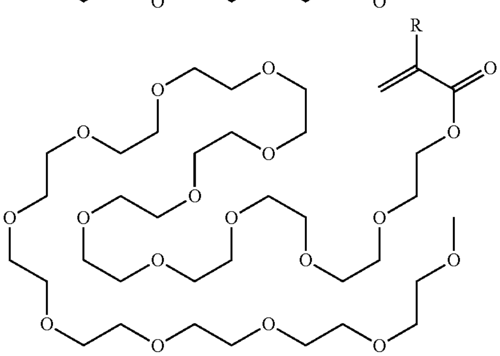
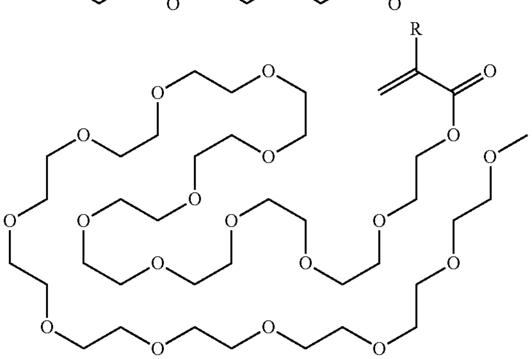

-continued
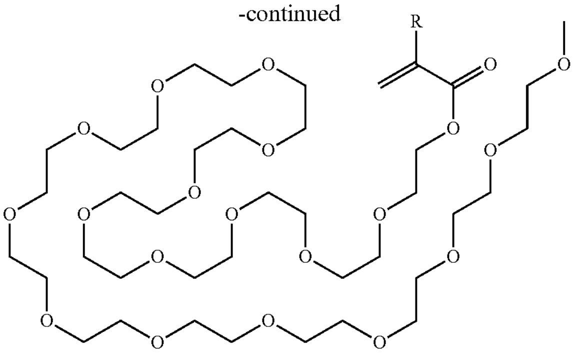
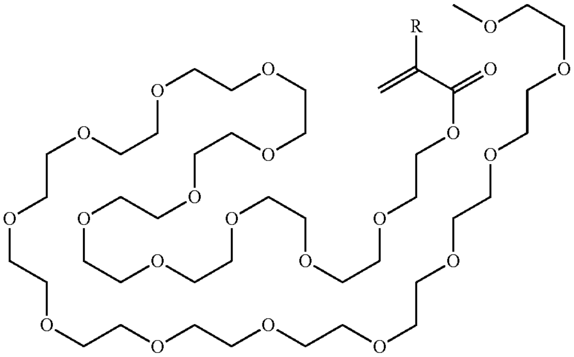
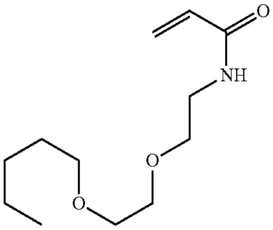
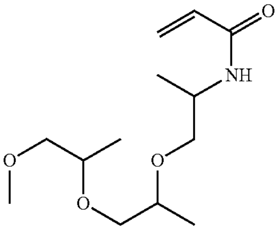
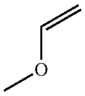
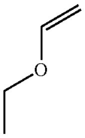
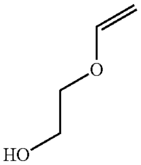
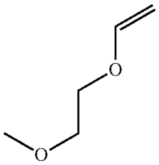
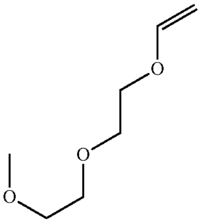
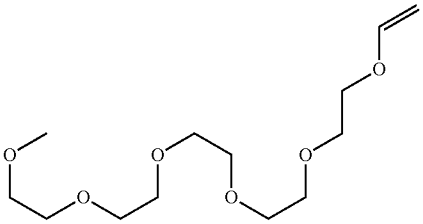
-continued
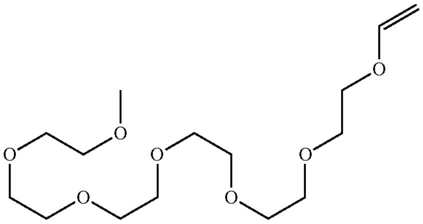
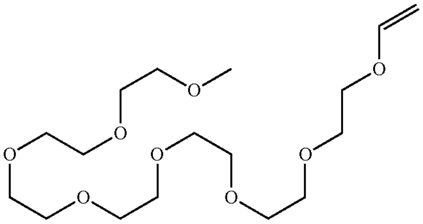
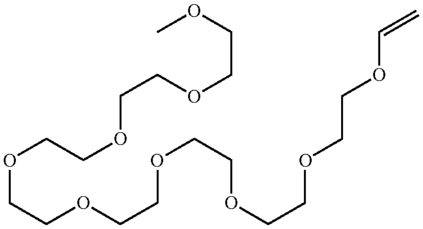
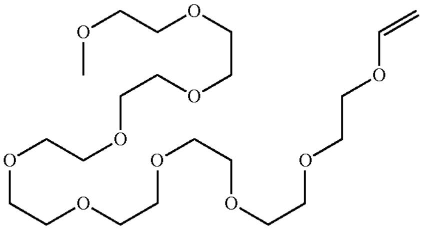
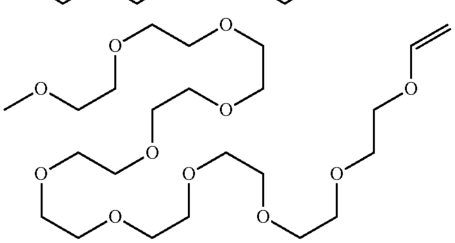
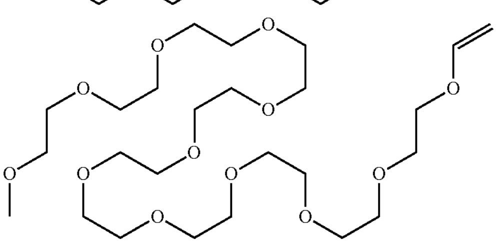
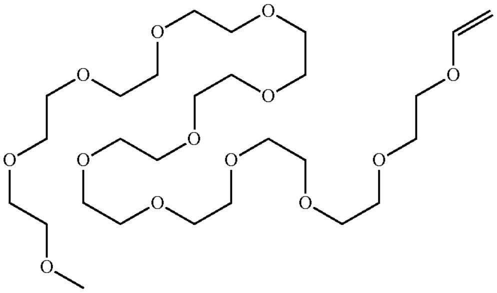

-continued
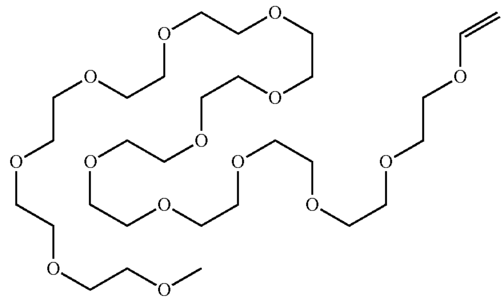
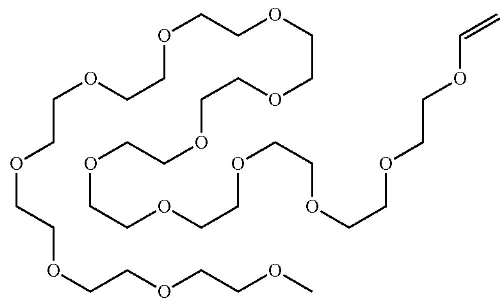
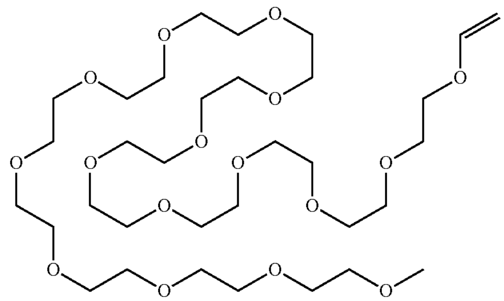
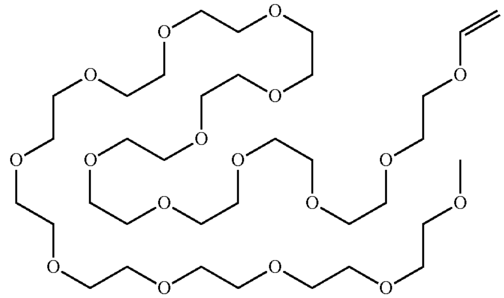
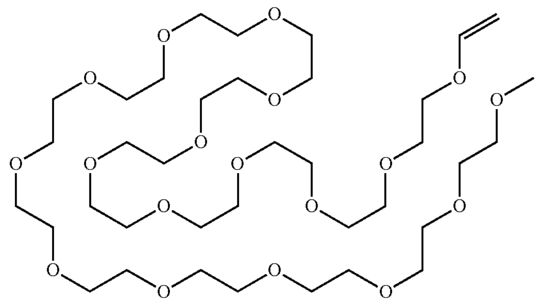
-continued
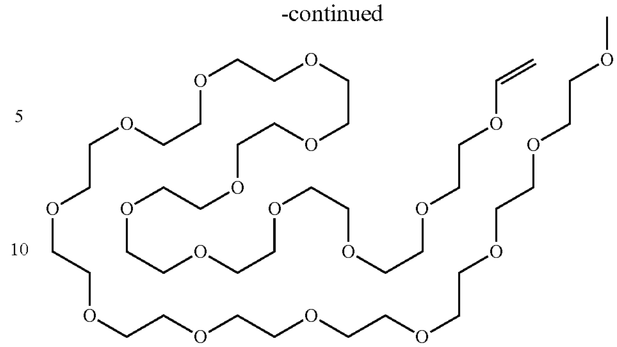
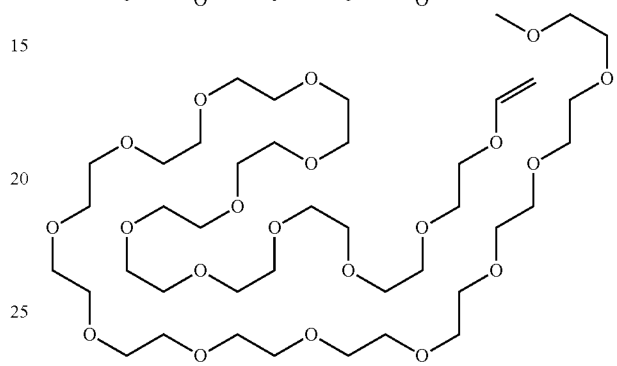
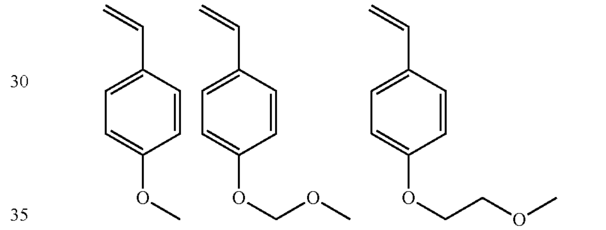
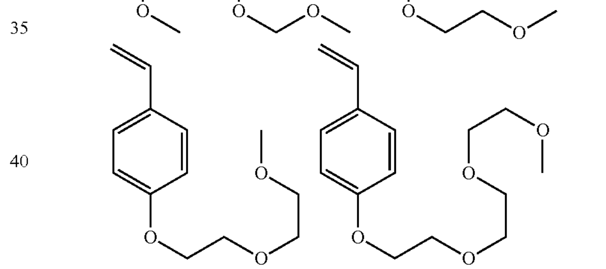
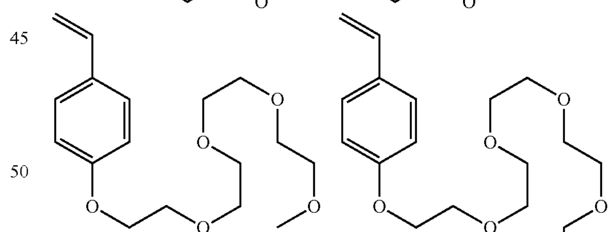
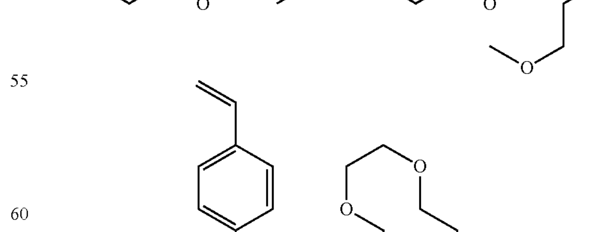
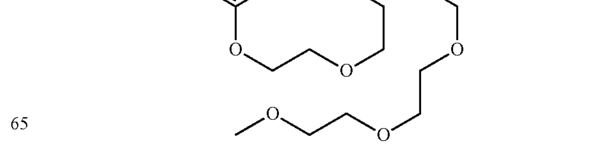

-continued

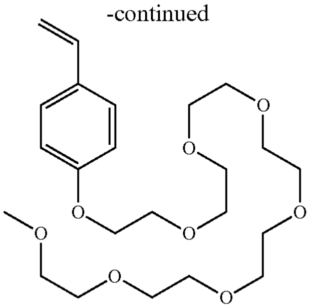

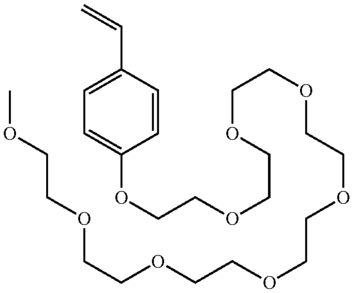

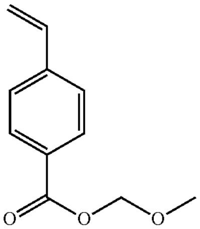

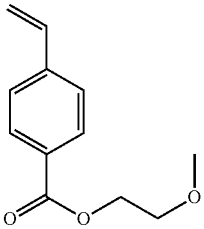

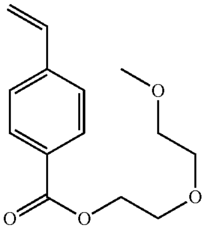

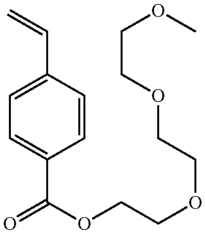

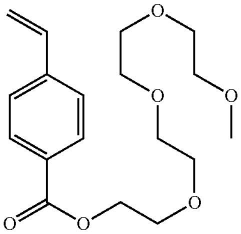

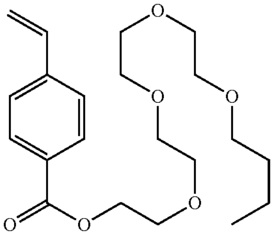

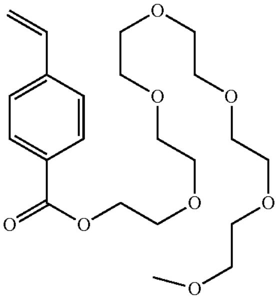

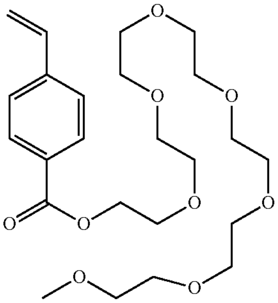

-continued

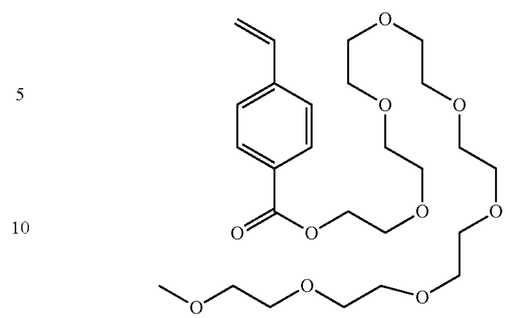

R represents a hydrogen atom or a methyl group.

(Repeating Unit-c)

In addition to the repeating units A1-1, A1-2, A2-1 to A2-7, and -b, it is also possible to copolymerize, in the component (B) of the inventive bio-electrode composition, a hydrophilic repeating unit-c having an ammonium salt, a betaine, an amide group, pyrrolidone, a lactone ring, a lactam ring, a sultone ring, sulfonic acid, a sodium salt of sulfonic acid, or a potassium salt of sulfonic acid in order to enhance electric conductivity. Specific examples of a monomer to give the hydrophilic repeating unit-c include the following. The copolymerization with the repeating unit containing such hydrophilic groups can increase the sensitivity of the dry electrode by increasing the sensitivity to ions released from the skin.

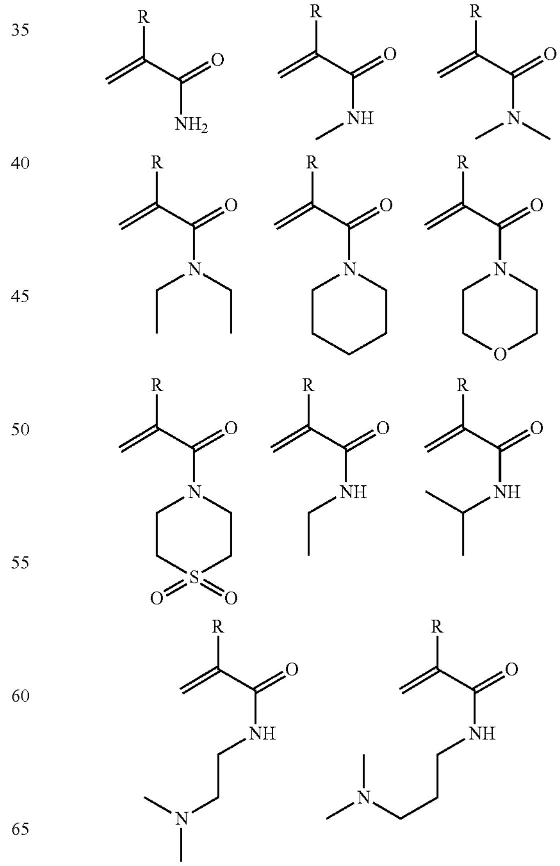

-continued
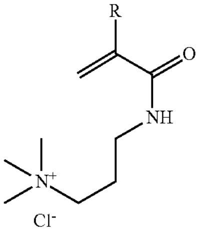
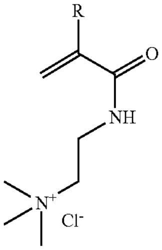
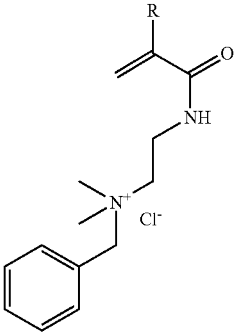
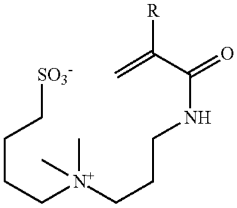
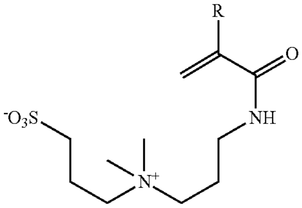
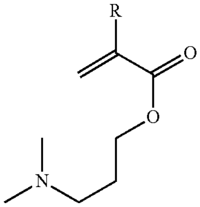
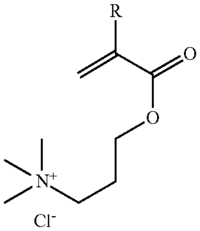
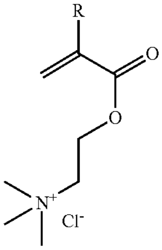
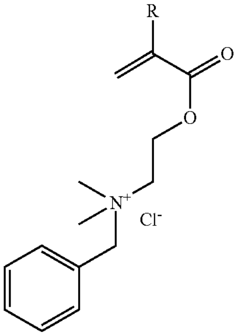
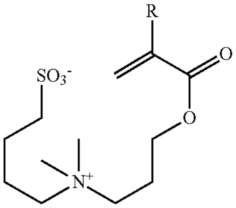
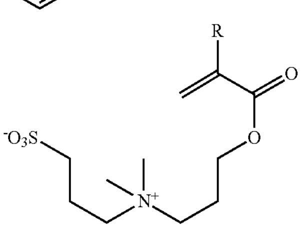
-continued
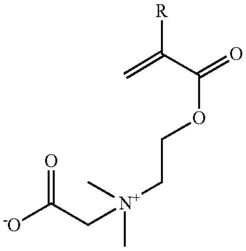
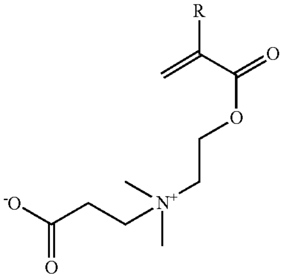
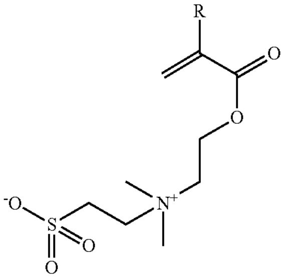
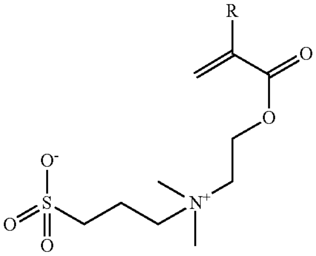
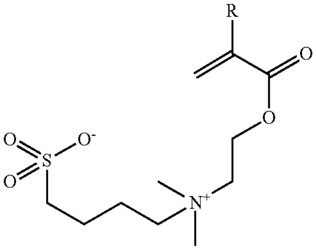
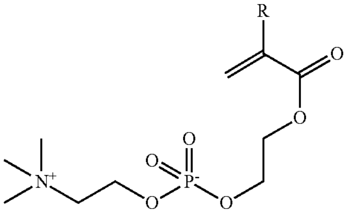
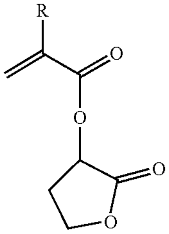
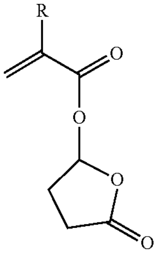
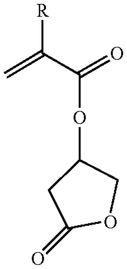

-continued
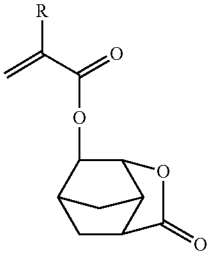
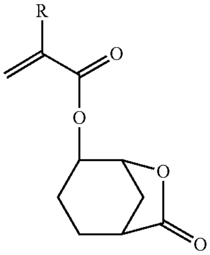
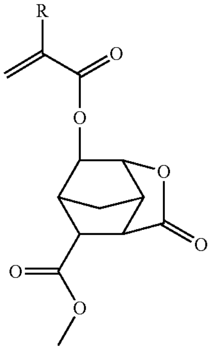
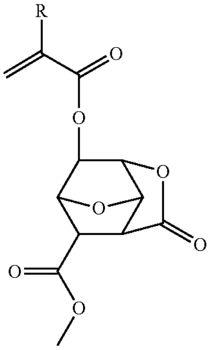
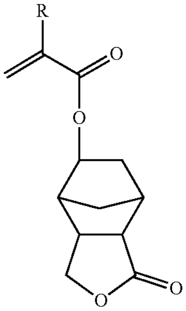
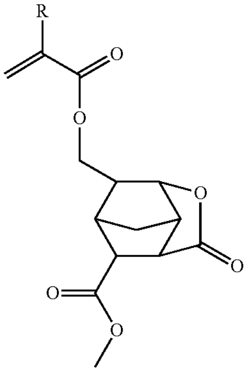
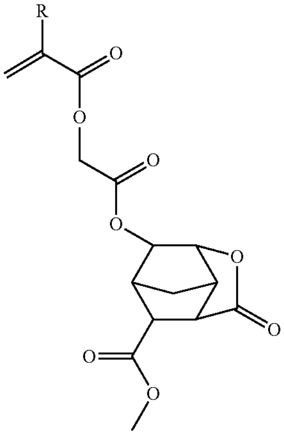
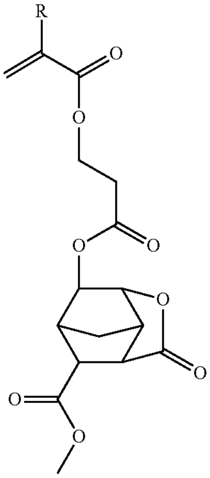
-continued
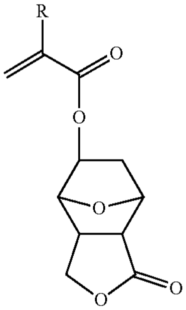
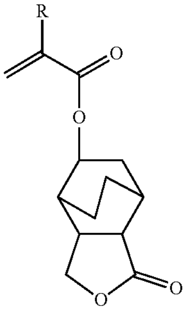
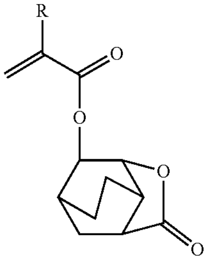
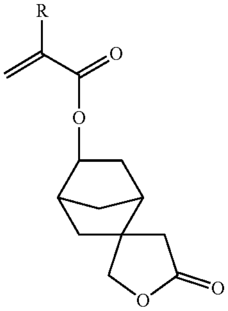
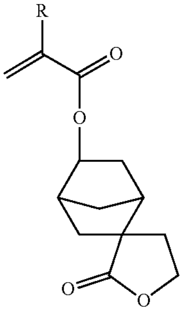
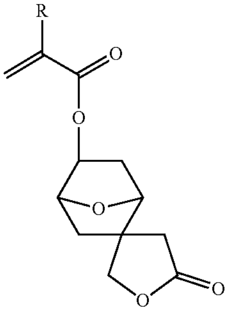
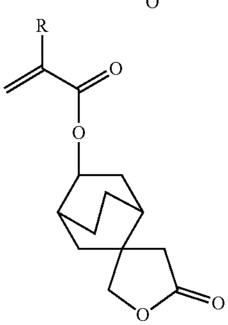
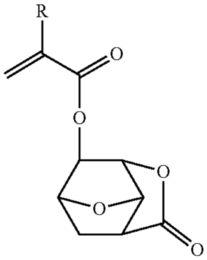
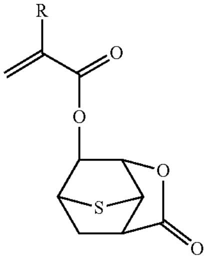
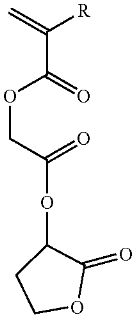
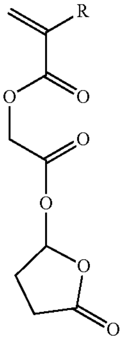

-continued
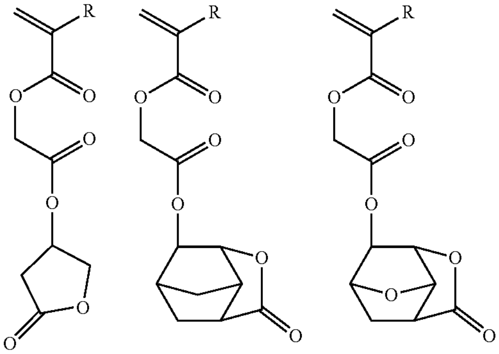
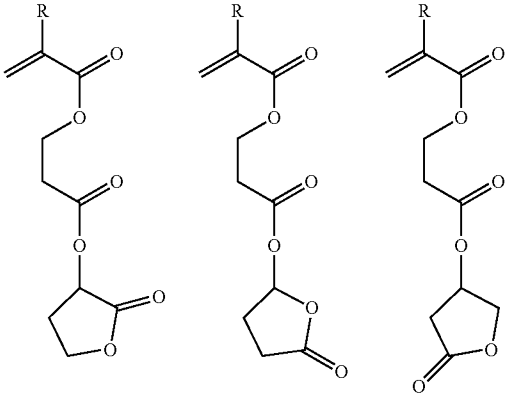
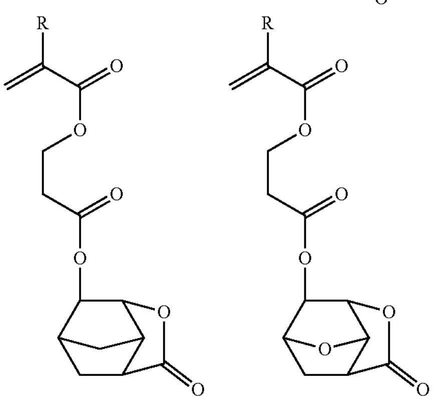
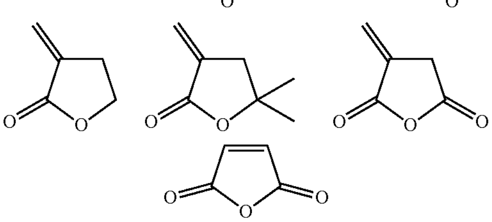
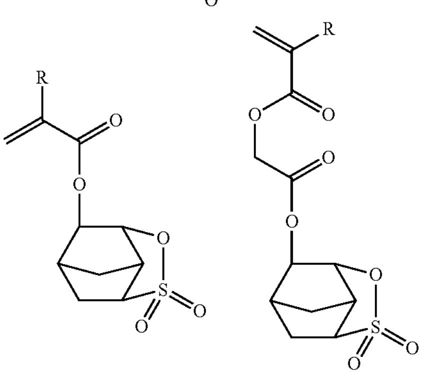
-continued
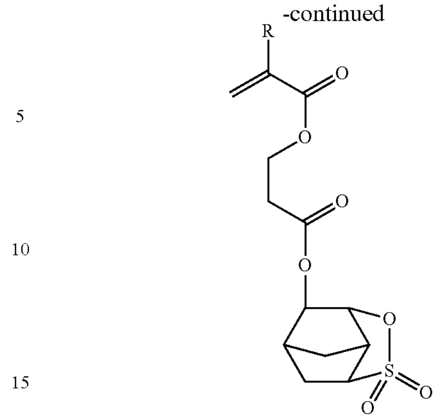
(Repeating Unit-d)
In addition to the repeating units selected from the repeating units A1-1, A1-2, A2-1 to A2-7, -b, and -c, the component (B) of the inventive bio-electrode composition can have a repeating unit-d containing fluorine.
Specific examples of a monomer to give the repeating unit-d containing fluorine include the following.
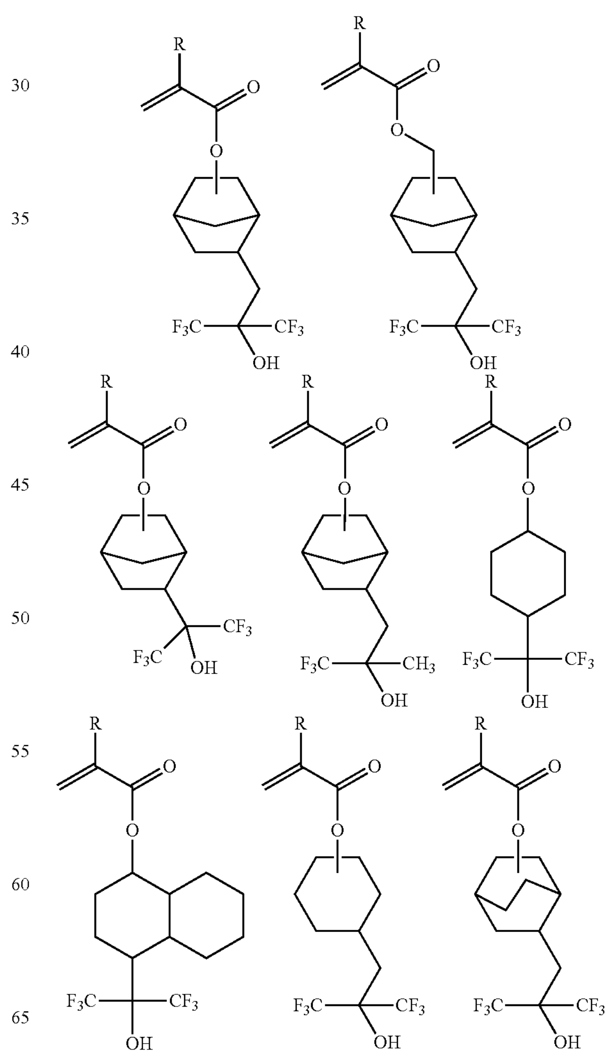

-continued
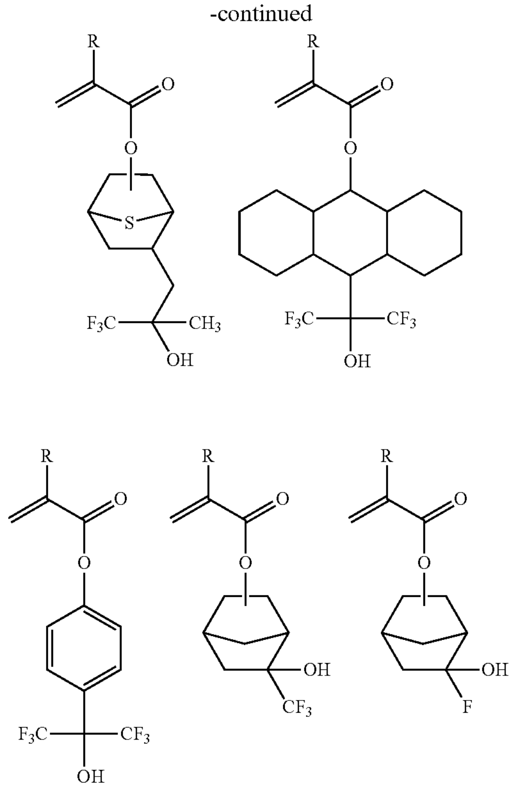
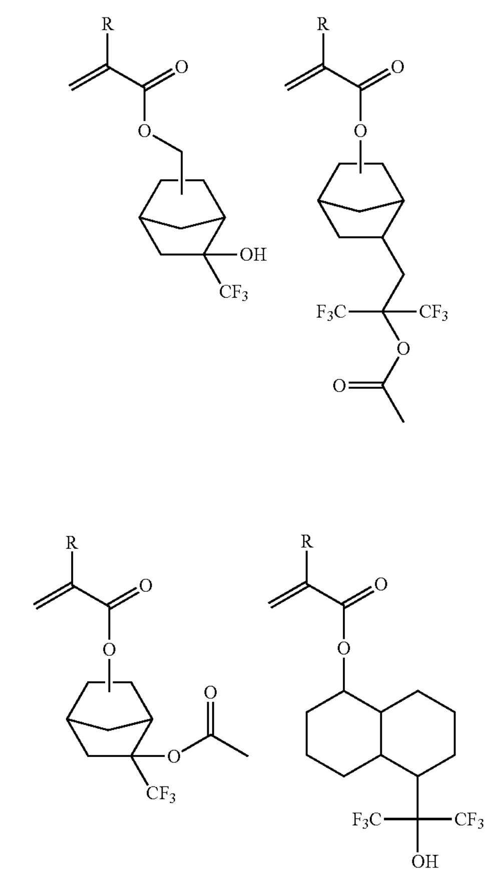
-continued
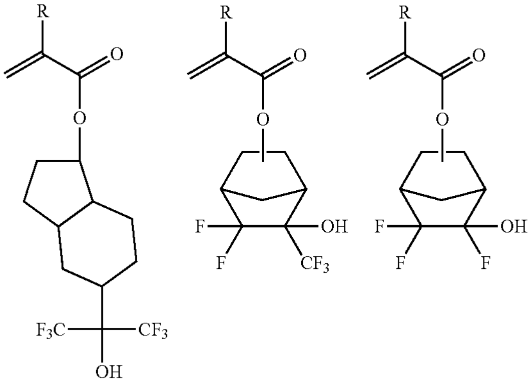
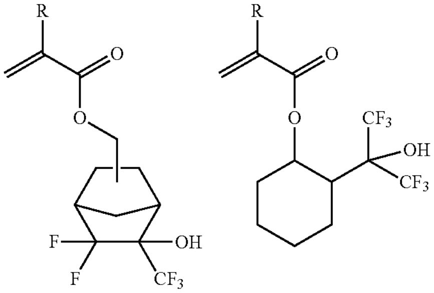
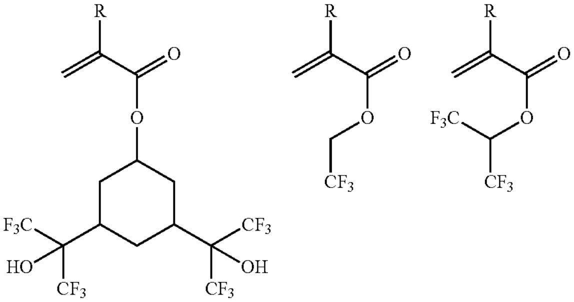
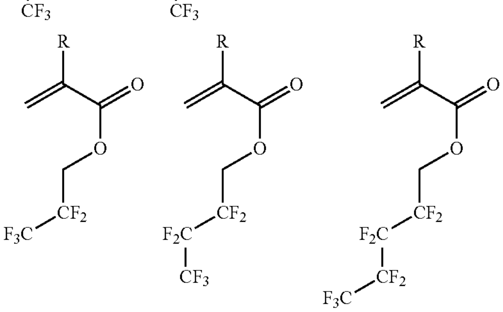
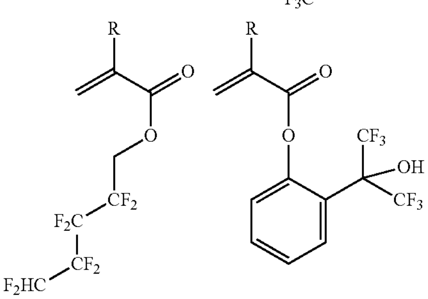

-continued
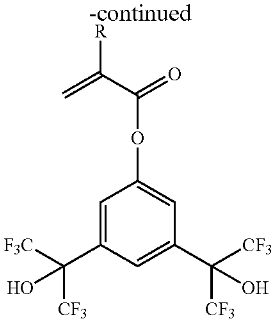
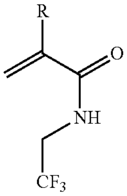
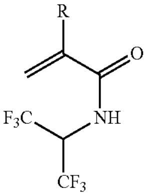
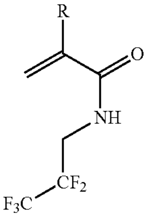
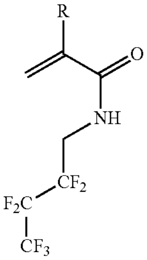
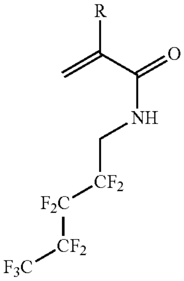
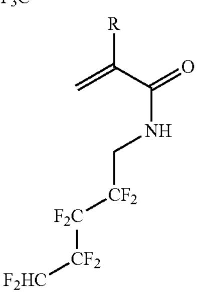
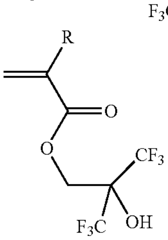
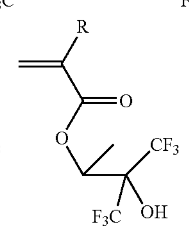
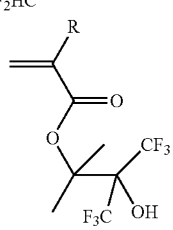
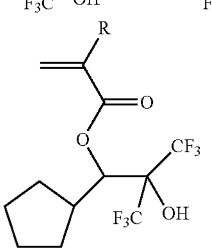
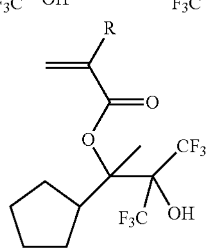
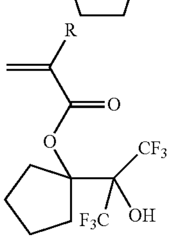
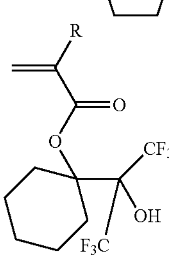
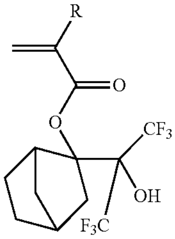
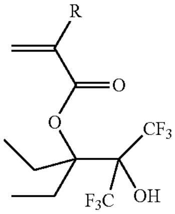
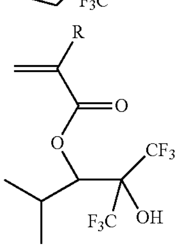
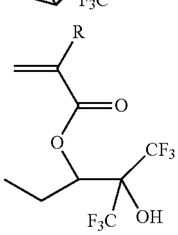
-continued
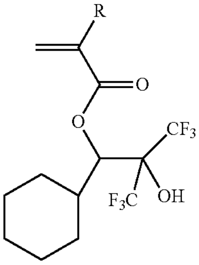
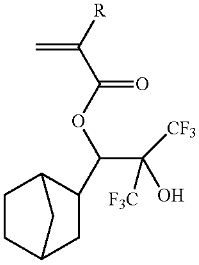
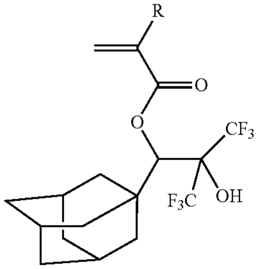
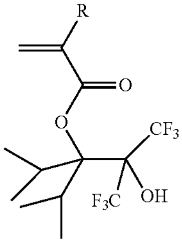
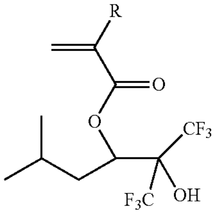
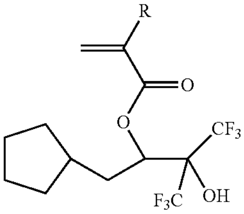
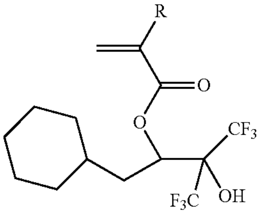
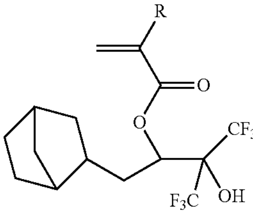
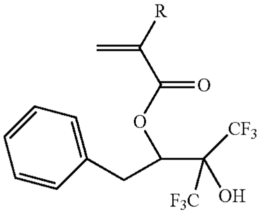
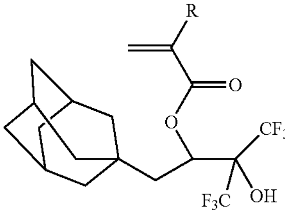
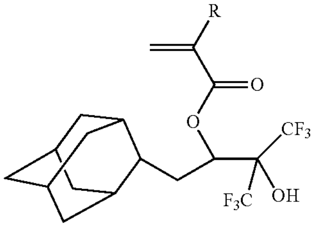
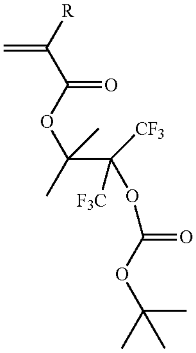

-continued
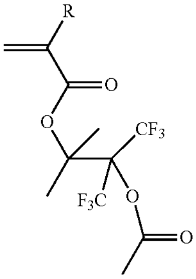
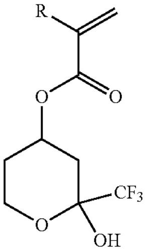
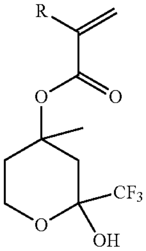
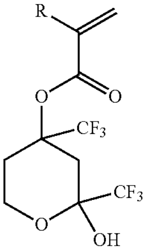
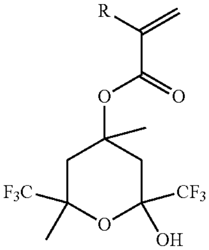
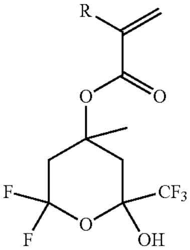
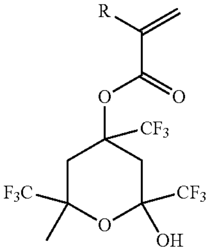
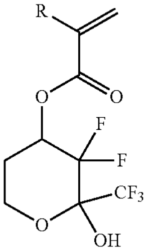
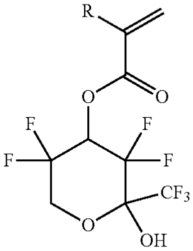
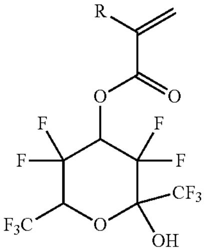
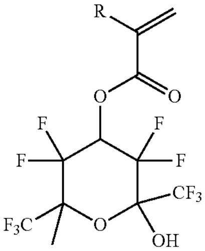
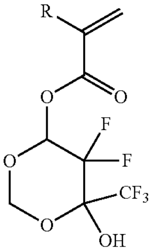
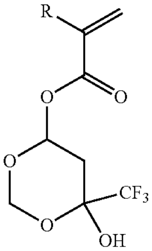
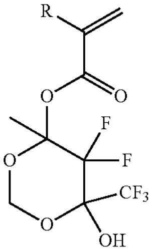
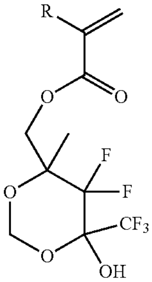
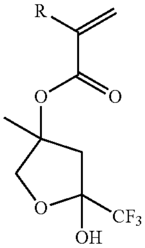
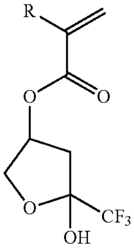
-continued
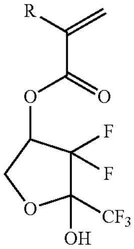
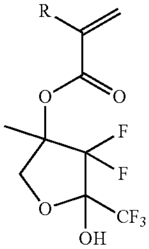
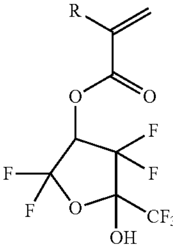
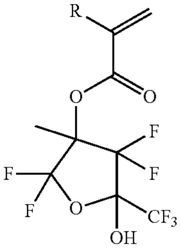
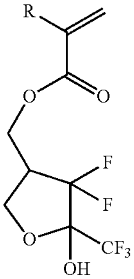
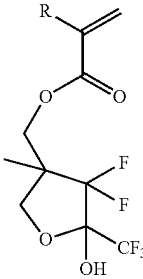
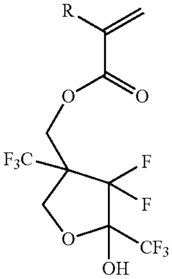
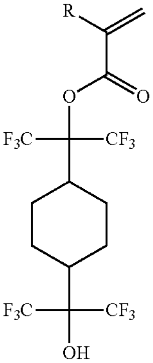
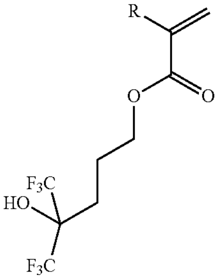
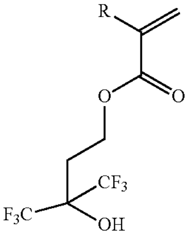
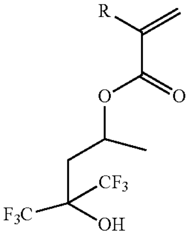
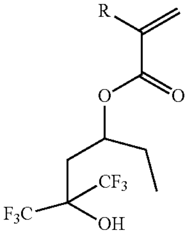
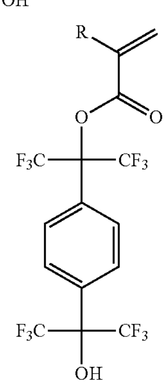
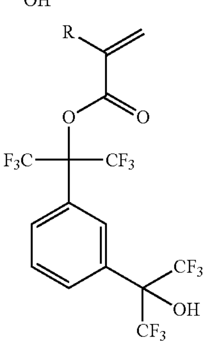

-continued
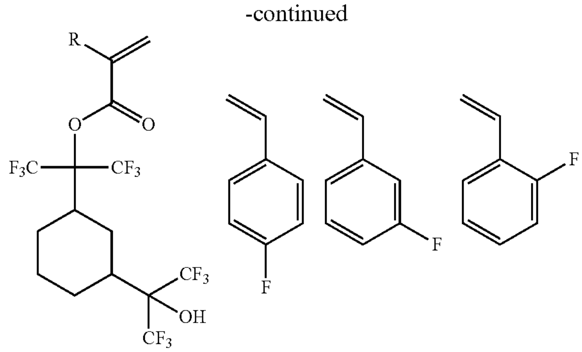
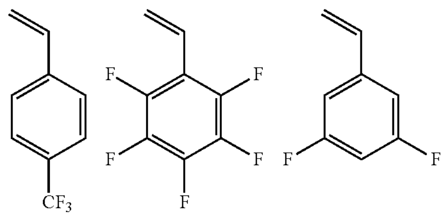
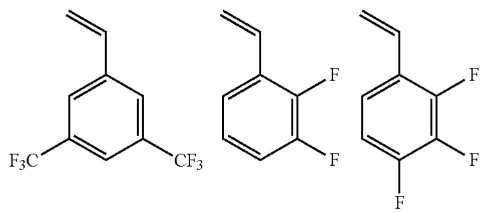
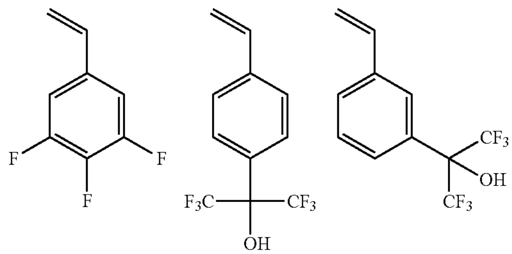
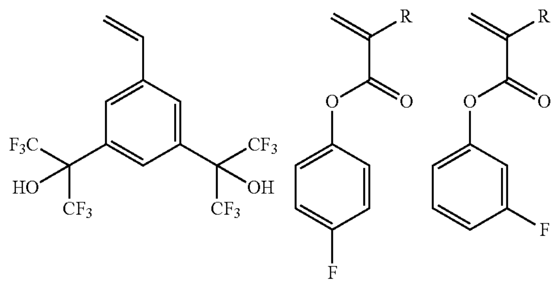
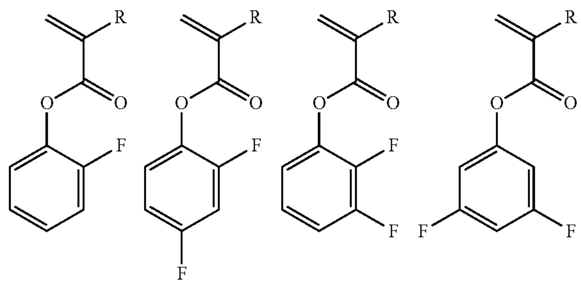
-continued
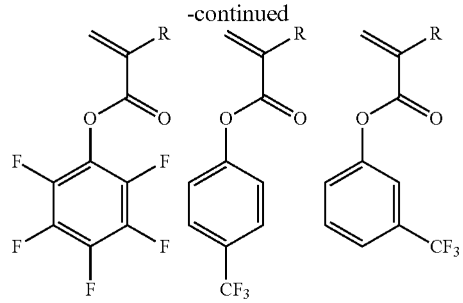
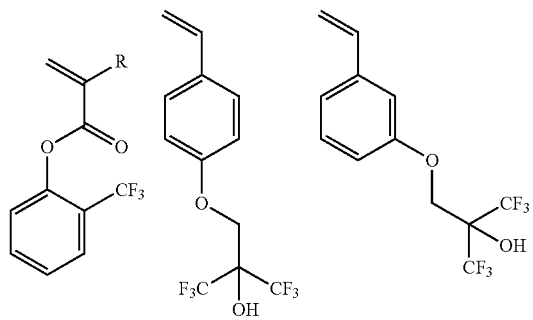
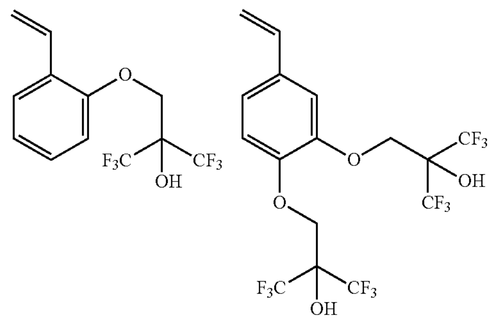
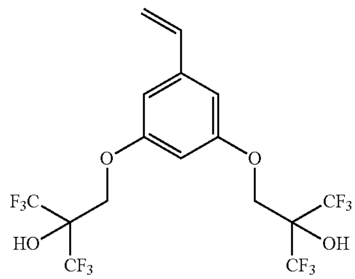
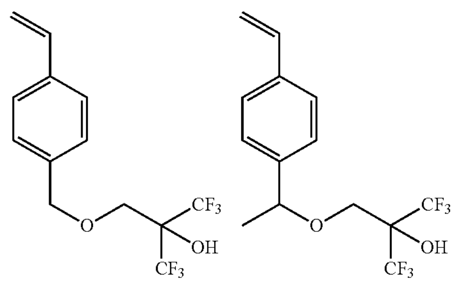

-continued
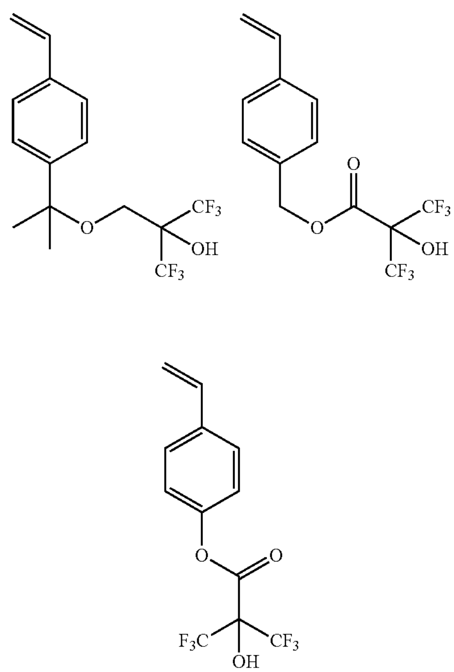
(Repeating Unit-e)
The component (B) can further include a repeating unit-e having a nitro group.
Specific examples of a monomer to give the repeating unit-e having a nitro group include the following.
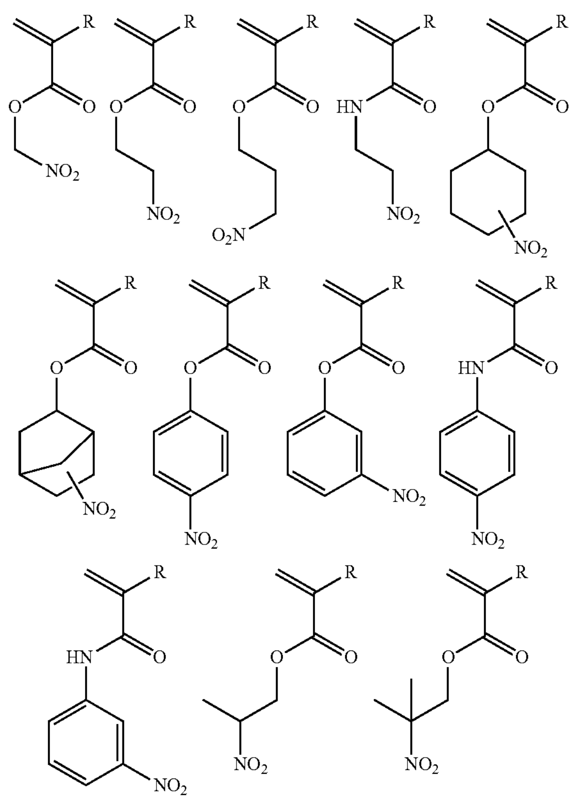
-continued
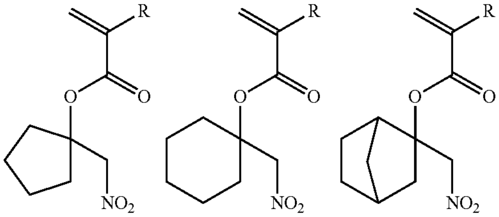
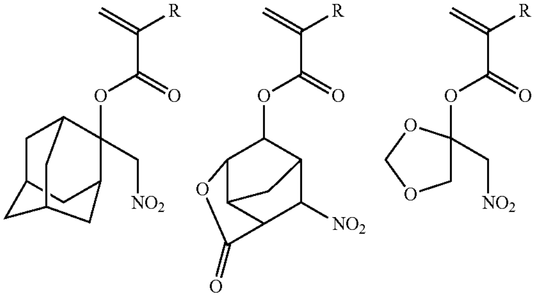
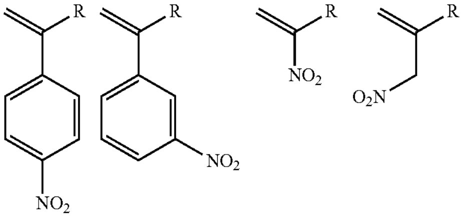
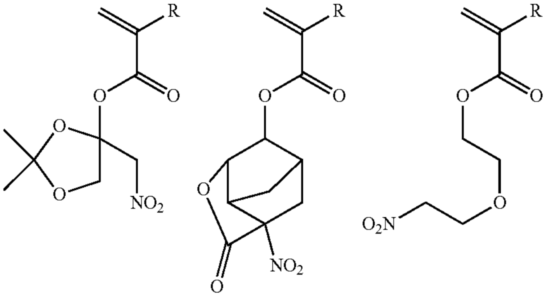
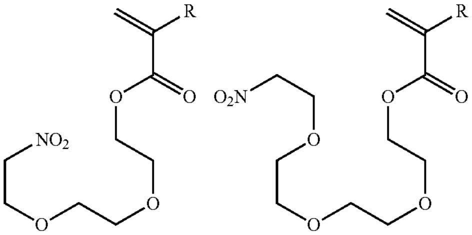
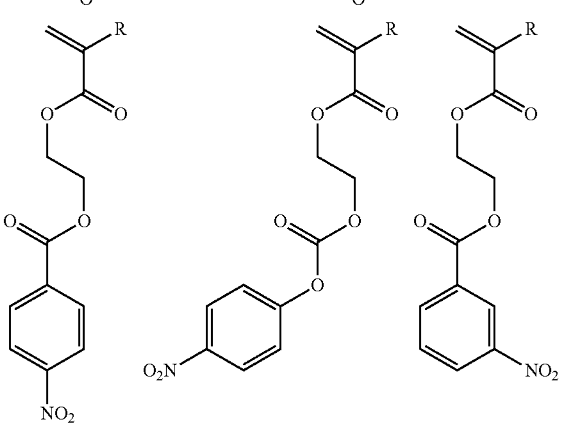

-continued
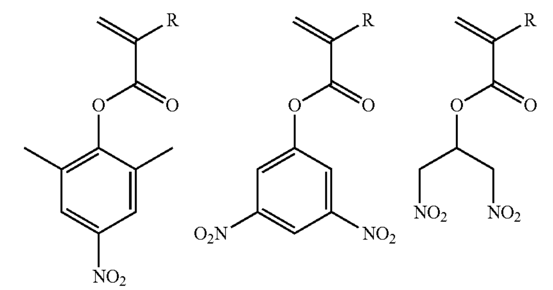
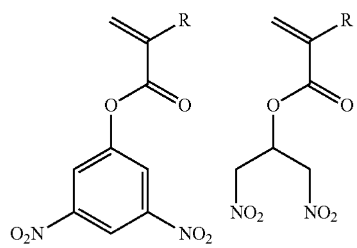
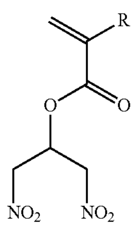
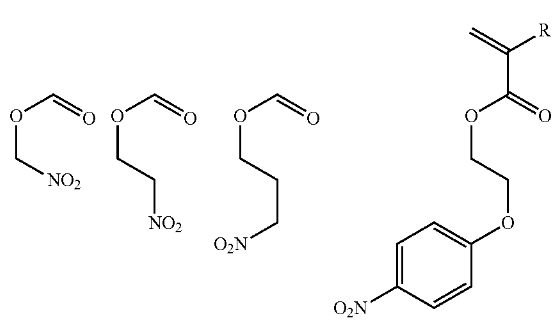
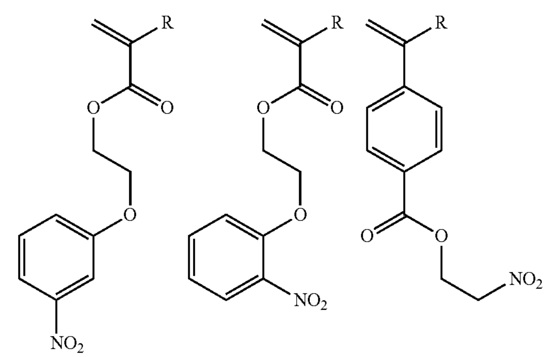
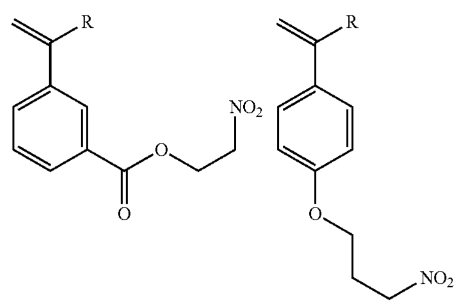
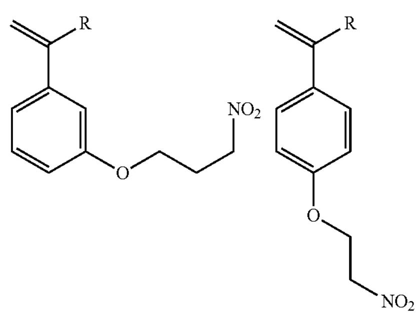
-continued
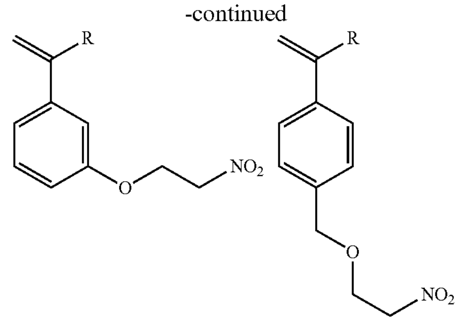
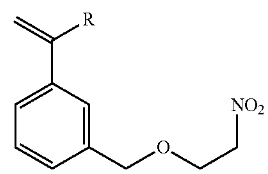
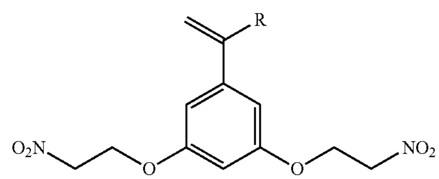
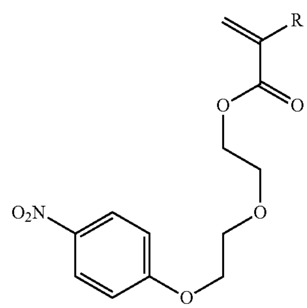
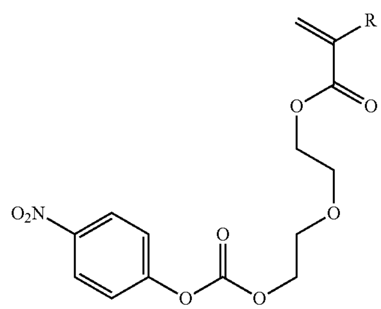
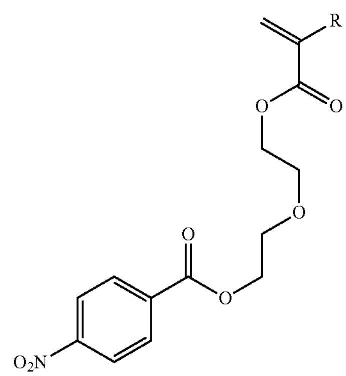

-continued
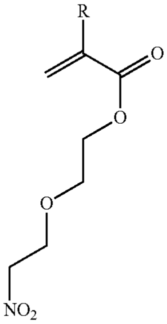
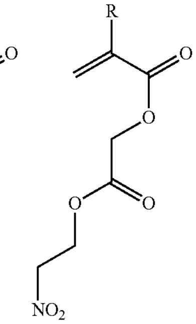
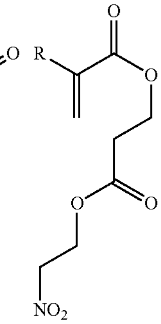
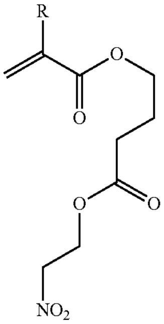
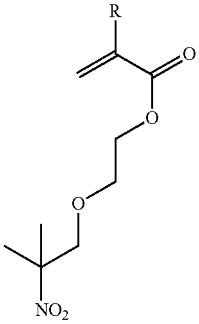
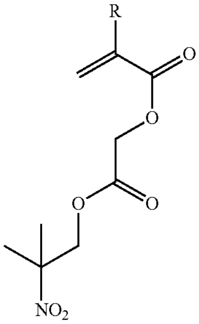
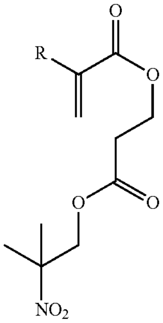
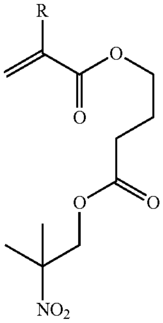
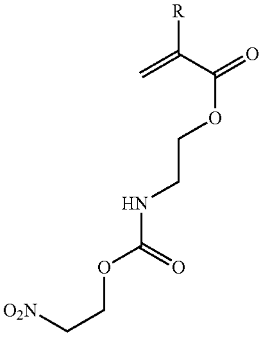
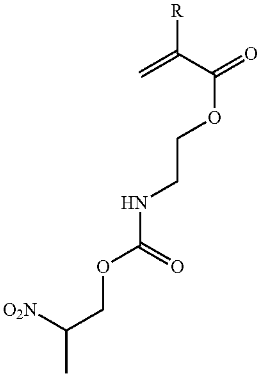
-continued
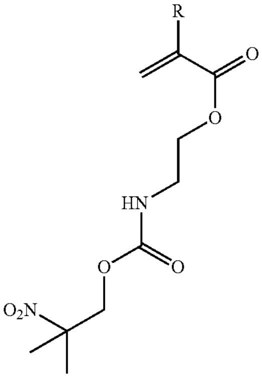
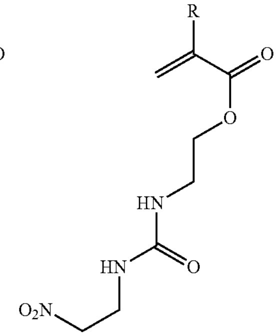
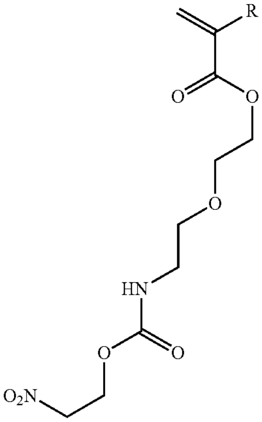
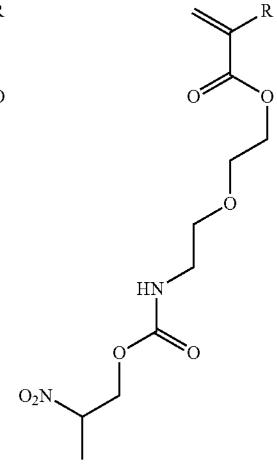
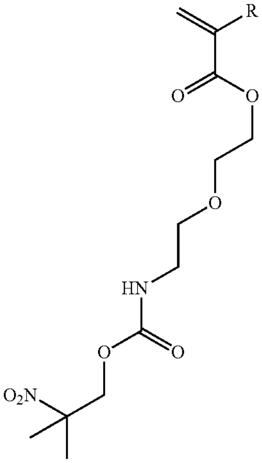
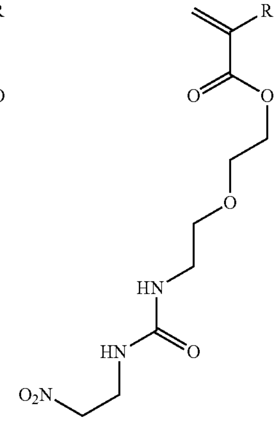
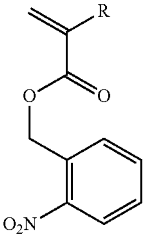
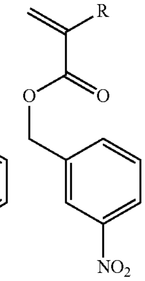
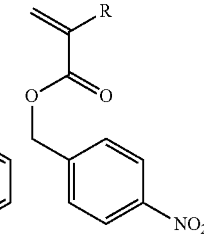

-continued
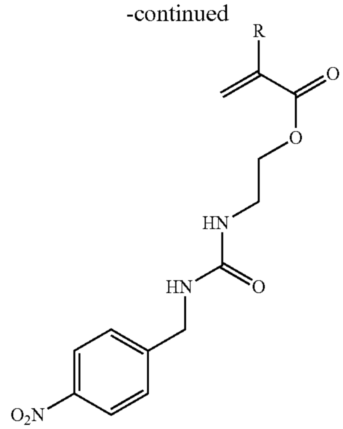
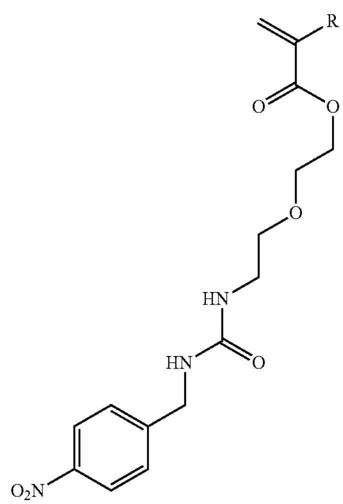
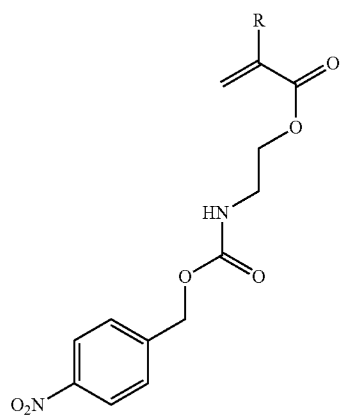
-continued
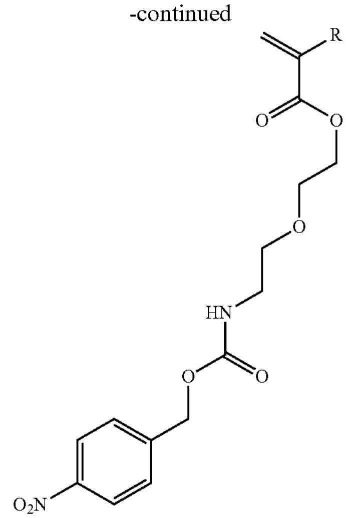
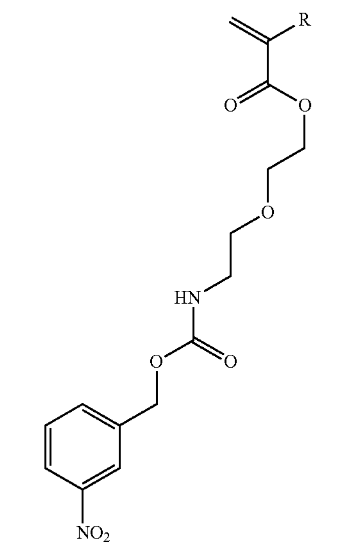
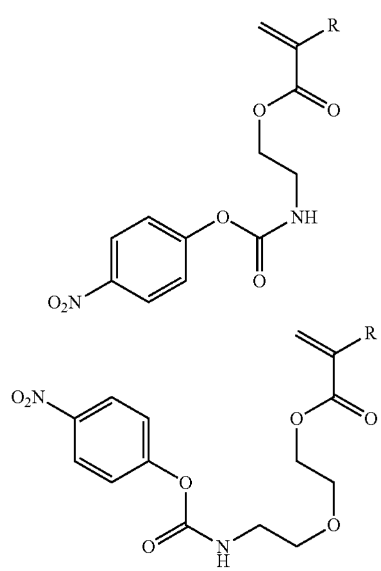

-continued
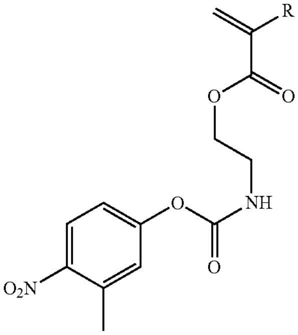
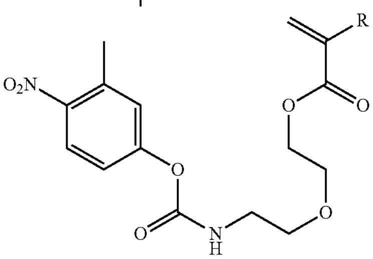
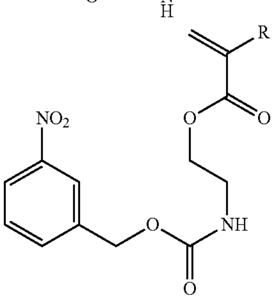
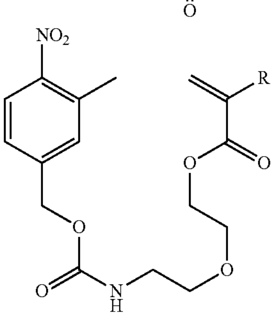
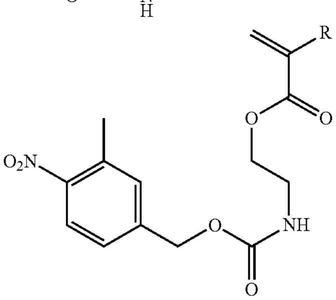
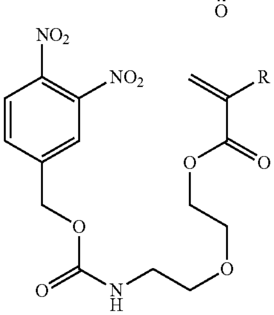
-continued
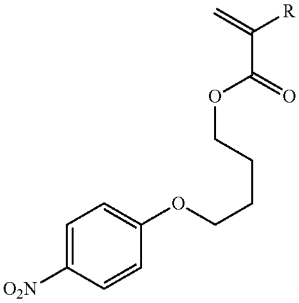
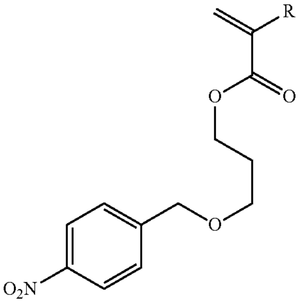
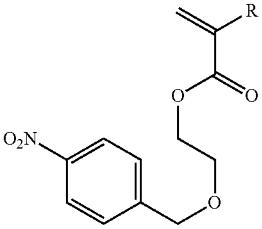
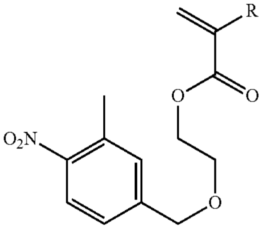
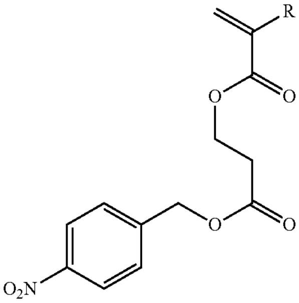
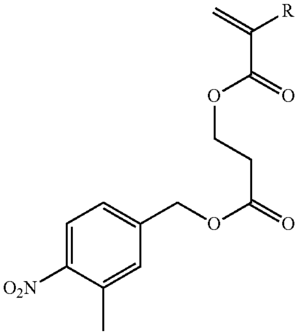
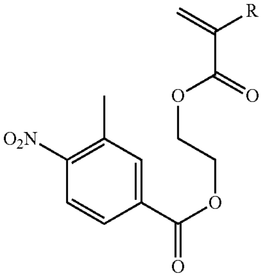

-continued
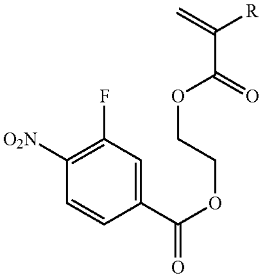
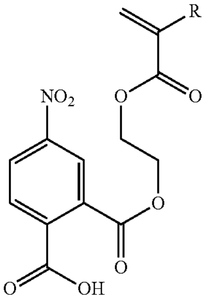
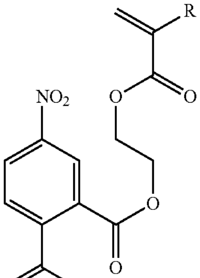
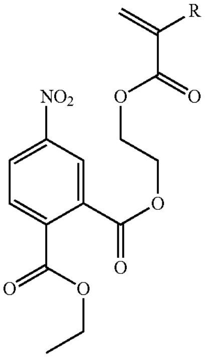
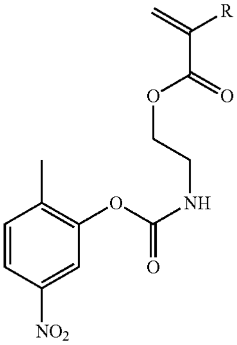
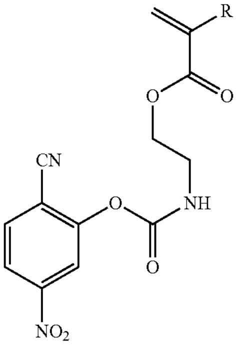
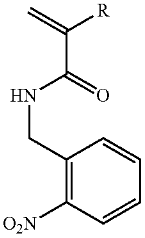
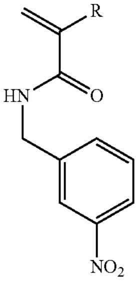
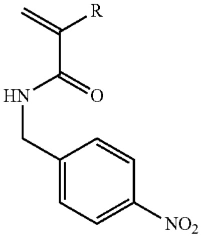
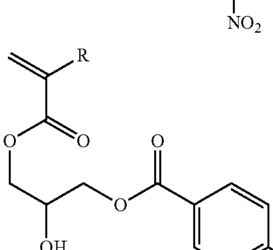
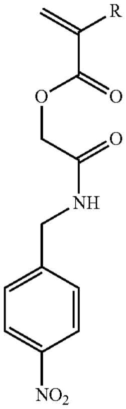
-continued
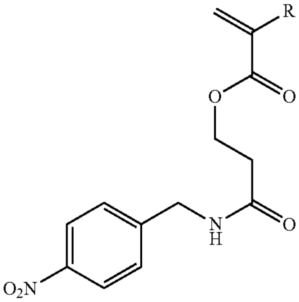
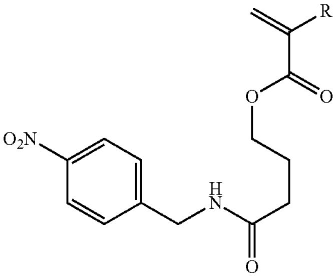
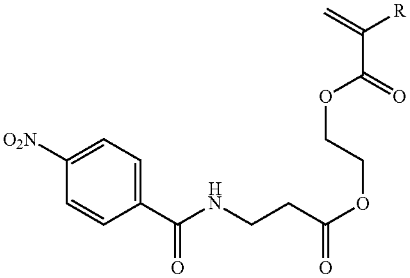
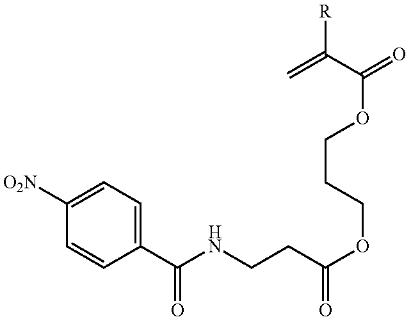
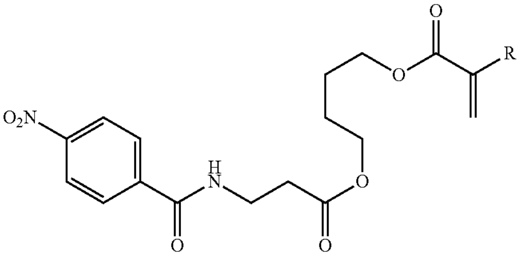

-continued
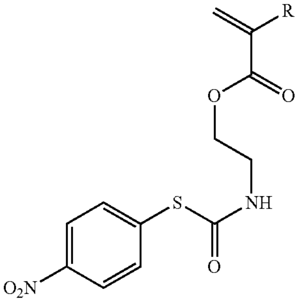
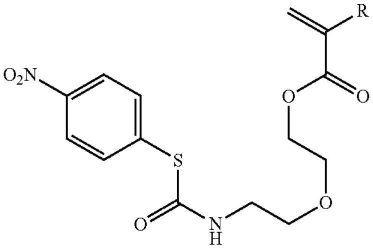
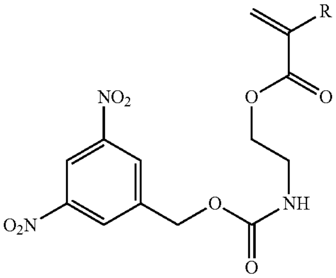
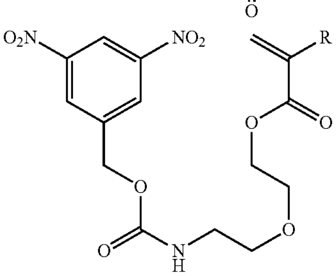
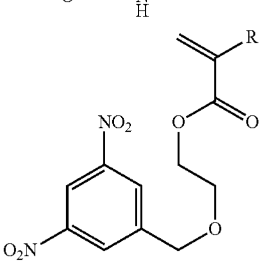
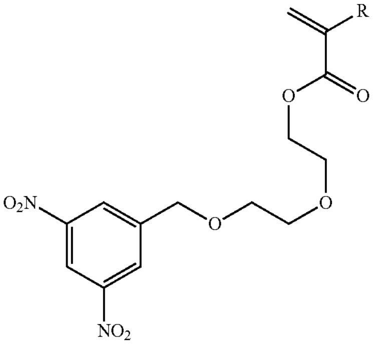
-continued
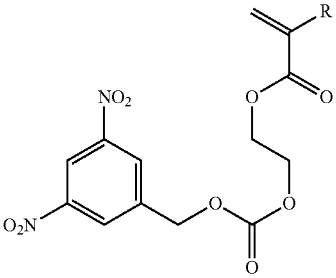
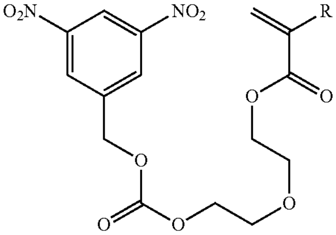
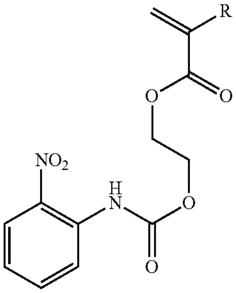
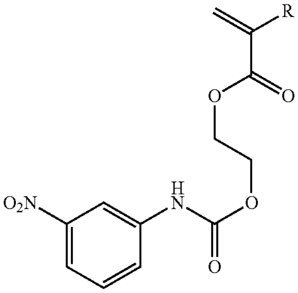
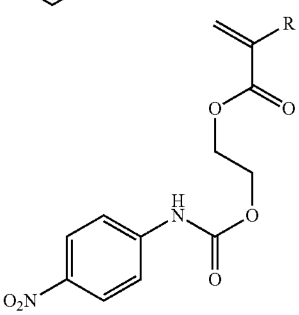
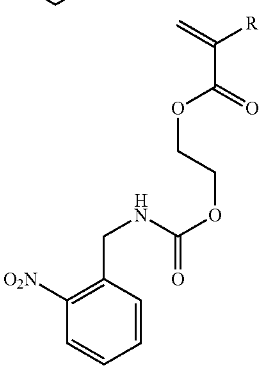
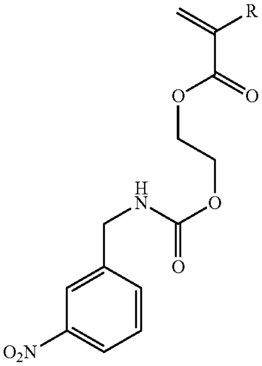
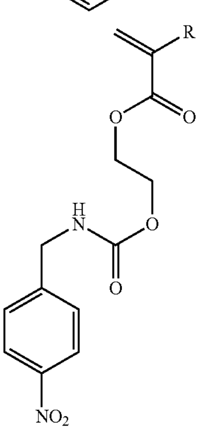

-continued
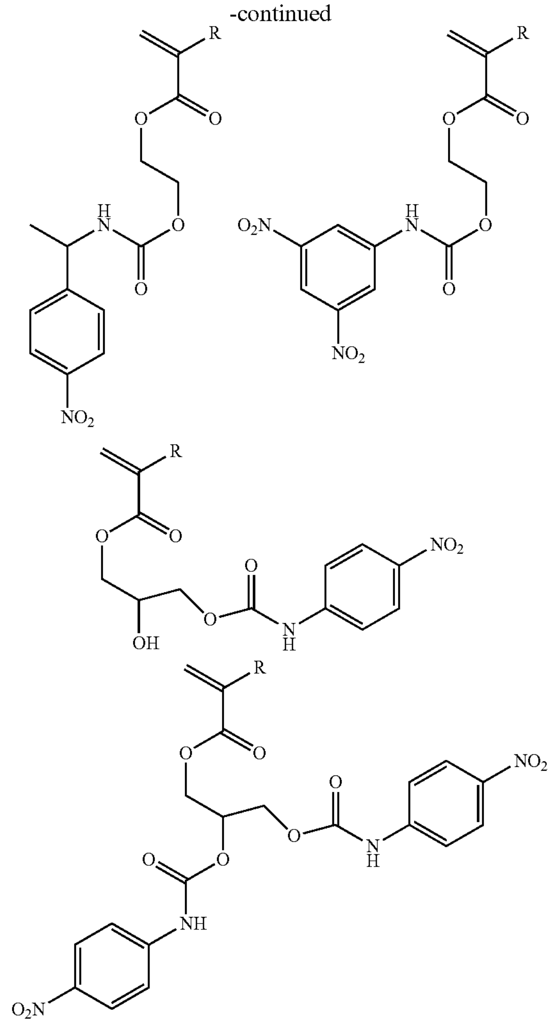
(Repeating Unit-f)
The component (B) can further include a repeating unit-f having a cyano group.
Specific examples of a monomer to give the repeating unit-f having a cyano group include the following.
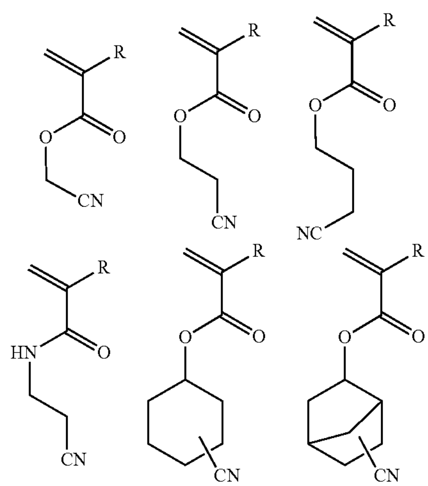
-continued
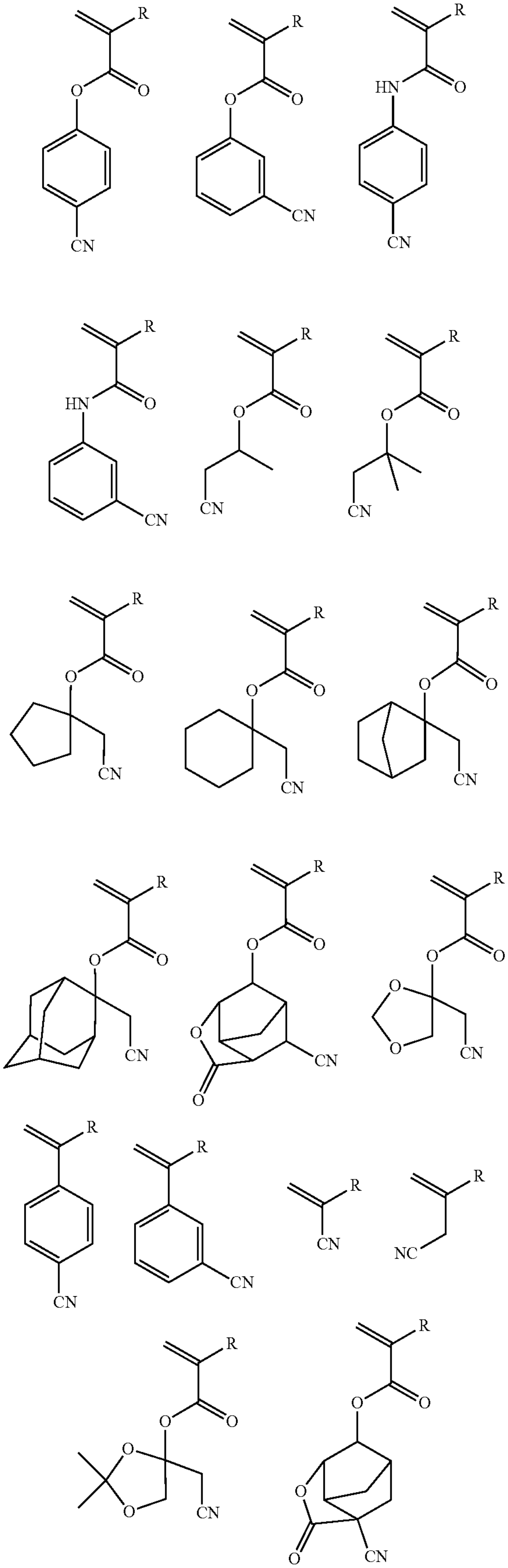

-continued
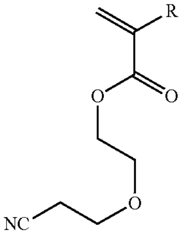
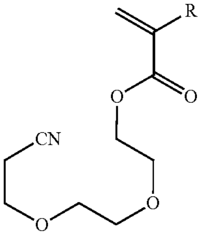
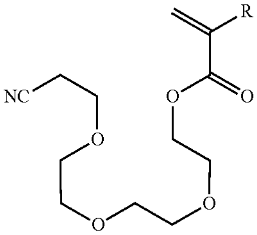
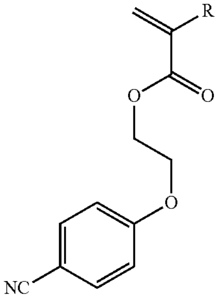
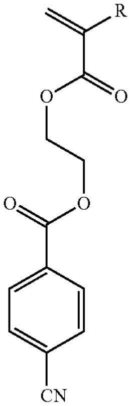
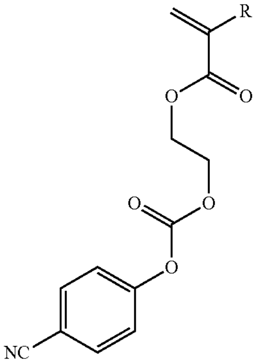
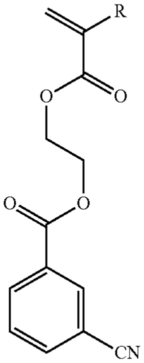
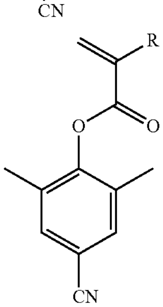
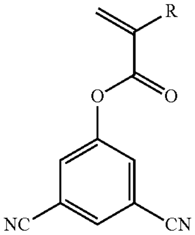
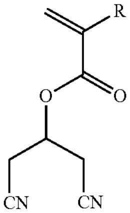
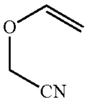
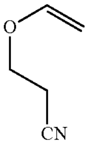
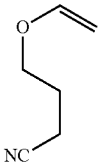
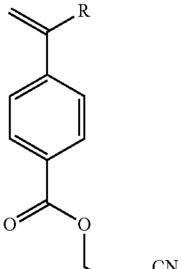
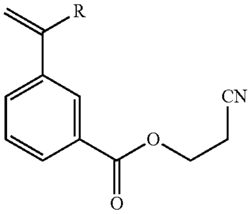
-continued
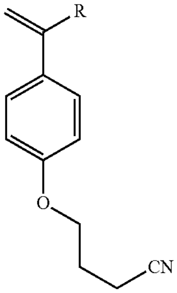
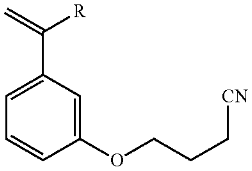
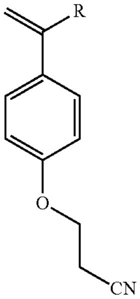
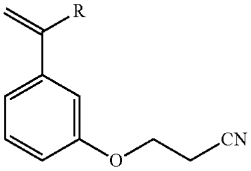
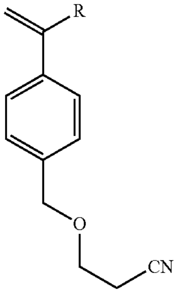
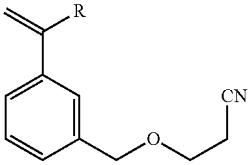
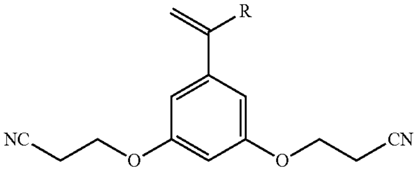
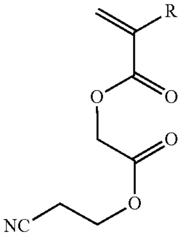
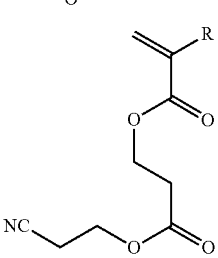
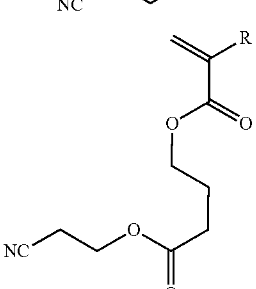
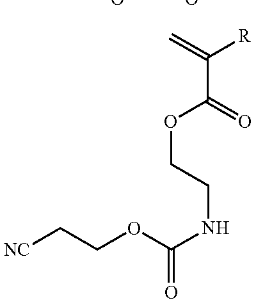

-continued

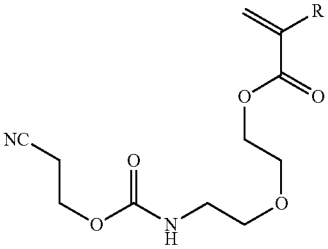

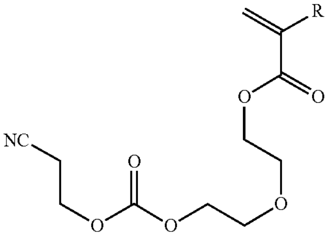

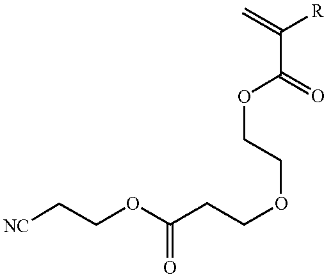

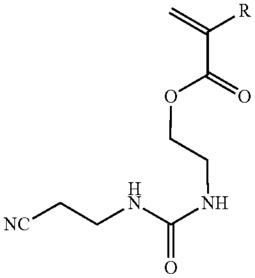

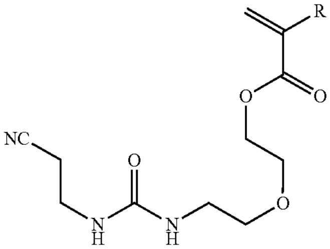

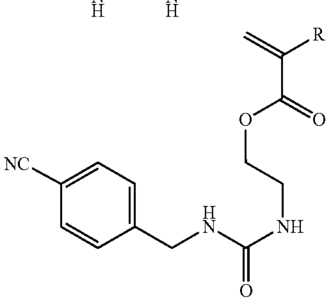

-continued

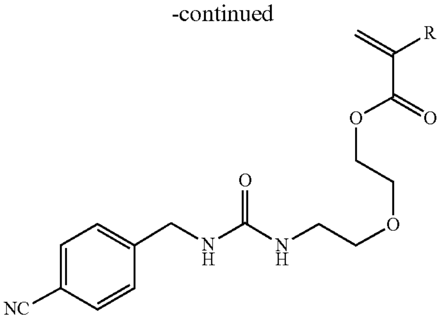

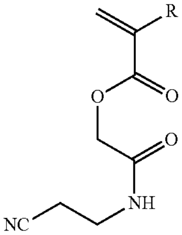

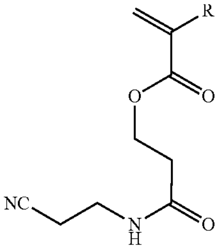

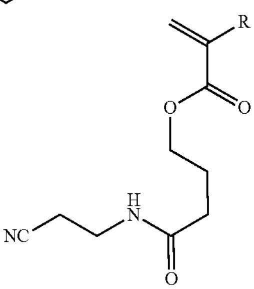

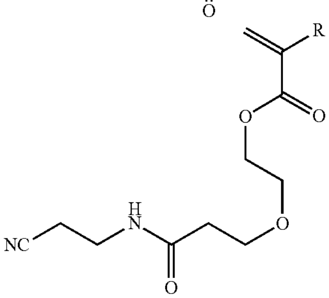

Here, R represents a hydrogen atom or a methyl group.

In addition, the dopant polymer (B) preferably contains, as the ammonium ion constituting the ammonium salt, an ammonium ion (ammonium cation) represented by the following general formula (3).

(3)

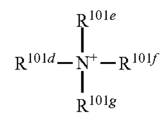

In the general formula (3), $R^{101d}$, $R^{101e}$, $R^{101f}$, and $R^{101g}$ each represent a hydrogen atom, a linear, branched, or cyclic alkyl group having 1 to 15 carbon atoms, a linear, branched, or cyclic alkenyl group or alkynyl group having 2 to 12 carbon atoms, or an aromatic group having 4 to 20 carbon atoms, $R^{101d}$, $R^{101e}$, $R^{101f}$, and $R^{101g}$ optionally having one or more selected from an ether group, a carbonyl group, an ester group, a hydroxy group, a carboxy group, an amino group, a nitro group, a sulfonyl group, a sulfinyl group, a halogen atom, and a sulfur atom. $R^{101d}$ and $R^{101e}$, or $R^{101d}$, $R^{101e}$, and $R^{101f}$ optionally form a ring together with a nitrogen atom bonded to $R^{101d}$ and $R^{101e}$, or $R^{101d}$, $R^{101e}$, and $R^{101f}$ and when a ring is formed, $R^{101d}$ and $R^{101e}$, or $R^{101d}$, $R^{101e}$, and $R^{101f}$ form an alkylene group having 3 to 10 carbon atoms or a heteroaromatic ring having, in the ring, the nitrogen atom in the general formula (3).

Specific examples of the ammonium ion represented by the general formula (3) include the following.

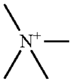
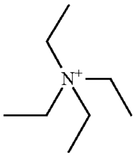
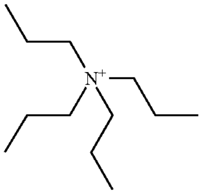
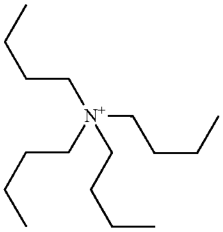
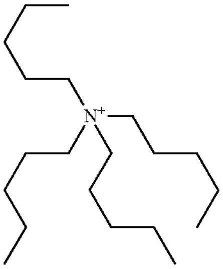
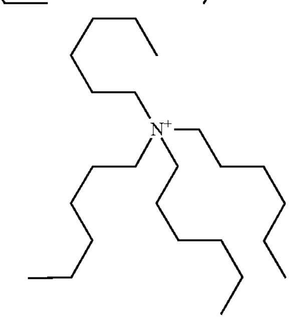
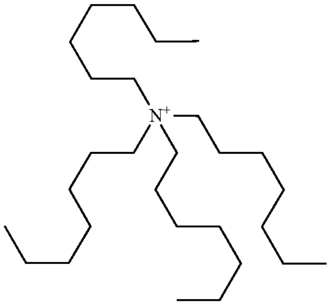
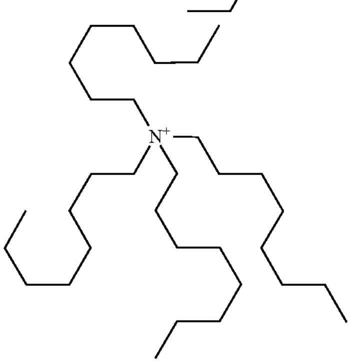

-continued

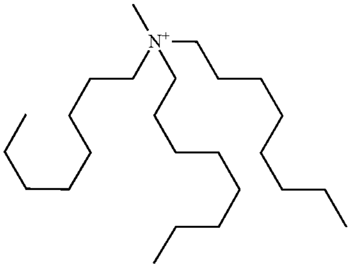
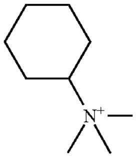
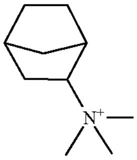
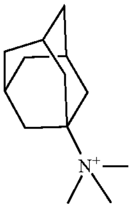
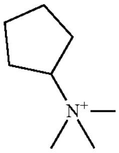
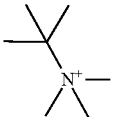
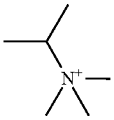
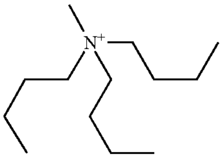
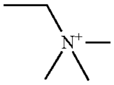
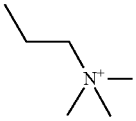
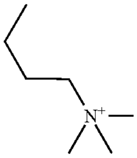
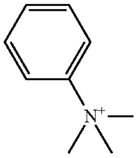
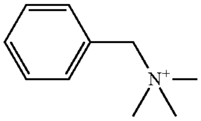
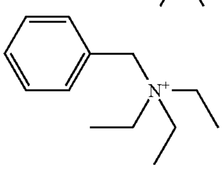
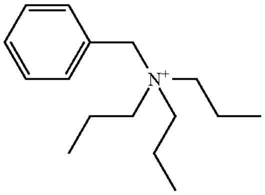
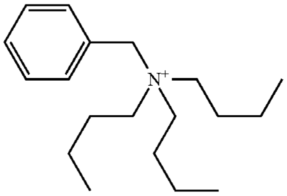
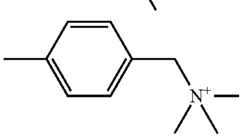
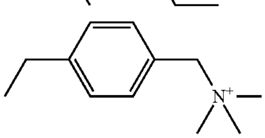
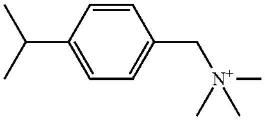
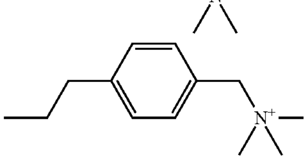
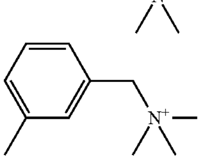
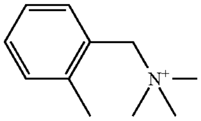
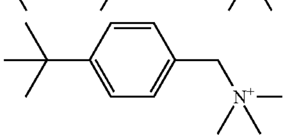

-continued
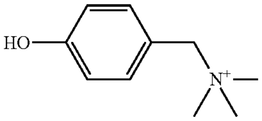
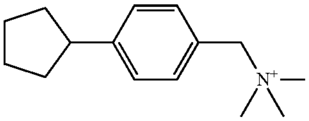
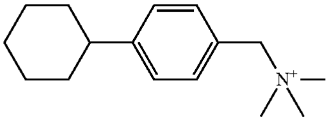
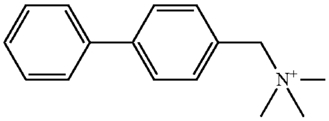
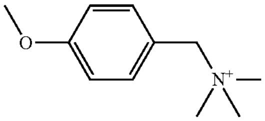
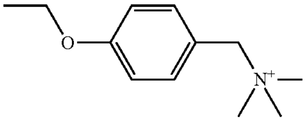
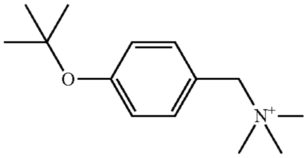
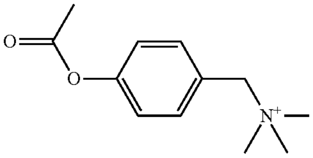
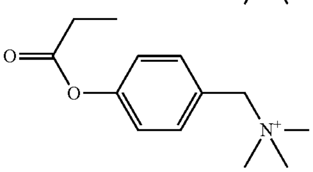
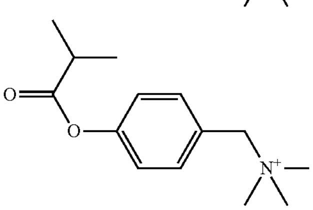
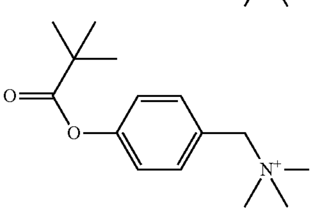
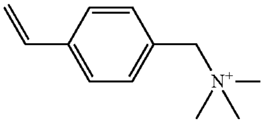
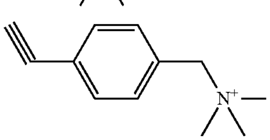
-continued
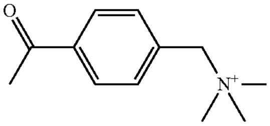
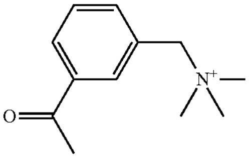
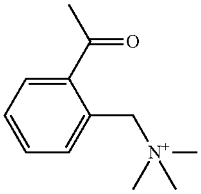
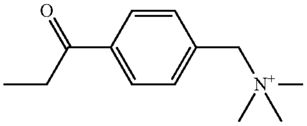
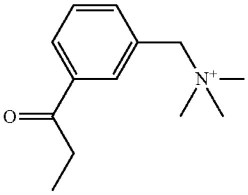
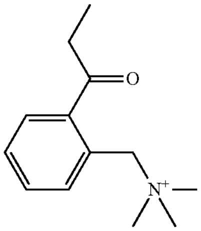
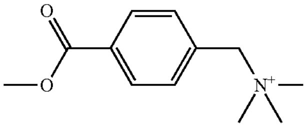
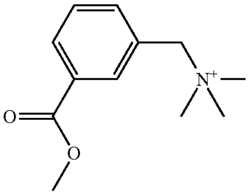
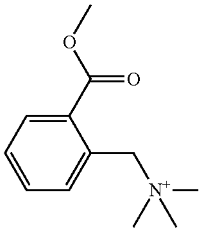
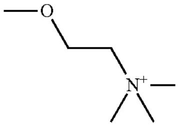
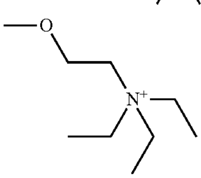
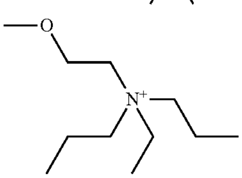
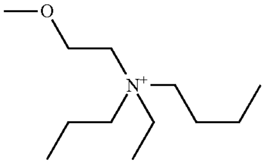
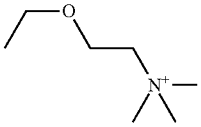
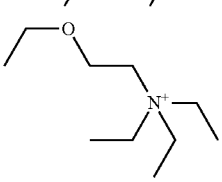
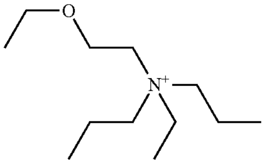
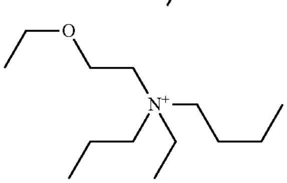
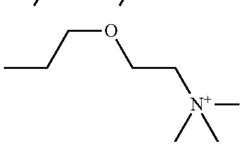

-continued
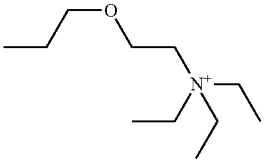
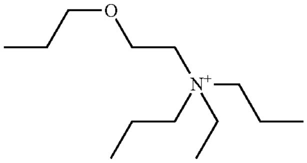
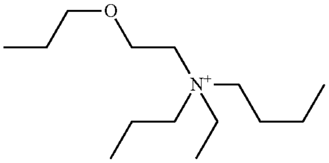
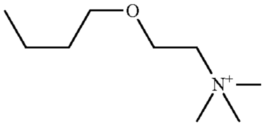
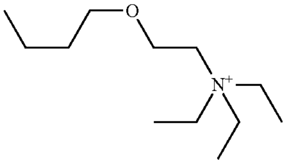
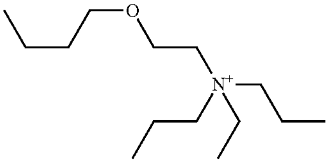
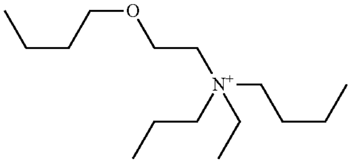
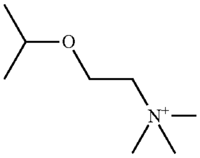
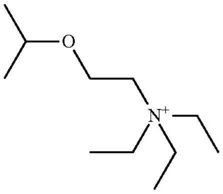
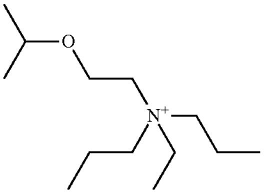
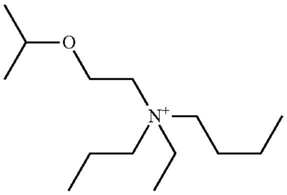
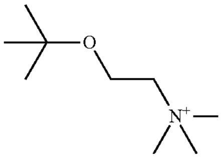
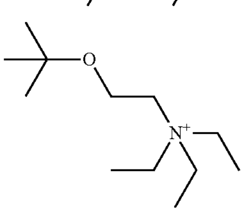
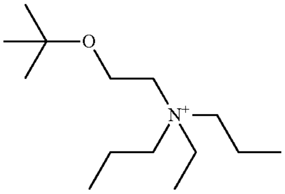
-continued
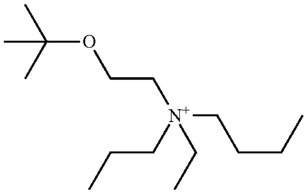
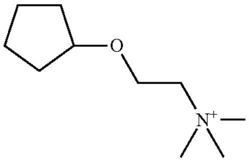
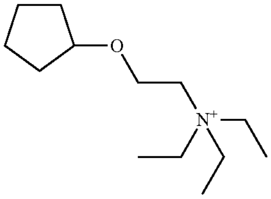
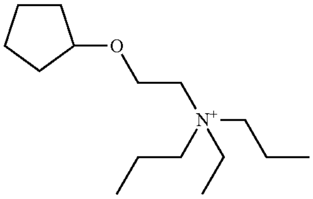
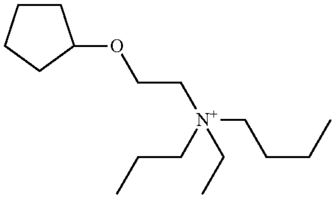
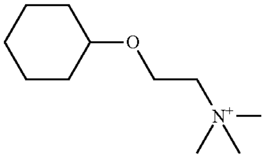
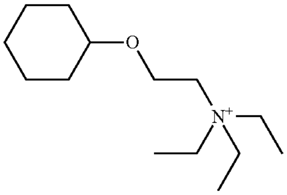
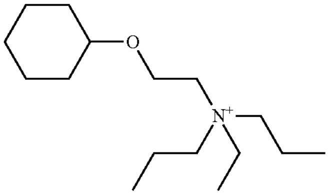
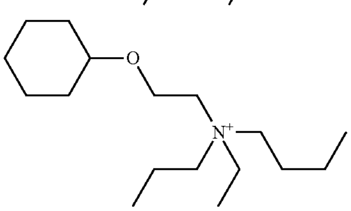
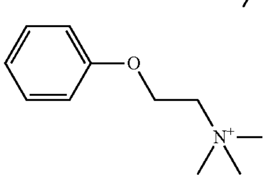
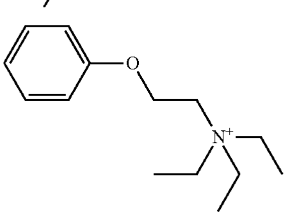

-continued
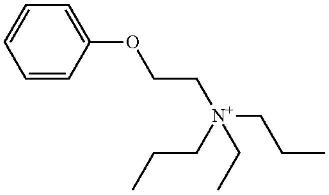
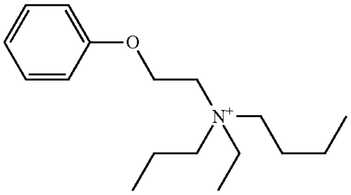
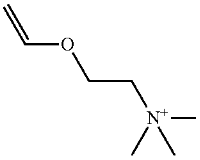
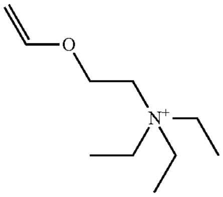
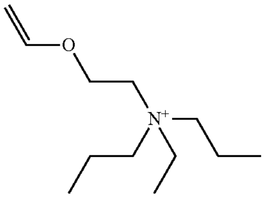
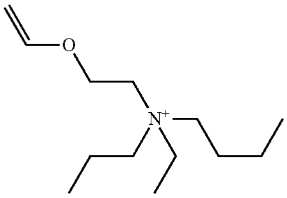
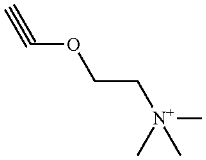
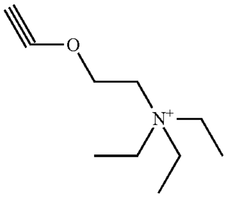
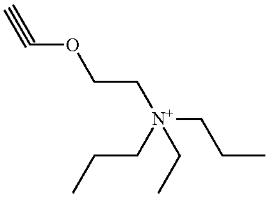
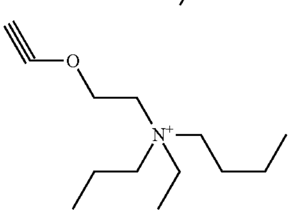
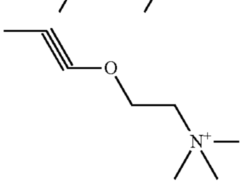
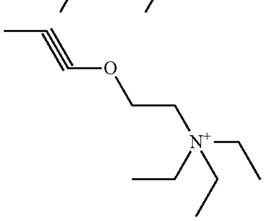
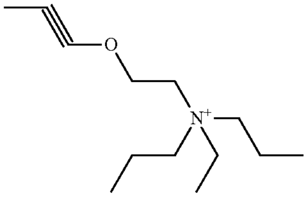
-continued
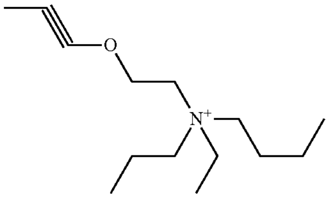
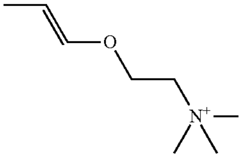
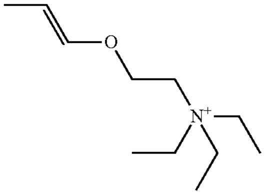
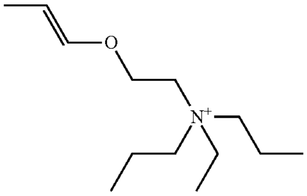
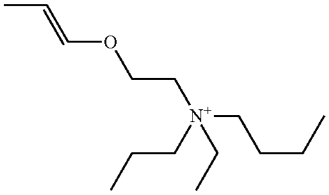
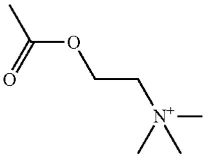
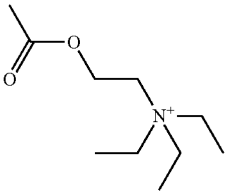
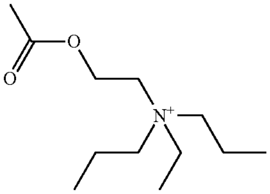
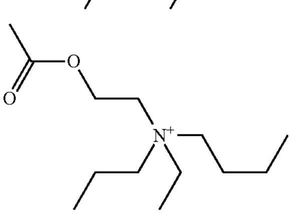
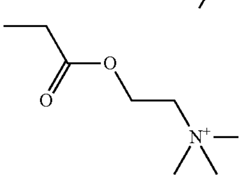
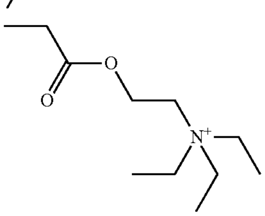

-continued
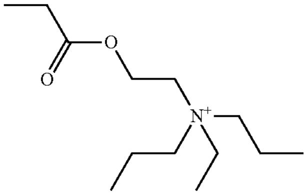
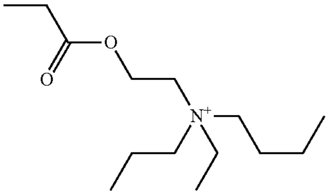
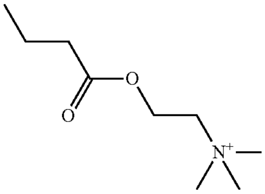
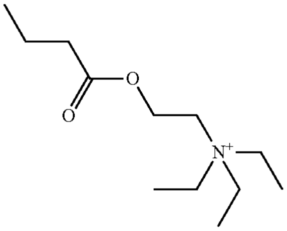
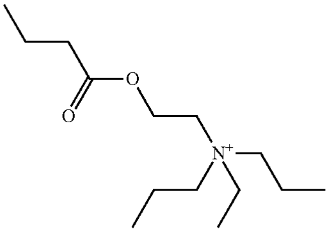
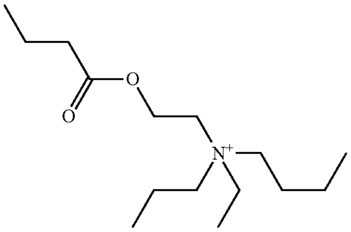
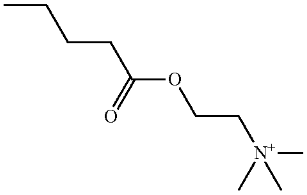
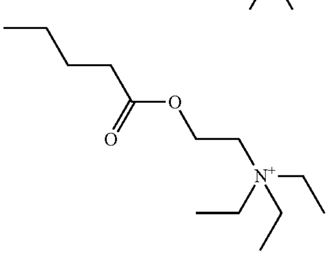
-continued
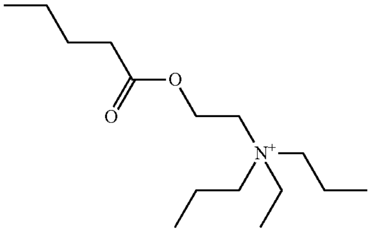
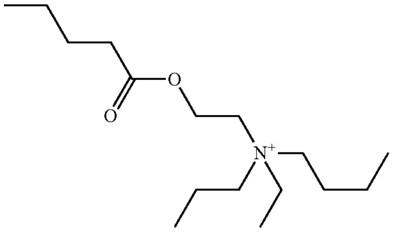
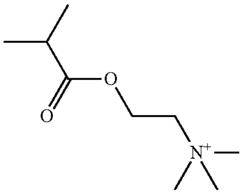
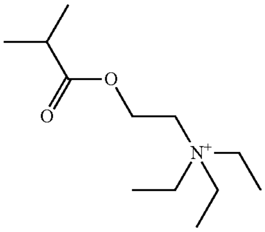
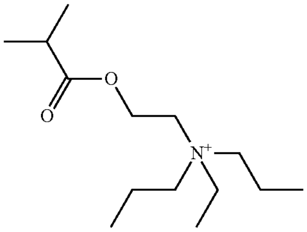
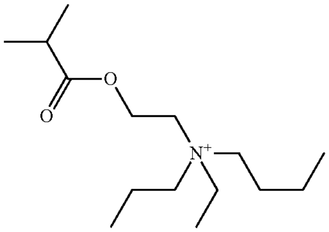
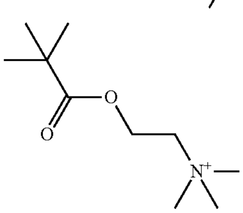
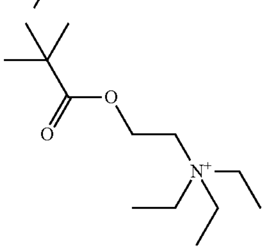
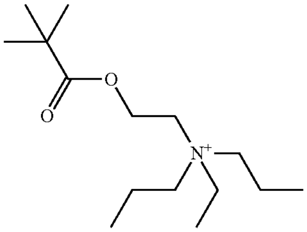

-continued
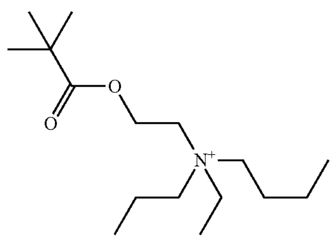
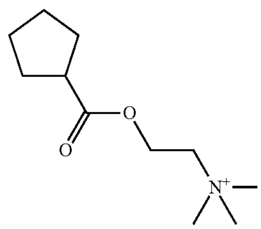
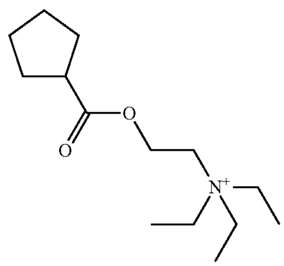
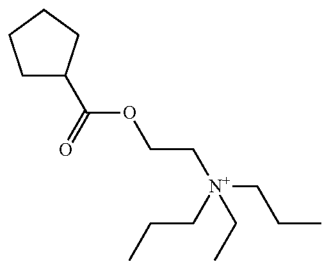
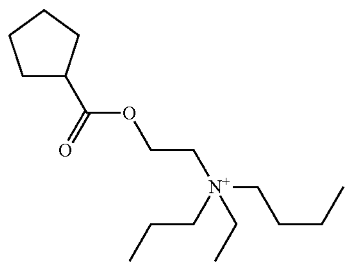
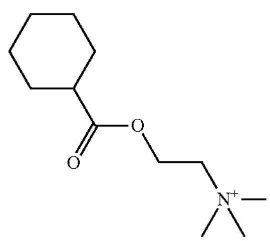
-continued
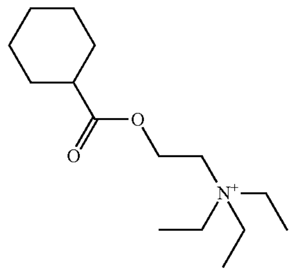
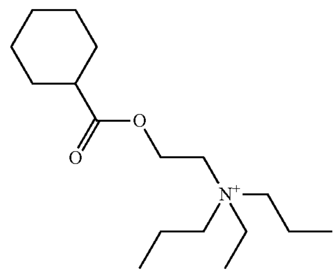
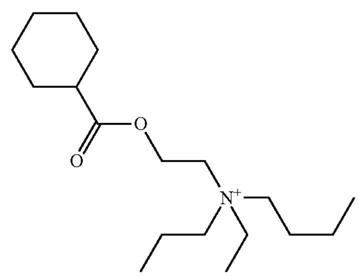
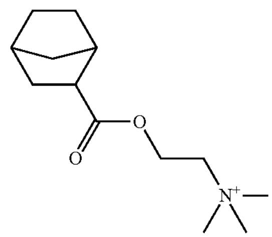
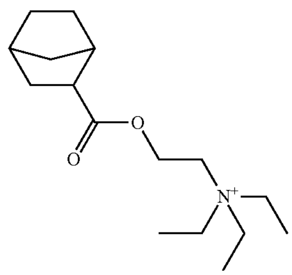
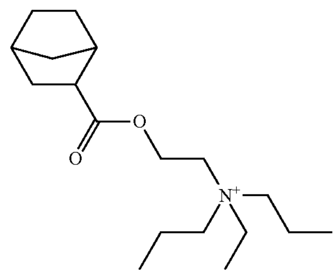

-continued
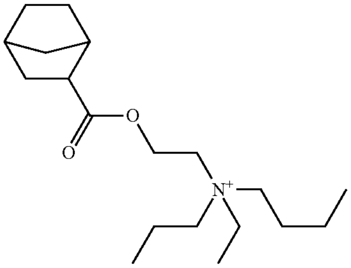
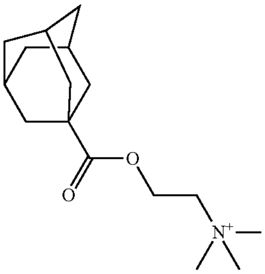
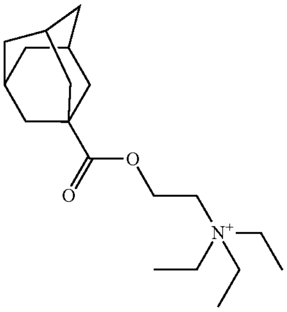
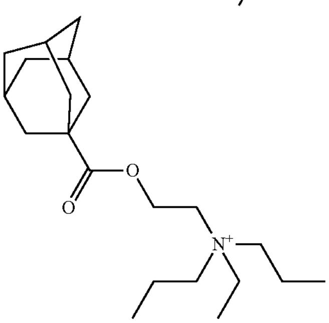
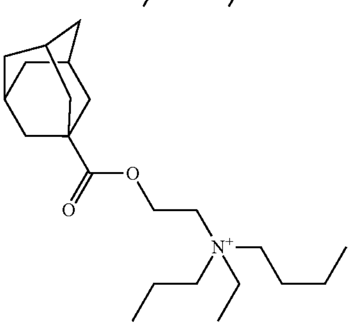
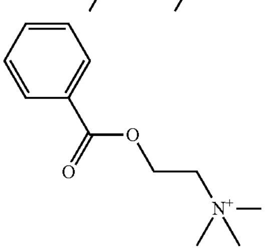
-continued
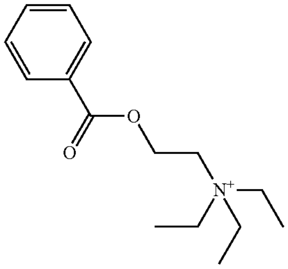
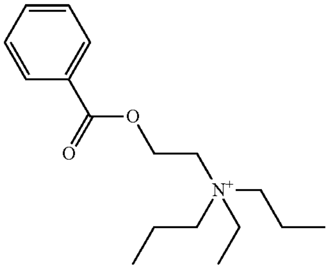
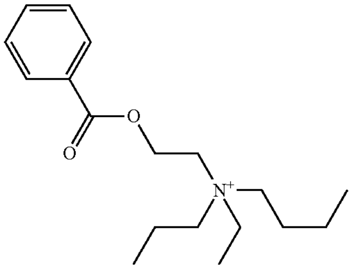
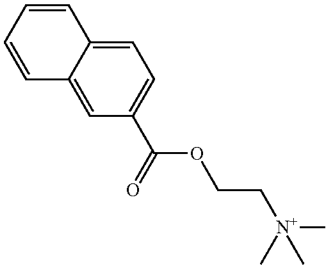
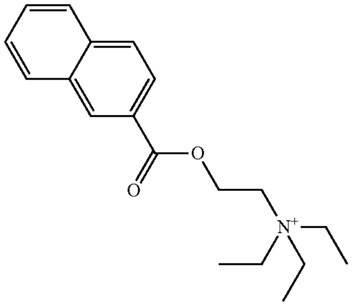
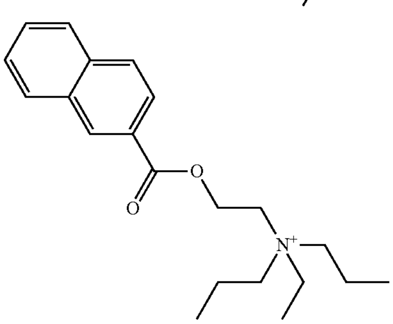

-continued
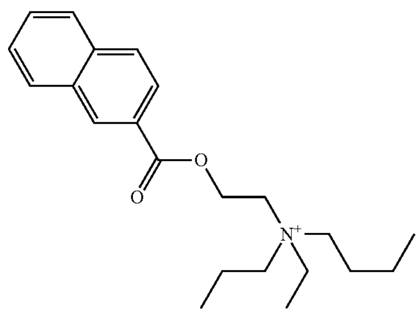
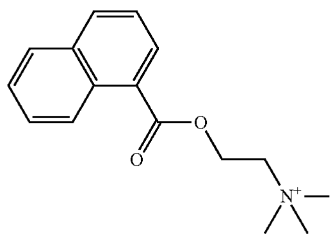
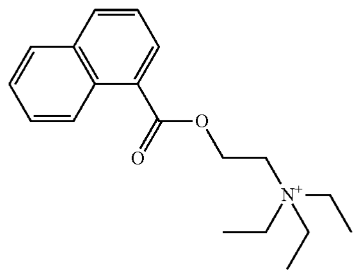
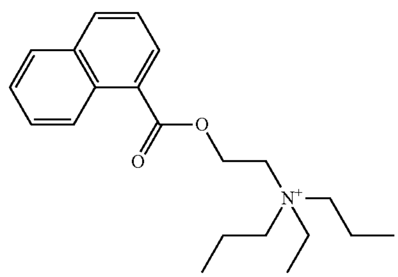
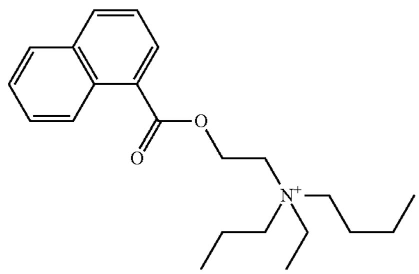
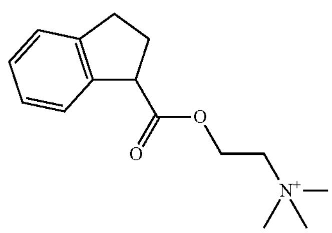
-continued
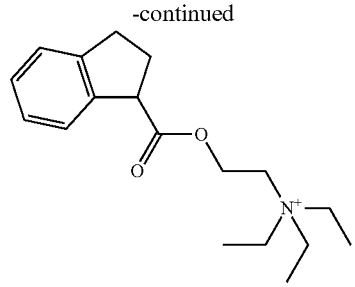
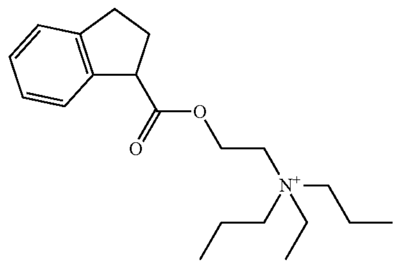
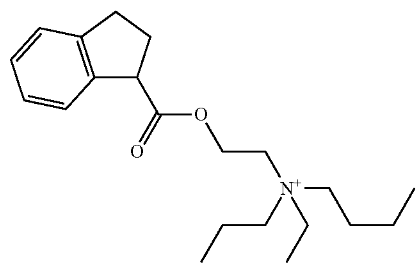
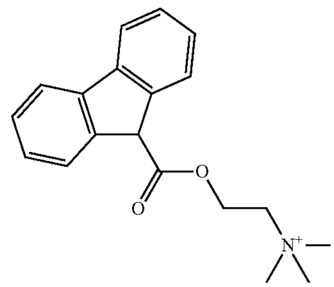
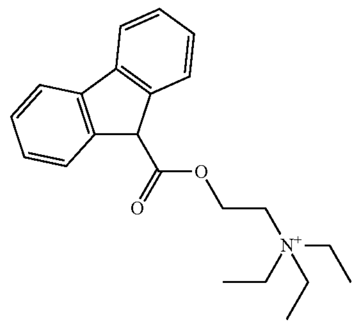
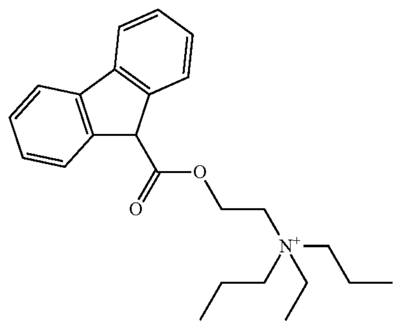

-continued
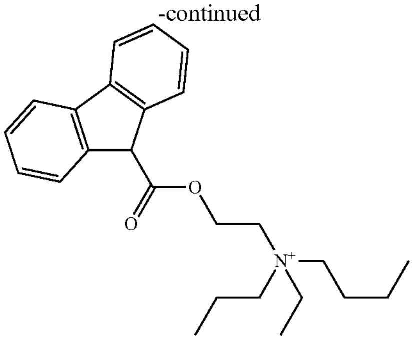
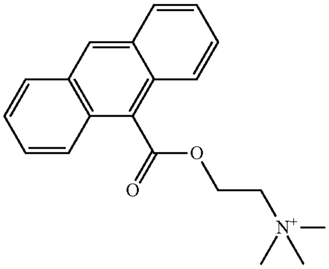
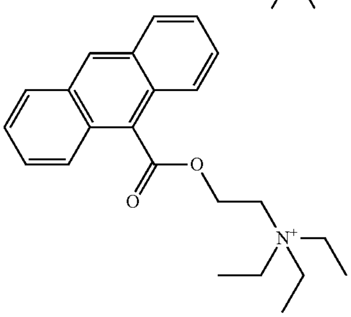
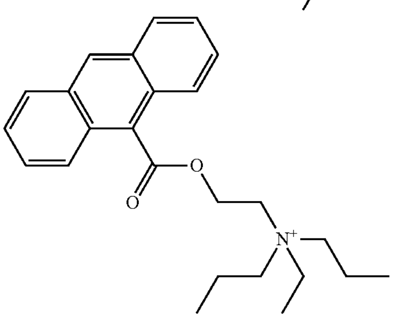
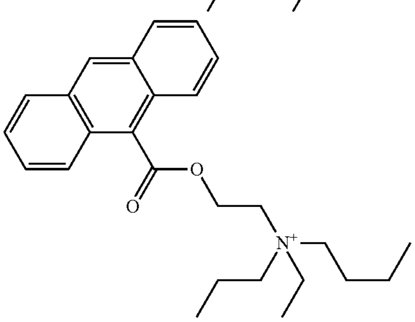
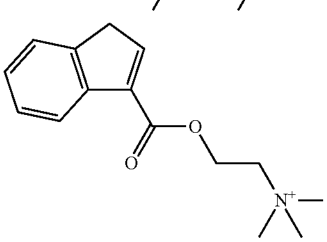
-continued
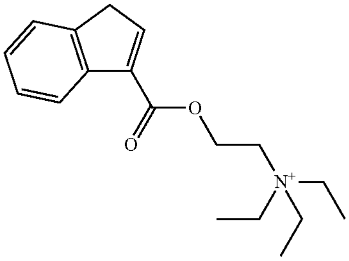
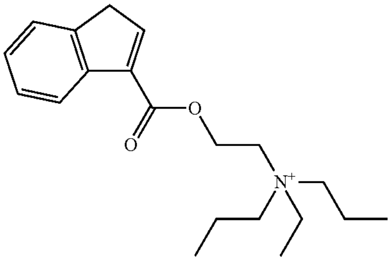
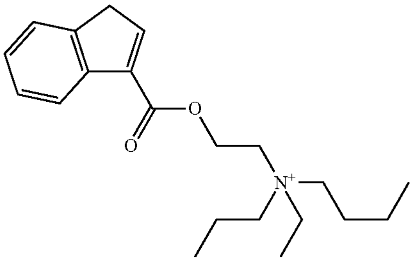
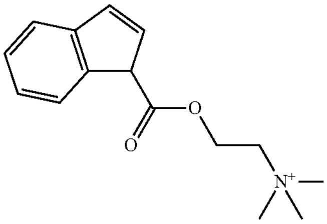
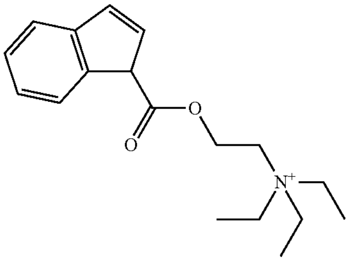
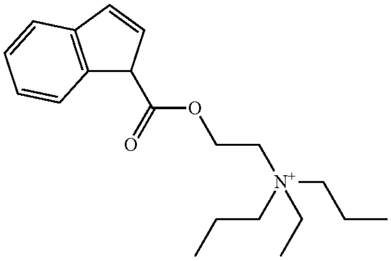

-continued
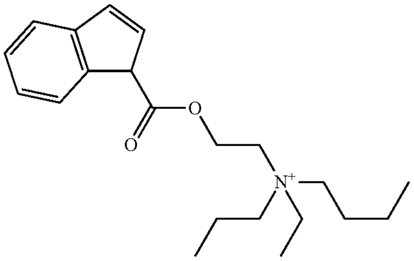
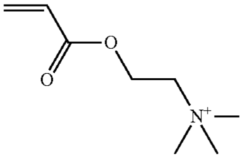
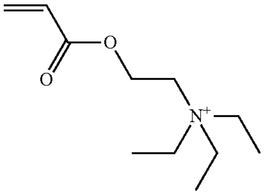
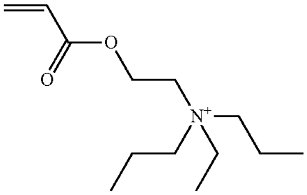
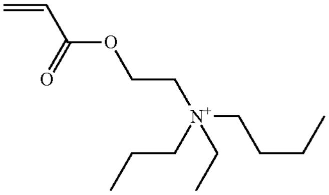
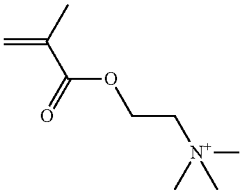
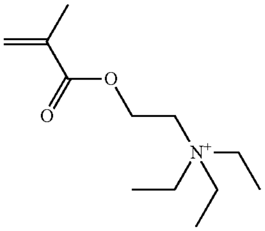
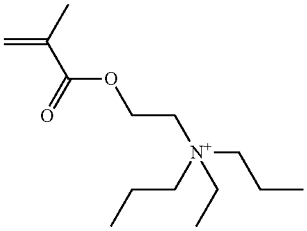
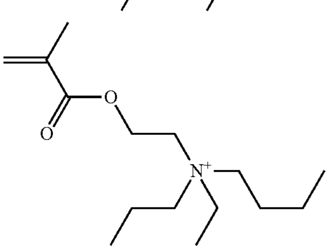
-continued
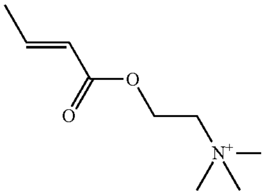
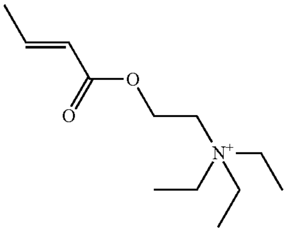
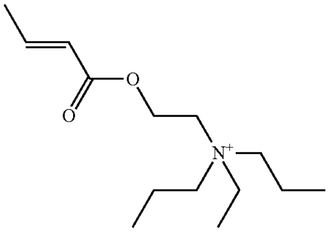
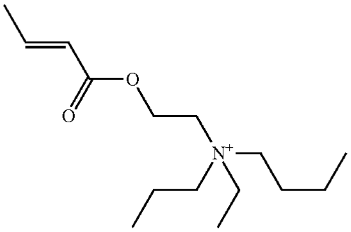
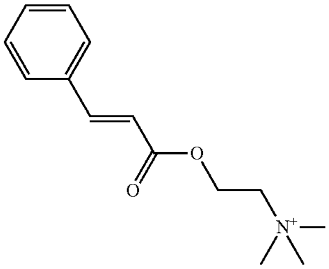
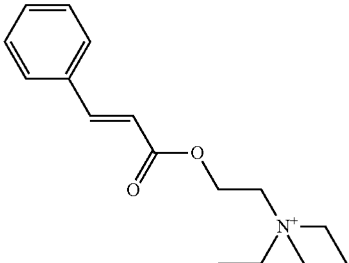
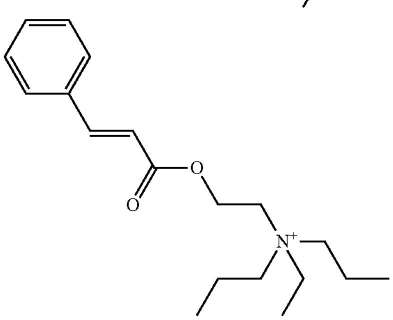

-continued
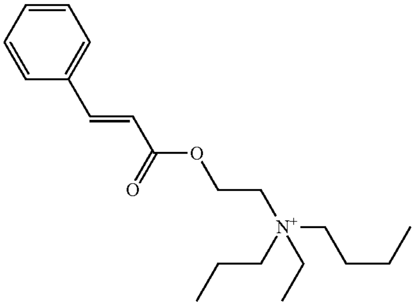
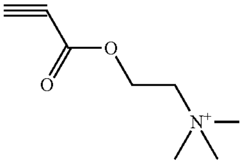
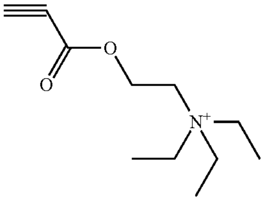
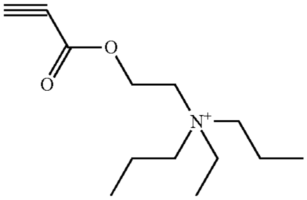
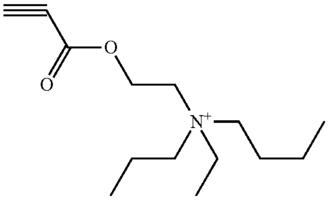
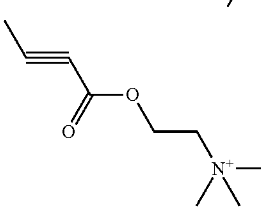
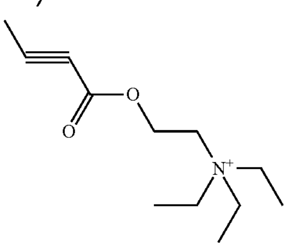
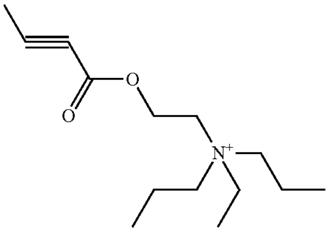
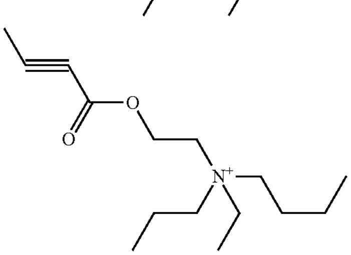
-continued
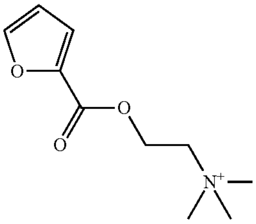
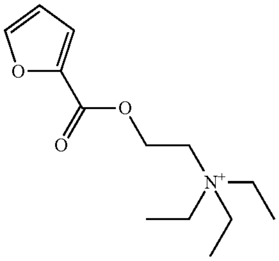
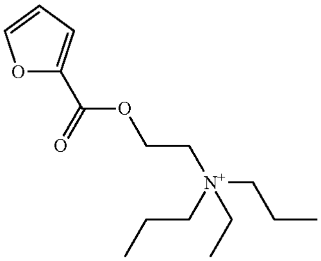
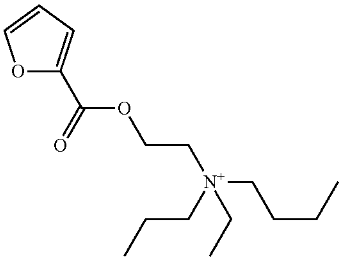
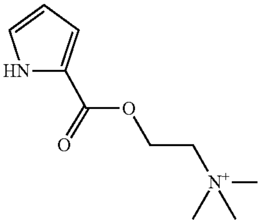
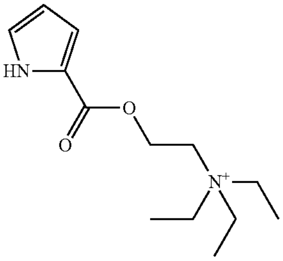
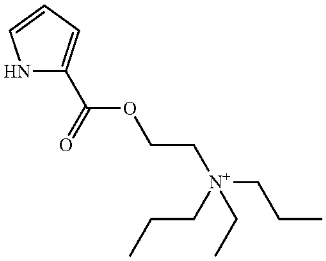
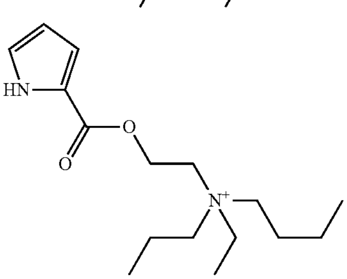

-continued
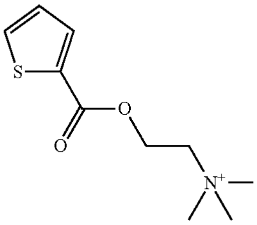
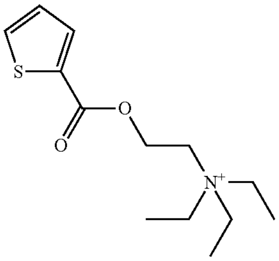
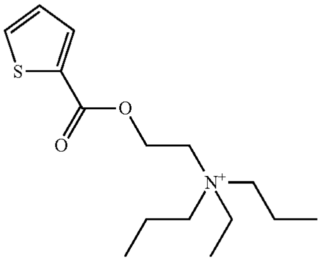
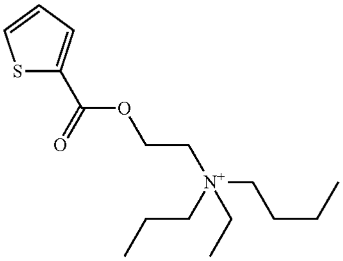
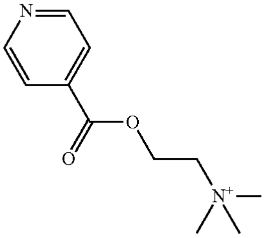
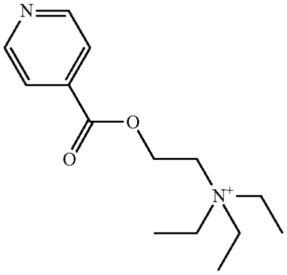
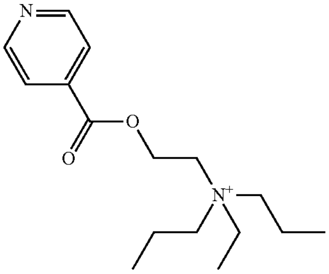
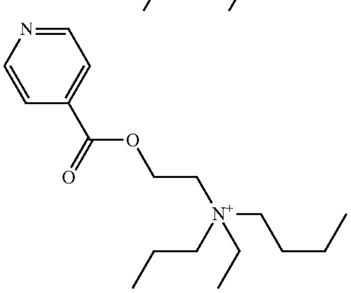
-continued
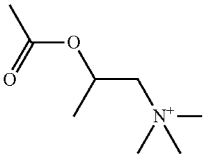
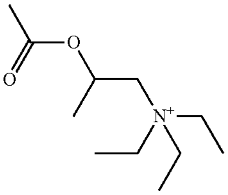
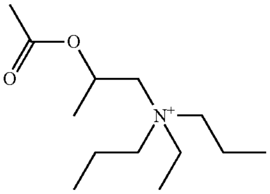
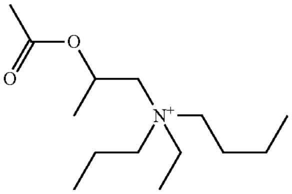
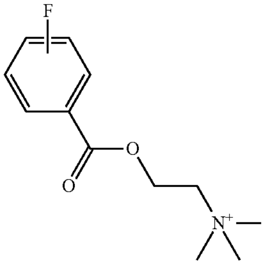
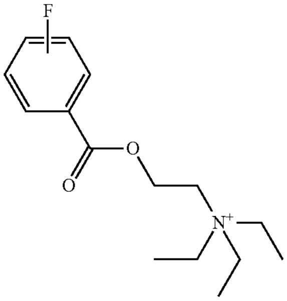
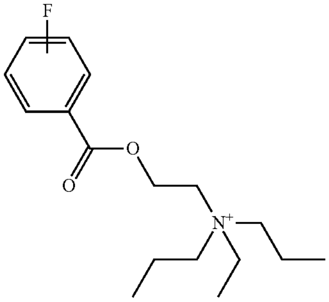
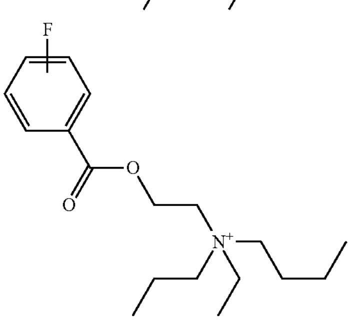
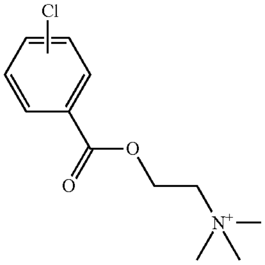
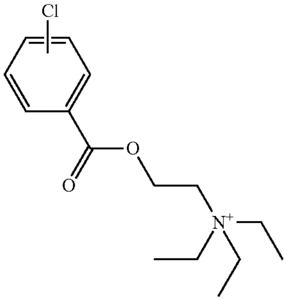

-continued
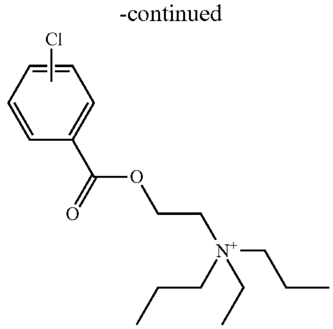
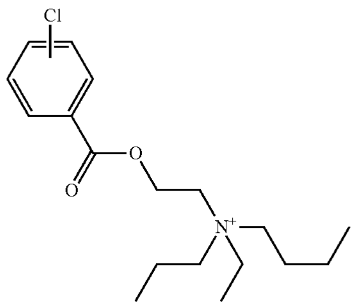
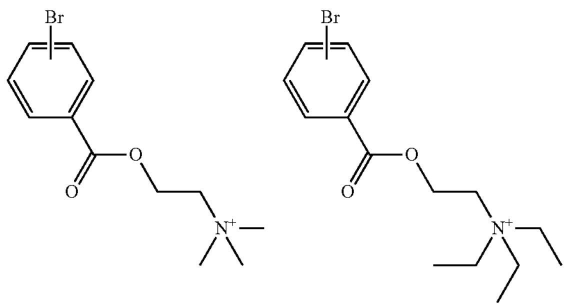
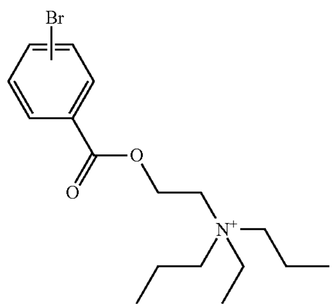
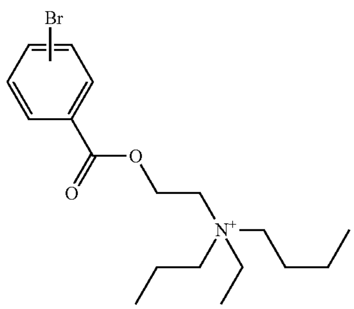
-continued
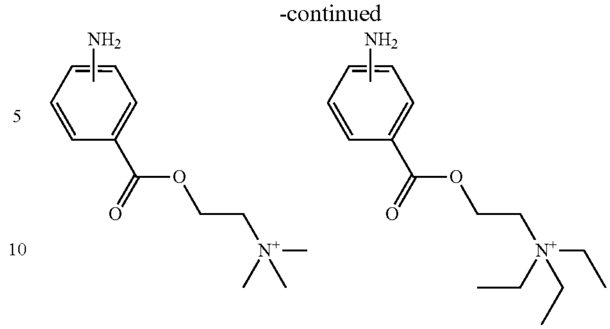
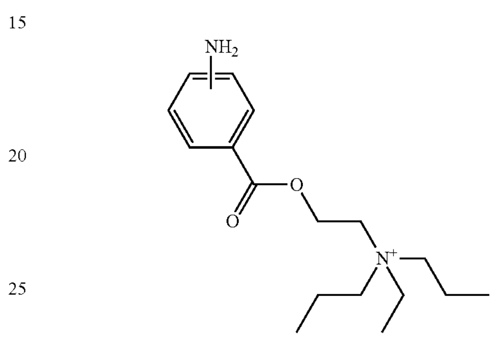
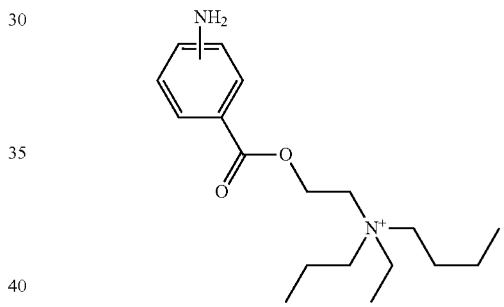
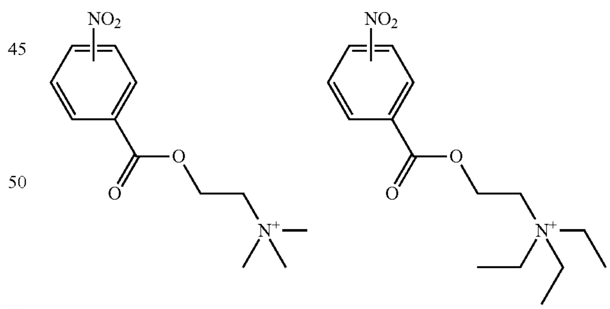
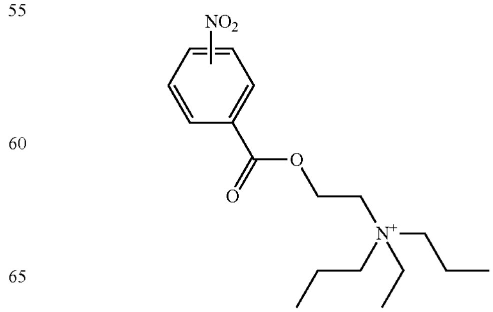

-continued
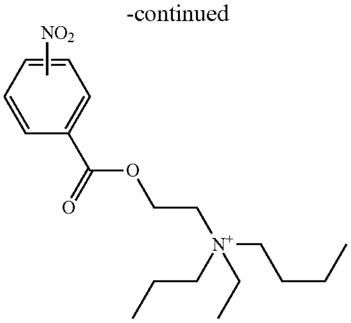
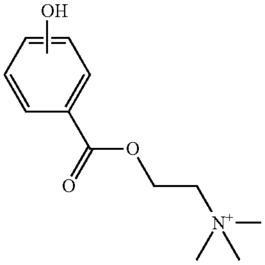
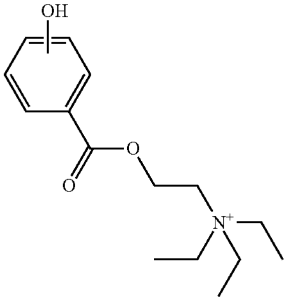
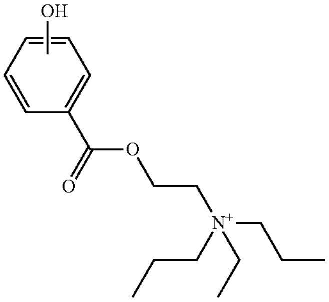
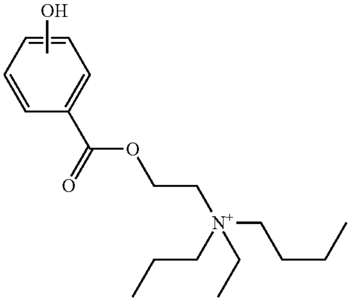
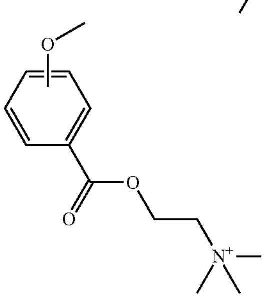
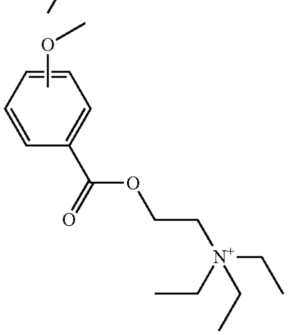
-continued
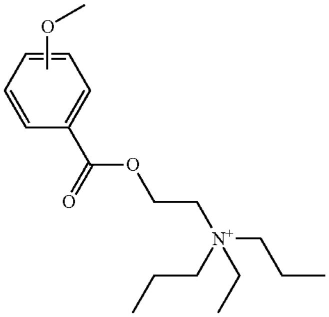
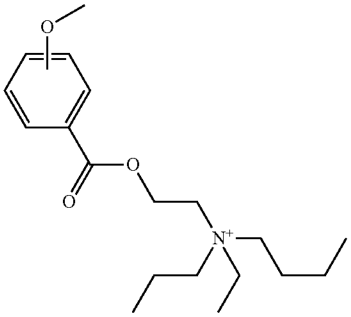
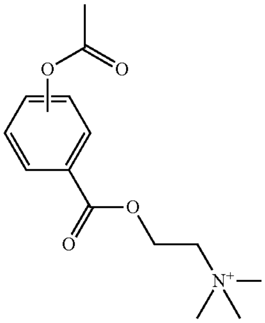
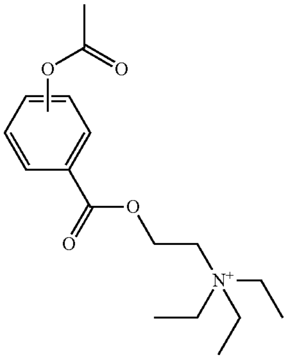
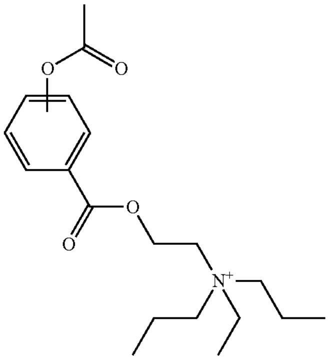
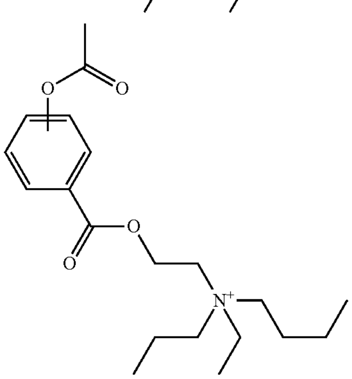

-continued
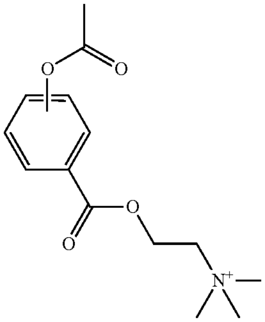
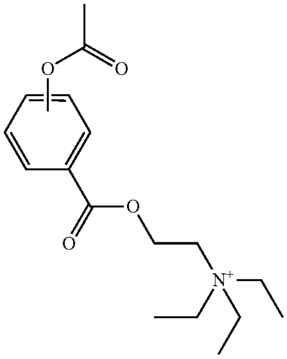
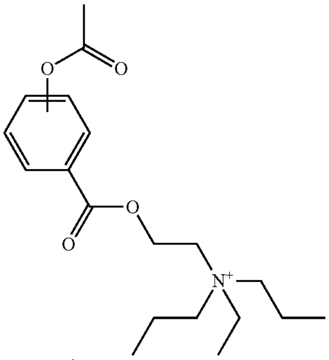
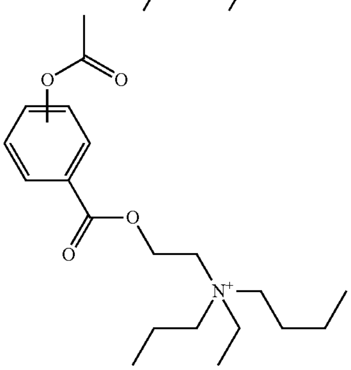
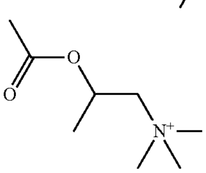
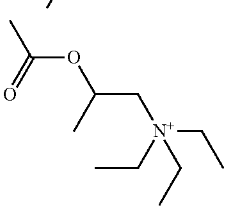
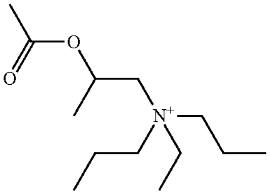
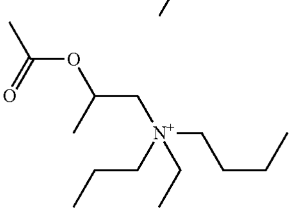
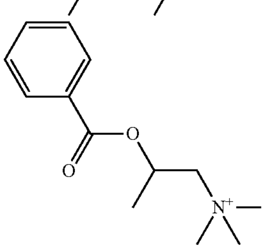
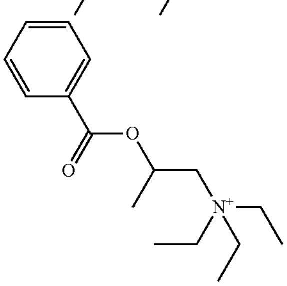
-continued
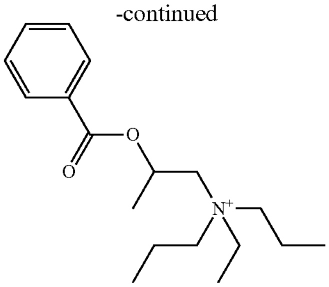
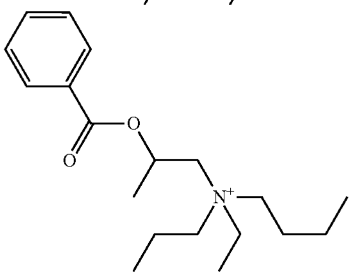
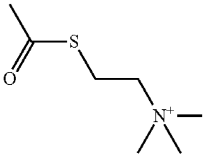
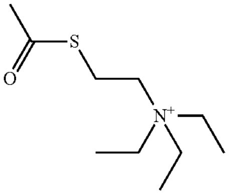
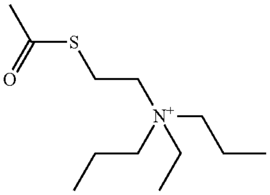
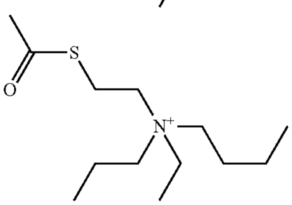
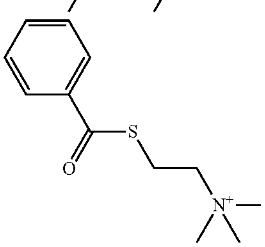
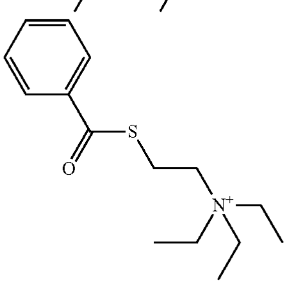
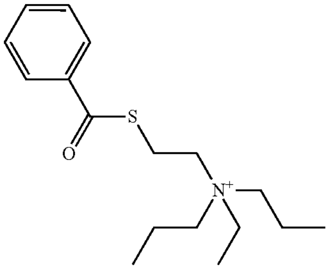
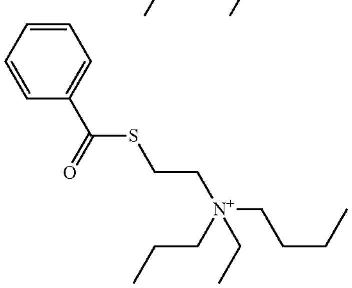

-continued
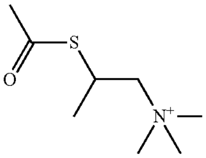
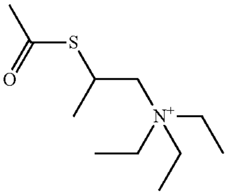
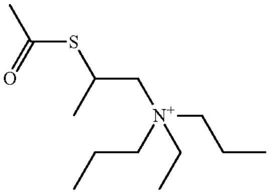
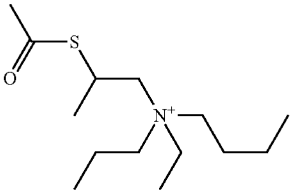
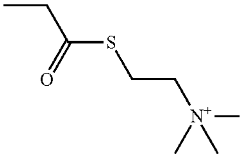
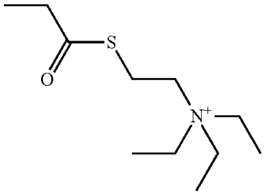
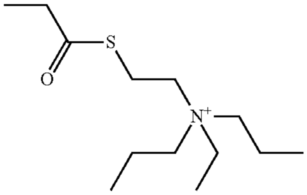
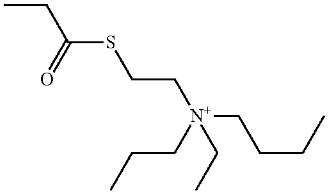
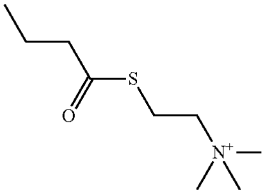
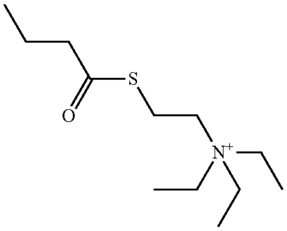
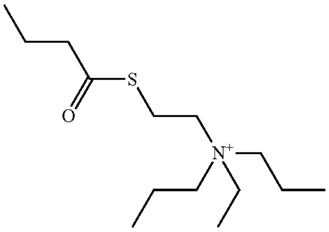
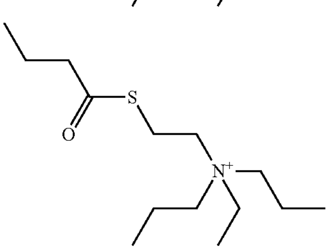
-continued
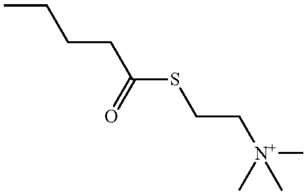
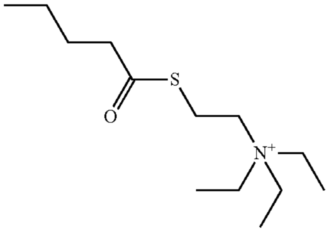
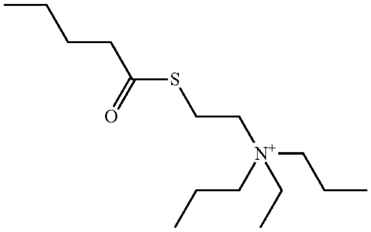
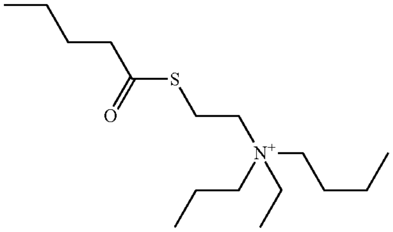
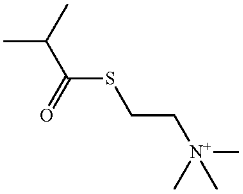
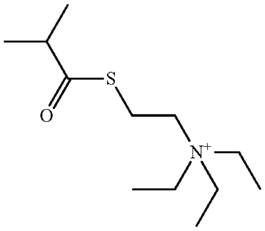
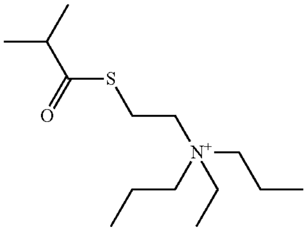
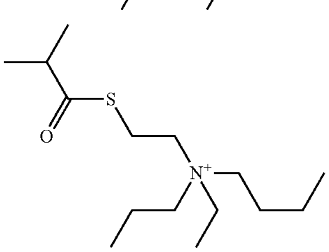

-continued
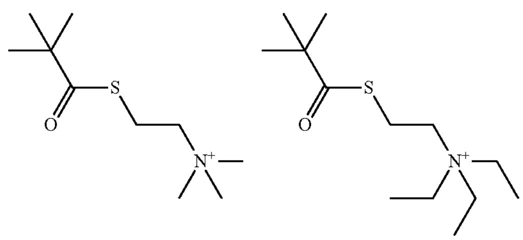
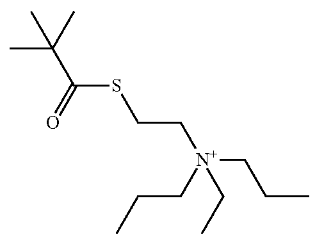
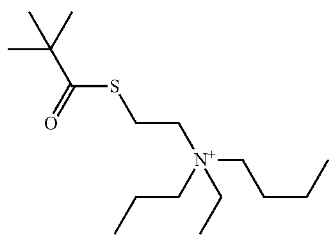
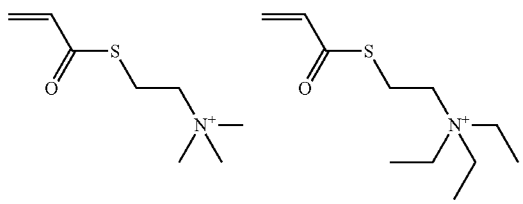
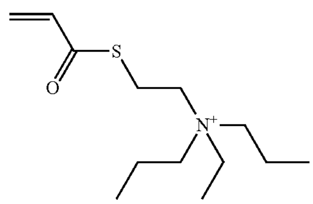
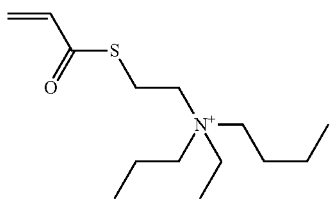
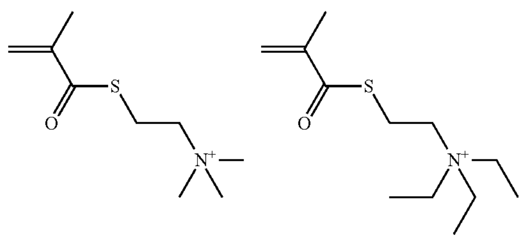
-continued
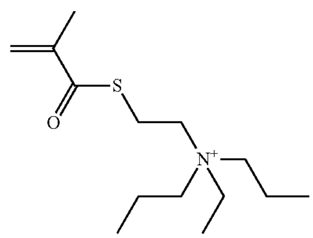
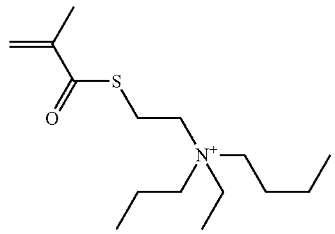
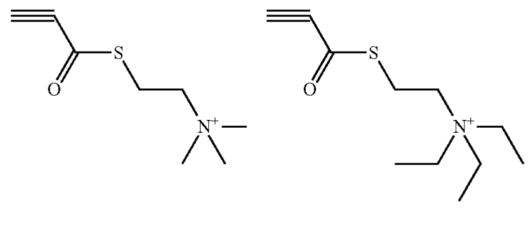
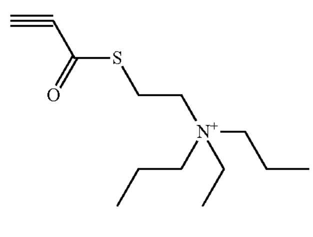
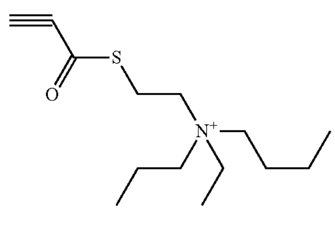
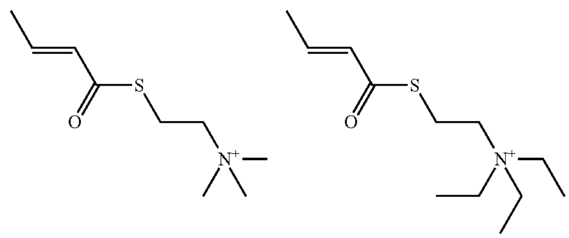
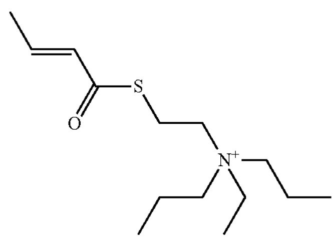

-continued
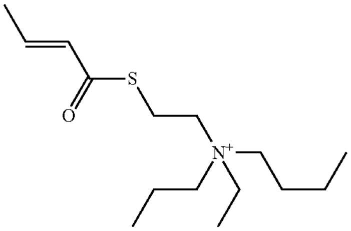
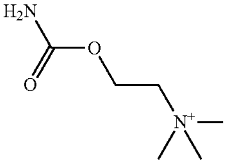
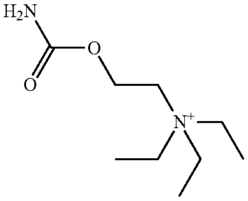
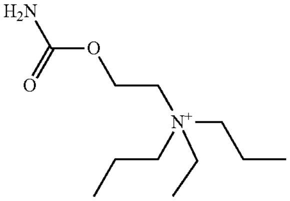
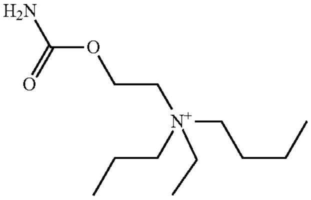
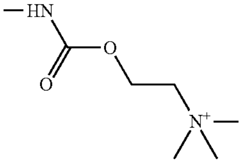
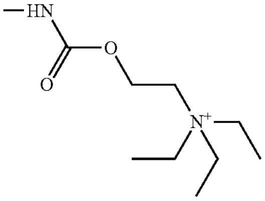
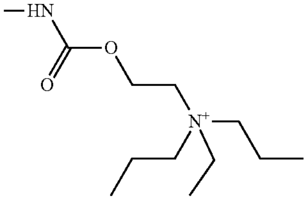
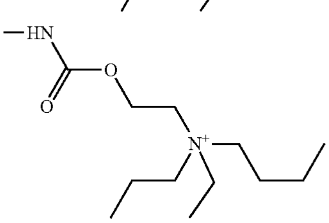
-continued
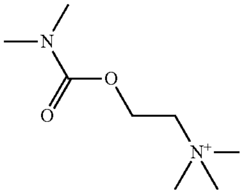
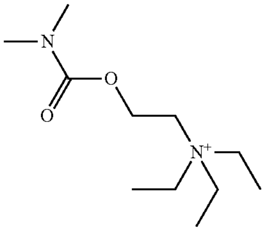
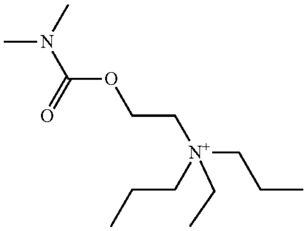
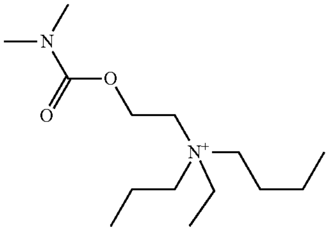
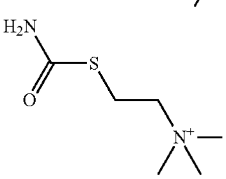
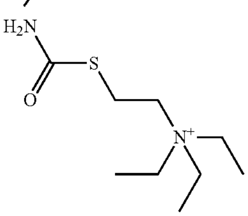
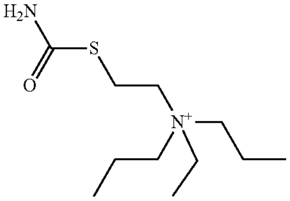
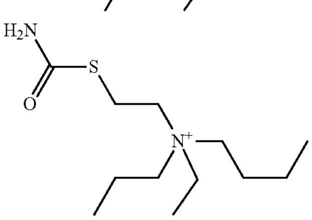
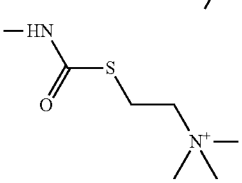
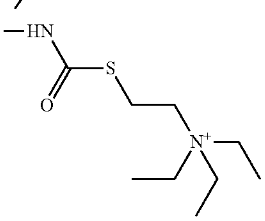
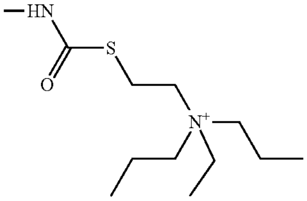

-continued
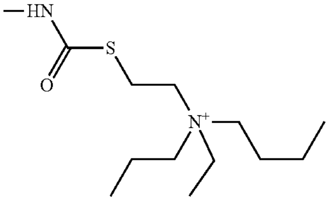
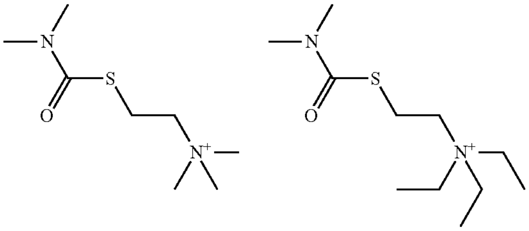
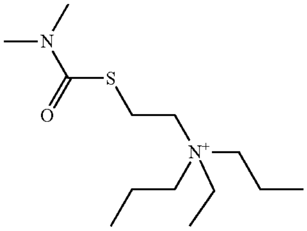
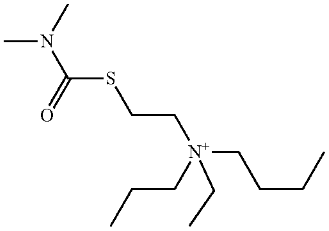
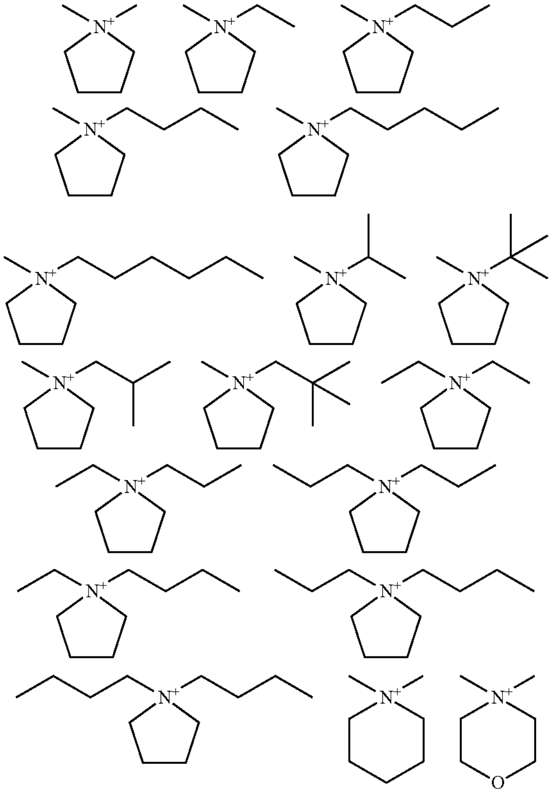
-continued
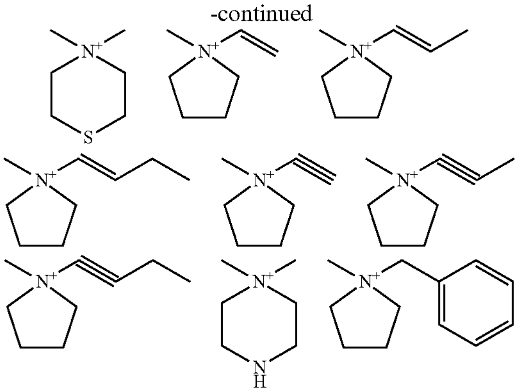
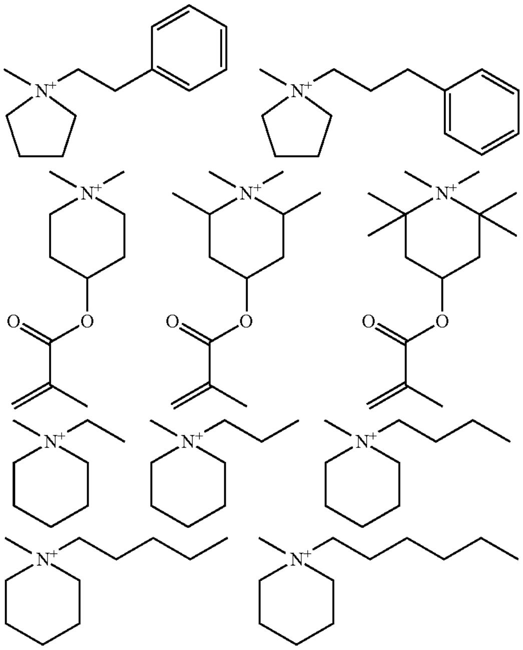
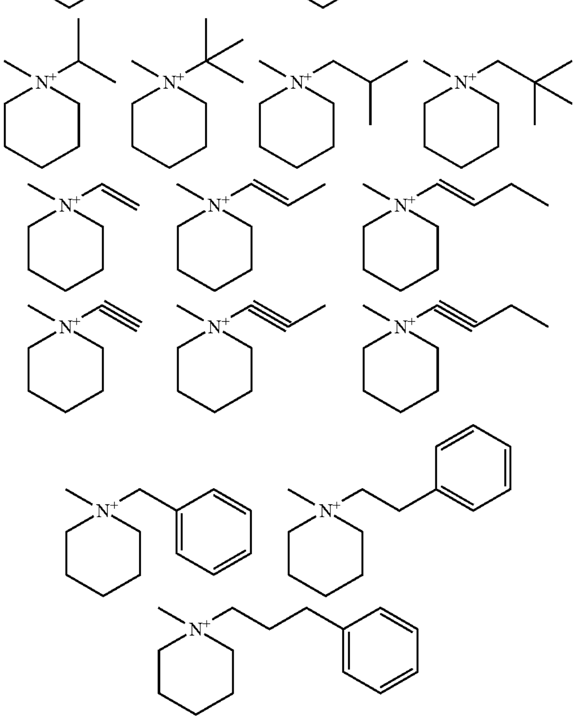

-continued
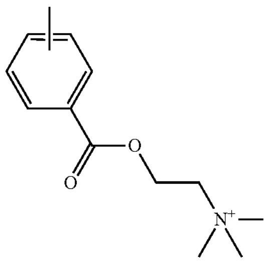
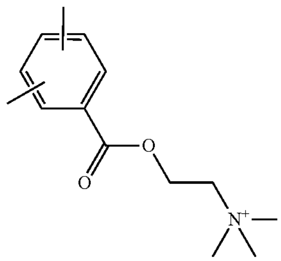
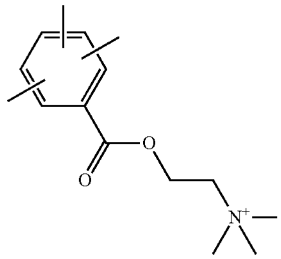
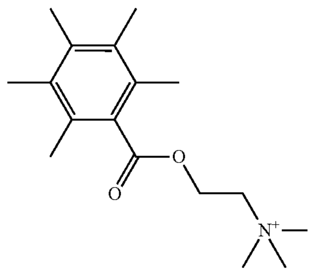
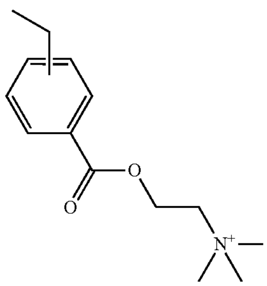
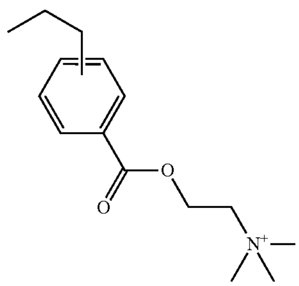
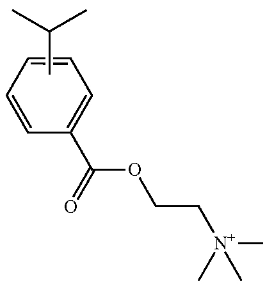
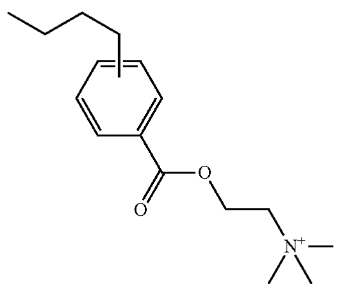
-continued
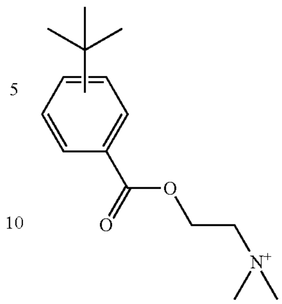
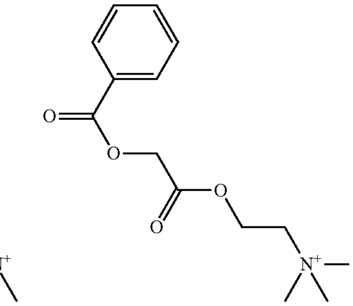
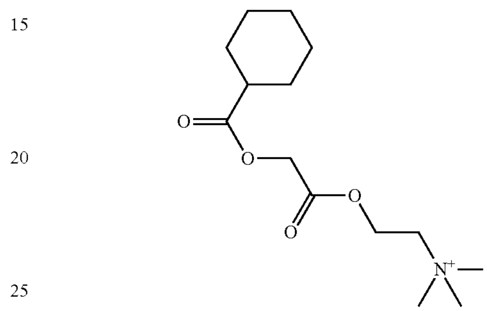
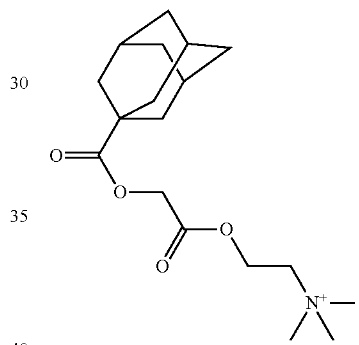
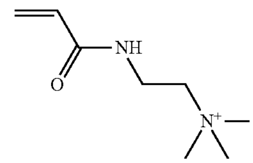
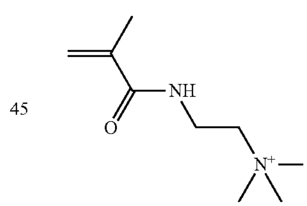
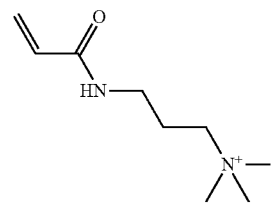
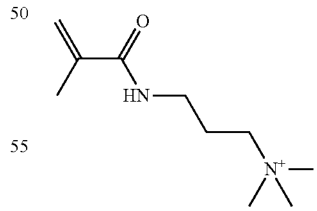
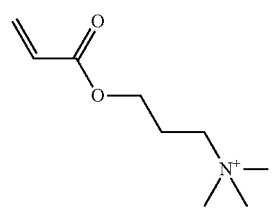
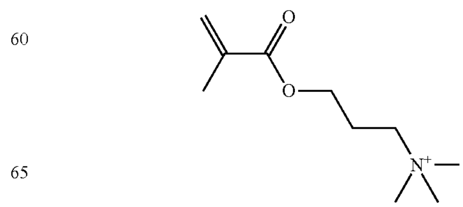

-continued
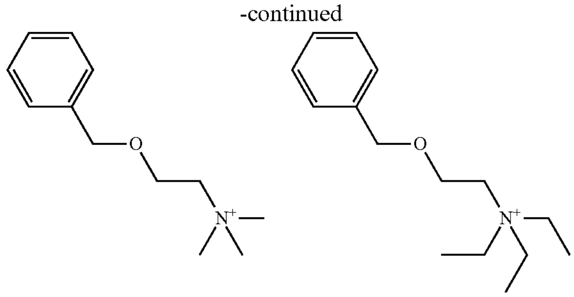
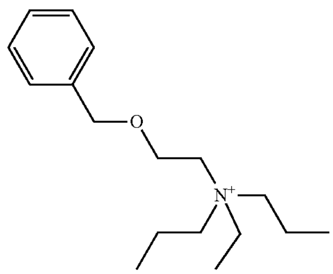
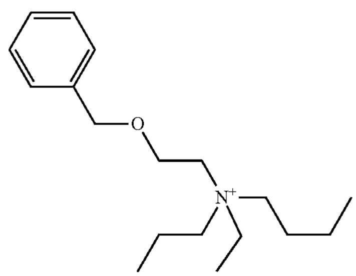
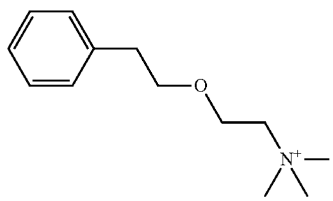
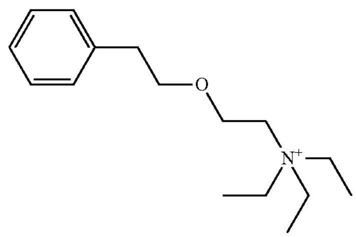
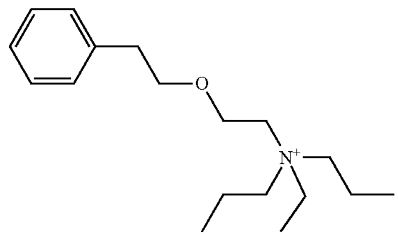
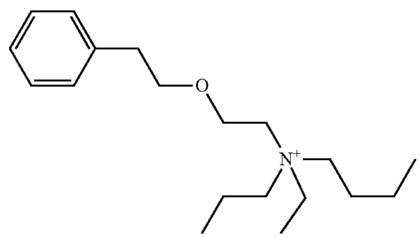
-continued
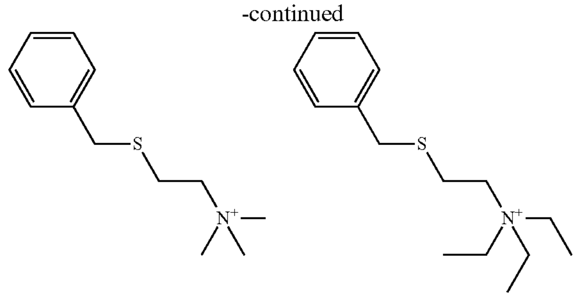
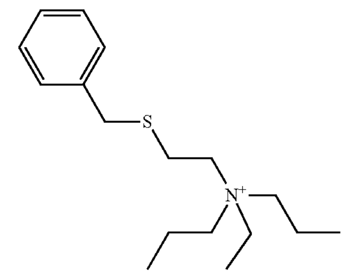
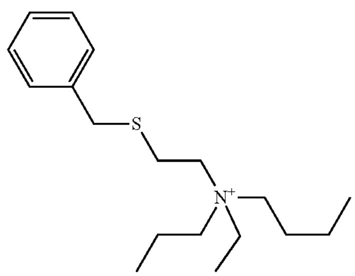
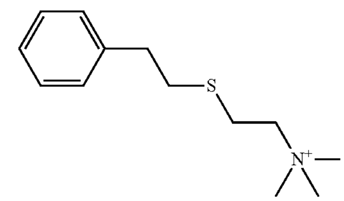
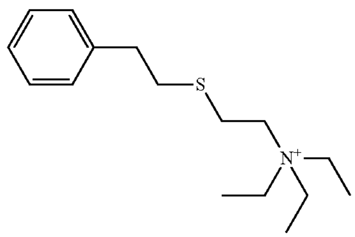
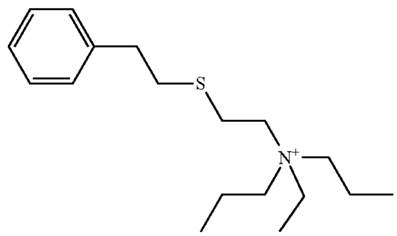
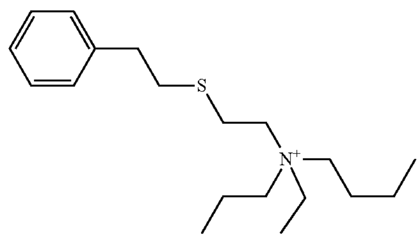

-continued
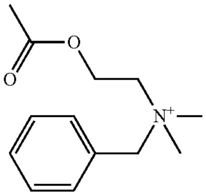
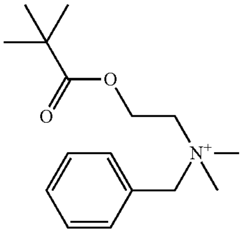
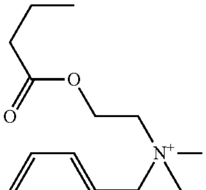
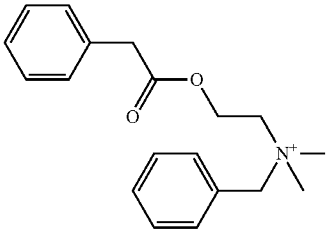
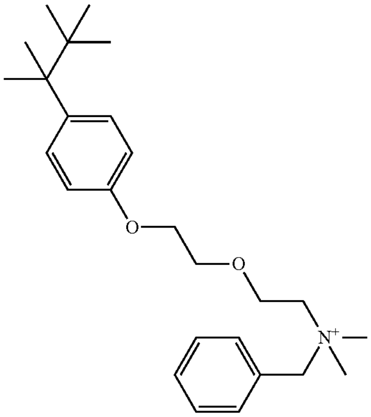
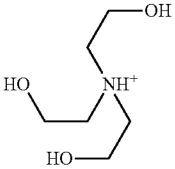
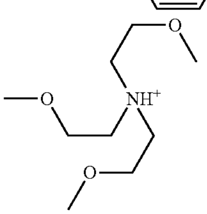
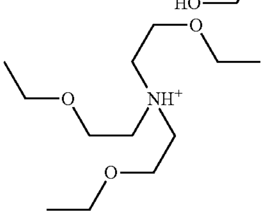
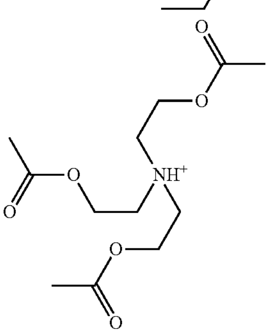
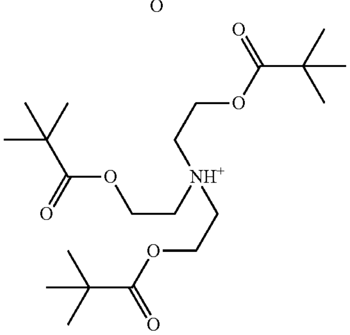
-continued
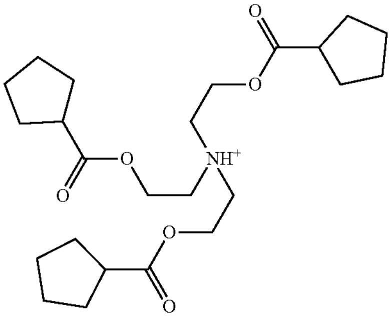
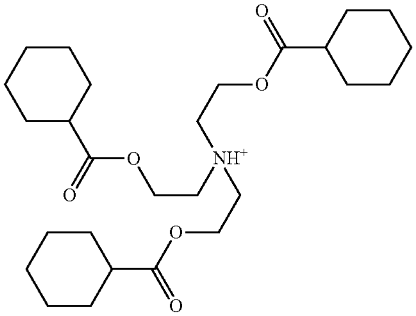
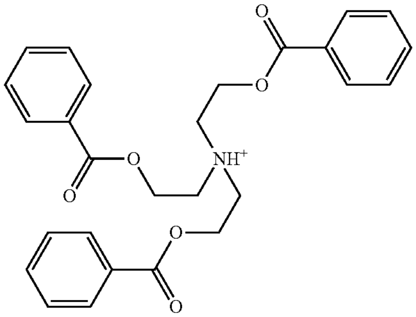
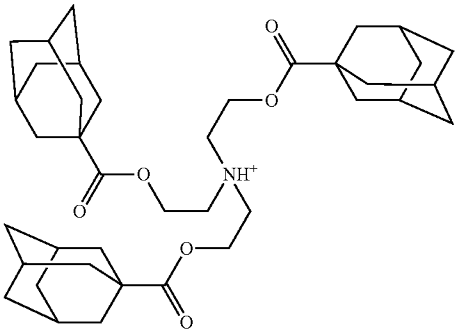
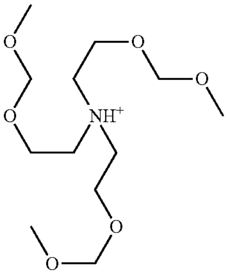
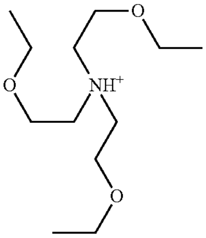

-continued
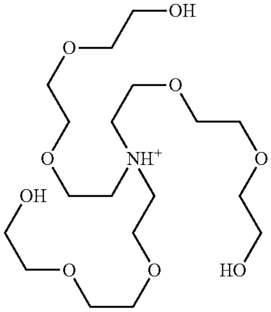
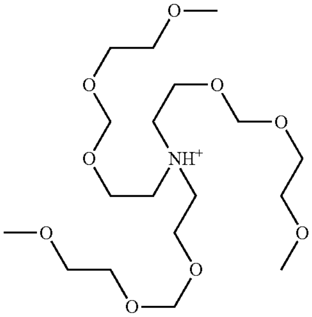
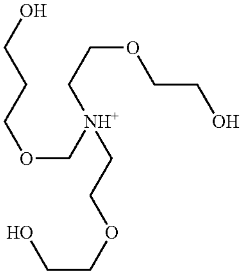
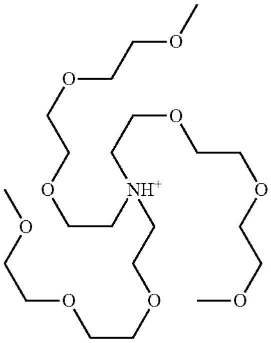
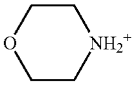
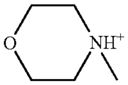
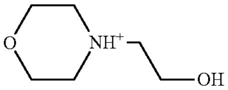
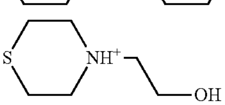
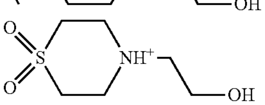
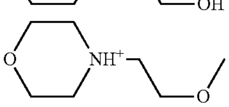
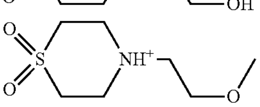
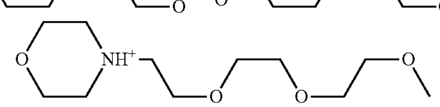
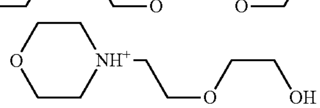
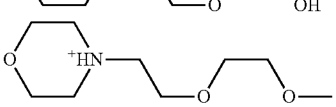
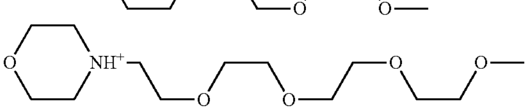
-continued
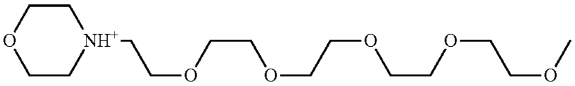
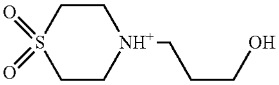
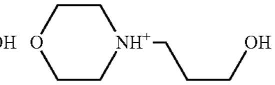
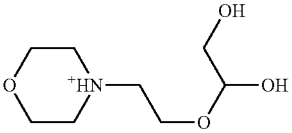
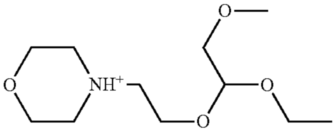
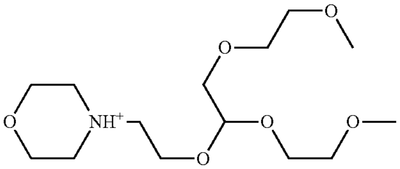
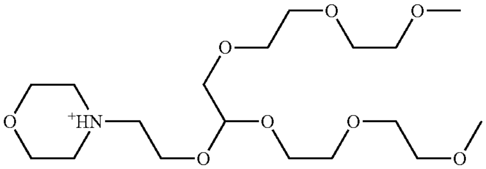
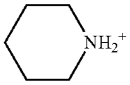
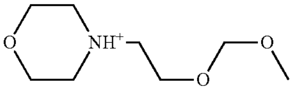
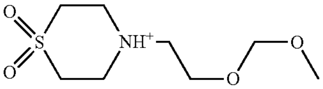
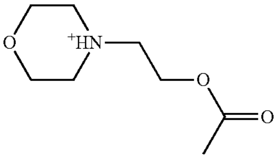
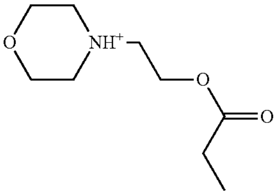
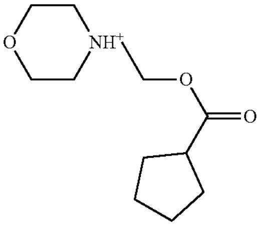
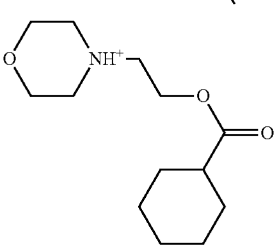
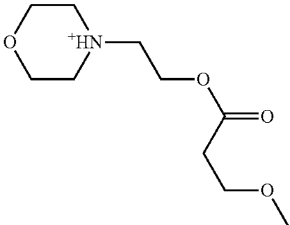

-continued
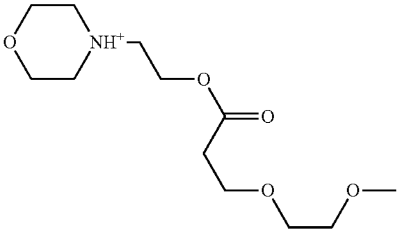
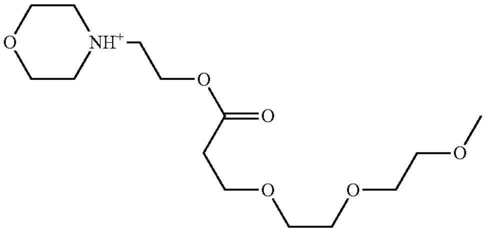
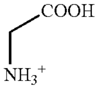
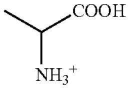
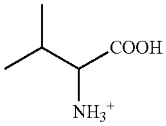
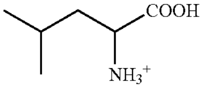
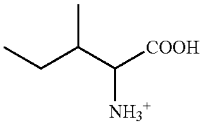
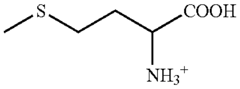
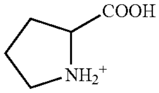
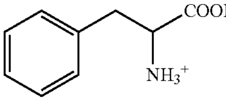
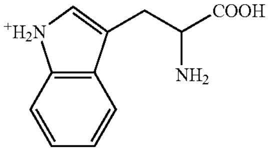
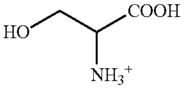
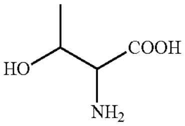
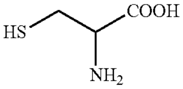
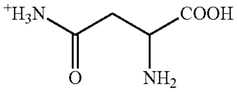
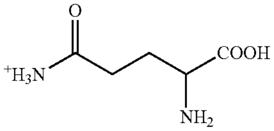
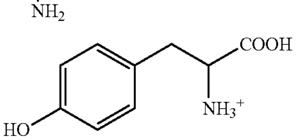
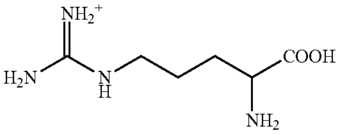
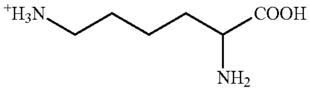
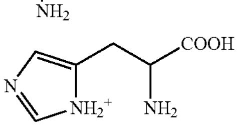
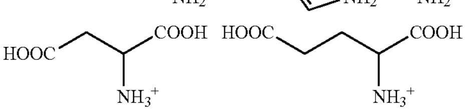
-continued
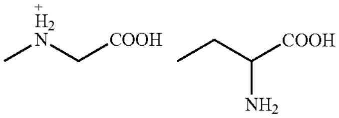
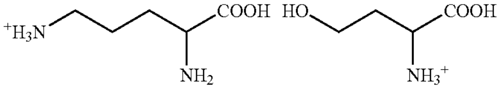
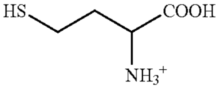
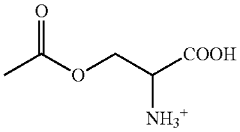
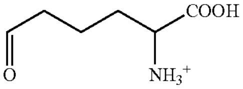
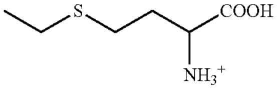
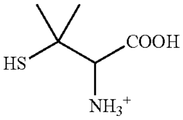
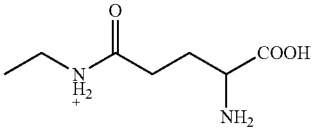
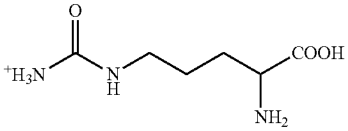
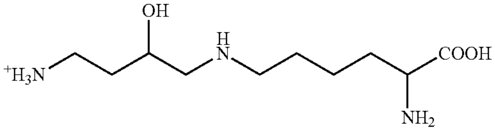
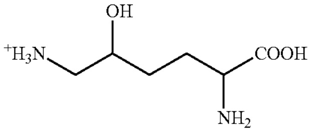
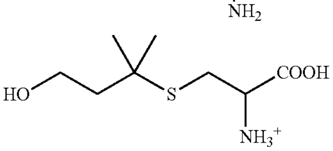
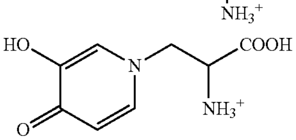
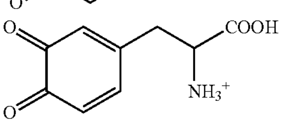
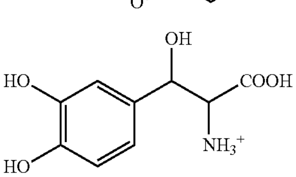
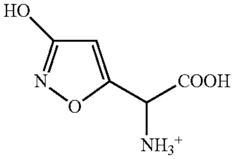
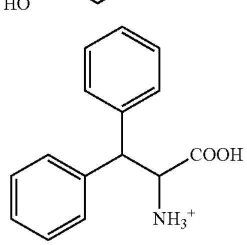
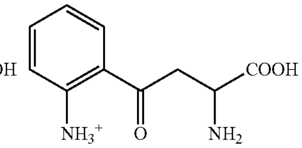

-continued

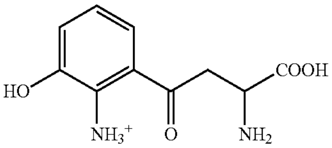
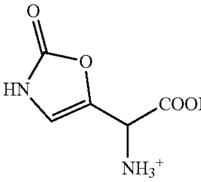
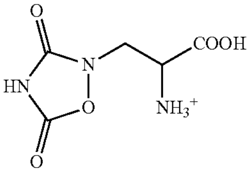
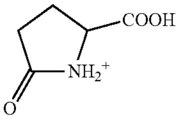
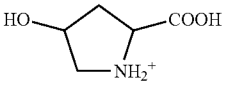
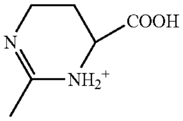
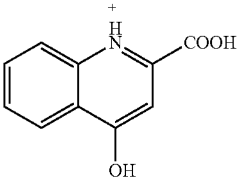
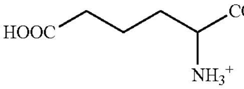
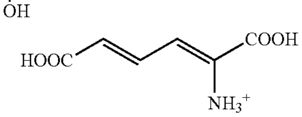
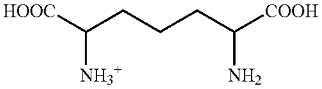
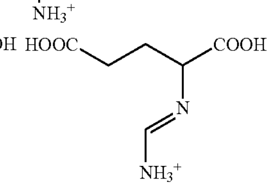
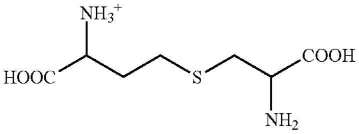
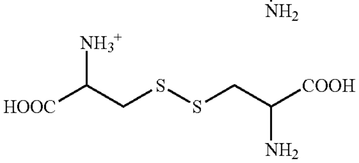
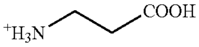
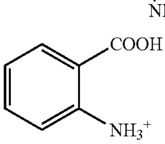
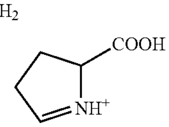
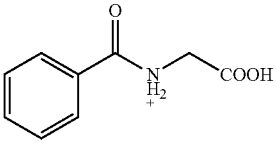
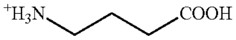
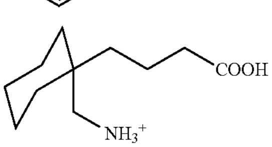
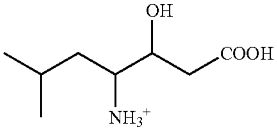
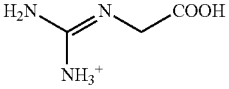
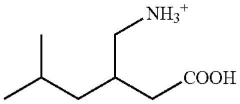

-continued

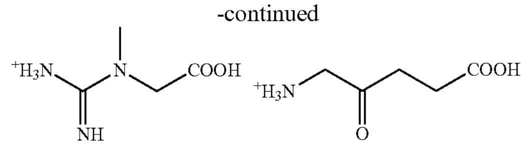

As a method for synthesizing the dopant polymer as the component (B), for example, desired monomers among the monomers providing the repeating units A1-1, A1-2, A2-1 to A2-7, -b, -c, -d, -e, and -f may be subjected to polymerization under heating in an organic solvent by adding a radical polymerization initiator to obtain a dopant polymer which is a (co)polymer.

The organic solvent to be used at the time of the polymerization may be exemplified by toluene, benzene, tetrahydrofuran, diethyl ether, dioxane, cyclohexane, cyclopentane, methyl ethyl ketone, γ-butyrolactone, etc.

The radical polymerization initiator may be exemplified by 2,2'-azobisisobutyronitrile (AIBN), 2,2'-azobis(2,4-dimethylvaleronitrile), dimethyl 2,2'-azobis(2-methylpropionate), benzoyl peroxide, lauroyl peroxide, etc.

The reaction temperature is preferably 50 to 80° C. The reaction time is preferably 2 to 100 hours, more preferably 5 to 20 hours.

In the component (B) dopant polymer, the monomers for providing the repeating units A1-1, A1-2, and A2-1 to A2-7 may be one kind or two or more kinds.

In addition, the monomers providing the repeating units A1-1, A1-2, A2-1 to A2-7, -b, -c, -d, -e, and -f may be randomly copolymerized, or each may be copolymerized in block.

When the random copolymerization is carried out by the radical polymerization, a common method is to mix monomers to be copolymerized and a radical polymerization initiator and polymerize the mixture under heating. Polymerization is initiated in the presence of a first monomer and a radical polymerization initiator, and then a second monomer is added. Thereby, one side of the polymer molecule has a structure in which the first monomer is polymerized, and the other side has a structure in which the second monomer is polymerized. In this case, however, the repeating units of the first and second monomers are mixedly present in the intermediate portion, and the form is different from that of the block copolymer. For forming the block copolymer by the radical polymerization, living radical polymerization is preferably used.

In the living radical polymerization method called the RAFT polymerization (Reversible Addition Fragmentation chain Transfer polymerization), the radical at the polymer end is always living, so that it is possible to form a di-block copolymer with a block of the repeating unit of the first monomer and a block of the repeating unit of the second monomer by: initiating the polymerization with the first monomer; and adding the second monomer when the first monomer is consumed. Further, a tri-block copolymer can also be formed by: initiating the polymerization with the first monomer; adding the second monomer when the first monomer is consumed; and then adding a third monomer.

When the RAFT polymerization is carried out, there is a characteristic that a narrow dispersion polymer whose molecular weight distribution (dispersity) is narrow is formed. In particular, when the RAFT polymerization is carried out by adding the monomers at a time, a polymer having a narrower molecular weight distribution can be formed.

Note that the component (B) dopant polymer has a molecular weight distribution (Mw/Mn) of preferably 1.0 to 2.0, particularly preferably a narrow dispersity of 1.0 to 1.5. When the dispersity is narrow, it is possible to prevent a decrease in the transmittance of an electro-conductive film formed from the electro-conductive polymer composite using such a dopant polymer.

For carrying out the RAFT polymerization, a chain transfer agent is necessary. Specific examples thereof include 2-cyano-2-propylbenzothioate, 4-cyano-4-phenylcarbonothioylthiopentanoic acid, 2-cyano-2-propyl dodecyl trithiocarbonate, 4-cyano-4-[(dodecylsulfanylthiocarbonyl)sulfanyl] pentanoic acid, 2-(dodecylthiocarbonothioylthio)-2-methylpropanoic acid, cyanomethyl dodecyl thiocarbonate, cyanomethyl methyl(phenyl)carbamothioate, bis(thiobenzoyl)disulfide, and bis(dodecylsulfanylthiocarbonyl)disulfide. Among these, 2-cyano-2-propylbenzothioate is particularly preferable.

The component (B) dopant polymer has a weight-average molecular weight of 1,000 to 500,000, preferably 2,000 to 200,000. If the weight-average molecular weight is less than 1,000, the heat resistance is poor, and the uniformity of the composite solution with the component (A) is degraded. Meanwhile, if the weight-average molecular weight exceeds 500,000, conductivity is degraded, and in addition, viscosity increases, so that workability is degraded, and dispersibility in water and an organic solvent is reduced.

Incidentally, the weight-average molecular weight (Mw) is a value measured in terms of polyethylene oxide, polyethylene glycol, or polystyrene, by gel permeation chromatography (GPC) using water, dimethylformamide (DMF), or tetrahydrofuran (THF) as an eluent.

Note that, as the monomer constituting the component (B) dopant polymer, a monomer having a sulfo group may be used. Alternatively, the polymerization reaction may be carried out using a monomer which is a lithium salt, a sodium salt, a potassium salt, an ammonium salt, or a sulfonium salt of a sulfo group; and after the polymerization, the resultant may be converted to a sulfo group by using an ion exchange resin. Here, the proportions of the repeating units A1-1, A1-2, A2-1 to A2-7, -b, -c, -d, -e, and -f in the dopant polymer (B) may be $0 \le (a1\text{-}1) < 1.0$, $0 \le (a1\text{-}2) < 1.0$, $0 < (a1\text{-}1)+(a1\text{-}2) < 1.0$, $0 \le (a2\text{-}1) < 1.0$, $0 \le (a2\text{-}2) < 1.0$, $0 \le (a2\text{-}3) < 1.0$, $0 \le (a2\text{-}4) < 1.0$, $0 \le (a2\text{-}5) < 1.0$, $0 \le (a2\text{-}6) < 1.0$, $0 \le (a2\text{-}7) < 1.0$, $0 \le (a2\text{-}1)+(a2\text{-}2)+(a2\text{-}3)+(a2\text{-}4)+(a2\text{-}5)+(a2\text{-}6)+(a2\text{-}7) < 1.0$, $0 \le b < 1.0$, $0 \le c < 1.0$, $0 \le d < 1.0$, $0 \le e < 1.0$, and $0 \le f < 1.0$; preferably $0 \le (a1\text{-}1) \le 0.9$, $0 \le (a1\text{-}2) \le 0.9$, $0.01 \le (a1\text{-}1)+(a1\text{-}2) \le 0.9$, $0 \le (a2\text{-}1) \le 0.99$, $0 \le (a2\text{-}2) \le 0.99$, $0 \le (a2\text{-}3) \le 0.99$, $0 \le (a2\text{-}4) \le 0.99$, $0 \le (a2\text{-}5) \le 0.99$, $0 \le (a2\text{-}6) \le 0.99$, $0 \le (a2\text{-}7) \le 0.99$, $0.1 \le (a2\text{-}1)+(a2\text{-}2)+(a2\text{-}3)+(a2\text{-}4)+(a2\text{-}5)+(a2\text{-}6)+(a2\text{-}7) \le 0.99$, $0 \le b \le 0.9$, $0 \le c \le 0.9$, $0 \le d \le 0.9$, $0 \le e \le 0.9$, and $0 \le f \le 0.9$; more preferably $0 \le (a1\text{-}1) \le 0.8$, $0 \le (a1\text{-}2) \le 0.8$, $0.01 (a1\text{-}1)+(a1\text{-}2) \le 0.8$, $0 \le (a2\text{-}1) \le 0.98$, $0 \le (a2\text{-}2) \le 0.98$, $0 \le (a2\text{-}3) \le 0.98$, $0 \le (a2\text{-}4) \le 0.98$, $0 \le (a2\text{-}5) \le 0.98$, $0 \le (a2\text{-}6) \le 0.98$, $0 \le (a2\text{-}7) \le 0.98$, $0.1 \le (a2\text{-}1)+(a2\text{-}2)+(a2\text{-}3)+(a2\text{-}4)+(a2\text{-}5)+(a2\text{-}6)+(a2\text{-}7) \le 0.98$, $0 \le b \le 0.7$, $0 \le c \le 0.7$, $0 \le d \le 0.7$, $0 \le e \le 0.7$, and $0 \le f \le 0.7$. "b", "c", "d", "e", and "f" each represent the proportions of the repeating units-b to -f respectively.

[Electro-Conductive Polymer Composite]

The electro-conductive polymer composite contains the component (A) π-conjugated polymer and the component (B) dopant polymer. The component (B) dopant polymer is coordinated to the component (A) π-conjugated polymer to form the composite.

The electro-conductive polymer composite preferably has dispersibility in water or an organic solvent, and can improve the spin-coating film formability and film flatness on an inorganic or organic substrate (a substrate having an inorganic film or an organic film formed on a surface thereof).

(Method for Manufacturing Electro-Conductive Polymer Composite)

The composite of the components (A) and (B) can be obtained, for example, by adding a raw-material monomer of the component (A) (preferably, pyrrole, thiophene, aniline, or a derivative monomer thereof) into an aqueous solution of the component (B) or a mixed solution of the component (B) in water and an organic solvent, and adding an oxidizing agent and, if necessary, an oxidizing catalyst thereto, to carry out oxidative polymerization.

The oxidizing agent and the oxidizing catalyst which can be used may be: a peroxodisulfate (persulfate), such as ammonium peroxodisulfate (ammonium persulfate), sodium peroxodisulfate (sodium persulfate), and potassium peroxodisulfate (potassium persulfate); a transition metal compound, such as ferric chloride, ferric sulfate, and cupric chloride; a metal oxide, such as silver oxide and cesium oxide; a peroxide, such as hydrogen peroxide and ozone; an organic peroxide, such as benzoyl peroxide; oxygen, etc.

As the reaction solvent to be used for carrying out the oxidative polymerization, water or a mixed solvent of water and a solvent may be used. The solvent herein used is preferably a solvent which is miscible with water, and can dissolve or disperse the components (A) and (B). Examples of the solvent include polar solvents, such as N-methyl-2-pyrrolidone, N,N'-dimethylformamide, N,N'-dimethylacetamide, dimethylsulfoxide, and hexamethylene phosphotriamide; alcohols, such as methanol, ethanol, propanol, and butanol; polyhydric aliphatic alcohols, such as ethylene glycol, propylene glycol, dipropylene glycol, 1,3-butylene glycol, 1,4-butylene glycol, D-glucose, D-glucitol, isoprene glycol, butanediol, 1,5-pentanediol, 1,6-hexanediol, 1,9-nonanediol, and neopentyl glycol; carbonate compounds, such as ethylene carbonate and propylene carbonate; cyclic ether compounds, such as dioxane and tetrahydrofuran; linear ethers, such as dialkyl ether, ethylene glycol monoalkyl ether, ethylene glycol dialkyl ether, propylene glycol monoalkyl ether, propylene glycol dialkyl ether, polyethylene glycol dialkyl ether, and polypropylene glycol dialkyl ether; heterocyclic compounds, such as 3-methyl-2-oxazolidinone; nitrile compounds, such as acetonitrile, glutaronitrile, methoxyacetonitrile, propionitrile, and benzonitrile; etc. One of these solvents may be used singly, or two or more kinds thereof may be used in mixture. The contained amount of these solvents miscible with water is preferably 50 mass % or less based on the whole reaction solvent.

After the synthesis of the electro-conductive polymer composite, a neutralization reaction can also be performed to provide a sodium ion, a potassium ion, an ammonium ion, or a sulfonium ion as the $M^+$ in the general formulae (2) and (2)-1 to (2)-4.

The composite of the components (A) and (B) obtained thus can be used, if necessary, after being subjected to fine pulverization with a homogenizer, a ball mill, or the like.

For fine pulverization, a mixing-dispersing machine which can provide high shearing force is preferably used. Examples of the mixing-dispersing machine include a homogenizer, a high-pressure homogenizer, a bead mill, etc. In particular, a high-pressure homogenizer is preferable.

Specific examples of the high-pressure homogenizer include Nanovater manufactured by Yoshida Kikai Co., Ltd., Microfluidizer manufactured by Powrex Corp., Artimizer manufactured by Sugino Machine Limited., etc.

Examples of a dispersing treatment using the high-pressure homogenizer include a treatment in which the composite solution before subjecting to the dispersing treatment is subjected to counter-collision with high pressure; a treatment in which the solution is passed through an orifice or slit with high pressure; etc.

Before or after fine pulverization, impurities may be removed by a method, such as filtration, ultrafiltration, and dialysis, followed by purification with a cation-exchange resin, an anion-exchange resin, a chelate resin, or the like.

Note that a total amount of the components (A) and (B) contained is preferably 0.05 to 5.0 mass % in the electro-conductive polymer composite solution. When the total amount of the components (A) and (B) contained is 0.05 mass % or more, sufficient conductivity is obtained. When the total amount contained is 5.0 mass % or less, a uniform conductive coating film is easily obtained.

The contained amount of the component (B) is preferably such that the amount of sulfo groups, sulfonamide groups, and sulfonimide groups in the component (B) is 0.1 to 10 mol, more preferably 1 to 7 mol, based on 1 mol of the component (A). When there is 0.1 mol or more of the sulfo groups in the component (B), the doping effect to the component (A) is high, and sufficient conductivity can be ensured. Meanwhile, when there is 10 mol or less of the sulfo groups in the component (B), the contained amount of the component (A) is also suitable, and sufficient conductivity can be achieved.

Examples of the organic solvent, which can be contained in the aqueous solution for the polymerization reaction or can dilute the monomer, include methanol, ethyl acetate, cyclohexanone, methyl amyl ketone, butanediol monomethyl ether, propylene glycol monomethyl ether, ethylene glycol monomethyl ether, butanediol monoethyl ether, propylene glycol monoethyl ether, ethylene glycol monoethyl ether, propylene glycol dimethyl ether, diethylene glycol dimethyl ether, propylene glycol monomethyl ether acetate, propylene glycol monoethyl ether acetate, ethyl pyruvate, butyl acetate, methyl 3-methoxypropionate, ethyl 3-ethoxypropionate, tert-butyl acetate, t-butyl propionate, propylene glycol mono-t-butyl ether acetate, γ-butyrolactone, mixtures thereof, etc.

Note that the amount of the organic solvent to be used is preferably 0 to 1,000 mL, particularly preferably 0 to 500 mL, based on 1 mol of the monomer. When the amount of the organic solvent is 1,000 mL or less, the reaction vessel does not become too large so that it is economical.

In the presence of the component (B) dopant polymer, after polymerizing the component (A) to obtain a composite, a neutralizer can also be added. When a neutralizer is added, the $M^+$ in the general formulae (2) and (2)-1 to (2)-4 becomes an ion other than a hydrogen ion. In a case where the $M^+$ in the general formulae (2) and (2)-1 to (2)-4 is a hydrogen ion, the acidity of a solution of the inventive bio-electrode is high if the proportion of hydrogen ions is large, so that when the bio-electrode is attached to the skin, the bio-electrode becomes acidic on the side of the skin due to perspiration, and causes skin allergy in some cases. In order to avoid this, a neutralization treatment is preferably performed. However, a small amount of hydrogen ions remaining in the $M^+$ can be tolerated.

(C) Crosslinking Agent

In the present invention, a crosslinking agent is contained in order to prevent the electro-conductive polymer composite from being delaminated or swelling in water. The crosslinking agent can be selected from an isocyanate group, a blocked isocyanate group, a carbodiimide group, and an aziridine group.

Examples of the crosslinking agents containing an isocyanate group include compounds having a plurality of isocyanate groups. Compounds having a plurality of isocyanate groups are disclosed in paragraphs [0082] and [0083] of Patent Document 11.

Specific examples of the crosslinking agents having a blocked isocyanate group include MEIKANATE series of Meisei Chemical Works, Ltd., Blonate series of DAIE INDUSTRY Co., Ltd., and ELASTRON series of DKS Co. Ltd. The blocked groups are removed by heating after application, isocyanate groups are generated, and the isocyanate groups react with the hydroxy groups and the carboxy groups of the dopant polymer.

Examples of the crosslinking agents having a carbodiimide group include V-02 and V-02-L2 of Nisshinbo Chemical Inc.

Examples of the crosslinking agents having an aziridine group include Chemitite DZ-22E and DZ-33 of NIPPON SHOKUBAI CO., LTD.

In particular, as a crosslinking agent that is stable in an aqueous bio-electrode solution, crosslinking agents that contain a blocked isocyanate group are preferable.

The contained amount is preferably 1 to 50 parts by mass based on a total of 100 parts by mass of the component A and the component B.

[Other Components]

(Surfactant)

In the present invention, a surfactant may be contained to increase wettability of the composite solution to a material to be processed, such as a substrate. Examples of such a surfactant include various surfactants such as nonionic, cationic, and anionic surfactants. Specific examples thereof include nonionic surfactants, such as polyoxyethylene alkyl ether, polyoxyethylene alkylphenyl ether, polyoxyethylene carboxylic acid ester, sorbitan ester, and polyoxyethylene sorbitan ester; cationic surfactants, such as alkyltrimethyl ammonium chloride and alkylbenzyl ammonium chloride; anionic surfactants, such as alkyl or alkylallyl sulfates, alkyl or alkylallyl sulfonate, and dialkyl sulfosuccinate; amphoteric ionic surfactants, such as amino acid type and betaine type; etc.

The contained amount is preferably 0.001 to 50 parts by mass based on a total of 100 parts by mass of the components A and B.

(Conductivity Enhancer)

In the present invention, a conductivity enhancer may be contained besides the main agent for the purpose of improving the conductivity of the electro-conductive polymer composite. Examples of such a conductivity enhancer include polar solvents, and specific examples include ethylene glycol, diethylene glycol, polyethylene glycol, glycerin, dimethylsulfoxide (DMSO), dimethylformamide (DMF), N-methyl-2-pyrrolidone (NMP), sulfolane, and mixtures thereof. The amount of the solvent to be contained is preferably 1.0 to 40.0 mass %, particularly preferably 3.0 to 30.0 mass % based on 100 parts by mass of a dispersion of the electro-conductive polymer composite.

The electro-conductive polymer composite as described above makes it possible to form an electro-conductive film having excellent filterability, excellent film formability by spin-coating, high transparency, and low surface roughness.

[Living Body Contact Layer]

The electro-conductive polymer composite (solution) obtained in the above manner can be applied to an electro-conductive base material of one or more selected from gold, silver, silver chloride, platinum, aluminum, magnesium, tin, tungsten, iron, copper, nickel, stainless steel, chromium, titanium, and carbon. Thus, a bio-electrode can be formed. Examples of methods for applying the electro-conductive polymer composite (solution) include: coating with a spin coater, etc.; bar coating, dipping, comma coating, spray coating, roll coating, screen printing, flexographic printing, gravure printing, ink-jet printing, etc. After the application, a bio-electrode can be formed by a heat treatment with a hot air circulation furnace, a hot plate, etc.

[(D) Resin]

The resin (D) contained in the inventive bio-electrode composition is made compatible with the above-described dopant polymer (B) (salt) and prevents elution of the electro-conductive polymer composite, and is a component for holding an electric conductivity improver such as a metal powder, a carbon powder, a silicon powder, and a lithium titanate powder. The resin is preferably one or more kinds selected from a (meth)acrylate resin, a (meth)acrylamide resin, a urethane resin, polyvinyl alcohol, polyvinylpyrrolidone, polyoxazoline, polyglycerin, polyglycerin-modified silicone, cellulose, polyethylene glycol, and polypropylene glycol.

The resin is preferably contained in an amount of 0 to 200 parts by mass based on a total of 100 parts by mass of the components A and B.

[Component (E)]

The inventive bio-electrode composition can further contain, as a component (E), one or more selected from a carbon powder, a metal powder, a silicon powder, and a lithium titanate powder. Out of the component (E), the carbon powder and the metal powder are contained in order to enhance electron conductivity, and the silicon powder and the lithium titanate powder are contained in order to enhance ion reception sensitivity.

[Metal Powder]

The inventive bio-electrode composition may also contain, in order to enhance electron conductivity, a metal powder selected from the group consisting of gold, silver, platinum, copper, tin, titanium, nickel, aluminum, tungsten, molybdenum, ruthenium, chromium, and indium. The metal powder is preferably contained in an amount of 1 to 50 parts by mass based on 100 parts by mass of the resin.

As the kind of the metal powder, gold, silver, and platinum are preferable from the viewpoint of electric conductivity, and silver, copper, tin, titanium, nickel, aluminum, tungsten, molybdenum, ruthenium, and chromium are preferable from the viewpoint of cost. From the viewpoint of biocompatibility, noble metals are preferable. From a comprehensive viewpoint including the above, silver is the most preferable.

The metal powder may have any shape, such as a spherical shape, a disk shape, a flaky shape, and a needle shape. The addition of a flaky powder or a needle-form powder brings the highest electric conductivity and is preferable. In the case of a flaky powder, the metal powder is preferably a flake having relatively low density and large specific surface area with a size of 100 μm or less, a tapped density of not more than 5 $g/cm^3$, and a specific surface area of not less than 0.5 $m^2/g$. In the case of a needle-form powder, the diameter is preferably 1 to 200 nm, and the length is preferably 1 to 500 μm.

The metal powder is preferably any of gold nanoparticles, silver nanoparticles, copper nanoparticles, gold nanowire, silver nanowire, and copper nanowire.

[Carbon Powder]

A carbon powder can be contained as an electric conductivity improver. Examples of the carbon powder include carbon black, graphite, carbon nanotube, carbon fiber, etc. The carbon nanotube may be either single layer or multi-layer, and the surface may be modified with an organic group(s). In particular, the carbon powder is preferably one or both of carbon black and carbon nanotube. The carbon powder is preferably contained in an amount of 1 to 50 parts by mass based on 100 parts by mass of the electro-conductive polymer composite.

[Silicon Powder]

The inventive bio-electrode composition may contain a silicon powder to enhance ion reception sensitivity. Examples of the silicon powder include powders of silicon, silicon monoxide, or silicon carbide. The particle size of the powder is preferably smaller than 100 μm, more preferably 1 μm or less. Since finer particles have a larger surface area, the resulting bio-electrode can receive a larger amount of ions and has higher sensitivity. The silicon powder is preferably contained in an amount of 1 to 50 parts by mass based on 100 parts by mass of the resin.

[Lithium Titanate Powder]

The inventive bio-electrode composition may contain a lithium titanate powder to enhance ion reception sensitivity. Examples of the lithium titanate powder include powders containing a compound shown by molecular formulae $Li_2TiO_3$, $LiTiO_2$, or $Li_4Ti_5Oi_2$ with a spinel structure. The lithium titanate powder preferably has a spinel structure. It is also possible to use carbon-incorporated lithium titanate particles. The particle size of the powder is preferably smaller than 100 μm, more preferably 1 μm or less. Since finer particles have a larger surface area, the bio-electrode can receive a larger amount of ions, and has higher sensitivity. The aforementioned powders may be composite powders with carbon. The lithium titanate powder is preferably contained in an amount of 1 to 50 parts by mass based on 100 parts by mass of the resin.

When an electro-conductive additive of silver nanowire or carbon nanotube having a needle-form or a fiber-form is contained in the electro-conductive polymer composite solution, sufficient electric conductivity as a bio-electrode can be ensured even without providing an underlying electro-conductive layer.

[Optional Components]

The inventive bio-electrode composition can contain optional components such as an ionic additive and a solvent.

[Ionic Additive]

The inventive bio-electrode composition may contain an ionic additive to enhance the ionic conductivity. In consideration of biocompatibility, examples of the ionic additive include sodium chloride, potassium chloride, calcium chloride, saccharin, acesulfame potassium, and salts disclosed in Patent Documents 12 to 15.

Ammonium salts of a fluorosulfonic acid, a fluoroimidic acid, and a fluoromethide acid are known as ionic liquids. Specific examples are disclosed in Non Patent Document 3. These ionic liquids can also be contained.

[Silicone Compound Having Polyglycerin Structure]

The inventive bio-electrode composition may also contain a silicone compound having a polyglycerin structure in order to improve the moisture-holding property of the film and improve the ionic conductivity and the sensitivity to ions released from the skin. The silicone compound having a polyglycerin structure is preferably contained in an amount of 0.01 to 100 parts by mass, more preferably 0.5 to 60 parts by mass based on 100 parts by mass of the components (A) and (B). One kind of the silicone compound having a polyglycerin structure may be used, or two or more kinds may be used in mixture.

The silicone compound having a polyglycerin structure is preferably shown by any of the following general formulae (4)' and (5)'.

(4)'

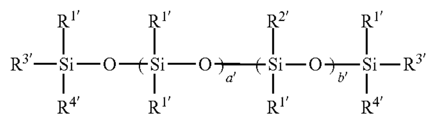

(4)'-1

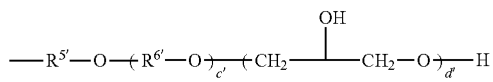

(4)'-2

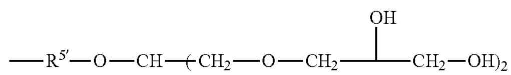

(5)'

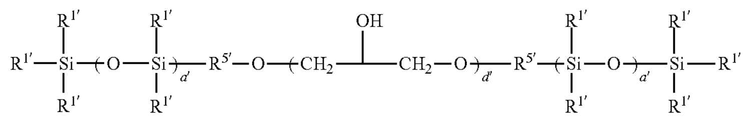

(6)'

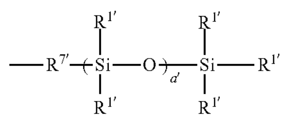

In the formulae (4)' and (5)', each $R^{1'}$ is identical to or different from one another, and independently represents a hydrogen atom, a phenyl group, a linear or branched alkyl group having 1 to 50 carbon atoms, or a silicone chain shown by the general formula (6)', and optionally contains an ether group. $R^{2'}$ represents a group having a polyglycerin group structure shown by the formula (4)'-1 or (4)'-2. Each $R^{3'}$ is identical to or different from the other, and independently represents the $R^{1'}$ group or the $R^{2'}$ group. Each $R^{4'}$ is identical to or different from the other, and independently represents the $R^{1'}$ group, the $R^{2'}$ group, or an oxygen atom. When $R^{4'}$ represents an oxygen atom, the $R^{4'}$ moieties bond to each other and optionally constitute an ether group to form a ring together with silicon atoms. Each a' is identical to or different from one another and represents 0 to 100, b' represents 0 to 100, and a'+b' is 0 to 200. Nevertheless, when b' is 0, at least one $R^{3'}$ is the $R^{2'}$ group. In the formulae (4)'-1 and (4)'-2, $R^{5'}$ represents an alkylene group having 2 to 10 carbon atoms or an aralkylene group having 7 to 10 carbon atoms. $R^{5'}$ in the formula (5)', $R^{6'}$, and $R^{7'}$ each represent an alkylene group having 2 to 6 carbon atoms, but $R^{7'}$ may represent an ether bond. c' represents 0 to 20. d' represents 1 to 20.

Examples of such a silicone compound having a polyglycerin structure include the following.

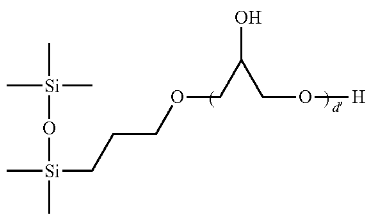

-continued

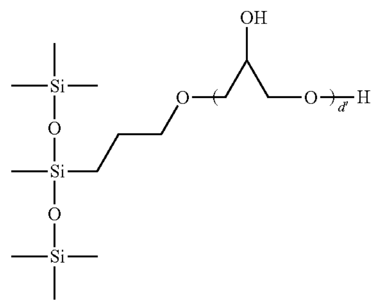

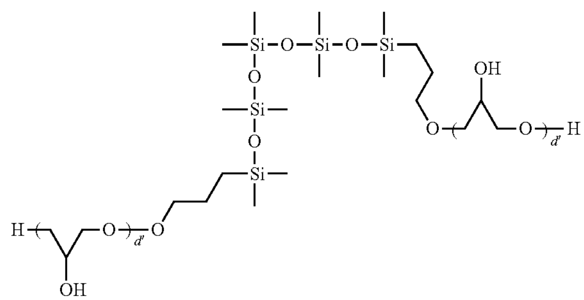

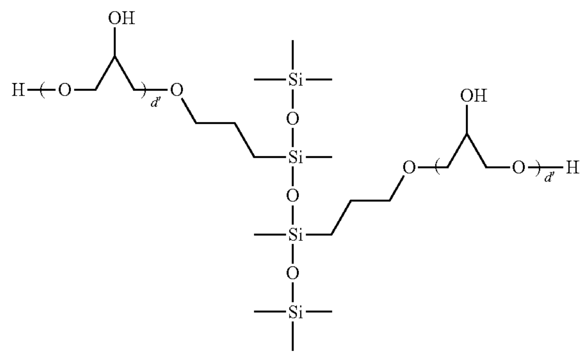

-continued
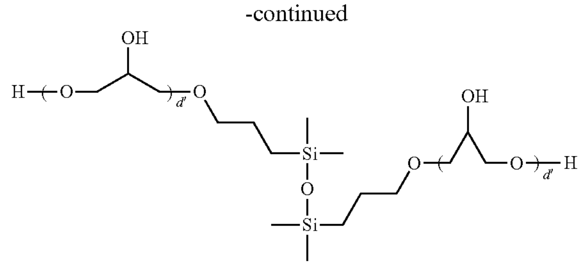
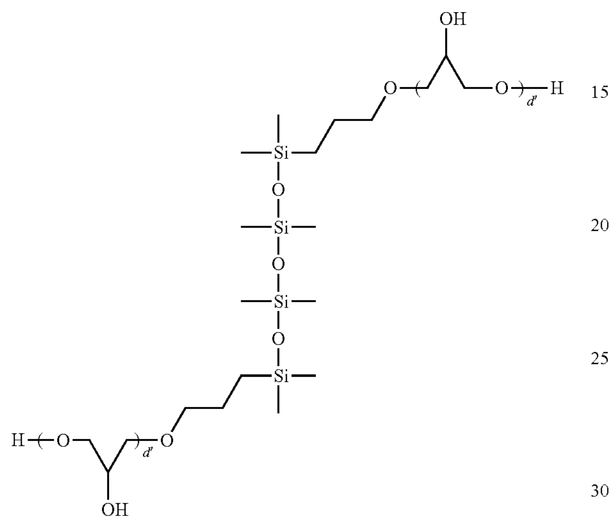
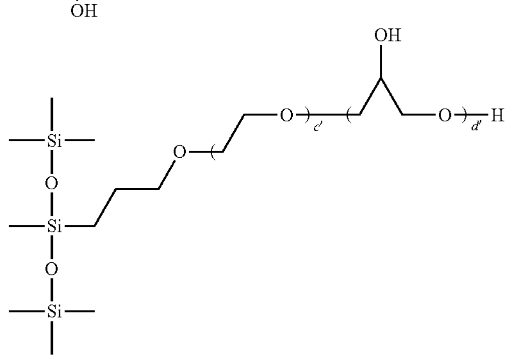
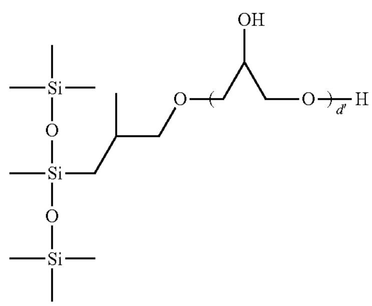
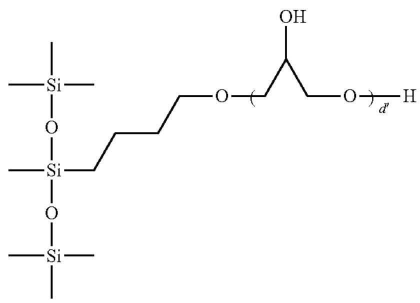
-continued
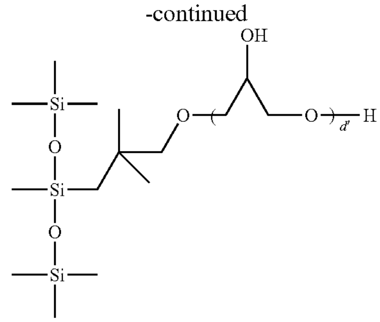
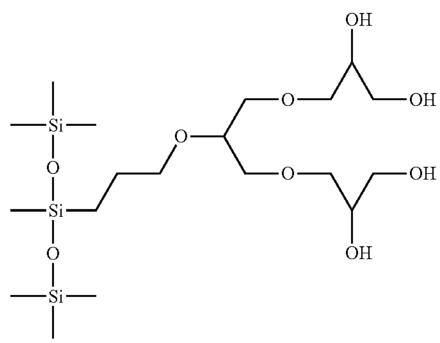
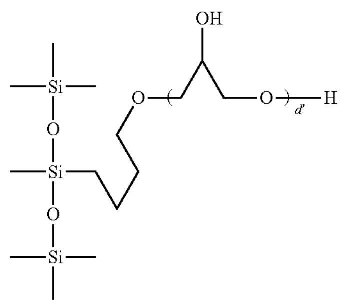
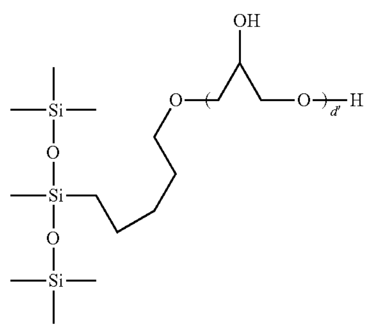
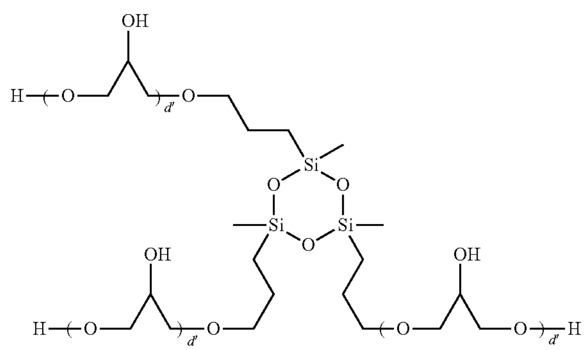

-continued
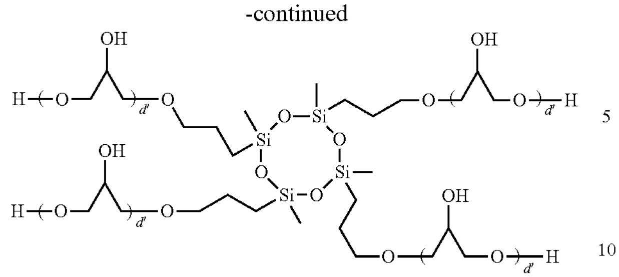
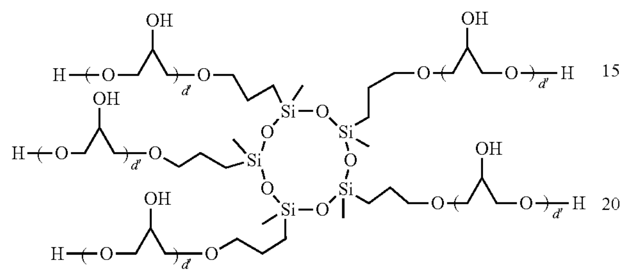
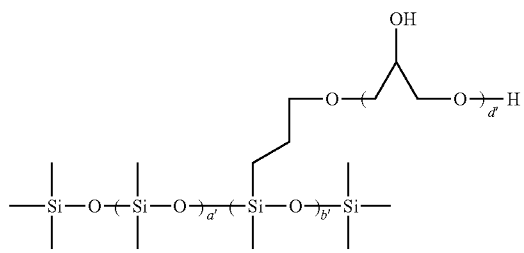
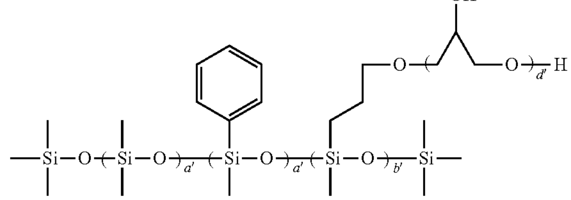
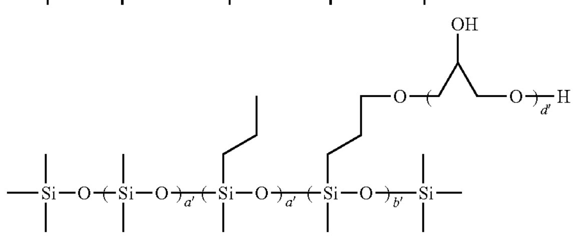
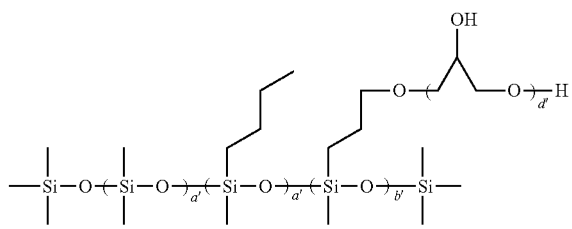
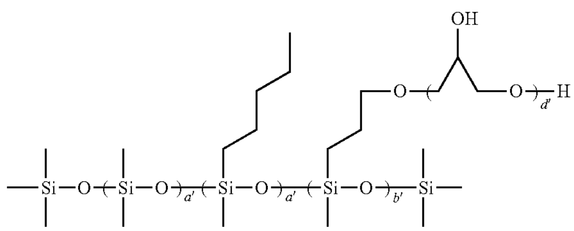
-continued
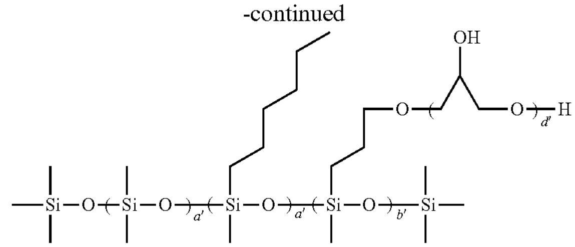
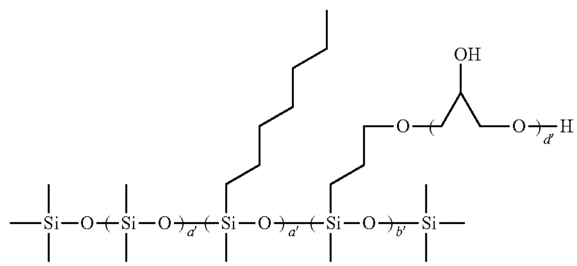
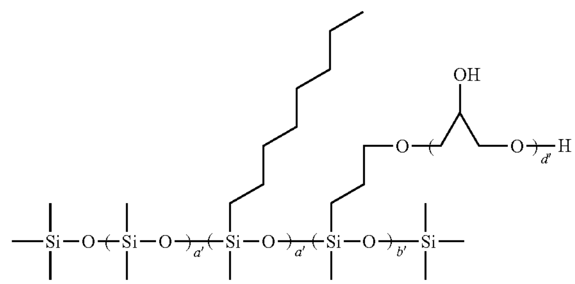
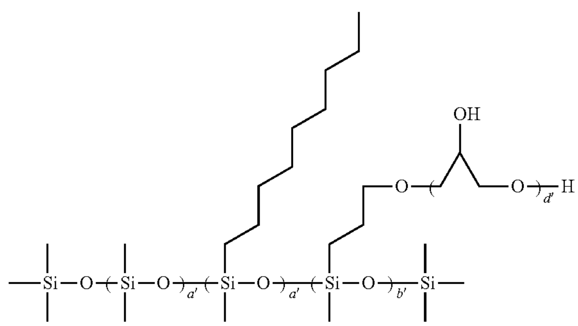
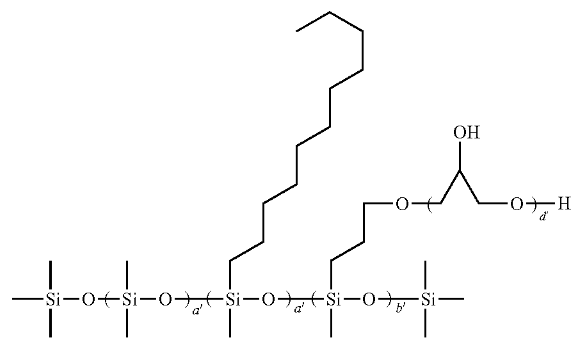

-continued
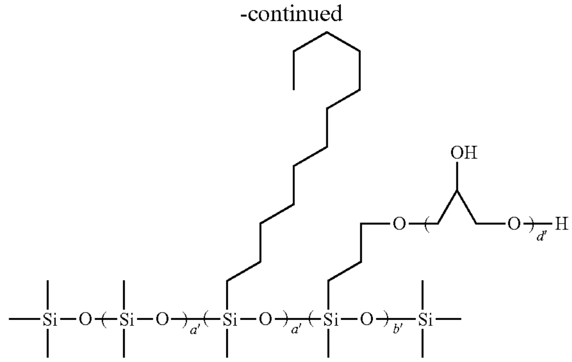
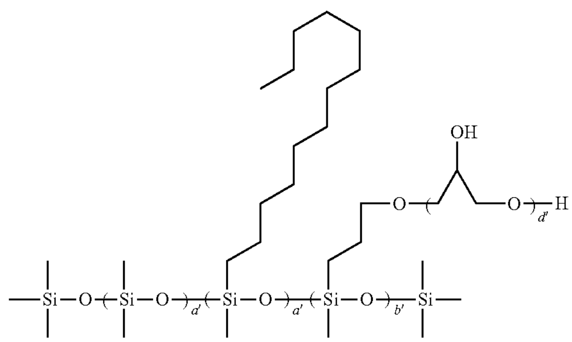
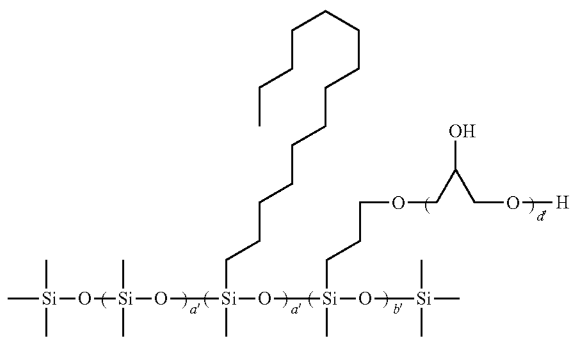
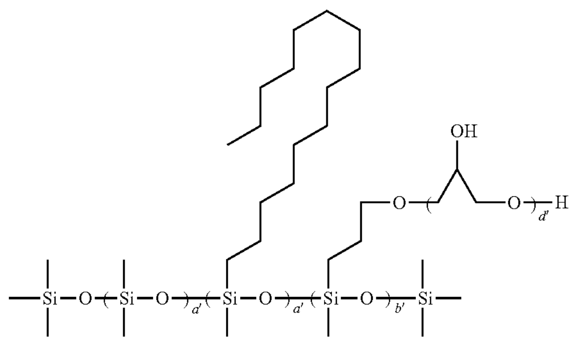
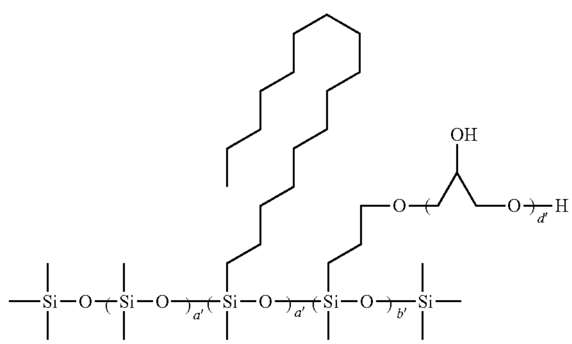
-continued
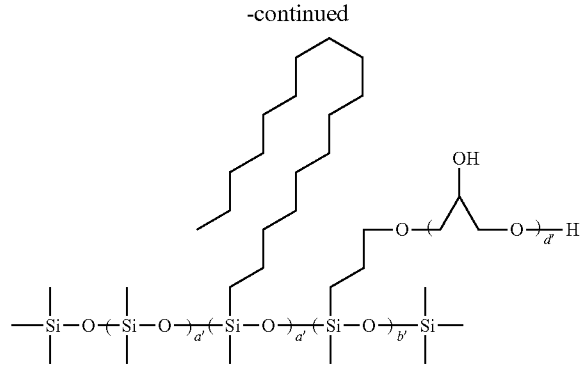
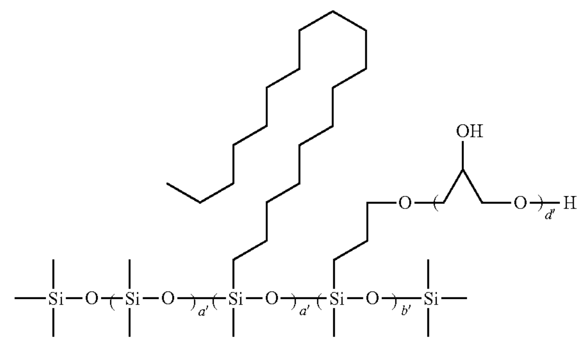
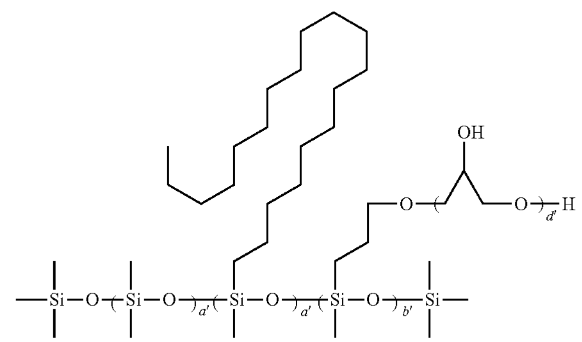
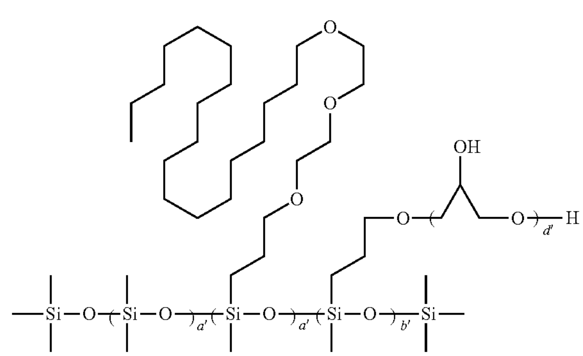
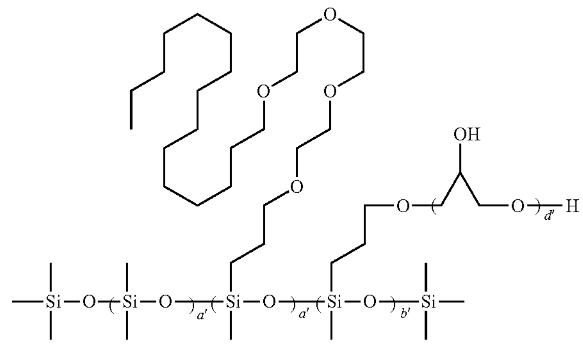

-continued
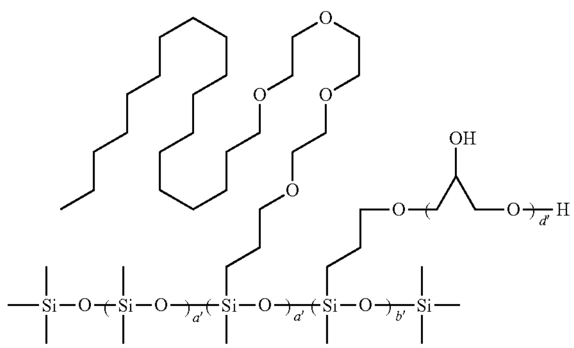
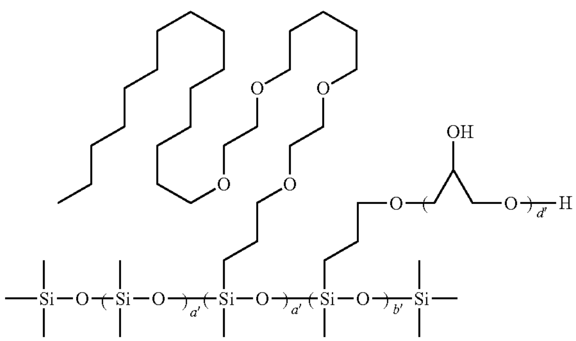
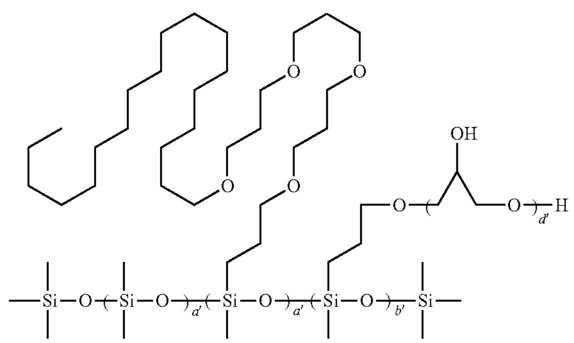
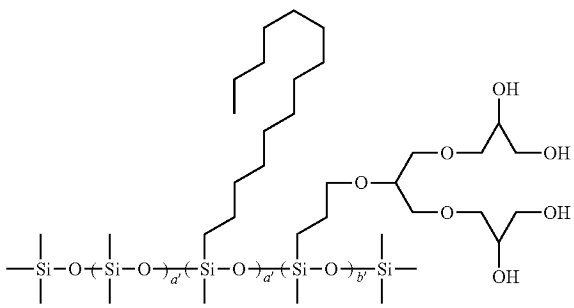
-continued
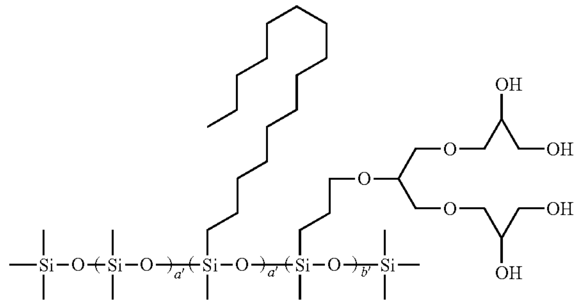
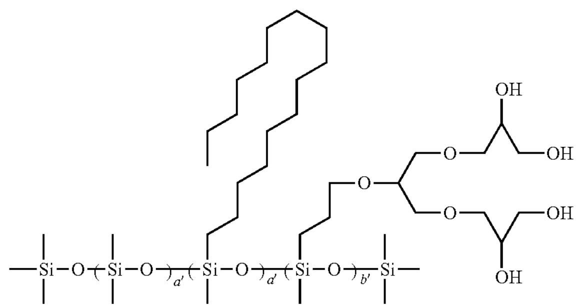
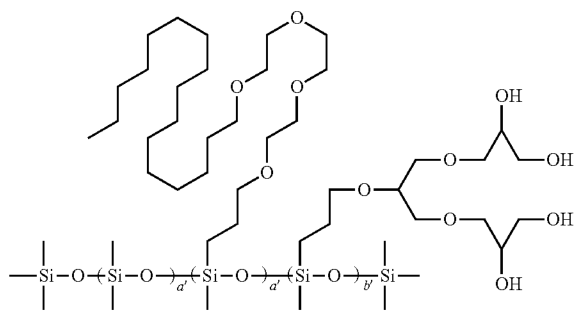
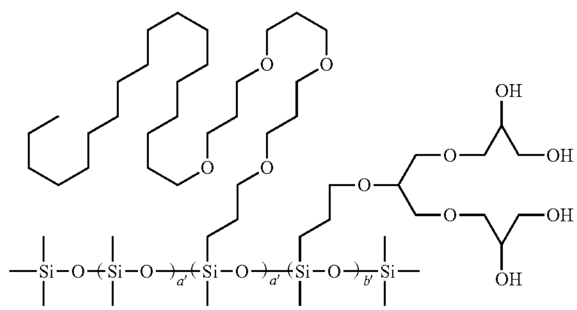

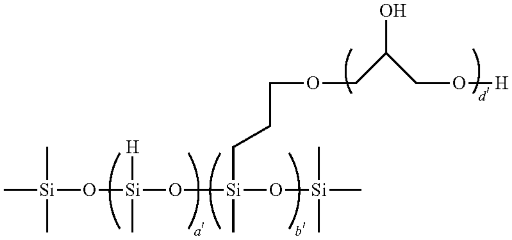
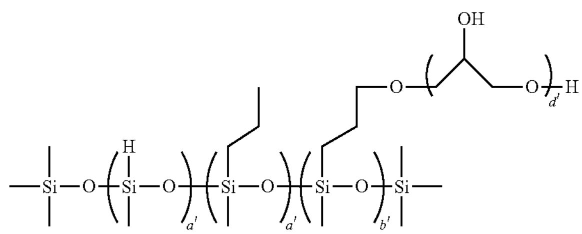
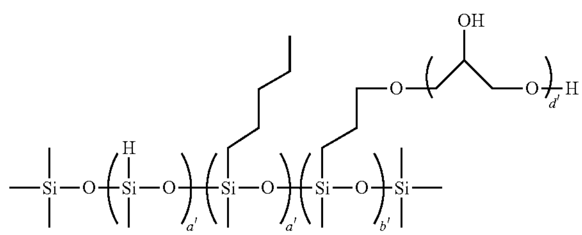
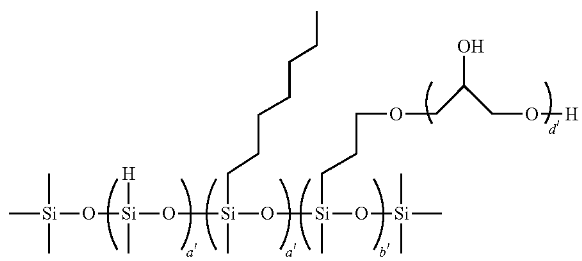
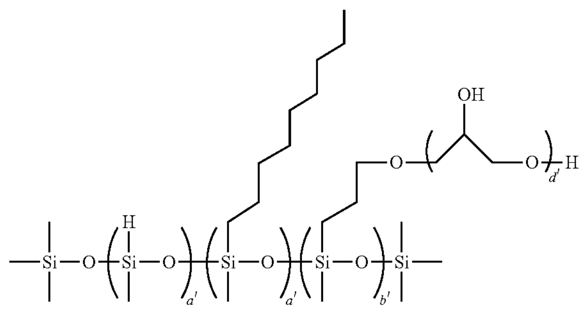
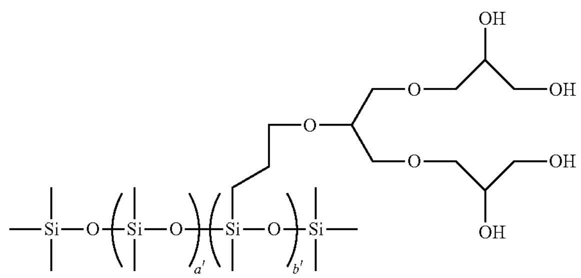
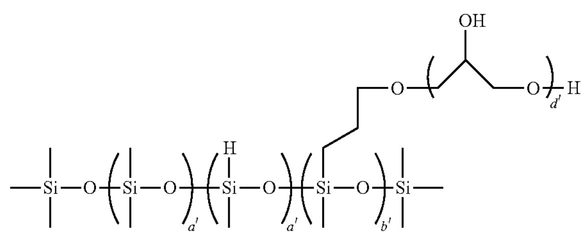
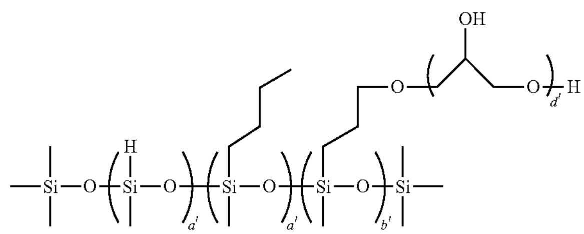
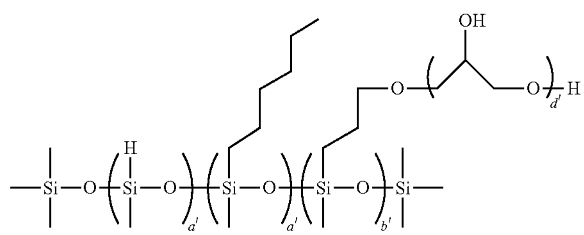
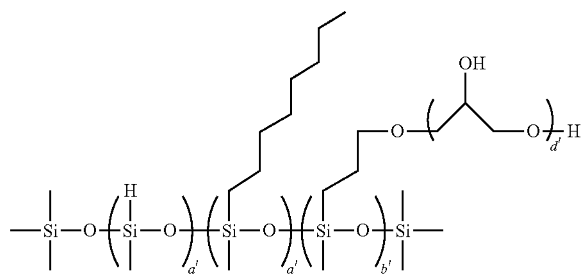
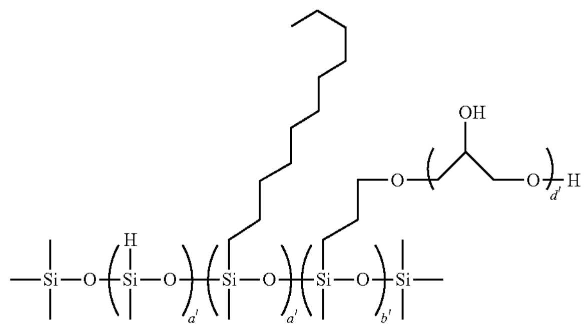
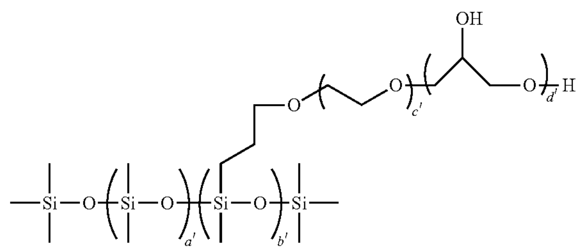

-continued
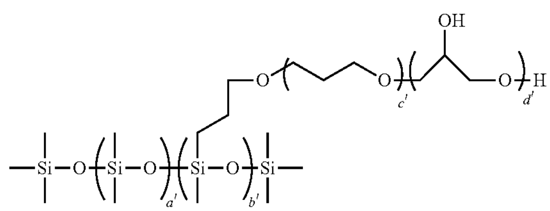
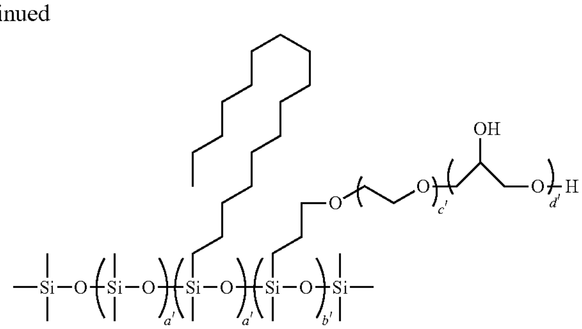
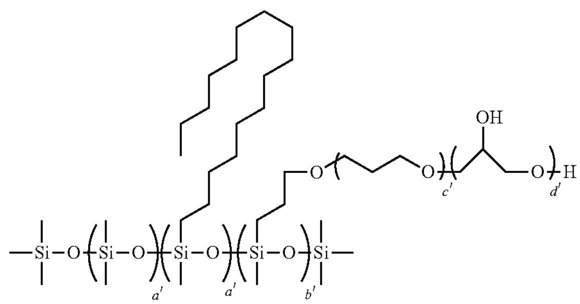
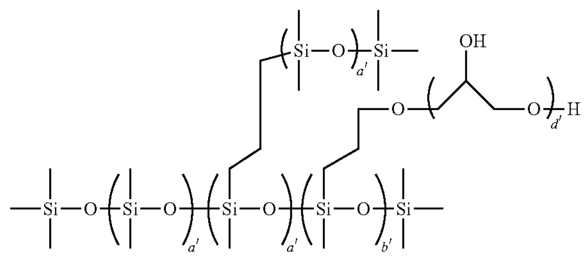
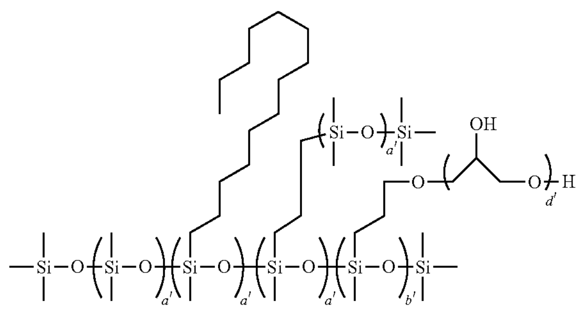
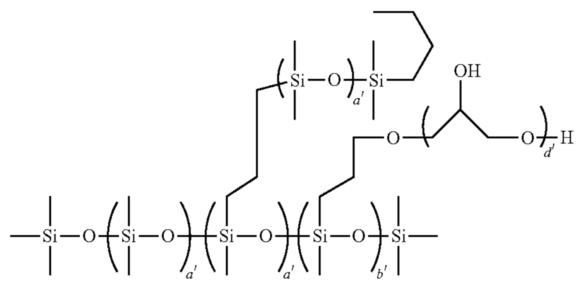
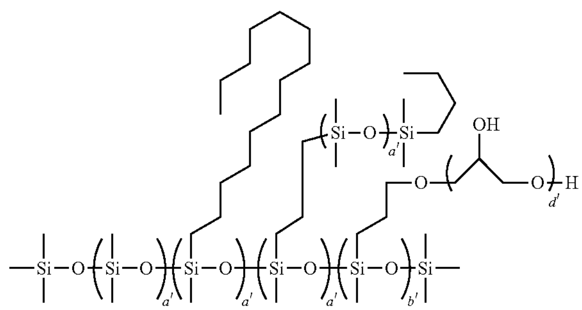
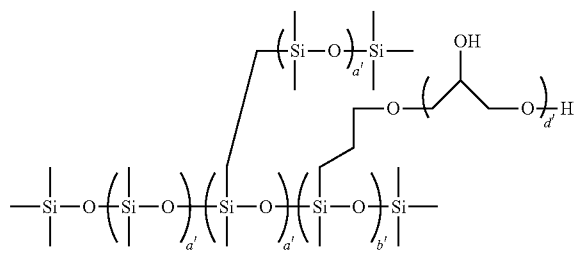
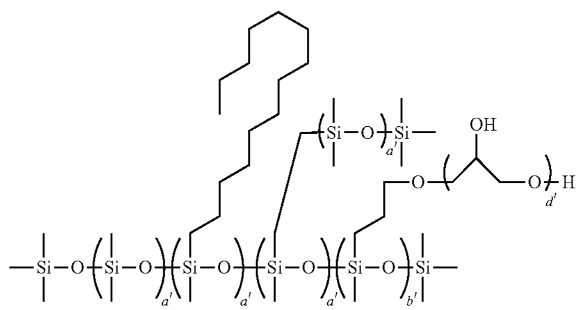
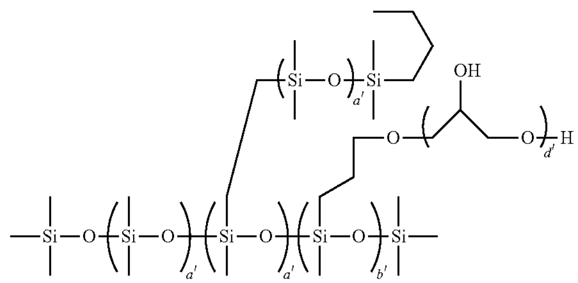

-continued

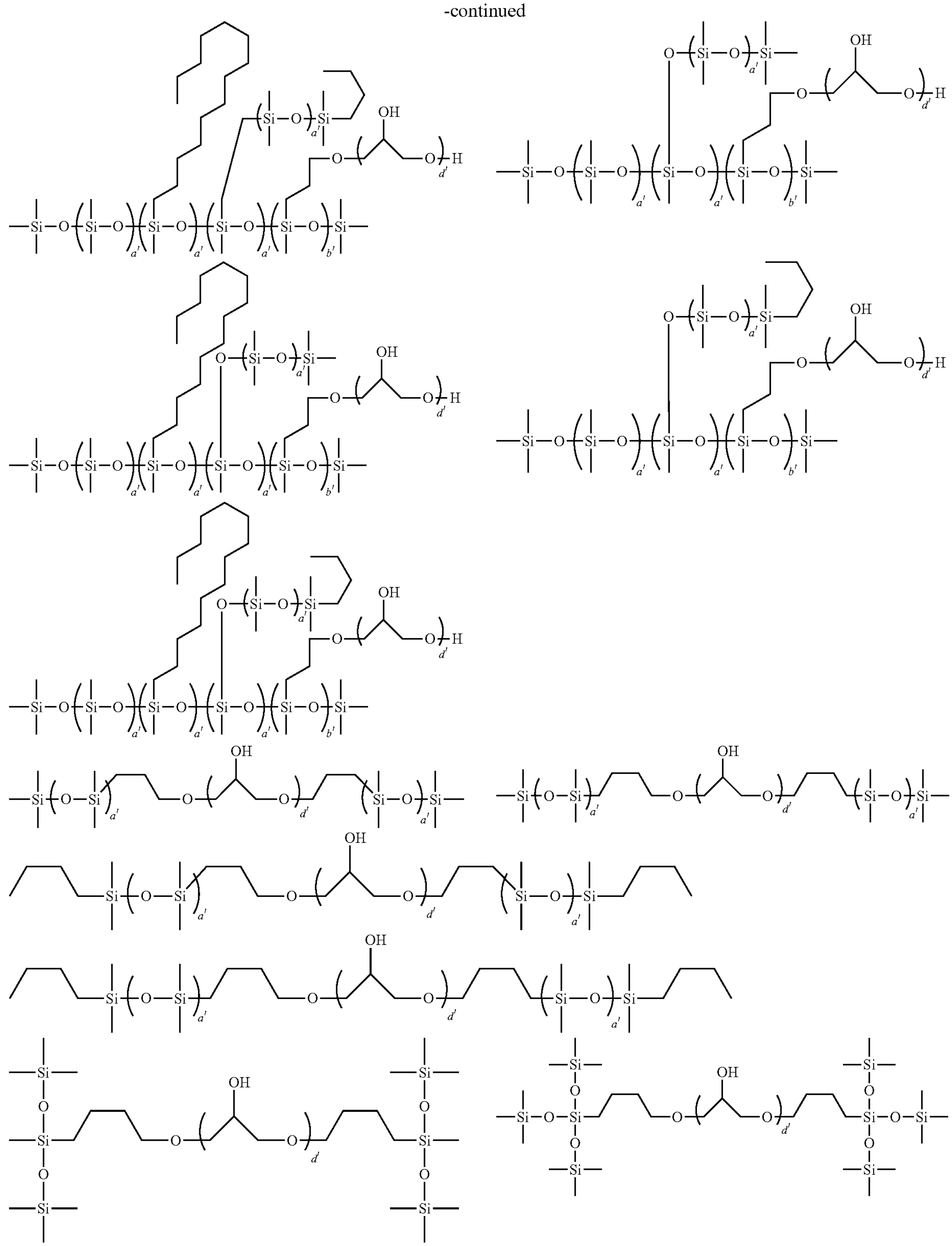

In the formulae, a', b', c', and d' are as defined above.

When such a silicone compound having a polyglycerin structure is incorporated, the resulting bio-electrode composition is capable of forming a living body contact layer that can exhibit better moisture-holding property and consequently exhibit better sensitivity to ions released from the skin.

[Solvent]

The inventive bio-electrode composition can also contain a solvent. Specific examples of the solvent include water, heavy water, alcohols, such as methanol, ethanol, propanol, and butanol; polyvalent aliphatic alcohols, such as ethylene glycol, propylene glycol, 1,3-propanediol, dipropylene glycol, 1,3-butylene glycol, 1,4-butylene glycol, D-glucose, D-glucitol, isoprene glycol, 1,2-butanediol, 1,3-butanediol, 1,4-butanediol, 2,3-butanediol, 1,2-pentanediol, 1,5-pentanediol, 1,2-hexanediol, 1,6-hexanediol, 1,9-nonanediol, and neopentyl glycol; linear ethers, such as dialkyl ether, ethylene glycol monoalkyl ether, ethylene glycol dialkyl ether, propylene glycol monoalkyl ether, propylene glycol dialkyl ether, polyethylene glycol dialkyl ether, and polypropylene glycol dialkyl ether; cyclic ether compounds, such as dioxane and tetrahydrofuran; polar solvents, such as cyclohexanone, methyl amyl ketone, ethyl acetate, butanediol monomethyl ether, propylene glycol monomethyl ether, ethylene glycol monomethyl ether, butanediol monoethyl ether, propylene glycol monoethyl ether, ethylene glycol monoethyl ether, propylene glycol dimethyl ether, diethylene glycol dimethyl ether, propylene glycol monomethyl ether acetate, propylene glycol monoethyl ether acetate, ethyl pyruvate, butyl acetate, methyl 3-methoxypropionate, ethyl 3-ethoxypropionate, tert-butyl acetate, t-butyl propionate, propylene glycol mono-t-butyl ether acetate, γ-butyrolactone, N-methyl-2-pyrrolidone, N,N'-dimethylformamide, N,N'-dimethylacetamide, dimethylsulfoxide, and hexamethylene phosphoric triamide; carbonate compounds, such as ethylene carbonate and propylene carbonate; heterocyclic compounds, such as 3-methyl-2-oxazolidinone; nitrile compounds, such as acetonitrile, glutaronitrile, methoxyacetonitrile, propionitrile, and benzonitrile; mixtures thereof, etc.

The solvent is preferably contained in an amount of 10 to 50,000 parts by mass based on 100 parts by mass of the resin.

<Method for Manufacturing Bio-Electrode>

The inventive method for manufacturing a bio-electrode is described below.

The inventive method for manufacturing a bio-electrode is for manufacturing a bio-electrode having an electro-conductive base material and a living body contact layer formed on the electro-conductive base material, the method including:

- applying the above-described bio-electrode composition onto the electro-conductive base material; and
- curing the bio-electrode composition to form the living body contact layer.

The present invention provides a method for manufacturing a bio-electrode by fabricating an electro-conductive base material and forming a living body contact layer containing an electro-conductive polymer composite on the electro-conductive base material on the side to be attached to the skin.

The method for applying the living body contact layer including the electro-conductive polymer composite onto the electro-conductive base material is not particularly limited, and there is a method of applying the layer directly and a method of applying the layer onto a different substrate and then transferring the layer. In either method, examples of the suitable method include dip coating, spray coating, spin coating, roll coating, flow coating, doctor coating, screen printing, flexographic printing, gravure printing, inkjet printing, etc.

A similar method to the method for applying the living body contact layer including the electro-conductive polymer composite can also be used as the method for forming the electro-conductive base material.

After applying the electro-conductive base material or after applying the living body contact layer containing the electro-conductive polymer composite, heating is performed for the purpose of evaporating the solvent and solidifying the film.

Note that the temperature at which to heat the living body contact layer containing the electro-conductive polymer composite after application is not particularly limited, and can be selected appropriately depending on the kind of the components (A) and (B) used in the bio-electrode composition. For example, the temperature is preferably about 50 to 250° C.

The temperature for heating after applying the electro-conductive base material is, when silver nanowire or the like is used as the electro-conductive base material, 200 to 600° C. in order to fuse the silver together. In this event, it is also possible to employ a flash annealing method, where high-intensity ultraviolet rays are applied for a short time, in order to avoid thermal decomposition of the base material.

Furthermore, in a case where a combination of heating and light irradiation is performed, it is possible to perform the heating and the light irradiation simultaneously, perform the light irradiation and then the heating, or perform the heating and then the light irradiation. It is also possible to perform air-drying to evaporate the solvent before heating the coating film.

Water droplets may be attached to the surface of the cured living body contact layer containing the electro-conductive polymer composite; alternatively, the surface may be sprayed with water vapor or mist. These treatments improve the compatibility with skin, and enable quick collection of biological signals. Water mixed with alcohol can be used to reduce the size of the droplets of the water vapor or mist. The film surface may be wetted by bringing an absorbent cotton or cloth containing water into contact therewith.

The water for making the surface of the cured living body contact layer containing the electro-conductive polymer composite wet may contain a salt. The water-soluble salt mixed with the water is preferably selected from the group consisting of sodium salts, potassium salts, calcium salts, magnesium salts, and betaines.

Specifically, the water-soluble salt can be a salt selected from the group consisting of sodium chloride, potassium chloride, calcium chloride, magnesium chloride, saccharin sodium salt, acesulfame potassium, sodium carboxylate, potassium carboxylate, calcium carboxylate, sodium sulfonate, potassium sulfonate, calcium sulfonate, sodium phosphate, potassium phosphate, calcium phosphate, magnesium phosphate, and betaines. It should be noted that the dopant polymer (B) described above is excluded from the water-soluble salt.

More specific examples of the water-soluble salt include, besides the aforementioned examples, sodium acetate, sodium propionate, sodium pivalate, sodium glycolate, sodium butyrate, sodium valerate, sodium caproate, sodium enanthate, sodium caprylate, sodium pelargonate, sodium caprate, sodium undecylate, sodium laurate, sodium tridecylate, sodium myristate, sodium pentadecylate, sodium palmitate, sodium margarate, sodium stearate, sodium benzoate, disodium adipate, disodium maleate, disodium phthalate, sodium 2-hydroxybutyrate, sodium 3-hydroxybutyrate, sodium 2-oxobutyrate, sodium gluconate, sodium methanesulfonate, sodium 1-nonanesulfonate, sodium 1-decanesulfonate, sodium 1-dodecanesulfonate, sodium 1-undecanesulfonate, sodium cocoyl isethionate, sodium lauroyl methylalanine, sodium methyl cocoyl taurate, sodium cocoyl glutamate, sodium cocoyl sarcosinate, sodium lauroyl methyl taurate, lauramidopropyl betaine, potassium isobutyrate, potassium propionate, potassium pivalate, potassium glycolate, potassium gluconate, potassium methanesulfonate, calcium stearate, calcium glycolate, calcium gluconate, calcium 3-methyl-2-oxobutyrate, and calcium methanesulfonate. The term betaines is a general term for inner salts. Specific examples thereof include amino acid compounds in each of which three methyl groups are added to an amino group. More specific examples include trimethylglycine, carnitine, and proline betaines.

The water-soluble salt can further contain a monohydric alcohol or polyhydric alcohol having 1 to 4 carbon atoms. The alcohol is preferably selected from the group consisting of ethanol, isopropyl alcohol, ethylene glycol, diethylene glycol, triethylene glycol, glycerin, polyethylene glycol, polypropylene glycol, polyglycerin, diglycerin, and a silicone compound having a polyglycerin structure. More preferably, the silicone compound having a polyglycerin structure is shown by the general formula (4)'.

In the pretreatment methods with the aqueous solution containing the salt, the bio-electrode film can be wetted by performing a spraying method, a droplet-dispensing method, etc. on the cured bio-electrode composition (living body contact layer). The bio-electrode film can also be wetted under a high-temperature, high-humidity condition like sauna. To prevent drying after the wetting, the bio-electrode film can be covered with a sheet. Since the sheet needs to be removed immediately before the bio-electrode is attached to the skin, the sheet may be coated with a release agent, or a peelable Teflon (registered trademark) film may be used as the sheet. For long-time storage, the dry electrode covered with the peelable sheet may be sealed in a bag that is covered with aluminum etc. To prevent drying in the bag covered with aluminum, it is preferable to include water therein, too.

To obtain highly accurate biological signals with high sensitivity in a shorter time by moisturizing the surface of the skin, it is effective to wipe the side of the skin where the bio-electrode is to be attached with a cloth containing water or an alcohol, such as ethanol and glycerin containing water, or spray the skin immediately before attachment. The wiping with a cloth containing water has an effect of removing the grease from the surface of the skin as well as moisturizing the skin. The sensitivity to biological signals can also be enhanced in this manner.

As has been described above, the inventive method for manufacturing a bio-electrode makes it possible to manufacture the inventive bio-electrode easily and at low cost, with the bio-electrode being excellent in electric conductivity and biocompatibility, light-weight, and capable of preventing significant reduction in the electric conductivity either when wetted with water or dried.

Example

Hereinafter, the present invention will be specifically described with reference to Examples and Comparative Examples, but the present invention is not limited thereto.

Monomer 1

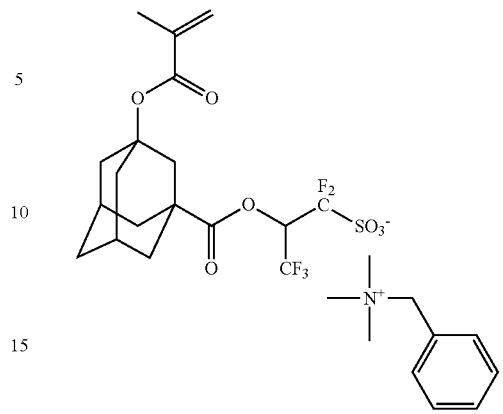

Under a nitrogen atmosphere, a solution was added dropwise over 4 hours to 37.5 g of methanol stirred at 64° C., the solution containing 49.1 g of Monomer 1, 1.0 g of hydroxyethylacrylate, and 4.19 g of dimethyl 2,2'-azobis(isobutyrate) dissolved in 112.5 g of methanol. The mixture was further stirred at 64° C. for 4 hours. After being cooled to room temperature, the mixture was added dropwise to 1,000 g of ethyl acetate under vigorous stirring. The formed solid product was collected by filtration, and dried under vacuum at 50° C. for 15 hours. Thus, 45.3 g of a white polymer was obtained.

The obtained white polymer was dissolved in 396 g of methanol, and the ammonium salt was converted to a sulfo group by using an ion exchange resin. When the obtained polymer was measured by $^{19}F$, $^{1}H$-NMR, and GPC, the following analytical results were obtained.

Weight-average molecular weight (Mw)=10,500

Molecular weight distribution (Mw/Mn)=1.59

This polymer compound is Dopant Polymer 1.

Dopant Polymer 1

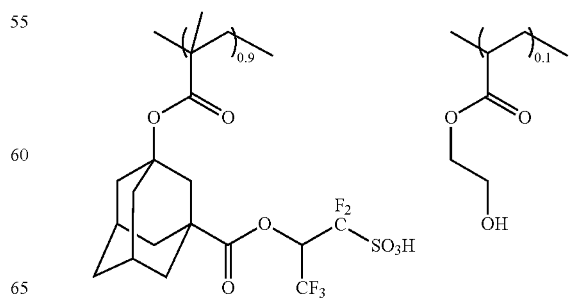

Dopant Polymers 2 to 32 shown below were polymerized by similar methods.
Dopant Polymer 2
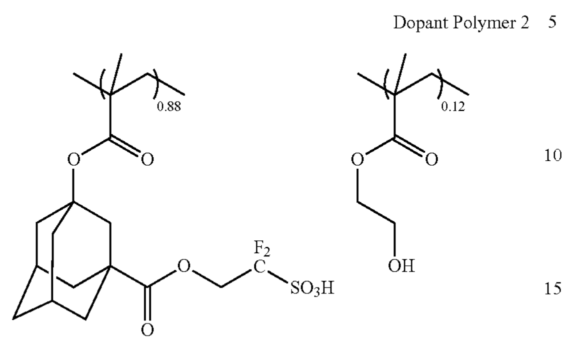
Mw = 12.000
Mw/Mn = 1.79
Dopant Polymer 3
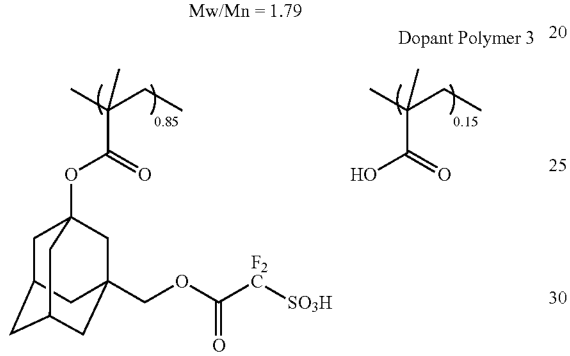
Mw = 9.700
Mw/Mn = 1.66
Dopant Polymer 4
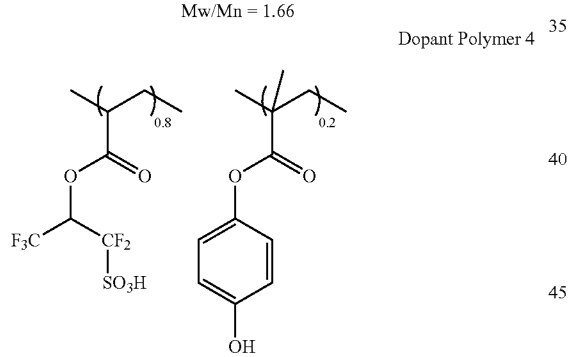
Mw = 12.500
Mw/Mn = 1.53
Dopant Polymer 5
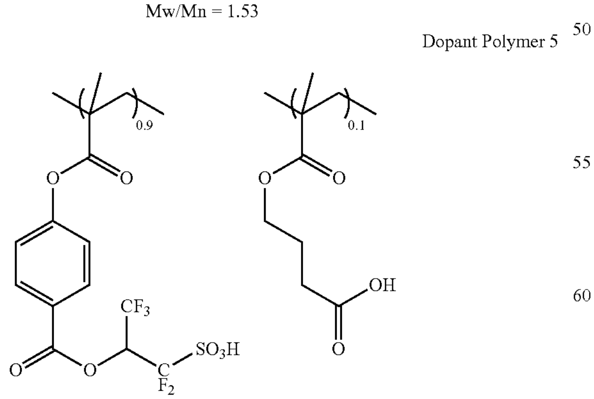
Mw = 8.900
Mw/Mn = 1.69
-continued
Dopant Polymer 6
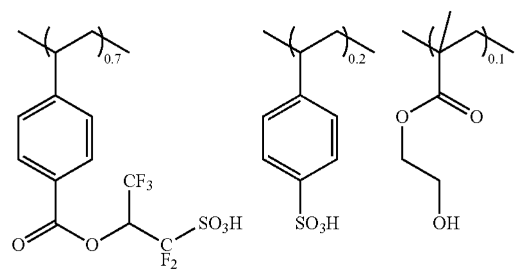
Mw = 10.800
Mw/Mn = 1.92
Dopant Polymer 7
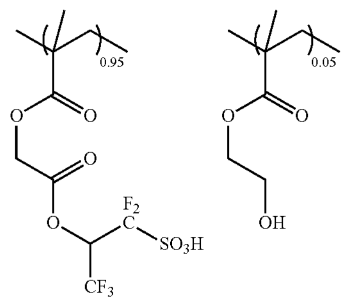
Mw = 14.500
Mw/Mn = 1.71
Dopant Polymer 8
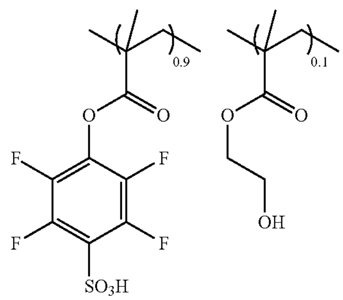
Mw = 14.500
Mw/Mn = 1.77
Dopant Polymer 9
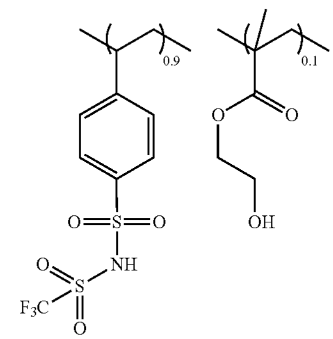
Mw = 10.300
Mw/Mn = 1.61

-continued
Dopant Polymer 10
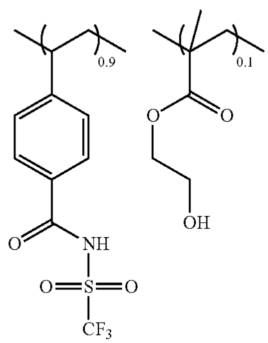
Mw = 9.200
Mw/Mn = 1.57
Dopant Polymer 11
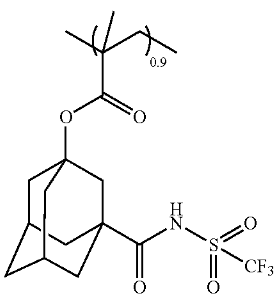
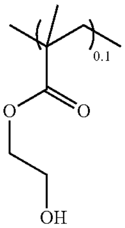
Mw = 11.100
Mw/Mn = 1.74
Dopant Polymer 12
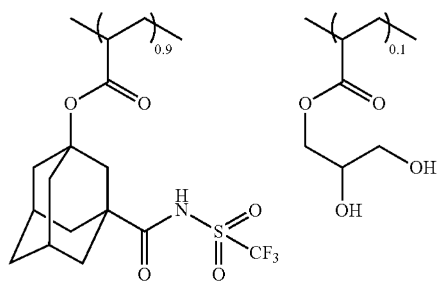
Mw = 16.100
Mw/Mn = 1.73
Dopant Polymer 13
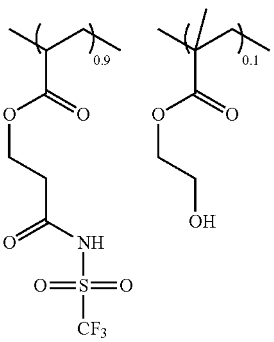
Mw = 14.200
Mw/Mn = 1.71
-continued
Dopant Polymer 14
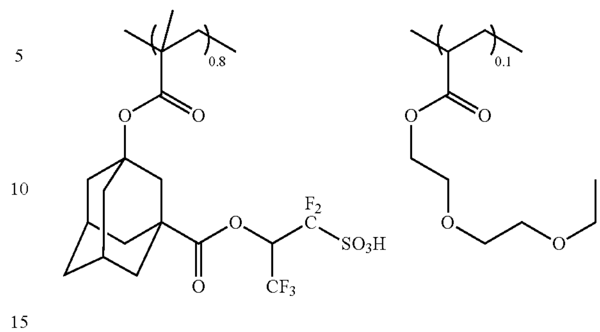
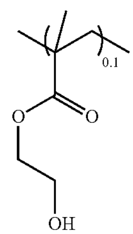
Mw = 14.500
Mw/Mn = 1.69
Dopant Polymer 15
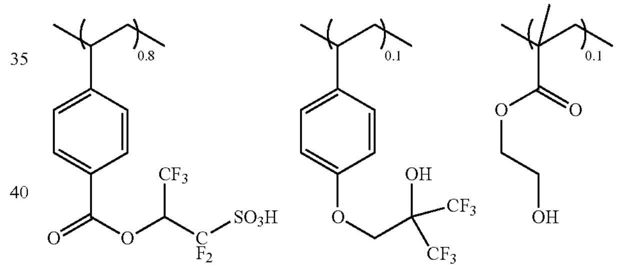
Mw = 11.400
Mw/Mn = 1.76
Dopant Polymer 16
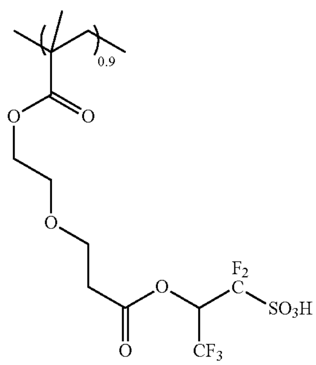
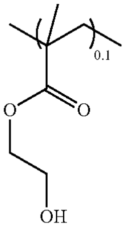
Mw = 13.500
Mw/Mn = 1.73

-continued
Dopant Polymer 17
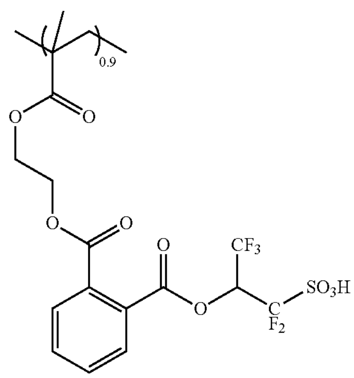
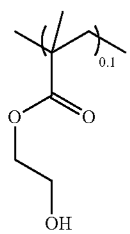
Mw = 12.600
Mw/Mn = 1.62
Dopant Polymer 18
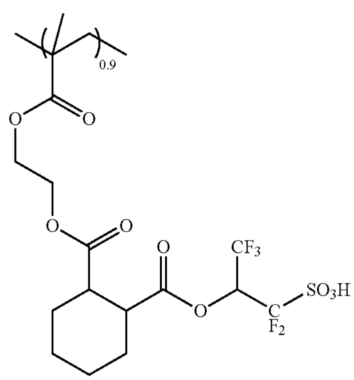
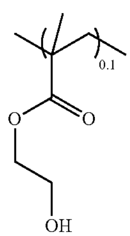
Mw = 10.600
Mw/Mn = 1.61
Dopant Polymer 19
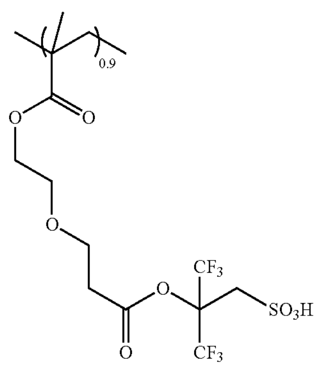
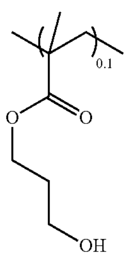
Mw = 12.600
Mw/Mn = 1.83
-continued
Dopant Polymer 20
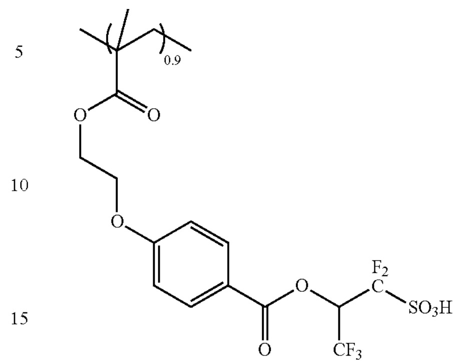
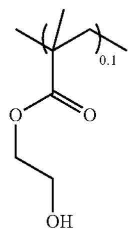
Mw = 12.600
Mw/Mn = 1.89
Dopant Polymer 21
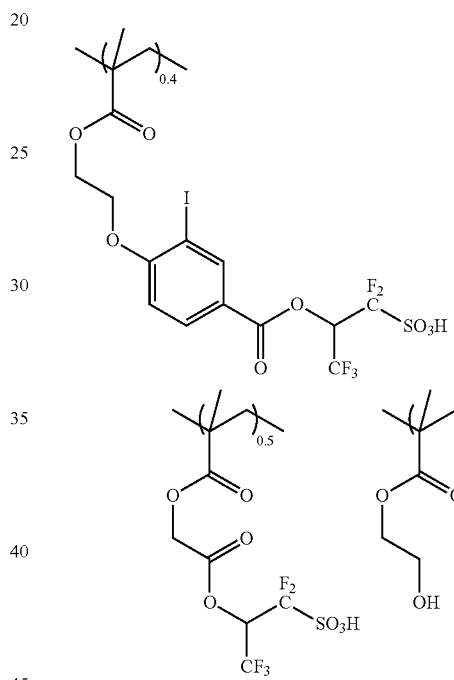
Mw = 11.900
Mw/Mn = 1.88
Dopant Polymer 22
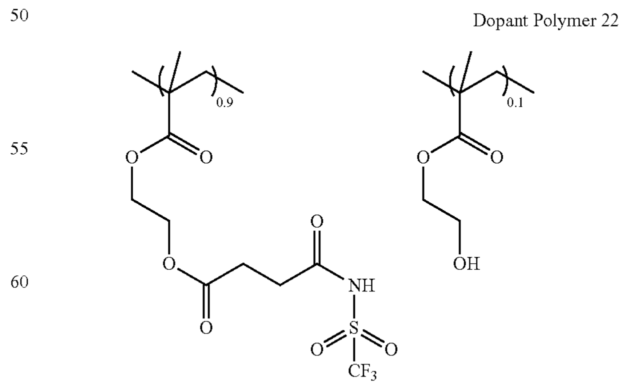
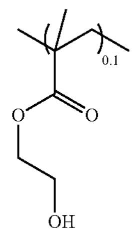
Mw = 12.800
Mw/Mn = 1.59

-continued
Dopant Polymer 23
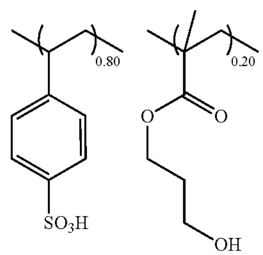
Mw = 12.800
Mw/Mn = 1.79
Dopant Polymer 24
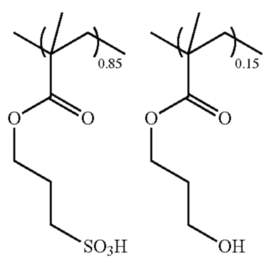
Mw = 14.500
Mw/Mn = 1.95
Dopant Polymer 25
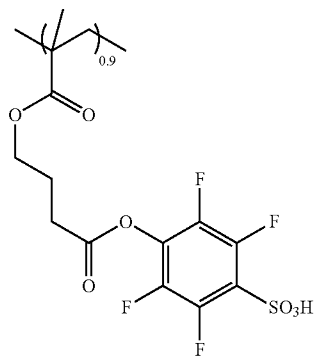
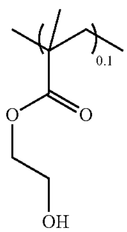
Mw = 14.100
Mw/Mn = 1.69
Dopant Polymer 26
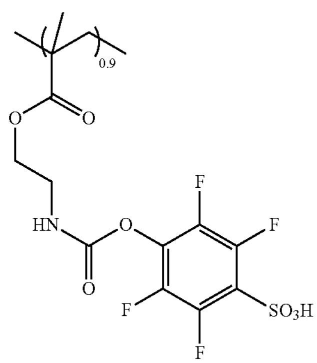
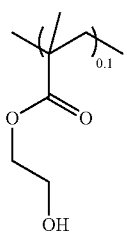
Mw = 12.100
Mw/Mn = 1.51
-continued
Dopant Polymer 27
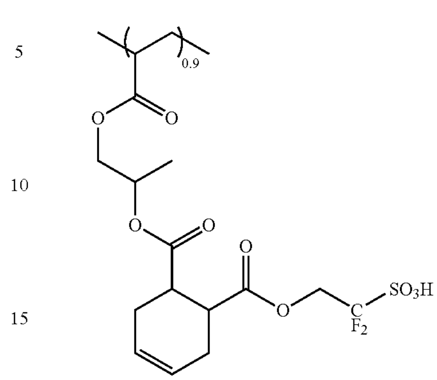
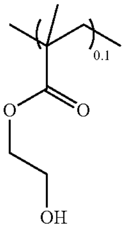
Mw = 14.100
Mw/Mn = 1.71
Dopant Polymer 28
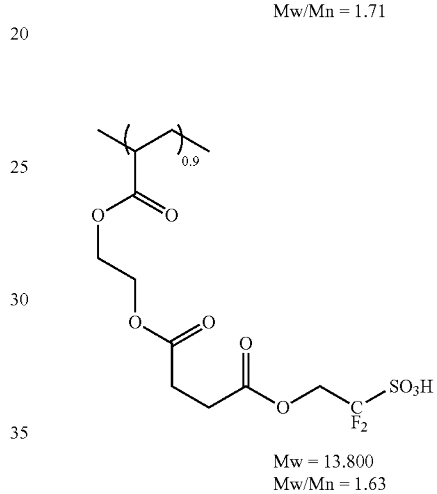
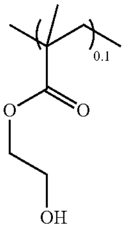
Mw = 13.800
Mw/Mn = 1.63
Dopant Polymer 29
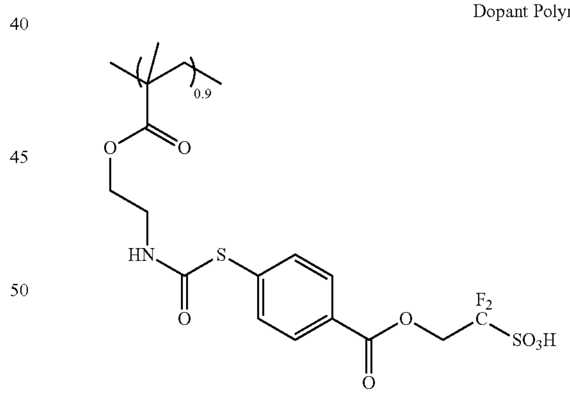
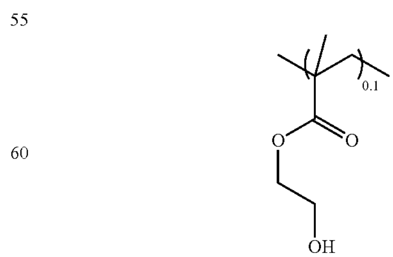
Mw = 13.800
Mw/Mn = 1.89

-continued

Dopant Polymer 30

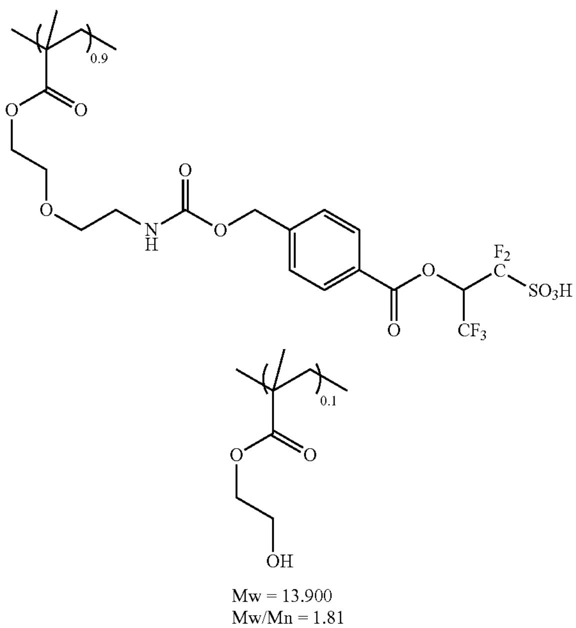

Mw = 13.900
Mw/Mn = 1.81

Dopant Polymer 31

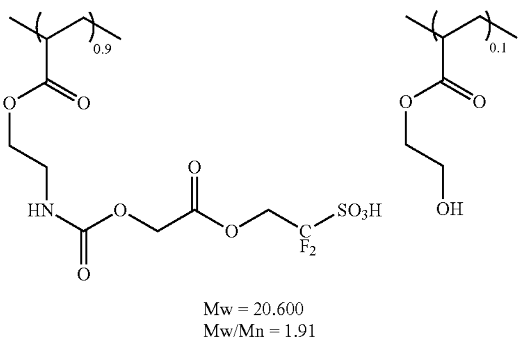

Mw = 20.600
Mw/Mn = 1.91

Dopant Polymer 32

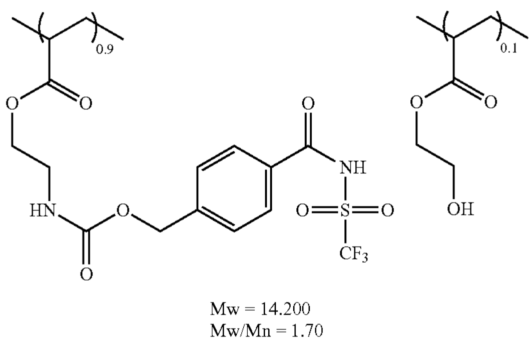

Mw = 14.200
Mw/Mn = 1.70

[Preparation of Electro-Conductive Polymer Composite Solution Containing Polythiophene as π-Conjugated Polymer]

Preparation Example 1

3.82 g of 3,4-ethylenedioxythiophene and a solution in which 15.0 g of Dopant Polymer 1 had been dissolved in 1,000 mL of ultrapure water were mixed at 30° C.

The obtained mixture solution was maintained at 30° C. under stirring. In this state, an oxidizing catalyst solution of 8.40 g of sodium persulfate and 2.3 g of ferric sulfate dissolved in 100 mL of ultrapure water was gradually added thereto and stirred for 4 hours to react these materials.

To the obtained reaction solution, 1,000 mL of ultrapure water was added, and about 1,000 mL of the solution was removed by using the ultrafiltration method. This operation was repeated three times.

Then, to the processed solution after the filtration treatment, 200 mL of sulfuric acid diluted to 10 mass % and 2,000 mL of ion exchanged water were added. About 2,000 mL of the processed solution was removed by using the ultrafiltration method, and 2,000 mL of ion exchanged water was added thereto. About 2,000 mL of the solution was removed by using the ultrafiltration method. This operation was repeated three times.

The obtained processed solution was refined with cation-exchange resin and anion-exchange resin, then 2,000 mL of ion exchanged water was further added thereto, and about 2,000 mL of the processed solution was removed by using the ultrafiltration method. This operation was repeated five times to obtain 1.0 mass % of Electro-Conductive Polymer Composite Solution 1.

The ultrafiltration conditions were as follows.

Molecular weight cutoff of ultrafiltration membrane: 30 K

Cross flow type

Flow amount of supplied liquid: 3,000 mL/minute

Membrane partial pressure: 0.12 Pa

Note that the ultrafiltration was carried out under the same conditions in the other Preparation Examples.

Preparation Example 2

3.02 g of 3-hydroxythiophene and a solution in which 15.0 g of Dopant Polymer 1 had been dissolved in 1,000 mL of pure water were mixed at 30° C.

The obtained mixture solution was maintained at 30° C. under stirring. In this state, an oxidizing catalyst solution of 8.40 g of sodium persulfate and 2.3 g of ferric sulfate dissolved in 100 mL of ultrapure water was gradually added thereto and stirred for 4 hours to react these materials.

To the obtained reaction solution, 1,000 mL of ultrapure water was added, and about 1,000 mL of the solution was removed by using the ultrafiltration method. This operation was repeated three times.

Then, to the processed solution after the filtration treatment, 200 mL of sulfuric acid diluted to 10 mass % and 2,000 mL of ion exchanged water were added. About 2,000 mL of the processed solution was removed by using the ultrafiltration method, and 2,000 mL of ion exchanged water was added thereto. About 2,000 mL of the solution was removed by using the ultrafiltration method. This operation was repeated three times.

The obtained processed solution was refined with cation-exchange resin and anion-exchange resin, then 2,000 mL of ion exchanged water was further added thereto, and about 2,000 mL of the processed solution was removed by using the ultrafiltration method. This operation was repeated five times to obtain 1.0 mass % of Electro-Conductive Polymer Composite Solution 2.

The Dopant Polymer 1 of Preparation Example 1 was changed to Dopant Polymer 2. Thus, Electro-Conductive Polymer Composite Solution 3 was obtained.

The Dopant Polymer 1 of Preparation Example 1 was changed to Dopant Polymer 3. Thus, Electro-Conductive Polymer Composite Solution 4 was obtained.

The Dopant Polymer 1 of Preparation Example 1 was changed to Dopant Polymer 4. Thus, Electro-Conductive Polymer Composite Solution 5 was obtained.

The Dopant Polymer 1 of Preparation Example 1 was changed to Dopant Polymer 5. Thus, Electro-Conductive Polymer Composite Solution 6 was obtained.

The Dopant Polymer 1 of Preparation Example 1 was changed to Dopant Polymer 6. Thus, Electro-Conductive Polymer Composite Solution 7 was obtained.

The Dopant Polymer 1 of Preparation Example 1 was changed to Dopant Polymer 7. Thus, Electro-Conductive Polymer Composite Solution 8 was obtained.

The Dopant Polymer 1 of Preparation Example 1 was changed to Dopant Polymer 8. Thus, Electro-Conductive Polymer Composite Solution 9 was obtained.

The Dopant Polymer 1 of Preparation Example 1 was changed to Dopant Polymer 9. Thus, Electro-Conductive Polymer Composite Solution 10 was obtained.

The Dopant Polymer 1 of Preparation Example 1 was changed to Dopant Polymer 10. Thus, Electro-Conductive Polymer Composite Solution 11 was obtained.

The Dopant Polymer 1 of Preparation Example 1 was changed to Dopant Polymer 11. Thus, Electro-Conductive Polymer Composite Solution 12 was obtained.

The Dopant Polymer 1 of Preparation Example 1 was changed to Dopant Polymer 12. Thus, Electro-Conductive Polymer Composite Solution 13 was obtained.

The Dopant Polymer 1 of Preparation Example 1 was changed to Dopant Polymer 13. Thus, Electro-Conductive Polymer Composite Solution 14 was obtained.

The Dopant Polymer 1 of Preparation Example 1 was changed to Dopant Polymer 14. Thus, Electro-Conductive Polymer Composite Solution 15 was obtained.

The Dopant Polymer 1 of Preparation Example 1 was changed to Dopant Polymer 15. Thus, Electro-Conductive Polymer Composite Solution 16 was obtained.

The Dopant Polymer 1 of Preparation Example 1 was changed to Dopant Polymer 16. Thus, Electro-Conductive Polymer Composite Solution 17 was obtained.

The Dopant Polymer 1 of Preparation Example 1 was changed to Dopant Polymer 17. Thus, Electro-Conductive Polymer Composite Solution 18 was obtained.

The Dopant Polymer 1 of Preparation Example 1 was changed to Dopant Polymer 18. Thus, Electro-Conductive Polymer Composite Solution 19 was obtained.

The Dopant Polymer 1 of Preparation Example 1 was changed to Dopant Polymer 19. Thus, Electro-Conductive Polymer Composite Solution 20 was obtained.

The Dopant Polymer 1 of Preparation Example 1 was changed to Dopant Polymer 20. Thus, Electro-Conductive Polymer Composite Solution 21 was obtained.

The Dopant Polymer 1 of Preparation Example 1 was changed to Dopant Polymer 21. Thus, Electro-Conductive Polymer Composite Solution 22 was obtained.

The Dopant Polymer 1 of Preparation Example 1 was changed to Dopant Polymer 22. Thus, Electro-Conductive Polymer Composite Solution 23 was obtained.

The Dopant Polymer 1 of Preparation Example 1 was changed to Dopant Polymer 23. Thus, Electro-Conductive Polymer Composite Solution 24 was obtained.

The Dopant Polymer 1 of Preparation Example 1 was changed to Dopant Polymer 24. Thus, Electro-Conductive Polymer Composite Solution 25 was obtained.

The Dopant Polymer 1 of Preparation Example 1 was changed to Dopant Polymer 25. Thus, Electro-Conductive Polymer Composite Solution 26 was obtained.

The Dopant Polymer 1 of Preparation Example 1 was changed to Dopant Polymer 26. Thus, Electro-Conductive Polymer Composite Solution 27 was obtained.

The Dopant Polymer 1 of Preparation Example 1 was changed to Dopant Polymer 27. Thus, Electro-Conductive Polymer Composite Solution 28 was obtained.

The Dopant Polymer 1 of Preparation Example 1 was changed to Dopant Polymer 28. Thus, Electro-Conductive Polymer Composite Solution 29 was obtained.

The Dopant Polymer 1 of Preparation Example 1 was changed to Dopant Polymer 29. Thus, Electro-Conductive Polymer Composite Solution 30 was obtained.

The Dopant Polymer 1 of Preparation Example 1 was changed to Dopant Polymer 30. Thus, Electro-Conductive Polymer Composite Solution 31 was obtained.

The Dopant Polymer 1 of Preparation Example 1 was changed to Dopant Polymer 31. Thus, Electro-Conductive Polymer Composite Solution 32 was obtained.

The Dopant Polymer 1 of Preparation Example 1 was changed to Dopant Polymer 32. Thus, Electro-Conductive Polymer Composite Solution 33 was obtained.

A crosslinking agent, a solvent, and additives were added to the electro-conductive polymer composite solution as shown in Tables 1 to 3. With the exception of Examples 23 and 24, the mixture was filtered using regenerated cellulose having a pore size of 1.0 μm. Thus, solutions were prepared.

(Measurement of Thickness of Living Body Contact Layer)

The electro-conductive polymer composite solution was applied to a Si substrate by spin-coating and baked on a hot plate at 125° C. for 30 minutes, and the film thickness was measured with an optical film thickness meter. Tables 1 to 3 show the results.

(Preparation of Electro-Conductive Base Material)

A thermoplastic urethane (TPU) film ST-604 (manufactured by Bemis Associates Inc.) was coated with an electro-conductive paste DOTITE FA-333 (manufactured by Fujikura Kasei Co., Ltd.) by screen printing. The coating film was baked in an oven at 120° C. for 10 minutes to print a padlock-keyhole-shaped electro-conductive pattern including a circular portion with a diameter of 18 mm to obtain an electro-conductive base material. A Teflon (registered trademark) adhesive masking tape was pasted to the rectangular portion of the padlock-keyhole shape, and the ST-604 film was attached to a quartz wafer. The electro-conductive polymer composite solution was applied to the electro-conductive base material by spin-coating and baked on a hot plate at 120° C. for 10 minutes. The Teflon (registered trademark) adhesive tape was then peeled off (FIG. 3).

The obtained bio-electrodes were immersed in pure water having a temperature of 40° C. for 1 hour while applying ultrasonic vibration. The bio-electrodes were taken out of the water and observed visually to see whether or not the living body contact layer had been delaminated.

(Measurement of Biological Signals)

The bio-electrodes were cut out in the manner shown in FIG. 4 (the portion to contact the skin being a circle with a diameter of 1.8 cm). A cellophane adhesive tape was attached to the backside of the bio-electrodes, and the bio-electrodes were attached to the arms in the manner shown in FIG. 5. Thus, ECG measurement was carried out. In FIG. 5, 31 is a positive electrode, 32 is a negative electrode, and 33 is an earth.

Crosslinking Agent 1: MEIKANATE CX SU-268A (available from Meisei Chemical Works, Ltd.)

Additives

Polyglycerin silicone 1

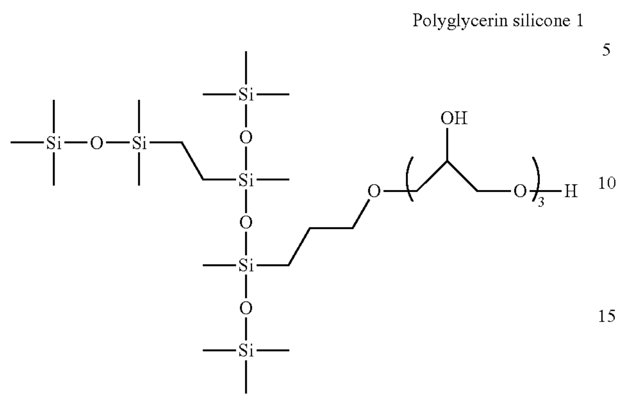

Fluoroalkyl-based nonionic surfactant FS-31 (available from DuPont)

Amine Compound 1

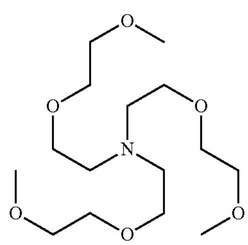

-continued

Amine Compound 2

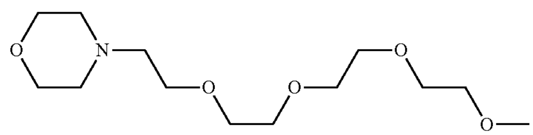

For the Silver Nanowire Solution 1 added to the electro-conductive polymer composite solution, silver nanowires having a diameter of 20 nm, a length of 12 μm, and a concentration of 5 mg/mL manufactured by Sigma-Aldrich Co., LLC. were used.

For the Silver Nanoparticle Solution 1 added to the electro-conductive polymer composite solution, silver nanoparticles having a diameter of 20 nm and a concentration of 0.02 mg/mL manufactured by Sigma-Aldrich Co., LLC. were used.

For the TPU base material, a thermoplastic urethane (TPU) film ST-604, manufactured by Bemis Associates Inc., was used.

As the PEDOT-PSS in the Comparative Examples, a high-conductivity grade product manufactured by Sigma-Aldrich Co., LLC. was used.

TABLE 1

| Example | Electro-conductive polymer composite solution (parts by mass) | Crosslinking Agent (parts by mass) | Solvent (parts by mass) | Additive (parts by mass) | Film delamination after immersion in water | Film thickness (nm) | ECG signals |
|---|---|---|---|---|---|---|---|
| Example 1 | Electro-Conductive Polymer Composite Solution 1 (100) | Crosslinking Agent 1 (0.2) | DMSO (5) | FS-31(0.2) Lysine(0.56) | None | 115 | Good |
| Example 2 | Electro-Conductive Polymer Composite Solution 1 (100) | Crosslinking Agent 1 (0.3) | DMSO (10) | FS-31(0.2) Histidine(0.60) | None | 121 | Good |
| Example 3 | Electro-Conductive Polymer Composite Solution 1 (100) | Crosslinking Agent 1 (0.2) | DMSO (5) | FS-31(0.2) Amine 1(1.24) | None | 112 | Good |
| Example 4 | Electro-Conductive Polymer Composite Solution 1 (100) | Crosslinking Agent 1 (0.25) | DMSO (5) | FS-31(0.2) Amine 2(1.06) | None | 111 | Good |
| Example 5 | Electro-Conductive Polymer Composite Solution 1 (100) | Crosslinking Agent 1 (0.2) | DMSO (5) | FS-31(0.2) Potassium hydroxide (0.21) | None | 105 | Good |
| Example 6 | Electro-Conductive Polymer Composite Solution 1 (100) | Crosslinking Agent 1 (0.2) | DMSO (5) | FS-31(0.2) Potassium hydrogencarbonate (0.38) | None | 110 | Good |
| Example 7 | Electro-Conductive Polymer Composite Solution 1 (100) | Crosslinking Agent 1 (0.2) | DMSO (5) | FS-31(0.2) | None | 111 | Good |
| Example 8 | Electro-Conductive Polymer Composite Solution 2 (100) | Crosslinking Agent 1 (0.2) | — | — | None | 113 | Good |
| Example 9 | Electro-Conductive Polymer Composite Solution 3 (100) | Crosslinking Agent 1 (0.2) | DMSO (5) | Polyglycerin silicone 1(5) | None | 121 | Good |

TABLE 1-continued

| Example | Electro-conductive polymer composite solution (parts by mass) | Crosslinking Agent (parts by mass) | Solvent (parts by mass) | Additive (parts by mass) | Film delamination after immersion in water | Film thickness (nm) | ECG signals |
|---|---|---|---|---|---|---|---|
| Example 10 | Electro-Conductive Polymer Composite Solution 4 (100) | Crosslinking Agent 1 (0.2) | DMSO (5) | — | None | 110 | Good |
| Example 11 | Electro-Conductive Polymer Composite Solution 5 (100) | Crosslinking Agent 1 (0.2) | Ethylene glycol (5) | Polyglycerin silicone 1(4) | None | 112 | Good |
| Example 12 | Electro-Conductive Polymer Composite Solution 6 (100) | Crosslinking Agent 1 (0.2) | Glycerin (5) | — | None | 117 | Good |
| Example 13 | Electro-Conductive Polymer Composite Solution 7 (100) | Crosslinking Agent 1 (0.2) | DMSO (5) | — | None | 119 | Good |
| Example 14 | Electro-Conductive Polymer Composite Solution 8 (100) | Crosslinking Agent 1 (0.2) | DMSO (5) | — | None | 115 | Good |
| Example 15 | Electro-Conductive Polymer Composite Solution 9 (100) | Crosslinking Agent 1 (0.2) | Ethylene glycol (5) | — | None | 113 | Good |
| Example 16 | Electro-Conductive Polymer Composite Solution 10 (100) | Crosslinking Agent 1 (0.2) | Ethylene glycol (5) | — | None | 125 | Good |
| Example 17 | Electro-Conductive Polymer Composite Solution 11 (100) | Crosslinking Agent 1 (0.2) | Ethylene glycol (5) | — | None | 126 | Good |
| Example 18 | Electro-Conductive Polymer Composite Solution 12 (100) | Crosslinking Agent 1 (0.2) | Ethylene glycol (5) | — | None | 122 | Good |
| Example 19 | Electro-Conductive Polymer Composite Solution 13 (100) | Crosslinking Agent 1 (0.2) | Ethylene glycol (5) | — | None | 125 | Good |

TABLE 2

| Example | Electro-Conductive Polymer Composite Solution (parts by mass) | Crosslinking Agent (parts by mass) | Solvent (parts by mass) | Additive (parts by mass) | Film delamination after immersion in water | Film thick-ness (nm) | ECG signals |
|---|---|---|---|---|---|---|---|
| Example 20 | Electro-Conductive Polymer Composite Solution 14 (100) | Crosslinking Agent 1 (0.2) | DMSO (5) | FS-31(0.2) Lysine(0.56) | None | 112 | Good |
| Example 21 | Electro-Conductive Polymer Composite Solution 15 (100) | Crosslinking Agent 1 (0.3) | DMSO (10) | FS-31(0.2) Histidine(0.60) | None | 109 | Good |
| Example 22 | Electro-Conductive Polymer Composite Solution 16 (100) | Crosslinking Agent 1 (0.2) | DMSO (5) | FS-31(0.2) Amine 1(1.24) Silver Nanowire 1(10) | None | 128 | Good |
| Example 23 | Electro-Conductive Polymer Composite Solution 17 (100) | Crosslinking Agent 1 (0.25) | DMSO (5) | FS-31(0.2) Amine 2(1.06) Silver Nanoparticle(10) | None | 119 | Good |
| Example 24 | Electro-Conductive Polymer Composite Solution 18 (100) | Crosslinking Agent 1 (0.2) | DMSO (5) | FS-31(0.2) Potassium hydroxide(0.21) | None | 106 | Good |
| Example 25 | Electro-Conductive Polymer Composite Solution 19 (100) | Crosslinking Agent 1 (0.2) | DMSO (5) | FS-31(0.2) Potassium hydrogencarbonate (0.38) | None | 108 | Good |
| Example 26 | Electro-Conductive Polymer Composite Solution 20 (100) | Crosslinking Agent 1 (0.2) | DMSO (5) | FS-31(0.2) | None | 101 | Good |
| Example 27 | Electro-Conductive Polymer Composite Solution 21 (100) | Crosslinking Agent 1 (0.2) | DMSO (5) | FS-31(0.2) | None | 102 | Good |
| Example 28 | Electro-Conductive Polymer Composite Solution 22 (100) | Crosslinking Agent 1 (0.2) | DMSO (5) | FS-31(0.2) | None | 105 | Good |
| Example 29 | Electro-Conductive Polymer Composite Solution 23 (100) | Crosslinking Agent 1 (0.2) | DMSO (5) | FS-31(0.2) | None | 108 | Good |

TABLE 2-continued

| Example | Electro-Conductive Polymer Composite Solution (parts by mass) | Crosslinking Agent (parts by mass) | Solvent (parts by mass) | Additive (parts by mass) | Film delamination after immersion in water | Film thick-ness (nm) | ECG signals |
|---|---|---|---|---|---|---|---|
| Example 30 | Electro-Conductive Polymer Composite Solution 24 (100) | Crosslinking Agent 1 (0.2) | — | — | None | 110 | Good |
| Example 31 | Electro-Conductive Polymer Composite Solution 25 (100) | Crosslinking Agent 1 (0.2) | DMSO (5) | — | None | 130 | Good |
| Example 32 | Electro-Conductive Polymer Composite Solution 26 (100) | Crosslinking Agent 1 (0.2) | DMSO (5) | — | None | 121 | Good |
| Example 33 | Electro-Conductive Polymer Composite Solution 27 (100) | Crosslinking Agent 1 (0.2) | DMSO (5) | — | None | 122 | Good |
| Example 34 | Electro-Conductive Polymer Composite Solution 28 (100) | Crosslinking Agent 1 (0.2) | DMSO (5) | — | None | 111 | Good |
| Example 35 | Electro-Conductive Polymer Composite Solution 29 (100) | Crosslinking Agent 1 (0.2) | DMSO (5) | — | None | 115 | Good |
| Example 36 | Electro-Conductive Polymer Composite Solution 30 (100) | Crosslinking Agent 1 (0.2) | DMSO (5) | — | None | 102 | Good |
| Example 37 | Electro-Conductive Polymer Composite Solution 31 (100) | Crosslinking Agent 1 (0.2) | DMSO (5) | — | None | 105 | Good |
| Example 38 | Electro-Conductive Polymer Composite Solution 32 (100) | Crosslinking Agent 1 (0.2) | DMSO (5) | — | None | 108 | Good |
| Example 39 | Electro-Conductive Polymer Composite Solution 33 (100) | Crosslinking Agent 1 (0.2) | DMSO (5) | — | None | 109 | Good |

TABLE 3

| Example | Electro-Conductive Polymer Composite Solution (parts by mass) | Crosslinking Agent (parts by mass) | Solvent (parts by mass) | Additive (parts by mass) | Film delamination after immersion in water | Film thickness (nm) | ECG signals |
|---|---|---|---|---|---|---|---|
| Comparative Example 1 | PEDOT-PSS solution (100) | Crosslinking Agent 1 (0.2) | DMSO (5) | — | Delaminated | 129 | — |
| Comparative Example 2 | Electro-Conductive Polymer Composite Solution 22 (100) | — | DMSO (5) | — | Delaminated | 101 | — |
| Comparative Example 3 | PEDOT-PSS solution (100) | — | DMSO (5) | — | Delaminated | 120 | — |

In Examples 1 to 39, where the inventive bio-electrode compositions were used, no delamination due to the immersion in water occurred, and the ECG signals were excellent as well. The ECG signal in Example 1 is shown in FIG. 6.

Signals having a wave form like the wave form in FIG. 6 were judged as good.

On the other hand, in Comparative Examples 1 and 3, where the dopant polymer did not contain a hydroxy group or a carboxy group, and in Comparative Example 2, where no crosslinking agent was contained, the living body contact layer was delaminated due to the immersion in water, and it was not possible to measure the ECG signals.

The present description includes the following embodiments.

[1]: A bio-electrode composition comprising:

an electro-conductive polymer composite including (A) a π-conjugated polymer and (B) a dopant polymer containing a repeating unit-a1 having a hydroxy group and/or a carboxy group and a repeating unit-a2 having a sulfonic acid, fluorosulfonimide, and N-carbonyl-fluorosulfonamide, the dopant polymer having a weight-average molecular weight of 1,000 to 500,000; and (C) a crosslinking agent.

[2]: The bio-electrode composition of the above [1], wherein the crosslinking agent has a reactive group selected from an isocyanate group, a blocked isocyanate group, a carbodiimide group, and an aziridine group.

[3]: The bio-electrode composition of the above [1] or [2], wherein the π-conjugated polymer (A) is a polymerized product of one or more precursor monomers selected from the group consisting of monocyclic aromatic compounds, polycyclic aromatic compounds, acetylenes, and derivatives thereof.

[4]: The bio-electrode composition of the above [3], wherein the monocyclic aromatic compounds are pyrroles, thiophenes, thiophenevinylenes, selenophenes, tellurophenes, phenylenes, phenylenevinylenes, or anilines, and the polycyclic aromatic compounds are acenes.

[5]: The bio-electrode composition of any one of the above [1] to [4], wherein the repeating unit-a1, having a hydroxy group and/or a carboxy group in the dopant polymer (B), has a repeating unit A1-1 and/or a repeating unit A1-2 represented by the following general formulae (1), (1)

A1-1

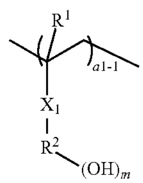

A1-2

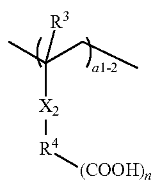

wherein $R^1$ and $R^3$ each independently represent a hydrogen atom or a methyl group; $X_1$ and $X_2$ each independently represent a single bond, a phenylene group, a naphthylene group, an ether group, an ester group, or an amide group; $R^2$ and $R^4$ each independently represent a single bond or a linear, branched, or cyclic hydrocarbon group having 1 to 20 carbon atoms and optionally having an ether group or an ester group; "m" and "n" each represent an integer of 1 to 5; and a1-1 and a1-2 satisfy $0 \leq (a1\text{-}1) < 1.0$, $0 \leq (a1\text{-}2) < 1.0$, and $0 < (a1\text{-}1) + (a1\text{-}2) < 1.0$.

[6]: The bio-electrode composition of any one of the above [1] to [5], wherein the dopant polymer (B) contains, as the repeating unit-a2, partial structures represented by the following general formulae (2)-1 to (2)-4, (2)-1

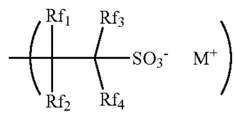

-continued (2)-2

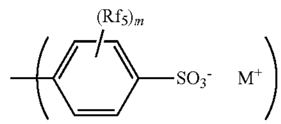

(2)-3

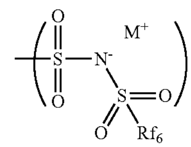

(2)-4

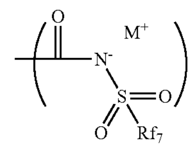

wherein $Rf_1$ to $Rf_4$ each represent a hydrogen atom, a fluorine atom, or a trifluoromethyl group, $Rf_1$ and $Rf_2$ optionally forming a carbonyl group together; $Rf_5$ represents a hydrogen atom, a fluorine atom, or a linear or branched alkyl group having 1 to 4 carbon atoms, optionally being substituted with a fluorine atom; $Rf_6$ and $Rf_7$ each represent a fluorine atom or a linear or branched alkyl group having 1 to 4 carbon atoms, having at least one fluorine atom; "m" represents an integer of 0 to 4; and $M^+$ represents an ion selected from a hydrogen ion, an ammonium ion, a sodium ion, and a potassium ion.

[7]: The bio-electrode composition of the above [6], wherein the dopant polymer (B) contains, as the repeating unit-a2, one or more repeating units selected from repeating units A2-1 to A2-7 represented by the following general formulae (2), (2)

A2-1

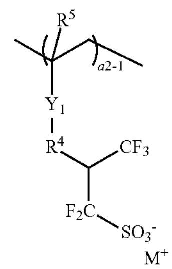

A2-2

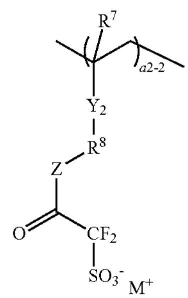

-continued

A2-3

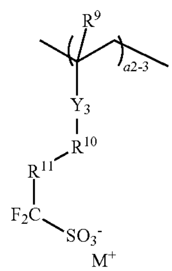

A2-4

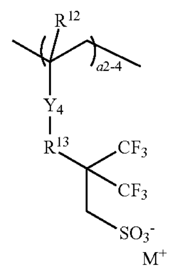

A2-5

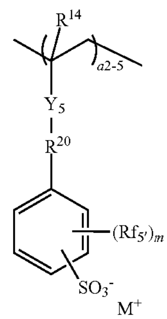

A2-6

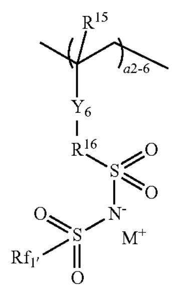

A2-7

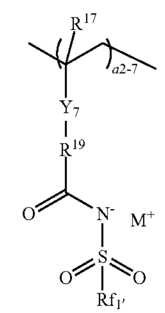

wherein $R^5$, $R^7$, $R^9$, $R^{12}$, $R^{14}$, $R^{15}$, and $R^{17}$ each independently represent a hydrogen atom or a methyl group; $R^6$, $R^8$, $R^{10}$, $R^{13}$, $R^{16}$, $R^{19}$, and $R^{20}$ each independently represent a single bond or a linear, branched, or cyclic hydrocarbon group having 1 to 13 carbon atoms, the hydrocarbon group optionally having one or more selected from an ester group, an ether group, an amide group, a carbamate group, a thiocarbamate group, and a urea group; $R^{11}$ represents a linear or branched alkylene group having 1 to 4 carbon atoms, one or two hydrogen atoms in $R^{11}$ optionally being substituted with a fluorine atom; $Y_1$, $Y_2$, $Y_3$, $Y_4$, $Y_6$, and $Y_7$ each independently represent a single bond, a phenylene group, a naphthylene group, an ether group, an ester group, or an amide group; $Y_5$ represents a single bond, an ether group, or an ester group; Z represents an oxygen atom or an —$NR^{18}$— group; $R^{18}$ represents a hydrogen atom, a linear, branched or cyclic alkyl group having 2 to 12 carbon atoms, or a phenyl group and optionally has one or more selected from an ether group, a carbonyl group, an ester group, and an amide group; Z optionally forms a ring together with $R^8$; $Rf_{1'}$ and $Rf_{5'}$ each represent a fluorine atom, a trifluoromethyl group, or a linear or branched alkyl group having 1 to 4 carbon atoms, having at least one fluorine atom; "m" represents an integer of 0 to 4; a2-1, a2-2, a2-3, a2-4, a2-5, a2-6, and a2-7 satisfy $0\leq(a2\text{-}1)<1.0$, $0\leq(a2\text{-}2)<1.0$, $0\leq(a2\text{-}3)<1.0$, $0\leq(a2\text{-}4)<1.0$, $0\leq(a2\text{-}5)<1.0$, $0\leq(a2\text{-}6)<1.0$, $0\leq(a2\text{-}7)<1.0$, and $0\leq(a2\text{-}1)+(a2\text{-}2)+(a2\text{-}3)+(a2\text{-}4)+(a2\text{-}5)+(a2\text{-}6)+(a2\text{-}7)<1.0$; $M^+$ represents an ion selected from a hydrogen ion, an ammonium ion, a sodium ion, and a potassium ion.

[8]: The bio-electrode composition of the above [7], wherein the $Rf_{1'}$ has at least one fluorine atom, and the $Rf_{5'}$ is a fluorine atom or a trifluoromethyl group in the general formulae (2).

[9]: The bio-electrode composition of the above [7] or [8], wherein the dopant polymer (B) contains, as the ammonium ion, an ammonium ion represented by the following general formula (3), (3)

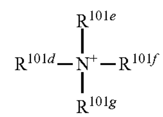

wherein $R^{101d}$, $R^{101e}$, $R^{101f}$, and $R^{101g}$ each represent a hydrogen atom, a linear, branched, or cyclic alkyl group having 1 to 15 carbon atoms, a linear, branched, or cyclic alkenyl group or alkynyl group having 2 to 12 carbon atoms, or an aromatic group having 4 to 20 carbon atoms, $R^{101d}$, $R^{101e}$, $R^{101f}$, and $R^{101g}$ optionally having one or more selected from an ether group, a carbonyl group, an ester group, a hydroxy group, a carboxy group, an amino group, a nitro group, a sulfonyl group, a sulfinyl group, a halogen atom, and a sulfur atom; and $R^{101d}$ and $R^{101e}$, or $R^{101d}$, $R^{101e}$, and $R^{101f}$ optionally form a ring together with a nitrogen atom bonded to $R^{101d}$ and $R^{101e}$, or $R^{101d}$, $R^{101e}$, and $R^{101f}$ and when a ring is formed, $R^{101d}$ and $R^{101e}$, or $R^{101d}$, $R^{101e}$, and $R^{101f}$ form an alkylene group having 3 to 10 carbon atoms or a heteroaromatic ring having, in the ring, the nitrogen atom in the general formula (3).

[10]: The bio-electrode composition of any one of the above [1] to [9], comprising, in addition to the components (A), (B), and (C), a component (D) containing one or more resins selected from a (meth)acrylate resin, a (meth)acrylamide resin, a urethane resin, polyvinyl alcohol, polyvinylpyrrolidone, polyoxazoline, polyglycerin, polyglycerin-modified silicone, cellulose, polyethylene glycol, and polypropylene glycol.

[11]: The bio-electrode composition of any one of the above [1] to [10], further comprising, as a component (E), one or more selected from a carbon powder, a metal powder, a silicon powder, and a lithium titanate powder.

[12]: The bio-electrode composition of the above [11], wherein the carbon powder is one or both of carbon black and carbon nanotube.

[13]: The bio-electrode composition of the above [11] or [12], wherein the metal powder is any of gold nanoparticles, silver nanoparticles, copper nanoparticles, gold nanowire, silver nanowire, and copper nanowire.

[14]: A bio-electrode comprising an electro-conductive base material and a living body contact layer formed on the electro-conductive base material, wherein the living body contact layer comprises the electro-conductive polymer composite comprised in the bio-electrode composition of any one of the above [1] to [13].

[15]: The bio-electrode of the above [14], wherein the electro-conductive base material comprises one or more selected from the group consisting of gold, silver, silver chloride, platinum, aluminum, magnesium, tin, tungsten, iron, copper, nickel, stainless steel, chromium, titanium, and carbon.

[16]: A method for manufacturing a bio-electrode having an electro-conductive base material and a living body contact layer formed on the electro-conductive base material, the method comprising:

applying the bio-electrode composition of any one of the above [1] to [13] onto the electro-conductive base material; and curing the bio-electrode composition to form the living body contact layer.

It should be noted that the present invention is not limited to the above-described embodiments. The embodiments are just examples, and any examples that have substantially the same feature and demonstrate the same functions and effects as those in the technical concept disclosed in claims of the present invention are included in the technical scope of the present invention.

The invention claimed is:

1. A bio-electrode composition comprising:

an electro-conductive polymer composite including (A) a π-conjugated polymer and (B) a dopant polymer containing a repeating unit-a1 having a hydroxy group and/or a carboxy group and a repeating unit-a2 having one or more selected from a sulfonic acid, fluorosulfonimide, and N-carbonyl-fluorosulfonamide, the dopant polymer having a weight-average molecular weight of 1,000 to 500,000; and (C) a crosslinking agent, having a reactive group selected from an isocyanate group, a blocked isocyanate group, a carbodiimide group, and an aziridine group, wherein the dopant polymer (B) contains, as the repeating unit-a1, a repeating unit A1-1 and/or a repeating unit A1-2 represented by the following general formulae (1), (1)

A1-1

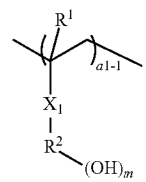

A1-2

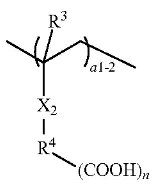

wherein $R^1$ and $R^3$ each independently represent a hydrogen atom or a methyl group, $X_1$ and $X_2$ each independently represent a single bond, a phenylene group, a naphthylene group, an ether group, an ester group, or an amide group; $R^2$ and $R^4$ each independently represent a single bond or a linear, branched, or cyclic hydrocarbon group having 1 to 20 carbon atoms and the hydrocarbon group is unsubstituted or substituted with an ether group or an ester group; "m" and "n" each represent an integer of 1 to 5, and a1-1 and a1-2 satisfy $0 \leq (a1\text{-}1) < 1.0$, $0 \leq (a1\text{-}2) < 1.0$, and $0 < (a1\text{-}1)+(a1\text{-}2) < 1.0$.

2. The bio-electrode composition according to claim 1, wherein the π-conjugated polymer (A) is a polymerized product of one or more precursor monomers selected from the group consisting of monocyclic aromatic compounds, polycyclic aromatic compounds, acetylenes, and derivatives thereof.

3. The bio-electrode composition according to claim 2, wherein the monocyclic aromatic compounds are pyrroles, thiophenes, thiophenevinylenes, selenophenes, tellurophenes, phenylenes, phenylenevinylenes, or anilines, and the polycyclic aromatic compounds are acenes.

4. The bio-electrode composition according to claim 1, wherein the dopant polymer (B) contains, as the repeating unit-a2, one or more partial structures selected from group represented by the following general formulae (2)-1 to (2)-5, (2)-1

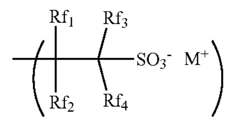

(2)-2

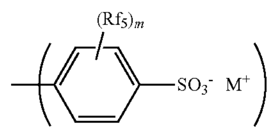

(2)-3

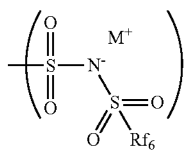

-continued (2)-4

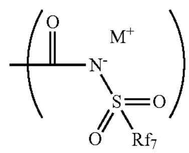

(2)-5

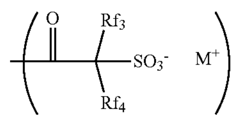

wherein $Rf_1$ to $Rf_4$ each represent a hydrogen atom, a fluorine atom, or a trifluoromethyl group; $Rf_5$ represents a hydrogen atom, a fluorine atom, or a linear or branched alkyl group having 1 to 4 carbon atoms, the alkyl group is unsubstituted or substituted with a fluorine atom; $Rf_6$ and $Rf_7$ each represent a fluorine atom or a linear or branched alkyl group having 1 to 4 carbon atoms, having at least one fluorine atom; "m" represents an integer of 0 to 4; and $M^+$ represents an ion selected from a hydrogen ion, an ammonium ion, a sodium ion, and a potassium ion.

5. The bio-electrode composition according to claim 4, wherein the dopant polymer (B) contains, as the repeating unit-a2, one or more repeating units selected from repeating units A2-1 to A2-7 represented by the following general formulae (2), (2)

A2-1

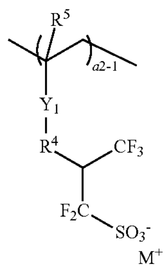

A2-2

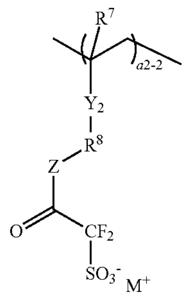

-continued

A2-3

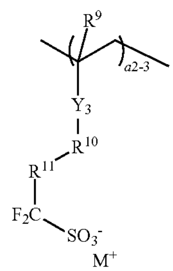

A2-4

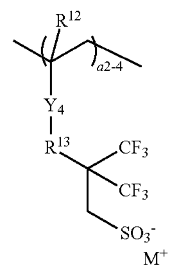

A2-5

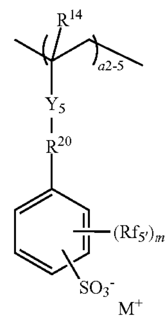

A2-6

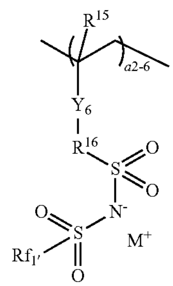

A2-7

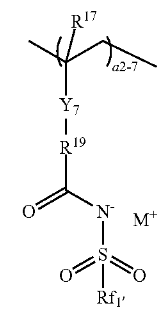

wherein $R^5$, $R^7$, $R^9$, $R^{12}$, $R^{14}$, $R^{15}$, and $R^{17}$ each independently represent a hydrogen atom or a methyl group; $R^6$, $R^8$, $R^{10}$, $R^{13}$, $R^{16}$, $R^{19}$, and $R^{20}$ each independently represent a single bond or a linear, branched, or cyclic hydrocarbon group having 1 to 13 carbon atoms, the hydrocarbon group is unsubstituted or substituted with one or more groups selected from an ester group, an ether group, an amide group, a carbamate group, a thiocarbamate group, and a urea group; $R^{11}$ represents a linear or branched alkylene group having 1 to 4 carbon atoms, one or two hydrogen atoms in $R^{11}$ being unsubstituted or substituted with a fluorine atom; $Y_1$, $Y_2$, $Y_3$, $Y_4$, $Y_6$, and $Y_7$ each independently represent a single bond, a phenylene group, a naphthylene group, an ether group, an ester group, or an amide group; $Y_5$ represents a single bond, an ether group, or an ester group; Z represents an oxygen atom or an —$NR^{18}$— group; $R^{18}$ represents a hydrogen atom, a linear, branched or cyclic alkyl group having 2 to 12 carbon atoms, or a phenyl group and is unsubstituted or substituted with one or more groups selected from an ether group, a carbonyl group, an ester group, and an amide group; Z forms a ring together with $R^8$; when Z is an —$NR^{18}$— group; $R^{18}$ represents a linear, branched or cyclic alkyl group having 2 to 12 carbon atoms, or a phenyl group and $R^6$ is a linear, branched, or cyclic hydrocarbon group having 1 to 13 carbon atoms; $Rf_{1'}$ and $Rf_{5'}$ each represent a fluorine atom, a trifluoromethyl group, or a linear or branched alkyl group having 1 to 4 carbon atoms, having at least one fluorine atom; "m" represents an integer of 0 to 4; a2-1, a2-2, a2-3, a2-4, a2-5, a2-6, and a2-7 satisfy $0 \leq (a2\text{-}1) < 1.0$, $0 \leq (a2\text{-}2) < 1.0$, $0 \leq (a2\text{-}3) < 1.0$, $0 \leq (a2\text{-}4) < 1.0$, $0 \leq (a2\text{-}5) < 1.0$, $0 \leq (a2\text{-}6) < 1.0$, $0 \leq (a2\text{-}7) < 1.0$, and $0 < (a2\text{-}1)+(a2\text{-}2)+(a2\text{-}3)+(a2\text{-}4)+(a2\text{-}5)+(a2\text{-}6)+(a2\text{-}7) < 1.0$;

$M^+$ represents an ion selected from a hydrogen ion, an ammonium ion, a sodium ion, and a potassium ion.

6. The bio-electrode composition according to claim 5, wherein the $Rf_{1'}$ has at least one fluorine atom, and the $Rf_{5'}$ is a fluorine atom or a trifluoromethyl group in the general formulae (2).

7. The bio-electrode composition according to claim 5, wherein the dopant polymer (B) contains, as the ammonium ion, an ammonium ion represented by the following general formula (3), (3)

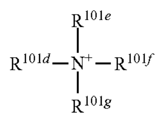

wherein $R^{101d}$, $R^{101e}$, $R^{101f}$, and $R^{101g}$ each represent a hydrogen atom, a linear, branched, or cyclic alkyl group having 1 to 15 carbon atoms, a linear, branched, or cyclic alkenyl group or alkynyl group having 2 to 12 carbon atoms, or an aromatic group having 4 to 20 carbon atoms, $R^{101d}$, $R^{101e}$, $R^{101f}$, and $R^{101g}$ are unsubstituted or substituted with one or more groups selected from an ether group, a carbonyl group, an ester group, a hydroxy group, a carboxy group, an amino group, a nitro group, a sulfonyl group, a sulfinyl group, a halogen atom, and a sulfur atom; and $R^{101d}$ and $R^{101a}$ form a ring together when $R^{101d}$ is a linear, branched, or cyclic alkyl group, a linear branched, or cyclic alkenyl group or alkynyl group, or an aromatic group and $R^{101e}$ is a linear, branched, or cyclic alkyl group, a linear, branched, or cyclic alkenyl group or alkynyl group, or an aromatic group, or when $R^{101d}$, $R^{101e}$, and $R^{101f}$ form a ring together when $R^{101d}$ is a linear, branched, or cyclic alkyl group, a linear branched, or cyclic alkenyl group or alkynyl group, or an aromatic group, $R^{101e}$ is a linear, branched, or cyclic alkyl group, a linear, branched, or cyclic alkenyl group or alkynyl group, or an aromatic group, and $R^{101f}$ is a linear, branched, or cyclic alkyl group, a linear, branched, or cyclic alkenyl group or alkynyl group, or an aromatic group when the ring is formed, $R^{101d}$ and $R^{101e}$, or $R^{101d}$, $R^{101e}$, and $R^{101f}$ form an alkylene group having 3 to 10 carbon atoms or a heteroaromatic ring having, in the ring, the nitrogen atom in the general formula (3).

8. The bio-electrode composition according to claim 1, comprising, in addition to the components (A), (B), and (C), a component (D) containing one or more resins selected from a (meth)acrylate resin, a (meth)acrylamide resin, a urethane resin, polyvinyl alcohol, polyvinylpyrrolidone, polyoxazoline, polyglycerin, polyglycerin-modified silicone, cellulose, polyethylene glycol, and polypropylene glycol.

9. The bio-electrode composition according to claim 1, further comprising, as a component (E), one or more selected from a carbon powder, a metal powder, a silicon powder, and a lithium titanate powder.

10. The bio-electrode composition according to claim 9, wherein the carbon powder is one or both of carbon black and carbon nanotube.

11. The bio-electrode composition according to claim 9, wherein the metal powder is any of gold nanoparticles, silver nanoparticles, copper nanoparticles, gold nanowire, silver nanowire, and copper nanowire.

12. A bio-electrode comprising an electro-conductive base material and a living body contact layer formed on the electro-conductive base material, wherein the living body contact layer comprises the electro-conductive polymer composite comprised in the bio-electrode composition according to claim 1.

13. The bio-electrode according to claim 12, wherein the electro-conductive base material comprises one or more selected from the group consisting of gold, silver, silver chloride, platinum, aluminum, magnesium, tin, tungsten, iron, copper, nickel, stainless steel, chromium, titanium, and carbon.

14. A method for manufacturing a bio-electrode having an electro-conductive base material and a living body contact layer formed on the electro-conductive base material, the method comprising:

applying the bio-electrode composition according to claim 1 onto the electro-conductive base material; and curing the bio-electrode composition to form the living body contact layer.

* * * * *